US011548875B2

(12) United States Patent
Goldstein et al.

(10) Patent No.: US 11,548,875 B2
(45) Date of Patent: Jan. 10, 2023

(54) INHIBITOR COMPOUNDS FOR MALE CONTRACEPTION

(71) Applicant: University of Washington, Seattle, WA (US)

(72) Inventors: Alex S. Goldstein, Seattle, WA (US); John K. Amory, Seattle, WA (US); Jisun Paik, Seattle, WA (US); Michael Haenisch, Seattle, WA (US); Nina Isoherranen, Seattle, WA (US); Piper Treuting, Seattle, WA (US); Charles H. Muller, Seattle, WA (US)

(73) Assignee: University of Washington, Seattle, WA (US)

( * ) Notice: Subject to any disclaimer, the term of this patent is extended or adjusted under 35 U.S.C. 154(b) by 29 days.

(21) Appl. No.: 17/262,877

(22) PCT Filed: Dec. 12, 2019

(86) PCT No.: PCT/US2019/066059
§ 371 (c)(1),
(2) Date: Jan. 25, 2021

(87) PCT Pub. No.: WO2020/123855
PCT Pub. Date: Jun. 18, 2020

(65) Prior Publication Data
US 2021/0332030 A1 Oct. 28, 2021

Related U.S. Application Data

(60) Provisional application No. 62/778,773, filed on Dec. 12, 2018, provisional application No. 62/778,786, filed on Dec. 12, 2018.

(51) Int. Cl.
*C07D 403/12* (2006.01)
*C07D 231/14* (2006.01)
*A61P 15/16* (2006.01)
*A61K 9/00* (2006.01)

(52) U.S. Cl.
CPC .......... *C07D 403/12* (2013.01); *A61K 9/0024* (2013.01); *A61P 15/16* (2018.01); *C07D 231/14* (2013.01)

(58) Field of Classification Search
CPC .............................. C07D 403/12; C07D 231/14
See application file for complete search history.

(56) References Cited

U.S. PATENT DOCUMENTS

| | | |
|---|---|---|
| 3,934,015 A | 1/1976 | Boris |
| 4,297,350 A | 10/1981 | Babcock |
| 2007/0281963 A1 | 12/2007 | Fukumoto |
| 2011/0178148 A1 | 7/2011 | Xia |

FOREIGN PATENT DOCUMENTS

| | | |
|---|---|---|
| CN | 103254133 | 8/2013 |
| WO | 2007020388 | 2/2007 |
| WO | 2007052843 | 5/2007 |
| WO | 2008137081 | 11/2008 |
| WO | 2011143657 | 11/2011 |
| WO | 2012100342 | 8/2012 |
| WO | 2013142408 | 9/2013 |

OTHER PUBLICATIONS

Haenisch M, Treuting PM, Brabb T, et al. Pharmacological inhibition of ALDH1A enzymes suppresses weight gain in a mouse model of diet-induced obesity. Obes Res Clin Pract. 2017.
Hammerschmidt SI, Ahrendt M, Bode U, et al. Stromal mesenteric lymph node cells are essential for the generation of gut-homing T cells in vivo. J Exp Med. 2008;205:2483-2490.
Heilig M, Egli M. Pharmacological treatment of alcohol dependence: target symptoms and target mechanisms. Pharmacol Ther 2006 111:855-876.
Heinemann K, Saad F, Wiesemes M, White S, Heinemann L. Attitudes towards male fertility control: results of a multinational survey on four continents. Human Repro 2005 20; 2:549-556.
Heller CG, Flageolle BY, Matson LJ. Histopathology of the human testes as affected by Bis (dichloroacetyl) diamines. Exp Mol Path 1963 2:107-114.
Heller CG, Moore DJ, Paulsen CA. Suppression of spermatogenesis and chronic toxicity in men by a new series of bis (dichloroacetyl) diamines. Toxicol Appl Pharmacol. 1961;3:1-11.
Henderson P, van Limbergen JE, Wilson DC, et al. Genetics of childhood-onset inflammatory bowel disease. Inflamm Bowel Dis. 2011;17:346-361.
Hill, D et al. 2,2,2-Trifluoroethyl Formate: A Versatile and Selective Reagent for the Formylation of Alcohols, Amines, and N-Hydroxylamines 2002 Organic Lett 4(1) 111-3.
Hogarth et al. Suppression of Stra8 Expression in the Mouse Gonad by WIN 18,446, Biol. Reprod. 84, 957-965 (2011).
Hong K, Zhang Y, Guo Y, et al. All-trans retinoic acid attenuates experimental colitis through inhibition of NF-kappaB signaling. Immunol Lett. 2014;162:34-40.
Hsu LH, Chang W-C, Yoshida A. Mouse type-2 retinaldehyde dehydrogenase (RALDH2): genomic organization, tissue-dependent expression, chromosome assignment and comparison to other types. Biochem Biophys Acta 2000 1492:289-293.
Huang, Xian-Feng, et al. Bioorganic & Medicinal Chemistry (2012), 20(16), 4895-4900.
Huang, Zhangjian, et al. Acyclic triaryl olefins possessing a sulfohydroxamic acid pharmacophore: synthesis, nitric oxide/nitroxyl release, cyclooxygenase inhibition, and anti-inflammatory studies. 2010 Organic and Biomolecular Chemistry 8(18)4124-36.

(Continued)

Primary Examiner — Shawquia Jackson
(74) Attorney, Agent, or Firm — Christensen O'Connor Johnson Kindness PLLC

(57) ABSTRACT

Pyrazole compounds and piperazine compounds that are inhibitors of ALDH1A1 and ALDH1A2 and methods for using the pyrazole compounds and piperazine compounds in male contraceptive compositions for preventing spermatogenesis.

23 Claims, 10 Drawing Sheets

(56) References Cited

OTHER PUBLICATIONS

Iwata M, Hirakiyama A, Eshima Y, et al. Retinoic acid imprints gut-homing specificity on T cells. Immunity. 2004;21:527-538.

Iwata M. Retinoic acid production by intestinal dendritic cells and its role in T-cell trafficking. Semin Immunol. 2009;21:8-13.

Jaensson E, Uronen-Hansson H, Pabst O, et al. Small intestinal CD103+ dendritic cells display unique functional properties that are conserved between mice and humans. The Journal of experimental medicine. 2008;205:2139-2149.

Jijon HB, Suarez-Lopez L, Diaz OE, et al. Intestinal epithelial cell-specific RARalpha depletion results in aberrant epithelial cell homeostasis and underdeveloped immune system. Mucosal Immunol. 2018;11:703-715.

Johansson-Lindbom B, Svensson M, Pabst O, et al. Functional specialization of gut CD103+ dendritic cells in the regulation of tissue-selective T cell homing. The Journal of experimental medicine. 2005;202:1063-1073.

Kabsch, W. (2010) Integration, scaling, space-group assignment and post-refinement. Acta Crystallogr., Sect. D: Biol. Crystallogr. 66, 133-144.

Kang SG, Wang C, Matsumoto S, et al. High and low vitamin A therapies induce distinct FoxP3+ T-cell subsets and effectively control intestinal inflammation Gastroenterology 2009;137:1391-1402 e1391-1396.

Kasimanickam, V. R. (2016) Expression of retinoic acid-metabolizing enzymes, ALDH1A1, ALDH1A2, ALDH1A3, CYP26A1, CYP26B1 and CYP26C1 in canine testis during post-natal development. Reprod Domest Anim 51, 901-909.

Kastner P, Mark M, Leid M, Gansmuller A, Chin W, Grondona JM, Décimo D, Krezel W, Dierich A, Chambon P. Abnormal spermatogenesis in RXR beta mutant mice Genes Dev 1006 10:80-92.

Khanna, M., Chen, C. H., Kimble-Hill, A., Parajuli, B., Perez-Miller, S., Baskaran, S., Kim, J., Dria, K., Vasiliou, V., Mochly-Rosen, D., and Huriey, T. D. (2011) Discovery of a novel class of covalent inhibitor for aldehyde dehydrogenases. J. Biol. Chem. 286, 43486-43494.

Kikonyogo A, Abriola DP, Dryjanski M, et al. Mechanism of inhibition of aldehyde dehydrogenase by citral, a retinoid antagonist. Eur J Biochem. 1999;262:704-712.

Kimble-Hill, A. C., Parajuli, B., Chen, C. H., Mochly-Rosen, D., and Hurley, T. D. (2014) Development of selective inhibitors for aldehyde dehydrogenases based on substituted indole 2,3-diones. J. Med. Chem. 57, 714-722.

Koch, M. F., Harteis, S., Blank, I. D., Pestel, G., Tietze, L. F., Ochsenfeld, C., Schneider, S., and Sieber, S. A. (2015) Structural, Biochemical, and Computational Studies Reveal the Mechanism of Selective Aldehyde Dehydrogenase 1A1 Inhibition by Cytotoxic Duocarmycin Analogues. Angew. Chern., Int. Ed. 54, 13550-13554.

Koppaka, V., Thompson, D. C., Chen, Y., Ellermann, M., Nicolaou, K. C., Juvonen, R. O., Petersen, D., Deitrich, R. A., Hurley, T. D., and Vasiliou, V. (2012) Aldehyde dehydrogenase inhibitors: a comprehensive review of the pharmacology, mechanism of action, substrate specificity, and clinical application. Pharmacol. Rev. 64, 520-539.

Koubova J, Menke D, Zhou Q, Capel B, Griswold MD, Page DC. Retinoic acid regulates sexspecific timing of meiotic initiation in mice Proc Natl Acad Sci USA 2006 103:2472-2479.

Kurmaeva, E.; Lord, J.D.; Zhang, S.; Bao, J.R.; Kevil, C.G.; Grisham, M.B.; Ostanin, D.V. T cell-associated alpha4beta7 but not alpha4beta1 integrin is required for the induction and perpetuation of chronic colitis. Mucosal Immunol. 2014, 7, 1354-1365.

Lagoutte, R., Patouret, R., and Winssinger, N. (2017) Covalent inhibitors: an opportunity for rational target selectivity. Curr. Opin. Chemn. Biol. 39, 54-63.

Lamb, A. L. and Newcomer, M. E. (1999) The structure of retinal dehydrogenase type II at 2.7 A resolution: Implications for retinal specificity,. Biochemistry 38, 6003-6011.

Li S-Q, Goldstein M, Shu J, Huber DH. The no-scalpel vasectomy. J Urol 1991;145:341-344.

Li Y, Gao Y, Cui T, et al. Retinoic Acid Facilitates Toll-Like Receptor 4 Expression to Improve Intestinal Barrier Function through Retinoic Acid Receptor Beta. Cell Physiol Biochem. 2017;42:1390-1406.

Li, K. et al. Inhibition of sperm capacitation and fertilizing capacity by adjudin is mediated by chloride and its channels in humans, Hum Reprod. Jan. 2013; 28(1):47-59.

Li, Xi et al. Synthesis, biological evaluation, and molecular docking studies of N,1,3-triphenyl-1 H-pyrazole-4-carboxamide derivatives as anticancer agents. 2012 Bioorg Med Chem Lett 22(11) 3589-93.

Liu Z, Geboes K, Colpaert S, et al. IL-15 is highly expressed in inflammatory bowel disease and regulates local T cell-dependent cytokine production. J Immunol 2000;164:3608-3615.

Liu, X., Wang, L., Cui, W., Yuan, X., Lin, L., Cao, Q., Wang, N., Li, Y., Guo, W., Zhang, X., Wu, C., and Yang, J. (2016) Targeting ALDH1A1 by disulfiram/copper complex inhibits non-small cell lung cancer recurrence driven by ALDH-positive cancer stem cells. Oncotarget 7, 58516-58530.

Lohnes D, Kastner P, Dierich A, Mark M, LeMeur M, Chambon P. Function of retinoic acid receptor gamma in the mouse. Cell 1993 73:643-658.

Lowe, E. D., Gao, G. Y., Johnson, L. N., and Keung, W. M. (2008) Structure of daidzin, a naturally occurring anti-alcohol-addiction agent, in complex with human mitochondrial aldehyde dehydrogenase. J. Med. Chem. 51, 4482-4487.

Lufkin T, Lohnes D, Mark M, Dierich A, Gorry P, Gaub MP, LeMeur M, Chambon P. High postnatal lethality and testis degeneration in retinoic acid receptor alpha mutant mice Proc Natl Acad Sci USA 1993 90:7225-7229.

Luo, M., Gates, K. S., Henzl, M. T., and Tanner, J. J. (2015) Diethylaminobenzaldehyde Is a Covalent, Irreversible Inactivator of ALDH7A1. ACS Chem. Biol. 10, 693-697.

Ma C, Battat R, Dulai PS, et al. Innovations in Oral Therapies for Inflammatory Bowel Disease. Drugs. 2019;79:1321-1335.

Macaluso FS, Orlando A, Cottone M. Anti-interieukin-12 and anti-interleukin-23 agents in Crohn's disease. Expert Opin Biol Ther. 2018.

Maggio-Price L, Treuting P, Zeng W, et al. Helicobacter infection is required for inflammation and colon cancer in SMAD3-deficient mice Cancer Res. 2006;66:828-838.

Marchitti SA, Brocker C, Stagos D, Vailiou V. Non-P450 aldehyde oxidizing enzymes: the aldehyde dehydrogenase superfamily. Expert Opin Drug Metab Toxicol 2008 4(6):697-720.

Martin CW, Anderson RA, Cheng L, et al. Potential impact of hormonal male contraception: cross-cultural implications for development of novel male preparations Human Repro 2000; 15:637-645.

McCaskey SJ, Rondini EA, Clinthorne JF, et al. Increased presence of effector lymphocytes during Helicobacter hepaticus-induced colitis World J Gastroenterol. 2012;18:1459-1469.

Meeker S, Seamons A, Paik J, et al. Increased dietary vitamin D suppresses MAPK signaling, colitis, and colon cancer. Cancer Res. 2014;74:4398-4408.

Mielke LA, Jones SA, Raverdeau M, et al. Retinoic acid expression associates with enhanced IL-22 production by gammadelta T cells and innate lymphoid cells and attenuation of intestinal inflammation. J Exp Med. 2013;210:1117-1124.

Milstein D, Stille JK, Mild, selective, general method of ketone synthesis from acid chlorides and organotin compounds catalyzed by palladium 1979 J Org Chem 44(10) 1613-18.

United States Patent and Trademark Office, International Search Report issued in PCT/US2019/066059, dated Apr. 20, 2020, 4 pages.

United States Patent and Trademark Office, Written Opinion of the International Searching Authority issued in PCT/US2019/066059, dated Apr. 20, 2020, 6 pages.

The International Bureau of WIPO, International Preliminary Report on Patentability issued in PCT/US2019/066059, dated Jun. 8, 2021, 7 pages.

Mora JR, Iwata M, von Andrian UH. Vitamin effects on the immune system: vitamins A and D take centre stage. Nat Rev Immunol. 2008;8:685-698.

(56) References Cited

OTHER PUBLICATIONS

Morales C, Griswold MD. Retinol-induced stage synchronization in seminiferous tubules of the rat. Endocrinology 1987 121:432-434.
Morgan, C. A. and Hurley, T. D. (2015) Characterization of two distinct structural classes of selective aldehyde dehydrogenase 1A1 inhibitors. J. Med. Chem. 58, 1964-1975.
Morgan, C. A., Parajuli, B., Buchman, C. D., Dria, K., and Hurley, T. D. (2015) N,N-diethylaminobenzaldehyde (DEAB) as a substrate and mechanism-based inhibitor for human ALDH isoenzymes. Chem.-Biol. Interact. 234, 18-28.
Moridani, M. Y., Khan, S., Chan, T., Teng, S., Beard, K., and O'Brien, P. J. (2001) Cytochrome P450 2E1 metabolically activates propargyl alcohol: propiolaldehyde-induced hepatocyte cytotoxicity. Chem.-Biol. Interact. 130-132, 931-942.
Mosli MH, Rivera-Nieves J, Feagan BG. T-cell trafficking and anti-adhesion strategies in inflammatory bowel disease: current and future prospects. Drugs. 2014;74:297-311.
Mruk, D et al., A male contraceptive targeting germ cell adhesion, Nat Med. Nov. 2006;12(11):1323-8.
Mucida D, Park Y, Kim G, et al. Reciprocal TH17 and regulatory T cell differentiation mediated by retinoic acid. Science 2007;317:256-260.
Munson L, Chassy LM, Asa C. Efficacy, safety and reversibility of bisdiamine as a male contraceptive in cats. Theriogenology 2004 62:81-92.
Murdoch, FE, et al. Male contraception: another holy grail, Bioorg Med Chem Lett. Jan. 15, 2014;24(2):419-24.
Napoli J. Retinoic acid: Its biosynthesis and metabolism. In: "Progress in Nucleic Acid Research and Molecular Biology" (Ed. K. Moldave), Academic Press, San Diego, 2000.
Nobrega JA, et al., Selective Preparation of a,a-Dichloroketones with Copper(II) Chloride, 2002 Syn Comm 32(24) 3711-7.
Nya-Ngatchou, J.J. et al. New approaches to male non-hormonal contraception, Contraception, 87(3), Mar. 2013, 296-299.
OD'Byrne SM, Blaner WS. Retinol and retinyl esters: biochemistry and physiology. J Lipid Res. 2013;54:1731-1743.
Oehlers SH, Flores MV, Hall CJ, et al. Retinoic acid suppresses intestinal mucus production and exacerbates experimental enterocolitis. Dis Model Mech. 2012;5:457-467.
Ohta, T. et al. Studies on the Oxidation of N-substituted—dibenz[b,f] azepines I. Oxidation with m-Chloroperbenzoic Acid. 1981 Chemical and Pharmaceutical Bulletin 29(5) 1221-30.
Oliveira LM, Teixeira FME, Sato MN. Impact of Retinoic Acid on Immune Cells and Inflammatory Diseases. Mediators Inflamm. 2018;2018:3067126.
Osani M, Cellular retinoic acid bioavailablility in various pathologies and its therapeuticsimplication. Pathol Int 2017, 67, 281-91.
Paik J et al. Vitamin A: overlapping delivery pathways to tissues from the circulation. J Nutr 2004 134:276-280.
Paik J, et al. Inhibition of retinoic acid biosynthesis by the bisdichloroacetyldiamine WIN 18,446 markedly suppresses spermatogenesis and alters retinoid metabolism in mice. J Biol Chem. 2014;289:15104-15117.
Perez-Aiea, M., McGrail, K., Sanchez-Redondo, S., Ferrer, B., Foumet, G., Cortes, J., Munoz, E., Hernandez-Losa, J., Tenbaum, S., Martin, G., Costello, R., Ceylan, I., Garcia-Patos, V., and Recio, J. A. (2017) ALDH1A3 is epigenetically regulated during melanocyte transformation and is a target for melanoma treatment. Oncogene 36, 5695-5708.
Perez-Miller, S. J. and Hurley, T. D. (2003) Coenzyme isomerization is integral to catalysis in aldehyde dehydrogenase. Biochemistry 42, 7100-7109.
Perlmann T. Retinoid metabolism: a balancing act. Nat Genet 2002 31:7-8.
Peyrin-Biroulet L, Demarest S, Nirula A. Bispecific antibodies: The next generation of targeted inflammatory bowel disease therapies. Autoimmun Rev. 2018.
Piccinino LJ, Mosher WD. Trends in contraceptive use in the United States: 1982:1995. Fam Plan Persp 1998;30:4-10.

Population Division of the Department of Economic and Social Affairs of the United Nations Secretariat. World Population prospects: the 2008 revision. Available at http://www.un.org/esa/population/ (Retrieved Sep. 30, 2011).
Qi et al. Synthesis and acrosin inhibitory activities of substituted ethyl 5-(4-aminophenyl)-1H-pyrazole-3-carboxylate derivatives, Bioorganic & Medicinal Chemistry Letters, vol. 21, Issue 19 (2011).
Quesada-Soriano, I., Primavera, A., Casas-Solvas, J. M., Tellez-Sanz, R., Baron, C., Vargas-Berenguel, A., Lo Bello, M., and Garcia-Fuentes, L. (2012) Identifying and characterizing binding sites on the irreversible inhibition of human glutathione S-transferase P1—1 by S-thiocarbamoylation. ChemBioChem 13, 1594-1604.
Rector, D. et al. Structure-Activity Relationships in a Broad-spectrum Anthelmintic Series. Acid Chloride Phenylhydrazones. 1. Aryl Substitutions and Chloride Variations.1981 J Med Chem 24, 532-8.
Reddy D, Siegel CA, Sands BE, et al. Possible association between isotretinoin and inflammatory bowel disease. Am J Gastroenterol. 2006;101:1569-1573.
Reniers DE, Howard JM. Isotretinoin-induced inflammatory bowel disease in an adolescent. The Annals of pharmacotherapy. 2001;35:1214-1216.
Rojas, R. J., Edmondson, D. E., Almos, T., Scott, R., and Massari, M. E. (2015) Reversible and irreversible small molecule inhibitors of monoamine oxidase B (MAO-B) investigated by biophysical techniques. Bioorg. Med. Chem. 23, 770-778.
Roosenboom B, Wahab PJ, Smids C, et al. Intestinal CD103+CD4+ and CD103+CD8+ T-Cell Subsets in the Gut of Inflammatory Bowel Disease Patients at Diagnosis and During Follow-up. Inflamm Bowel Dis. 2019.
Sanders TJ, McCarthy NE, Giles EM, et al. Increased production of retinoic acid by intestinal macrophages contributes to their inflammatory phenotype in patients with Crohn's disease. Gastroenterology. 2014;146:1278-1288 e1271-1272.
Sarma, M. et al. D-π-A-A-π-D Prototype 2,2'-Bipyridine Dyads Exhibiting Large Structure and Environment-Sensitive Fluorescence: Synthesis, Photophysics, and Computation, 2012 J. Org. Chem. 77, 432-44.
Schulze GE, Clay RJ, Mezza LE, Bregman CL, Buroker RA, Frantz JD. BMS-189453, a novel retinoid receptor antagonist, is a potent testicular toxin. Toxicol Sci 2001 59:297-308.
Seamons A, Treuting PM, Brabb T, et al. Characterization of dextran sodium sulfate-induced inflammation and colonic tumorigenesis in Smad3(-/-) mice with dysregulated TGFbeta PloS one. 2013;8:e79182.
Shah I, Ahman E. Unsafe abortion in 2008: global and regional level and trends. Reprod Health Matters 2010; 18:90-101.
Shen, M. L., Johnson, K. L., Mays, D. C., Lipsky, J. J., and Naylor, S. (2001) Determination of in vivo adducts of disulfiram with mitochondrial aldehyde dehydrogenase. Biochem. Pharmacol. 61, 537-545.
Siiteri JE, Karl AF, Linder CC, Griswold MD. Testicular synchrony: evaluation and analysis of different protocols. Biol Reprod 1992 46:284-289.
Silva, EJ et al., Characterization of EPPIN's semenogelin I binding site: a contraceptive drug target, Biol Reprod. Sep. 7, 2012;87(3):56.
Singh AK, Dominic CJ. Effect of N'N'-bis(dichloroacetyl)-1,8-octamethylenediamine (WIN 18,446) on the testis and epididymis of the musk shrew (*Sunus murinus*). Indian J Exp Biol 1980 18:1217-1220.
Singh AK, Dominic CJ. Testicular toxicity of WIN 18,446 in the laboratory mouse. Reproductive Toxicology 1995 9 (5):475-481.
Singh S, Darroch ME, Ashford LS, Vlassoff M. Adding it up: the costs and benefits of investing in family planning and maternal and newborn health. New York (NY). Alan Guttmacher Institute, 2009.
Singh S, Sedgh G, Hussain R. Unintended pregnancy: worldwide levels, trends and outcomes. Stud Fam Plann 2010 41(4):241-250.
Speidel JJ, Grossman RA. Addressing global health, economic, and environmental problems through family planning. Obstet Gynecol 2011; 117:1394-1398.
Sun, H., Tawa, G., and Wallqvist, A. (2012) Classification of scaffold-hopping approaches. Drug Discovery Today 17, 310-324.

(56) References Cited

OTHER PUBLICATIONS

Teletin M, Vernet M, Ghyselinck NB, Mark M. Roles of Retinoic Acid in Germ Cell Differentiation. Curr Topics Dev Biol 2017;125:191-225.
Tomita, H., Tanaka, K., Tanaka, T., and Hara, A. (2016) Aldehyde dehydrogenase 1A1 in stem cells and cancer. Oncotarget 7, 11018-11032.
Torrence, A.E.; Brabb, T.; Viney, J.L.; Bielefeldt-Ohmann, H.; Treuting, P.; Seamons, A.; Drivdahl, R.; Zeng,W.; Maggio-Price, L. Serum biomarkers in a mouse model of bacterial-induced inflammatory bowel disease. Inflamm. Bowel Dis. 2008, 14, 480-490.
Troncone E, Marafini I, Stolfi C, et al. Transforming Growth Factor-beta1/Smad7 in Intestinal Immunity, Inflammation, and Cancer Front Immunol. 2018;9:1407.
Trussell J, Vaughan B. Contraceptive failure, method-related discontinuation and resumption of use: results from the 1995 National Survey of Family Growth. Fam Plann Perspect 1999;31:64-72.
Tsuruta JK et al., Therapeutic ultrasound as a potential male contraceptive: power, frequency and temperature required to deplete rat testes of meiotic cells and epididymides of sperm determined using a commercially available system, Reprod Biol Endocrinol. Jan. 30, 2012;10:7.
Van Pelt AM, de Rooij DG. Synchronization of the seminiferous epithelium after vitamin a replacement in vitamin A deficient mice. Biol Reprod 1990 43:363-367.
Vernet N, Dennefeld C, Rochett-Egly C, Oulad-Abdelghani M, Chambon P, Ghyselinck NB, Mark M. Retinoic acid metabolism and signaling pathways in the adult and developing mouse testis. Endocrinology 2006 147:96-110.
Vicente-Suarez I, Larange A, Reardon C, et al. Unique lamina propria stromal cells imprint the functional phenotype of mucosal dendritic cells. Mucosal Immunol. 2015;8:141-151.
Wang X, Penzes P, Napoli J. Cloning of a cDNA encoding an aldehyde dehydrogenase and its expression in *Escherichia coli*. J Biol Chem 1996 27:16288-16291.
Wang, B., Chen, X., Wang, Z., Xiong, W., Xu, T., Zhao, X., Cao, Y., Guo, Y., Li, L., Chen, S., Huang, S., Wang, X., Fang, M., and Shen, Z. (2017) Aldehyde dehydrogenase 1A1 increases NADH levels and promotes tumor growth via glutathione/dihydrolipoic acid-dependent NAD(+) reduction. Oncotarget 8, 67043-67055.
Wei et al. Synthesis and acrosin inhibitory activities of 5-phenyl-1H-pyrazole-3-carboxylic acid amide derivatives, Bioorganic & Medical Chemistry Letters vol. 23, Issue 14 (2013).
Wendt, M. et al. Ortho selectivity in SNAr substitutions of 2,4-dihaloaromatic compounds. Reactions with piperidine 2010, Tetrahedron Letters 51, 641-644.
Wenzl, M. V., Beretta, M., Griesberger, M., Russwurm, M., Koesling, D., Schmidt, K., Mayer, B., and Gorren, A. C. (2011) Site-directed mutagenesis of aldehyde dehydrogenase-2 suggests three distinct pathways of nitroglycerin biotransformation. Mol. Pharmacol. 80, 258-266.
Wolbach SB, Howe PR. Tissue changes following deprivation of fat soluble A Vitamin. J Exp Med 1925 42:753-777.
World Health Organization Task Force on Methods for the Regulation of Male Fertility. Contraceptive efficacy of testosterone-induced azoospermia and oligozoospermia in normal men. Fertil Steril 1996 65:821-829.
Xu M, Pokrovskii M, Ding Y, et al. c-Maf-dependent regulatory T cells mediate immunological tolerance to a gut pathobiont. Nature. 2018;554:373-377.
Yokoyama, Y., Zhu, H., Lee, J. H., Kossenkov, A. V., Wu, S. Y., Wickramasinghe, J. M., Yin, X., Palozola, K. C., Gardini, A., Showe, L. C., Zaret, K. S., Liu, Q., Speicher, D., Conejo-Garcia, J. R., Bradner, J. E., Zhang, Z., Sood, A. K., Ordog, T., Bitler, B. G., and Zhang, R. (2016) BET Inhibitors Suppress ALDH Activity by Targeting ALDH1A1 Super-Enhancer in Ovarian Cancer. Cancer Res. 76, 6320-6330.
Zeng R, Bscheider M, Lahl K, et al. Generation and transcriptional programming of intestinal dendritic cells: essential role of retinoic acid. Mucosal Immunol. 2016;9:183-193.

Zheng, LP et al. Sperm-specific ion channels: targets holding the most potential for male contraceptives in development, Contraception. Oct. 2013:88(4):485-91.
Zhu, Y.; Richardson, J.A.; Parada, L.F.; Gra , J.M. Smad3 mutant mice develop metastatic colorectal cancer. Cell 1998, 94, 703-714.
PubChem, (Oct. 7, 2005), Database accession No. 1307900.
PubChem, (Oct. 26, 2006), Database accession No. 11450561.
PubChem, (Jul. 10, 2005), Database accession No. 1287551.
PubChem, (Jul. 29, 2005), Database accession No. 2959384.
Abdelhamid L, Luo XM. Retinoic Acid, Leaky Gut, and Autoimmune Diseases. Nutrients. 2018;10.
Abunada, N.M., et al. Molecules(2008), 13(7), 1501-1517.
Adams, P. D., Afonine, P. V., Bunkoczi, G., Chen, V. B., Davis, I. W., Echols, N., Headd, J. J., Hung, L. W., Kapral, G. J., Grosse-Kunstleve, R. W., McCoy, A. J., Moriarty, N. W., Oeffner, R., Read, R. J., Richardson, D. C., Richardson, J. S., Terwilliger, T. C., and Zwart, P. H. (2010) PHENIX: a comprehensive Python-based system for macromolecular structure solution. Acta Crystallogr., Sect. D: Biol. Crystallogr. 66, 213-221.
Akiyama, T. et al. 1-Aminoisoindole as a useful_-system elongation unit. 2009 Tetrahedron 65, 4345-50.
Allen, E. M., Anderson, D. G., Florang, V. R., Khanna, M., Hurley, T. D., and Doorn, J. A. (2010) Relative inhibitory potency of molinate and metabolites with aldehyde dehydrogenase 2: implications for the mechanism of enzyme inhibition. Chem. Res. Toxicol. 23, 1843-1850.
Alnouti Y, Klaassen CD. Tissue distribution, ontogeny and regulation of aldehyde dehydrogenase (Aldh) enzymes mRNA by prototypical microsomal enzyme inducers in mice. Toxicol Sci 2008 101:51-64.
Amory JK, Muller CH, Shimshoni AJ, Isoherranen N, Paik J, Moreb JS, Amory DW, Evanoff R, Goldstein AS, Griswold MD. Suppression of spermatogenesis by bisdichloroacetyldiamines is mediated by inhibition of testicular retinoic acid biosynthesis. Journal of Andrology 2011; 32(1):111-119.
Amory, J. K. (2016) Male contraception. Fertil. Steril. 106, 1303-1309.
Amory, J. K., Arnold, S., Lardone, M. C., Piottante, A., Ebensperger, M., Isoherranen, N., Muller, C. H., Walsh, T., and Castro, A. (2014) Levels of the retinoic acid synthesizing enzyme aldehyde dehydrogenase-1A2 are lower in testicular tissue from men with infertility. Fertil. Steril. 101, 960-966.
Arnold SL, Kent T, Hogarth CA, Schlatt S, Prasad B, Haenisch M, Walsh T, Muller CH, Griswold MD, Amory JK, Isoherranen N. Importance of ALDH1A enzymes in determining human testicular retinoic acid concentrations. Journal of Lipid Research 2015 56:342-57.
Arnold, S. L., Kent, T., Hogarth, C. A., Griswold, M. D., Amory, J. K., and Isoherranen, N. (2015) Pharmacological inhibition of ALDH1A in mice decreases all-trans retinoic acid concentrations in a tissue specific manner. Biochem. Pharmacol. 95, 177-192.
Asa C, Zaneveld LJD, Munson L, Callahan M, Byers AP. Efficacy, safety and reversibility of a bisdiamine male-directed oral contraceptive in grey wolves (*Canis lupus*). J Zoo Wild Med 1996 27:501-506.
Bai A, Lu N, Guo Y, et al. All-trans retinoic add down-regulates inflammatory responses by shifting the Treg/Th17 profile in human ulcerative and murine colitis. J Leukoc Biol. 2009;86:959-969.
Bawa, S. et al. One pot synthesis of diphenyl pyrazolylmethylanilines via reductive amination using NaBH4/I2 and their antimicrobial screening, Monatshefte fuer Chemie (2011), 142(6), 637-642.
Beedle MT, Stevison F, Zhong G, Topping T, Hogarth C, Isoherranen N, Griswold MD. Sources of All-Trans Retinal Oxidation Independent of the Aldehyde Dehydrogenase 1A Isozymes Exist in the Postnatal Testis. Biol Reprod. Sep. 21, 2018. doi: 10.1093/biolre/ioy200. [Epub ahead of print].
Beyler AL, Potts GO, Coulston F, Surrey AR. The selective testicular effects of certain bis-(dichloroacetyl) diamines. Endocrinology 1961 69:819-833.
Bhimani, K.B. et al., Journal of the Institution of Chemists (India) (2005), 77(4), 119-121.

(56) References Cited

OTHER PUBLICATIONS

Bishop PD, Griswold MD, Uptake and metabolism of retinol in cultured Sertoli cells: evidence for a kinetic model. Biochemistry 1987 26:7511-7518.

Bowles J, Knight D, Smith C, Wilhelm D, Richman J, Mamiya S, Yashiro K, Chawengsaksophak K, Wilson MJ, Rossant J, Hamada H, Koopman P. Retinoid signaling determines cell fate in mice. Science 2006 312:596-600.

Bratenko, M.K et al. 4-Functionally Substituted 3-Heterylpyrazoles: III. 3-Aryl(heteryl)pyrazole-4-carboxylic Acids and Their Derivatives 2001 Russian J Org Chem 37(4) 552-5.

Brooks NL, van der Horst G. Short-term effects on N'N-bis(dichloroacetyl),-1,8-octamethylenediamine (WIN 18,446) on the testes, selected sperm parameters and fertility of male CBA mice. Laboratory Animals 2003 (37:363-373.

Buchman, C. D. and Hurley, T. D. (2017) Inhibition of the Aldehyde Dehydrogenase 1/2 Family by Psoralen and Coumarin Derivatives J. Med. Chem. 60, 2439-2455.

Busch K, Ludvigsson JF, Ekstrom-Smedby K, et al. Nationwide prevalence of inflammatory bowel disease in Sweden: a population-based register study Aliment Pharmacol Ther. 2014;39:57-68.

Chang, J. S., Hsiao, J. R., and Chen, C. H. (2017) ALDH2 polymorphism and alcohol-related cancers in Asians: a public health perspective J. Biomed. Sci. 24, 19.

Cho JH, Brant SR. Recent insights into the genetics of inflammatory bowel disease. Gastroenterology. 2011;140:1704-1712.

Chung SS, Sung W, Wang X, Wolgemuth DJ. Retinoic acid receptor alpha is required for synchronization of spermatogenic cycles and its absence results in progressive breakdown of the spermatogenic process. Dev Dyn 2004 230:754-66.

Chung SS, Wang X, Roberts SS, Griffey SM, Reczek PR, Wolgemuth DJ. Oral administration of a retinoic Acid receptor antagonist reversibly inhibits spermatogenesis in mice. Endocrinology. 2011 152(6):2492-502.

Chung SS, Wang X, Wolgemuth DJ. Male sterility in mice lacking retinoic acid receptor alpha involves specific abnormalties in spermiogenesis. Differentiation 2005 73:188-198.

Clark, D. W. and Palle, K. (2016) Aldehyde dehydrogenases in cancer stem cells: potential as therapeutic targets. Ann. Transl Med. 4, 518.

Collins CB, Aheme CM, Kominsky D, et al. Retinoic acid attenuates ileitis by restoring the balance between T-helper 17 and T regulatory cells. Gastroenterology. 2011;141:1821-1831.

Coombes JL, Siddiqui KR, Arancibia-Carcamo CV, et al. A functionally specialized population of mucosal CD103+ DCs induces Foxp3+ regulatory T cells via a TGF-beta and retinoic acid-dependent mechanism. The Journal of experimental medicine. 2007;204:1757-1764.

Coperet, C. et al. A Simple and Efficient Method for the Preparation of Pyridine N-Oxides1998 J Org Chem 63, 1740-1.

Coulston F, Beyler AL, Drobeck HP. The biologic actions of a new series of bis(dichloroacetyl) diamines. Toxicol Appl Pharmacol 1960 2:715-721.

Crockett SD, Gulati A, Sandler RS, et al. A causal association between isotretinoin and inflammatory bowel disease has yet to be established. Am J Gastroenterol. 2009;104:2387-2393.

D'Ambrosio, K., Pailot, A., Talfoumier, F., Didierjean, C., Benedetti, E., Aubry, A., Branlant, G., and Corbier, C. (2006) The first crystal structure of a thioacylenzyme intermediate in the ALDH family: new coenzyme conformation and relevance to catalysis,. Biochemistry 45, 2978-2986.

DeMaster, E. G., Redfern, B., and Nagasawa, H. T. (1998) Mechanisms of inhibition of aldehyde dehydrogenase by nitroxyl, the active metabolite of the alcohol deterrent agent cyanamide. Biochem. Pharmacol. 55, 2007-2015.

DePaolo RW, Abadie V, Tang F, et al. Co-adjuvant effects of retinoic acid and IL-15 induce inflammatory immunity to dietary antigens. Nature. 2011;471:220-224.

Dorman E, Bishai D. Demand for male contraception. Expert Rev Pharmacoecon Outcomes Res 2012 12(5): 605-613.

Dufour JM, Kim KH. Cellular and subcellular localization of six retinoid receptors in rat testis during postnatal devlopment: identification of potential heterimeric receptors. Biol Reprod 1999 61:1300-1308.

Eberhardson M, Hedin C, Carlson M, et al. Toward Improved Control of Inflammatory Bowel Disease. Scand J Immunol. 2018:e12745.

Emsley, P., Lohkamp, B., Scott, W. G., and Cowtan, K. (2010) Features and development of Coot. Acta Crystallogr., Sect. D: Biol. Crystallogr. 66, 486-501.

Evans-Marin HL, Cong Y. Gut Homing Molecule Regulation of the Pathogenesis and Treatment of Inflammatory Bowel Diseases. Inflamm Allergy Drug Targets. 2015;14:4-12.

Feagins LA. Role of transforming growth factor-beta in inflammatory bowel disease and colitis-associated colon cancer. Inflamm Bowel Dis. 2010;16:1963-1968.

Feng T, Cong Y, Qin H, et al. Generation of mucosal dendritic cells from bone marrow reveals a critical role of retinoic acid. J Immunol. 2010;185:5915-5925.

Fierce, Y., de Morais Vieira, M., Piantedosi, R., Wyss, A., Blaner, W. S., and Paik, J. (2008) In vitro and in vivo characterization of retinoid synthesis from beta-carotene. Archives of biochemistry and biophysics 472, 126-138.

Frey-Wagner I, Fischbeck A, Cee A, et al. Effects of retinoids in mouse models of colitis: benefit or danger to the gastrointestinal tract? Inflamm Bowel Dis. 2013;19:2356-2365.

Ghyselinck NB, Vernet N, Dennefeld C, Giese N, Nau H, Chambon P, Viville S, Mark M. Retinoids and spermatogenesis: lessons from mutant mice lacking the plasma retinol binding protein. Dev Dyn 2006 235:1608-1622.

Grimes, DA et al., Steroid hormones for contraception in men, Database Syst Rev. Mar. 14, 2012;3:CD004316.

Griswold, M. D., Hogarth, C. A., Bowles, J., and Koopman, P. (2012) Initiating meiosis: the case for retinoic acid. Biol. Reprod. 86, 35.

317  3-Me-2-carbonylthiophene
318  4-Me-2-carbonylthiophene
319  5-Me-2-carbonylthiophene
320  3-carbonylthiophene

| 323 | 5-Et |
| 324 | 3-Cl |
| 325 | 5-Cl |
| 326 | 3-OCH$_2$CH$_3$ |
| 327 | 4,5-CH$_3$ |
| 328 | 5-CO$_2$H |
| 329 | 3-OCH$_3$ |
| 330 | 3-NBoc |
| 331 | 3-NH$_2$.HCl |
| 332 | 3-NAc |
| 333 | 5-CF$_3$ |
| 334 | 5-F |
| 335 | 3-OH |

| 336 | R=OH |

| | |
|---|---|
| 339 | C6H5 |
| 340 | 2-ClPh |
| 341 | 3-ClPh |
| 342 | 4-ClPh |
| 343 | N-methyl-1H-pyrrol-2-yl |
| 344 | 2-pyrrole |
| 345 | 4-OCH3Ph |
| 346 | 4-N(CH3)2Ph |
| 347 | N-acetyl-2-pyrrole |

INHIBITOR COMPOUNDS FOR MALE CONTRACEPTION

CROSS-REFERENCE TO RELATED APPLICATIONS

This application is a National Stage of International Application No. PCT/US2019/066059 filed Dec. 12, 2019, which claims the benefit of U.S. Provisional Application No. 62/778,773, filed Dec. 12, 2018, and U.S. Provisional Application No. 62/778,786, filed Dec. 12, 2018, each of which is expressly incorporated herein by reference in its entirety.

STATEMENT OF GOVERNMENT LICENSE RIGHTS

This invention was made with government support under Grant Nos. R01 HD098039, U01 HD060408, and U54 HD042454 awarded by the National Institutes of Health. The government has certain rights in the invention.

BACKGROUND OF THE INVENTION

The world's population exceeds seven billion, is increasing by 80 million yearly and will likely reach 9-10 billion by 2050. Population growth is a leading cause of environmental degradation and human suffering from poverty and hunger. Much of this population growth is unintended. In 2008, 41% of all pregnancies worldwide were unplanned, and 20% of all pregnancies ended in abortion, leading to 47,000 maternal deaths from unsafe abortions. In the United States, the unintended pregnancy rate is 48%, and 18% of all pregnancies end in abortion, accounting for 1.1 million abortions annually. This high rate of unintended pregnancy is due to inadequate use of and/or access to methods of contraception. Access to contraception dramatically reduces population growth and abortion rates, resulting in positive improvements in newborn and maternal health. In addition to the attenuation in world population growth, the use of modern contraception and better maternity care worldwide has the potential to avert 1.7 million newborn deaths and 251,000 maternal deaths each year. Therefore, there is a great need for better access to existing contraceptives, better contraceptive education, and more contraceptive options both in the United States and around the world.

Male Contraception

In the United States, 30% of all currently practiced contraception is male-directed with 20% of all couples using condoms and 10% of couples relying on vasectomy. Both of these methods have significant drawbacks. Condoms, while providing some protection against sexually transmitted infections, have a marginal contraceptive efficacy, and vasectomy, which is expensive and difficult to effectively reverse, is most appropriately considered an irreversible method of male contraception. A male contraceptive analogous to the estrogen/progesterone pills used by women would be welcomed by a large majority of men, and according to one analysis the market for such a contraceptive could exceed 40 million men in US and Western Europe.

Inhibition of Testicular Retinoic Acid Biosynthesis Reversibly Inhibits Spermatogenesis It has recently been discovered that inhibition of testicular retinoic acid biosynthesis allows for safe, reversible, non-hormonal inhibition of spermatogenesis. This line of investigation begins fifty years ago, when the oral administration of bisdichloroacetyldiamines (BDADs), such as WIN 18,446 were shown to safely, completely and reversibly inhibit spermatogenesis in many species including mice, rats, cats, shrews, dogs, monkeys and man. Histologic examination of testicular biopsies from men in these studies revealed a complete arrest of spermatogenesis, with an absence of forms beyond spermatogonia. Since these compounds had no effect on the endocrine function of the testes, and were not androgenic themselves, it was concluded that the inhibition of spermatogenesis exhibited by WIN 18,446 was not hormonal in nature. At least sixty men were administered WIN 18,446 for up to one year with achievement of sperm concentrations below 1 million sperm/ml of ejaculate—a sperm concentration associated with excellent contraceptive efficacy in trials of male hormonal contraceptives. Unfortunately, subjects taking WIN 18,446 experienced a "disulfiram reaction" consisting of nausea, vomiting, palpitations and sweating, when they drank alcohol. Because of this, further development of these compounds was abandoned without an understanding of the mechanism by which BDADs such as WIN 18,446 inhibited spermatogenesis.

In 2011, it was discovered that WIN 18,446 suppresses spermatogenesis by inhibiting testicular retinoic acid biosynthesis. Using a rabbit model, it was shown that oral administration of WIN 18,446 induced reversible azoospermia. This reduction in spermatogenesis was preceded by a reduction in intratesticular retinoic acid, the biosynthesis of which was potently inhibited by WIN 18,446 (see FIGS. 1A-1C).

These findings demonstrated that WIN 18,446 functioned as an oral, non-hormonal male contraceptive by inhibiting the testicular biosynthesis of retinoic acid and suggested that inhibition of the testicular retinal dehydrogenase (ALDH1A1 and ALDH1A2) responsible for testicular retinoic acid biosynthesis was a promising target for male contraceptive development. Since 2011, there has been a focus on identifying novel inhibitors (i.e., distinct from WIN 18,446) of ALDH1A1 and ALDH1A2, that didn't inhibit other ALDHs isozymes, to develop as male contraceptives.

Retinoic Acid and Spermatogenesis

It has been known since 1925 that vitamin-A is required for normal spermatogenesis. Nutritional studies in rats and genetic studies in mice demonstrate a requirement for vitamin-A and its metabolites at puberty for initiation of spermatogenesis and in adults for maintenance of spermatogenesis. Dietary beta-carotene (the vegetable form of vitamin-A) and retinol (the animal form of vitamin-A) are adsorbed in the intestine and mostly stored in the liver as retinyl-esters. Retinol is released via esterases and transported via a serum retinol binding protein-transthyretin complex to tissues, where it is converted to retinoic acid (RA), the main effector of vitamin-A activity by alcohol and aldehyde dehydrogenases.

In the seminiferous tubules, both germ and Sertoli cells synthesize retinoic acid from retinal via aldehyde dehydrogenases. Retinoic acid binds one of several retinoic acid receptors (RARs or RXRs), which regulate gene expression. Male RAR and RXR knockout animals are sterile due to various problems in spermiation. The importance of retinoic acid to spermatogenesis has also been demonstrated in animal models using experimental compounds that antagonize binding of retinoic acid to its receptors. For example, BMS-189453, a compound that non-selectively inhibits the binding of retinoic acid to RAR receptors, potently inhibits spermatogenesis after oral doses as low as 5 mg/kg for seven days, with mice becoming infertile after four weeks of treatment. However, this compound leads to hepatic inflammation, likely due to the fact that its antagonism of RAR is not testes specific. In mice, retinoic acid appears to be essential for the conversion of undifferentiated spermatogonia to A1 or differentiating spermatogonia. In the vitamin-A deficient mouse model, spermatogenesis can be synchronously initiated by vitamin-A supplementation, suggesting that the entry of spermatogonia into meiosis requires access to retinoic acid. This effect is mediated by the induction of the 45 kD protein STRA8 ("stimulated by retinoic acid-8") within the developing germ cells. The induction of Stra8 expression leads to the expression of Scp3 and Dmc1, known markers of meiosis. In summary, testicular retinoic acid appears to be the key signal that triggers spermatogonial differentiation and meiosis. Therefore, inhibition of retinoic acid biosynthesis in the testes is a logical target for male contraceptive development.

Testicular Retinoic Acid is synthesized by ALDH1A2, which is Testis Specific and by ALDH1A1. Nineteen isozymes of aldehyde dehydrogenase have been identified in the human. These enzymes catalyze the nicotinamide-dependent oxidation of a large array of aldehydes to their corresponding acids. Human and rodent ALDH1A1/1A2 sequences are highly conserved, sharing ~70% identity at the amino acid level. In mice, expression of the Aldh1a1 gene is evident in the testes, liver and lung; Aldh1a2 expression is predominantly in the testes and ovaries, while Aldh1a3 is expressed at very low levels in multiple tissues. Work in human testicular tissue samples indicates that ALDH1A1 and ALDH1A2 each contribute about 50% of intratesticular retinoic acid production in men, with ALDH1A3 contributing less than 1%.

A need exists for novel compounds that are effective inhibitor of both ALDH1A1 and ALDH1A2, without inhibiting other ALDH isozymes, for suppression of intratesticular retinoic acid biosynthesis and spermatogenesis. The present invention seeks t fulfill this need and provides further related advantages.

SUMMARY OF THE INVENTION

The present invention provides specific inhibitors of ALDH1A1 and ALDH1A2 for male contraception. In one aspect, pyrazole compounds as inhibitors of ALDH1A1 and ALDH1A2 are provided. In another aspect, piperazine compounds as inhibitors of ALDH1A1 and ALDH1A2 are provided. In further aspects, the invention provides methods for using the pyrazole compounds and piperazine compounds for male contraception to prevent spermatogenesis.

In one aspect, the invention provides pyrazole compounds that are inhibitors of ALDH1A1 and ALDH1A2. In one embodiment, the pyrazole compound is a compound of formula (I):

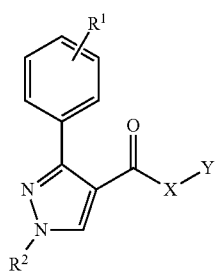

(I)

or a pharmaceutically acceptable salt thereof, wherein $R^1$ is selected from the group consisting of:
(a) $NO_2$,
(b) $SO_2R^a$, wherein $R^a$ is C1-C6 linear or branched alkyl or alkenyl,
(c) C1-C6 linear or branched alkyl, optionally substituted with hydroxy,
(d) C1-C6 linear or branched haloalkyl,
(e) C1-C6 linear or branched alkoxy,
(f) $C(=O)R^a$, wherein $R^a$ is hydrogen, C1-C6 linear or branched alkyl or alkenyl, optionally substituted with one or two halo groups, or $NR^cR^d$, wherein $R^c$ and $R^d$ are independently selected from hydrogen and C1-C3 linear or branched alkyl,
(g) $CO_2R^b$, wherein $R^b$ is hydrogen, or C1-C6 linear or branched alkyl,
(h) $O(C=O)R^a$, wherein $R^a$ is C1-C6 linear or branched alkyl, and
(i) $NH(R^e)$ or $N(R^a)(R^e)$, wherein in $R^a$ is C1-C6 linear or branched alkyl, and wherein $R^e$ is selected from
  (i) hydrogen,
  (ii) $C(=O)H$,
  (iii) $C(=O)R^f$, wherein $R^f$ is C1-C6 linear or branched alkyl or cyclo alkyl, optionally substituted with one or two halo groups,
  (iv) $C(=O)(CH_2)_2O$,
  (v) $C(=O)CH=CH_2$,
  (vi) $C(=O)(CH_2)_nOH$, wherein n is 1, 2, 3, or 4, and
  (vii) $SO_2R^g$, wherein $R^g$ is C1-C6 linear or branched alkyl;

$R^2$ is selected from the group consisting of:
(a) phenyl optionally substituted with
  (i) halo,
  (ii) C1-C6 linear or branched alkoxy,
  (iii) C1-C6 linear or branched haloalkyloxy,
  (iv) $C(=O)R^a$, wherein $R^a$ is C1-C6 linear or branched alkyl, or $R^a$ is $NR^cR^d$, wherein $R^c$ and $R^d$ are independently selected from is hydrogen and C1-C3 linear or branched alkyl, or $R^c$ is hydrogen and $R^d$ is hydroxy,
  (v) $CO_2R^b$, wherein $R^b$ is hydrogen or C1-C6 linear or branched alkyl, and
  (vi) cyano,
(b) C1-C6 linear or branched alkyl, and
(c) C1-C6 linear or branched haloalkyl;
X is O, NH, or $CH_2$; and
Y is phenyl optionally substituted with
(a) halo,
(b) C1-C6 linear or branched alkyl,
(c) C1-C6 linear or branched alkoxy,
(d) C1-C6 linear or branched haloalkyl,
(e) $(C=O)R^a$, wherein is C1-C6 linear or branched alkyl,
(f) $O(C=O)R^a$, wherein is C1-C6 linear or branched alkyl,
(g) $NR^cR^d$, wherein $R^c$ and $R^d$ are independently selected from hydrogen and C1-C6 linear or branched alkyl or $R^c$ is hydrogen and $R^d$ is C1-C6 linear or branched alkyl,
(h) cyano, and
(i) hydroxy,
with the proviso that when $R^1$ is $SO_2CH_3$, $R^2$ is phenyl or 4-cyanophenyl, and X is NH, Y is not ethoxy- or fluoro-substituted phenyl.

In another aspect, the invention provides piperazine compounds that are inhibitors of ALDH1A1 and ALDH1A2. In one embodiment, the piperazine compound is a compound of formula (IV):

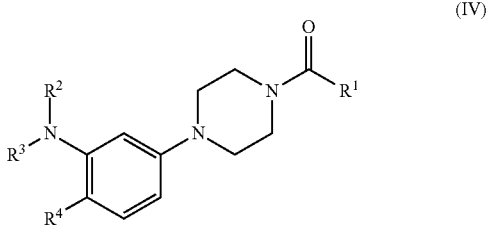

(IV)

or a pharmaceutically acceptable salt thereof, wherein $R^1$ is selected from the group consisting of substituted or unsubstituted phenyl, substituted or unsubstituted thiophenyl, substituted or unsubstituted pyrrolyl, and substituted or unsubstituted furanyl, wherein the phenyl, thiophenyl, pyrrolyl, or furanyl is substituted with a substituent selected from the group selected from:

(a) C1-C6 linear or branched alkyl,
(b) C1-C6 linear or branched haloalkyl,
(c) C1-C6 linear or branched alkoxy,
(d) halo,
(e) hydroxy,
(f) C(=O)$R^a$, wherein $R^a$ is C1-C6 linear or branched alkyl,
(g) CO$_2R^b$, wherein $R^b$ is hydrogen, C1-C6 linear or branched alkyl, and
(h) N$R^cR^d$, wherein $R^c$ is hydrogen or C1-C3 linear or branched alkyl, and $R^d$ is hydrogen, C1-C3 linear or branched alkyl, acetyl, or a N-protecting group;

$R^2$ and $R^3$ taken together with the nitrogen atom to which they are attached form a 4-, 5-, 6-, or 7-membered ring; and $R^4$ is selected from the group consisting of:
(a) NO$_2$,
(b) NH($R^e$), wherein $R^e$ is selected from
  (i) C(=O)$R^f$, wherein $R^f$ is C1-C6 linear or branched alkyl, optionally substituted with one or two halo groups,
  (ii) C(=O)(CH$_2$)$_2$O,
  (ii) C(=O)CH=CH$_2$, and
(c) N($R^g$)C(=O)$R^f$, wherein $R^g$ is C1-C6 linear or branched alkyl, and $R^f$ is C1-C6 linear or branched alkyl optionally substituted with one or two halo groups, with the proviso that when $R^1$ is 2-thiophenyl or 2-(3-ethoxythiophenyl), and $R^2$ and $R^3$ taken together with the nitrogen atom to which they are attached form a 5-membered ring, $R^4$ is not NO$_2$, and with the proviso that when $R^1$ is phenyl, 4-chlorophenyl, or 4-methoxyphenyl, and $R^2$ and $R^3$ taken together with the nitrogen atom to which they are attached form a 5-membered ring, $R^4$ is not NO$_2$.

In another aspect, the invention provides pharmaceutical compositions comprising a pyrazole compound or a piperazine compound described herein, or a pharmaceutically acceptable salt thereof, and a pharmaceutically acceptable carrier.

In a further aspect, the invention provides implantable devices comprising a pyrazole compound or a piperazine compound described herein, or a pharmaceutically acceptable salt thereof.

In other aspects, methods for using the pyrazole compounds and piperazine compounds described herein are provided.

In one embodiment, the invention provides a method for inhibiting ALDH1A1 and ALDH1A2 in a subject, comprising administering a therapeutically effective amount of a pyrazole compound or a piperazine compound described herein, or a pharmaceutically acceptable salt thereof, to subject in need thereof.

In another embodiment, the invention provides a method for preventing spermatogenesis in a subject, comprising administering a therapeutically effective amount of a pyrazole compound or a piperazine compound described herein, or a pharmaceutically acceptable salt thereof, to subject in need thereof.

DESCRIPTION OF THE DRAWINGS

The foregoing aspects and many of the attendant advantages of this invention will become more readily appreciated as the same become better understood by reference to the following detailed description, when taken in conjunction with the accompanying drawings.

DETAILED DESCRIPTION OF THE INVENTION

Figure 1A:
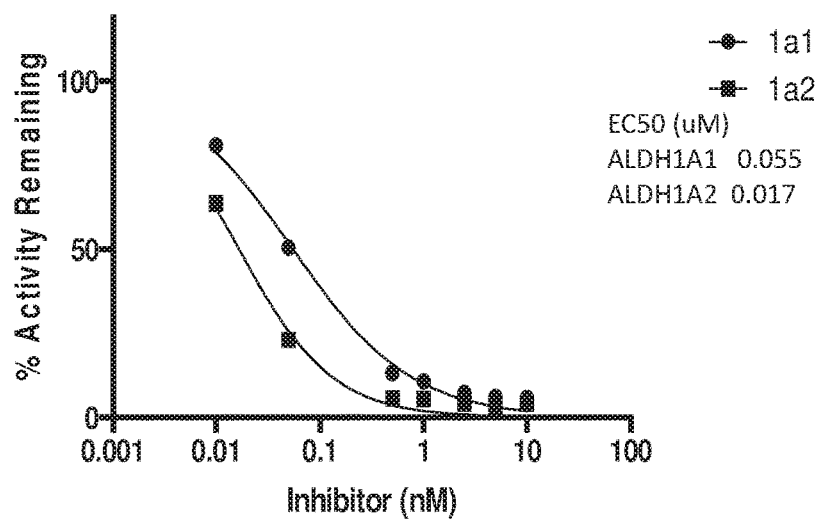
FIG. 1A illustrates the effective of WIN 18,446 on retinoic acid biosynthesis by inhibition of ALDH1A1 and the testicular aldehyde dehydrogenase (ALDH1A2). H1299 cells stably transfected with either ALDH1A1 or ALDH1A2 were used to determine efficacy of WIN 18,446. Cells were seeded at 4×10$^4$ on 96 well plates and cultured overnight. Cells were then treated with 1 μM retinal and varying concentrations of WIN 18,446 (0-10 μM) for about 24 hrs. Retinoic acid production was measured in media by LC/MS. All experiments were conducted in triplicate. Values are means±SEM (note error bars are contained within the symbol in most instances).
Figure 1B:
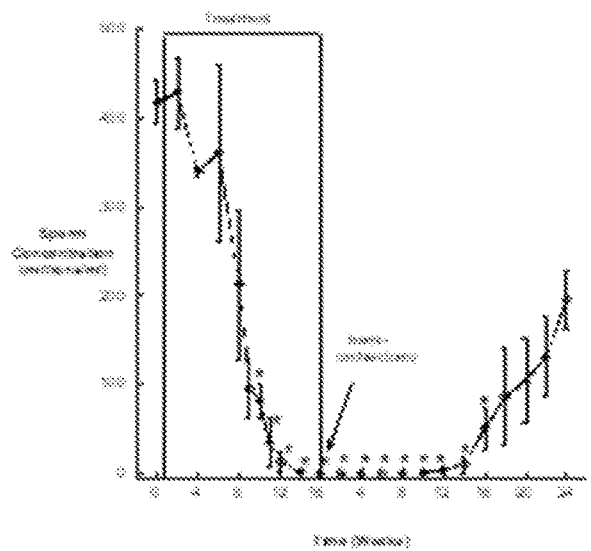
FIG. 1B shows ejaculated sperm concentrations in New Zealand white rabbits treated with 200 mg/kg WIN 18,446 orally for 16 weeks (N=4). All animals were azoospermic between week 16 of treatment and week 8 of recovery. Animals underwent a hemi-orchiectomy at the end of treatment, which accounts for the 50% reduction in sperm output at the end of recovery. *p<0.05 compared with baseline.
Figure 1C:
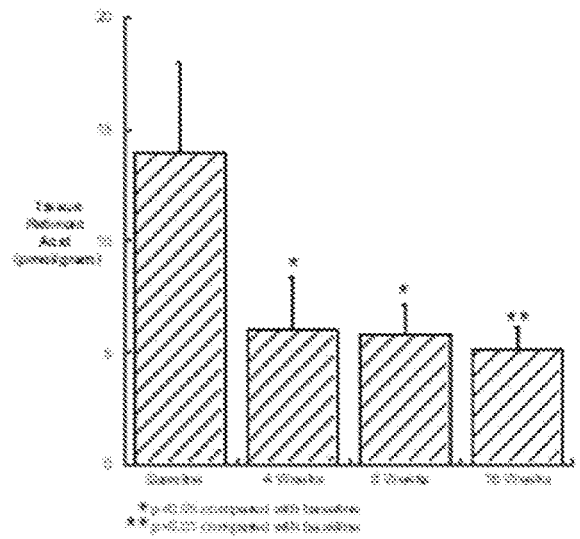
FIG. 1C compares testicular tissue retinoic acid concentration (pmol/g of tissue) in New Zealand white rabbits treated with 200 mg/kg WIN 18,446 daily, orally over time (N=4/group). Note the reduction in intra-testicular retinoic acid before the reduction in ejaculated sperm concentrations was observed (FIG. 1B). There were no significant changes in serum testosterone concentrations. All values are means±SEM. *p<0.05 compared with placebo, **p<0.01.
Figure 2:
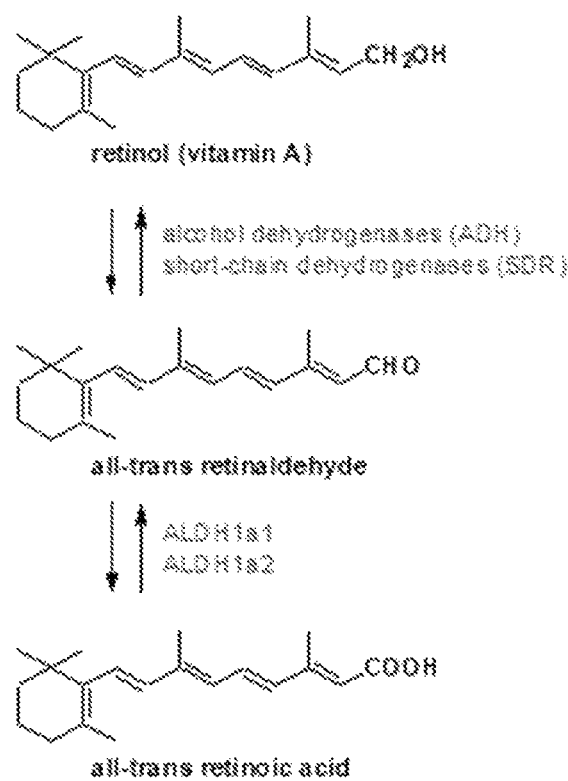
FIG. 2 illustrates the biosynthesis of retinoic acid. The first enzymatic step is catalyzed by alcohol dehydrogenases and leads to the generation of all-trans retinaldehyde. The second enzymatic step is catalyzed by aldehyde dehydrogenases and leads to the generation of all-trans retinoic acid.

Contraception is the most important tool to prevent unintended population growth and abortion, and increased use of contraception could decrease infant and maternal mortality and stabilize world population. New contraceptive technologies, especially effective male contraceptives, are likely to be widely used and accepted and would dramatically change the way in which contraception is provided around the world. Blocking testicular retinoic acid biosynthesis via inhibition of ALDH1A has been demonstrated to function as an oral, reversible, non-hormonal male contraceptive. Localized tissue retinoic acid levels are tightly controlled and RA does not readily cross the testis-blood-barrier. Since retinoic acid is essential for spermatogenesis, inhibition of ALDH1A1 and ALHD1A2 is an attractive, potent and specific approach to male contraceptive development. Successful development of a novel inhibitor of ALDH1A1 and ALDH1A2 has the potential to provide effective contraception in men and substantially reduce the risk of unintended pregnancy worldwide.

The present invention provides specific inhibitors of ALDH1A1 and ALDH1A2 for male contraception. In one aspect, pyrazole compounds as inhibitors of ALDH1A1 and ALDH1A2 are provided. In another aspect, piperazine compounds as inhibitors of ALDH1A1 and ALDH1A2 are provided. In further aspects, the invention provides methods for using the pyrazole compounds and piperazine compounds for male contraception to prevent spermatogenesis.

Pyrazole Compounds

In one aspect, the invention provides pyrazole compounds that are inhibitors of ALDH1A1 and ALDH1A2.

In one embodiment, the invention provides compounds having formula (I):

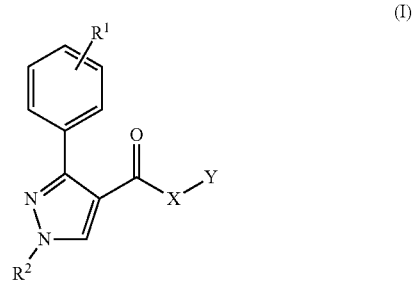

or pharmaceutically acceptable salts thereof, wherein $R^1$ is selected from the group consisting of:
(a) $NO_2$,
(b) $SO_2R^a$, wherein $R^a$ is C1-C6 linear or branched alkyl (e.g., $SO_2CH_3$) or alkenyl (e.g., $SO_2CH=CH_2$),
(c) C1-C6 linear or branched alkyl (e.g., methyl), optionally substituted with hydroxy (e.g., $CH_2OH$),
(d) C1-C6 linear or branched haloalkyl (e.g. trifluoromethyl, chloromethyl, bromomethyl),
(e) C1-C6 linear or branched alkoxy (e.g. methoxy),
(f) $C(=O)R^a$, wherein $R^a$ is hydrogen (e.g., CHO), C1-C6 linear or branched alkyl (e.g., $C(=O)CH_3$) or alkenyl ($C(=O)CH=CH_2$) optionally substituted with one or two halo groups (e.g., $C(=O)CH_2X$ or $C(=O)CHX_2$, where X is chloro or fluoro), or $NR^cR^d$, wherein $R^c$ and $R^d$ are independently selected from hydrogen and C1-C3 linear or branched alkyl (e.g., $CONH_2$),
(g) $CO_2R^b$, wherein $R^b$ is hydrogen (e.g., $CO_2H$), or C1-C6 linear or branched alkyl (e.g., $CO_2CH_3$),
(h) $O(C=O)R^a$, wherein $R^a$ is C1-C6 linear or branched alkyl (e.g., $O(C=O)CH_3$), and
(i) $NH(R^e)$ or $N(R^a)(R^e)$, wherein $R^a$ is C1-C6 linear or branched alkyl (e.g., methyl, ethyl), and wherein $R^e$ is selected from
  (i) hydrogen,
  (ii) $C(=O)H$,
  (iii) $C(=O)R^f$, wherein $R^f$ is C1-C6 linear or branched alkyl (e.g., $C(=O)CH_3$) or cycloalkyl (e.g., $C_3H_5$), optionally substituted with one or two halo groups (e.g., $C(=O)CH_2X$ or $C(=O)CHX_2$, where X is chloro or fluoro),
  (iv) $C(=O)(CH_2)_2O$,
  (v) $C(=O)CH=CH_2$,
  (vi) $C(=O)(CH_2)_nOH$, wherein n is 1, 2, 3, or 4 (e.g., $C(=O)CH_2OH$), and
  (vii) $SO_2R^g$, wherein $R^g$ is C1-C6 linear or branched alkyl (e.g., $SO_2CH_3$);
$R^2$ is selected from the group consisting of:
(a) phenyl optionally substituted with
  (i) halo (e.g., chloro, fluoro, difluoro),
  (ii) C1-C6 linear or branched alkoxy,
  (iii) C1-C6 linear or branched haloalkyloxy (e.g., $OCF_3$),
  (iv) $C(=O)R^a$, wherein $R^a$ is C1-C6 linear or branched alkyl (e.g., $O(C=O)CH_3$), or $R^a$ is $NR^cR^d$, wherein $R^c$ and $R^d$ are independently selected from is hydrogen and C1-C3 linear or branched alkyl (e.g., $C(=O)N(CH_3)_2$, $C(=O)NH(CH_3)$, $C(=O)NH_2$), or $R^c$ is hydrogen and $R^d$ is hydroxy (e.g., $C(=O)NHOH$),
  (v) $CO_2R^b$, wherein $R^b$ is hydrogen (e.g., $CO_2H$) or C1-C6 linear or branched alkyl (e.g., $CO_2CH_3$), and (vi) cyano, (b) C1-C6 linear or branched alkyl (e.g., methyl), and (c) C1-C6 linear or branched haloalkyl (e.g. trifluoromethyl);

X is O, NH, or $CH_2$; and

Y is phenyl optionally substituted with (a) halo (e.g., chloro, fluoro, difluoro), (b) C1-C6 linear or branched alkyl (e.g., methyl, ethyl), (c) C1-C6 linear or branched alkoxy (e.g., methoxy, ethoxy), (d) C1-C6 linear or branched haloalkyl (e.g., trifluoromethyl), (e) (C=O)$R^a$, wherein is C1-C6 linear or branched alkyl (e.g., C(=O)$CH_3$), (f) O(C=O)$R^a$, wherein is C1-C6 linear or branched alkyl (e.g., OC(=O)$CH_3$), (g) $NR^cR^d$, wherein $R^c$ and $R^d$ are independently selected from hydrogen and C1-C6 linear or branched alkyl (e.g., $NH_2$, NH($CH_3$), NH(iPr), NH(Pr), NH(s-Bu), NH(tBu)) or $R^c$ is hydrogen and $R^d$ is C1-C6 linear or branched alkyl (e.g., NH(C=O)$CH_3$), (h) cyano, and (i) hydroxy, with the proviso that when $R^1$ is $SO_2CH_3$, $R^2$ is phenyl or 4-cyanophenyl, and X is NH, Y is not ethoxy- or fluoro-substituted phenyl.

The proviso specifically excludes Compounds 232 and 249 (see Table 1) from the definition of the compounds of formula (I). It will be appreciated that compounds useful in the methods of the invention are as defined above except without the specified proviso (i.e., Compounds 232 and 249 are useful in the methods).

In certain embodiments, $R^1$ is C(=O)$R^f$, wherein $R^f$ is C1-C6 linear or branched alkyl, optionally substituted with one or two halo groups (e.g., C(=O)$CH_3$, C(=O)$CH_2$Cl or C(=O)$CHCl_2$). In other embodiments, $R^1$ is NHC(=O)$R^f$, wherein $R^f$ is C1-C6 linear or branched alkyl, optionally substituted with one or two halo groups (e.g., NH(C=O)$CH_2$Cl or NN(C=O)$CHCl_2$). In further embodiments, $R^1$ is $CH_2$Br or $SO_2$CH=$CH_2$.

In certain embodiments, $R^2$ is phenyl optionally substituted with cyano, CHO, aldoxime (CH=NOH), hydroxymethyl ($CH_2OH$), amide ($NH_2$), substituted amide (NH($R^a$) and N($R^a$)$_2$), hydroxamic acid ((C=O)N($R^a$)OH)), or ester ($CO_2R^a$), wherein $R^a$ at each occurrence is C1-C6 linear or branched alkyl.

In certain embodiments, X is NH and Y is phenyl optionally substituted with halo (e.g., fluoro) and/or hydroxy (e.g., F, OH-disubstituted). In other embodiments, X is O and Y is methyl or ethyl.

In another embodiment, the invention provides compounds having formula (II):

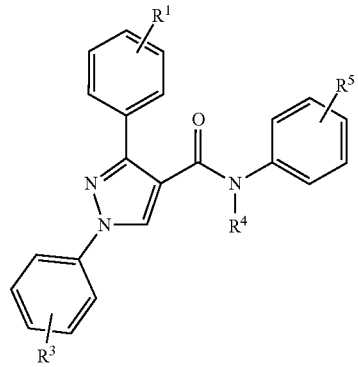

(II)

or pharmaceutically acceptable salts thereof, wherein
$R^1$ is $SO_2R^a$, wherein $R^a$ is C1-C6 linear or branched alkyl or alkenyl, C(=O)$R^f$, wherein $R^f$ is C1-C6 linear or branched alkyl, optionally substituted with one or two halo groups, or NHC(=O)$R^f$, wherein $R^f$ is C1-C6 linear or branched alkyl, optionally substituted with one or two halo groups;

$R^3$ is hydrogen, cyano, CHO, oxime (CH=NOH), hydroxymethyl ($CH_2OH$), $CO_2H$, $CO_2R^a$, $NH_2$, NH($R^a$), or N($R^a$)$_2$, wherein $R^a$ at each occurrence is C1-C6 linear or branched alkyl;

$R^4$ is hydrogen; and $R^5$ is fluoro or hydroxy.

In certain of these embodiments, $R^1$ is C(=O)$CHCl_2$ (e.g., 4-C(=O)$CHCl_2$) or NHC(=O)$CHCl_2$ (e.g., 4-NHC(=O)$CHCl_2$).

In certain of these embodiments, $R^3$ is cyano (e.g., 4-cyano).

In certain of these embodiments, $R^5$ is fluoro (e.g., 3-F).

In a further embodiment, the invention provides compounds having formula (III):

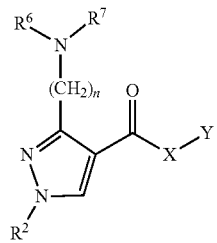

(III)

or pharmaceutically acceptable salts thereof, wherein
$R^2$, X, and Y are as described above for formula (I), $R^6$ is hydrogen or C1-C6 linear or branched alkyl (e.g., methyl, ethyl), $R^7$ is C(=O)$R^f$, wherein $R^f$ is C1-C6 linear or branched alkyl substituted with one or two halo groups (e.g., C(=O)$CHCl_2$ or C(=O)$CH_2$Cl), and n is 1, 2, 3, 4, 5, or 6.

In certain of these embodiments, $R^2$ is phenyl.

In certain of these embodiments, X is NH and Y is phenyl optionally substituted with halo (e.g., fluoro). In other embodiments, X is O and Y is methyl or ethyl.

In certain of these embodiments, $R^6$ is hydrogen, methyl, or ethyl, $R^7$ is C(=O)$CHCl_2$, and n is 1.

Representative pyrazole compounds of the invention are identified in Table 1.

The preparation of representative pyrazole compounds of the invention is described below.

Piperazine Compounds

In another aspect, the invention provides piperazine compounds that are inhibitors of ALDH1A1 and ALDH1A2.

In one embodiment, the invention provides compounds having formula (IV):

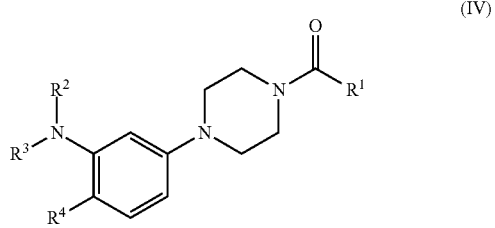

(IV)

or pharmaceutically acceptable salts thereof, wherein $R^1$ is selected from the group consisting of substituted or unsubstituted phenyl, substituted or unsubstituted thiophenyl, substituted or unsubstituted pyrrolyl, and substituted or unsubstituted furanyl, wherein the phenyl, thiophenyl, pyrrolyl, or furanyl is substituted with a substituent selected from the group selected from:

(a) C1-C6 linear or branched alkyl (e.g., methyl, ethyl), (b) C1-C6 linear or branched haloalkyl (e.g. trifluoromethyl), (c) C1-C6 linear or branched alkoxy (e.g. methoxy, ethoxy), (d) halo (e.g., chloro, fluoro), (e) hydroxy, (f) C(=O)$R^a$, wherein $R^a$ is C1-C6 linear or branched alkyl (e.g., C(=O)CH$_3$), (g) CO$_2$$R^b$, wherein $R^b$ is hydrogen, C1-C6 linear or branched alkyl (e.g., CO$_2$H), and (h) $NR^cR^d$, wherein $R^c$ is hydrogen or C1-C3 linear or branched alkyl, and $R^d$ is hydrogen, C1-C3 linear or branched alkyl, acetyl, or a N-protecting group (e.g., CO$_2$H, CO$_2$CH$_3$, C(=O)CH$_3$, Boc, N(CH$_3$)$_2$);

$R^2$ and $R^3$ taken together with the nitrogen atom to which they are attached for a 4-, 5-, 6-, or 7-membered ring (e.g., pyrrolidinyl, piperidinyl, azepanyl); and $R^4$ is selected from the group consisting of:

(a) NO$_2$, (b) NH($R^e$), wherein $R^e$ is selected from (i) C(=O)$R^f$, wherein $R^f$ is C1-C6 linear or branched alkyl (e.g., C(=O)CH$_3$) optionally substituted with one or two halo groups (e.g., C(=O)CH$_2$X or C(=O)CHX$_2$, where X is chloro or fluoro), (ii) C(=O)(CH$_2$)$_2$O, (ii) C(=O)CH=CH$_2$, and (c) N($R^g$)C(=O)$R^f$, wherein $R^g$ is C1-C6 linear or branched alkyl, and $R^f$ is C1-C6 linear or branched alkyl optionally substituted with one or two halo groups (e.g., N(CH$_3$)C(=O)CHCl$_2$, N(iPr)C(=O)CHCl$_2$), with the proviso that when $R^1$ is 2-thiophenyl or 2-(3-ethoxythiophenyl), and $R^2$ and $R^3$ taken together with the nitrogen atom to which they are attached form a 5-membered ring, $R^4$ is not NO$_2$, and with the proviso that when $R^1$ is phenyl, 4-chlorophenyl, or 4-methoxyphenyl, and $R^2$ and $R^3$ taken together with the nitrogen atom to which they are attached form a 5-membered ring, $R^4$ is not NO$_2$.

The provisos specifically exclude Compounds 326, 339, 342, and 345 (see Table 2) from the definition of the compounds of formula (IV). It will be appreciated that compounds useful in the methods of the invention are as defined above except without the specified provisos (i.e., Compounds 326, 339, 342, and 345 are useful in the methods).

In certain embodiments, the phenyl ring of formula (IV) is further substituted with one or more C1-C6 linear or branched alkyl groups (e.g., methyl).

In certain of these embodiments, substituted phenyl is phenyl substituted with C1-C6 linear or branched alkyl, C1-C6 linear or branched alkoxy, or halo.

In certain of these embodiments, substituted thiophenyl is thiophenyl substituted with C1-C6 linear or branched alkyl, C1-C6 linear or branched alkoxy, halo, or $NR^cR^d$, wherein $R^c$ is hydrogen or C1-C3 linear or branched alkyl, and $R^d$ is hydrogen, C1-C3 linear or branched alkyl, or acetyl.

In certain of these embodiments, substituted pyrrolyl is N—C1-C6 alkylpyrrolyl (e.g., N-methylpyrrolyl) or N—C1-C6 acylpyrrolyl (e.g., N-acetylpyrrolyl).

In certain of the above embodiments, $R^2$ and $R^3$ taken together with the nitrogen atom to which they are attached form a 5-, 6-, or 7-membered ring (e.g., pyrrolidinyl, piperidinyl, azepanyl). In certain of these embodiments, $R^2$ and $R^3$ taken together with the nitrogen atom to which they are attached form a 5-membered ring (i.e., pyrrolidinyl).

In certain of the above embodiments, $R^4$ is NO$_2$. In other of the above embodiments, $R^4$ is NHC(=O)CHCl$_2$.

In one embodiment, the invention provides a piperazine compound of formula (IV), or a pharmaceutically acceptable salt thereof, wherein $R^1$ is chloro-substituted phenyl, $R^2$ and $R^3$ taken together with the nitrogen atom to which they are attached form a 5-, 6-, or 7-membered ring, and $R^4$ is NHC(=O)CHCl$_2$. In further of these embodiments, $R^2$ and $R^3$ taken together with the nitrogen atom to which they are attached for a 5-membered ring (e.g., pyrrolidinyl).

In another embodiment, the invention provides a piperazine compound of formula (IV), or a pharmaceutically acceptable salt thereof, wherein $R^1$ is pyrrolyl or substituted pyrrolyl (e.g., N-methyl-2-pyrrolyl), $R^2$ and $R^3$ taken together with the nitrogen atom to which they are attached form a 5-, 6-, or 7-membered ring, and $R^4$ is NHC(=O)CHCl$_2$. In further of these embodiments, $R^2$ and $R^3$ taken together with the nitrogen atom to which they are attached for a 5-membered ring (e.g., pyrrolidinyl).

In a further embodiment, the invention provides a piperazine compound of formula (IV), or a pharmaceutically acceptable salt thereof, wherein $R^1$ is thiophenyl substituted with C1-C6 linear or branched alkyl, C1-C6 linear or branched alkoxy, or $NR^cR^d$, wherein $R^c$ is hydrogen or C1-C3 linear or branched alkyl, and $R^d$ is hydrogen, C1-C3 linear or branched alkyl, or acetyl; $R^2$ and $R^3$ taken together with the nitrogen atom to which they are attached for a 5-, 6-, or 7-membered ring; and $R^4$ is NHC(=O)CHCl$_2$. In further of these embodiments, $R^2$ and $R^3$ taken together with the nitrogen atom to which they are attached for a 5-membered ring (e.g., pyrrolidinyl).

Representative piperazine compounds of the invention are identified in Table 2.

The preparation of representative piperazine compounds of the invention is described below.

Implantable Devices

In another aspect, the invention provides an implantable device that includes a pyrazole compound of the invention or a pharmaceutically acceptable salt thereof, or a piperazine compound of the invention or a pharmaceutically acceptable salt thereof. Representative implantable devices include those useful for the administration of female contraceptives, including, for example, silastic implants (e.g., for administering Nexplanon®).

Methods of Using the Pyrazole and Piperazine Compounds

In further aspect, the invention provides methods for using the pyrazole and piperazine compounds of the invention.

In one embodiment, the invention provides a method for inhibiting ALDH1A1 in a subject, comprising administering a therapeutically effective amount of a pyrazole compound or a piperazine compound as described herein, or a pharmaceutically acceptable salt thereof, to subject in need thereof.

In a related embodiment, the invention provides methods for treating diseases or conditions that are treatable by inhibiting ALDH1A1. In these methods, a therapeutically effective amount of a pyrazole compound or a piperazine compound as described herein, or a pharmaceutically acceptable salt thereof, is administered to subject in need thereof.

In another embodiment, the invention provides a method for inhibiting ALDH1A2 in a subject, comprising administering a therapeutically effective amount of a pyrazole compound or a piperazine compound as described herein, or a pharmaceutically acceptable salt thereof, to subject in need thereof.

In a related embodiment, the invention provides methods for treating diseases or conditions that are treatable by inhibiting ALDH1A2. In these methods, a therapeutically effective amount of a pyrazole compound or a piperazine compound as described herein, or a pharmaceutically acceptable salt thereof, is administered to subject in need thereof.

In a further embodiment, the invention provides a method for inhibiting ALDH1A1 and ALDH1A2 in a subject, comprising administering a therapeutically effective amount of a pyrazole compound or a piperazine compound as described herein, or a pharmaceutically acceptable salt thereof, to subject in need thereof.

In a related embodiment, the invention provides methods for treating diseases or conditions that are treatable by inhibiting the invention provides methods for treating diseases or conditions that are treatable by inhibiting ALDH1A1 and ALDH1A2.

In yet another aspect, the invention provides a method for preventing spermatogenesis in a subject, comprising administering a therapeutically effective amount of a pyrazole compound or a piperazine compound as described herein, or a pharmaceutically acceptable salt thereof, to subject in need thereof.

In the context of the present invention, preventing spermatogenesis results in effective male contraception. It will be appreciated that administering a therapeutically effective amount of a pyrazole compound, a piperazine compound, or a pharmaceutically acceptable salt thereof, as described herein, may also result in reducing, diminishing, or inhibiting spermatogenesis in a subject to a level sufficient to provide effective male contraception.

In certain embodiments of the methods of the invention, the pyrazole compound, piperazine compound, or a pharmaceutically acceptable salt thereof, is administered systemically, intravenously, subcutaneously, intramuscularly, or topically.

In other embodiments of the methods of the invention, the pyrazole compound, piperazine compound, or a pharmaceutically acceptable salt thereof, is administered by release from an implantable device.

Definitions

As used herein, the term "patient" or "subject" encompasses mammals and non-mammals. Examples of mammals include, but are not limited to, any member of the Mammalian class: humans, non-human primates such as chimpanzees, and other apes and monkey species; farm animals such as cattle, horses, sheep, goats, swine; domestic animals such as rabbits, dogs, and cats; laboratory animals including rodents, such as rats, mice and guinea pigs, and the like. Examples of non-mammals include, but are not limited to, birds, fish, reptiles, amphibians and the like. The term does not denote a particular age.

As used herein, the term "spermatogenesis" is the process in which spermatozoa are produced from male primordial germ cells by way of mitosis and meiosis.

Chemical moieties referred to as univalent chemical moieties (e.g., alkyl, aryl, and the like) also encompass structurally permissible multivalent moieties, as understood by those skilled in the art. For example, while an "alkyl" moiety generally refers to a monovalent radical (e.g., $CH_3CH_2-$), in appropriate circumstances an "alkyl" moiety can also refer to a divalent radical (e.g., $-CH_2CH_2-$, which is equivalent to an "alkylene" group). Similarly, under circumstances where a divalent moiety is required, those skilled in the art will understand that the term "aryl" refers to the corresponding divalent arylene group.

Terms used herein may be preceded and/or followed by a single dash, "—", or a double dash, "=", to indicate the bond order of the bond between the named substituent and its parent moiety; a single dash indicates a single bond and a double dash indicates a double bond. In the absence of a single or double dash it is understood that a single bond is formed between the substituent and its parent moiety; further, substituents are intended to be read "left to right" unless a dash indicates otherwise. For example, C1-C6alkoxycarbonyloxy and —OC(O)C1-C6alkyl indicate the same functionality; similarly -arylalkyl and -alkylaryl indicate the same functionality.

All atoms are understood to have their normal number of valences for bond formation (e.g., 4 for carbon, 3 for N, 2 for O, and 2, 4, or 6 for S, depending on the atom's oxidation state). On occasion a moiety can be defined, for example, as $(A)_aB$, wherein a is 0 or 1. In such instances, when a is 0 the moiety is B and when a is 1 the moiety is AB.

Where a substituent can vary in the number of atoms or groups of the same kind (e.g., alkyl groups can be C1, C2, C3, and the like), the number of repeated atoms or groups can be represented by a range (e.g., C1-C6 alkyl) which includes each and every number in the range and any and all sub ranges. For example, C1-C3 alkyl includes C1, C2, C3, C1-2, C1-3, and C2-3 alkyl.

"Alkoxy" refers to an alkyl group, as defined herein, appended to the parent molecular moiety through an oxygen atom. Representative examples of alkoxy include, but are not limited to, methoxy, ethoxy, propoxy, 2-propoxy, butoxy, tert-butoxy, pentyloxy, and hexyloxy.

The term "alkyl" as used herein, means a straight or branched chain hydrocarbon containing from 1 to 10 carbon atoms unless otherwise specified. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, and n-decyl. When an "alkyl" group is a linking group between two other moieties, then it may also be a straight or branched chain; examples include, but are not limited to —CH$_2$—, —CH$_2$CH$_2$—, —CH$_2$CH$_2$CHC (CH$_3$)—, —CH$_2$CH(CH$_2$CH$_3$)CH$_2$—.

The term "alkenyl" as used herein, means a straight or branched chain hydrocarbon containing from 2 to 10 carbons, unless otherwise specified, and containing at least one carbon-carbon double bond. Representative examples of alkenyl include, but are not limited to, ethenyl, 2-propenyl, 2-methyl-2-propenyl, 3-butenyl, 4-pentenyl, 5-hexenyl, 2-heptenyl, 2-methyl-1-heptenyl, 3-decenyl, and 3,7-dimethylocta-2,6-dienyl.

The term "alkynyl" as used herein, means a straight or branched chain hydrocarbon group containing from 2 to 10 carbon atoms and containing at least one carbon-carbon triple bond. Representative examples of alkynyl include, but are not limited, to acetylenyl, 1-propynyl, 2-propynyl, 3-butynyl, 2-pentynyl, and 1-butynyl.

The term "aryl," as used herein, means a phenyl (i.e., monocyclic aryl), or a bicyclic ring system containing at least one phenyl ring or an aromatic bicyclic ring containing only carbon atoms in the aromatic bicyclic ring system. The bicyclic aryl can be azulenyl, naphthyl, or a phenyl fused to a monocyclic cycloalkyl, a monocyclic cycloalkenyl, or a monocyclic heterocyclyl. The bicyclic aryl is attached to the parent molecular moiety through any carbon atom contained within the phenyl portion of the bicyclic system, or any carbon atom with the napthyl or azulenyl ring. The fused monocyclic cycloalkyl or monocyclic heterocyclyl portions of the bicyclic aryl are optionally substituted with one or two oxo and/or thia groups. Representative examples of the bicyclic aryls include, but are not limited to, azulenyl, naphthyl, dihydroinden-1-yl, dihydroinden-2-yl, dihydroinden-3-yl, dihydroinden-4-yl, 2,3-dihydroindol-4-yl, 2,3-dihydroindol-5-yl, 2,3-dihydroindol-6-yl, 2,3-dihydroindol-7-yl, inden-1-yl, inden-2-yl, inden-3-yl, inden-4-yl, dihydronaphthalen-2-yl, dihydronaphthalen-3-yl, dihydronaphthalen-4-yl, dihydronaphthalen-1-yl, 5,6,7,8-tetrahydronaphthalen-1-yl, 5,6,7,8-tetrahydronaphthalen-2-yl, 2,3-dihydrobenzofuran-4-yl, 2,3-dihydrobenzofuran-5-yl, 2,3-dihydrobenzofuran-6-yl, 2,3-dihydrobenzofuran-7-yl, benzo[d][1,3]dioxol-4-yl, benzo[d][1,3]dioxol-5-yl, 2H-chromen-2-on-5-yl, 2H-chromen-2-on-6-yl, 2H-chromen-2-on-7-yl, 2H-chromen-2-on-8-yl, isoindoline-1,3-dion-4-yl, isoindoline-1,3-dion-5-yl, inden-1-on-4-yl, inden-1-on-5-yl, inden-1-on-6-yl, inden-1-on-7-yl, 2,3-dihydrobenzo[b][1,4]dioxan-5-yl, 2,3-dihydrobenzo[b][1,4]dioxan-6-yl, 2H-benzo[b][1,4]oxazin3 (4H)-on-5-yl, 2H-benzo[b][1,4]oxazin3 (4H)-on-6-yl, 2H-benzo[b][1,4]oxazin3 (4H)-on-7-yl, 2H-benzo[b][1,4]oxazin3 (4H)-on-8-yl, benzo[d]oxazin-2 (3H)-on-5-yl, benzo[d]oxazin-2(3H)-on-6-yl, benzo[d]oxazin-2(3H)-on-7-yl, benzo[d]oxazin-2 (3H)-on-8-yl, quinazolin-4(3H)-on-5-yl, quinazolin-4(3H)-on-6-yl, quinazolin-4(3H)-on-7-yl, quinazolin-4(3H)-on-8-yl, quinoxalin-2(1H)-on-5-yl, quinoxalin-2(1H)-on-6-yl, quinoxalin-2(1H)-on-7-yl, quinoxalin-2(1H)-on-8-yl, benzo[d]thiazol-2(3H)-on-4-yl, benzo[d]thiazol-2 (3H)-on-5-yl, benzo[d]thiazol-2 (3H)-on-6-yl, and, benzo[d]thiazol-2 (3H)-on-7-yl. In certain embodiments, the bicyclic aryl is (i) naphthyl or (ii) a phenyl ring fused to either a 5 or 6 membered monocyclic cycloalkyl, a 5 or 6 membered monocyclic cycloalkenyl, or a 5 or 6 membered monocyclic heterocyclyl, wherein the fused cycloalkyl, cycloalkenyl, and heterocyclyl groups are optionally substituted with one or two groups which are independently oxo or thia.

An "aralkyl" or "arylalkyl" group comprises an aryl group covalently attached to an alkyl group, either of which independently is optionally substituted. Preferably, the aralkyl group is aryl(C1-C6)alkyl, including, without limitation, benzyl, phenethyl, and naphthylmethyl.

The term "cycloalkyl" as used herein, means a monocyclic or a bicyclic cycloalkyl ring system. Monocyclic ring systems are cyclic hydrocarbon groups containing from 3 to 8 carbon atoms, where such groups can be saturated or unsaturated, but not aromatic. In certain embodiments, cycloalkyl groups are fully saturated. Examples of monocyclic cycloalkyls include cyclopropyl, cyclobutyl, cyclopentyl, cyclopentenyl, cyclohexyl, cyclohexenyl, cycloheptyl, and cyclooctyl. Bicyclic cycloalkyl ring systems are bridged monocyclic rings or fused bicyclic rings. Bridged monocyclic rings contain a monocyclic cycloalkyl ring where two non-adjacent carbon atoms of the monocyclic ring are linked by an alkylene bridge of between one and three additional carbon atoms (i.e., a bridging group of the form —(CH$_2$)$_w$—, where w is 1, 2, or 3). Representative examples of bicyclic ring systems include, but are not limited to, bicyclo[3.1.1]heptane, bicyclo[2.2.1]heptane, bicyclo[2.2.2]octane, bicyclo[3.2.2]nonane, bicyclo[3.3.1]nonane, and bicyclo[4.2.1]nonane. Fused bicyclic cycloalkyl ring systems contain a monocyclic cycloalkyl ring fused to either a phenyl, a monocyclic cycloalkyl, a monocyclic cycloalkenyl, a monocyclic heterocyclyl, or a monocyclic heteroaryl. The bridged or fused bicyclic cycloalkyl is attached to the parent molecular moiety through any carbon atom contained within the monocyclic cycloalkyl ring. Cycloalkyl groups are optionally substituted with one or two groups which are independently oxo or thia. In certain embodiments, the fused bicyclic cycloalkyl is a 5 or 6 membered monocyclic cycloalkyl ring fused to either a phenyl ring, a 5 or 6 membered monocyclic cycloalkyl, a 5 or 6 membered monocyclic cycloalkenyl, a 5 or 6 membered monocyclic heterocyclyl, or a 5 or 6 membered monocyclic heteroaryl, wherein the fused bicyclic cycloalkyl is optionally substituted by one or two groups which are independently oxo or thia.

The term "heterocyclyl" as used herein, means a monocyclic heterocycle or a bicyclic heterocycle. The monocyclic heterocycle is a 3, 4, 5, 6 or 7 membered ring containing at least one heteroatom independently selected from the group consisting of O, N, and S where the ring is saturated or unsaturated, but not aromatic. The 3 or 4 membered ring contains 1 heteroatom selected from the group consisting of O, N and S. The 5 membered ring can contain zero or one double bond and one, two to four heteroatoms selected from the group consisting of O, N and S. The 6 or 7 membered ring contains zero, one or two double bonds and one, two or three heteroatoms selected from the group consisting of O, N and S. The monocyclic heterocycle is connected to the parent molecular moiety through any carbon atom or any nitrogen atom contained within the monocyclic heterocycle. Representative examples of monocyclic heterocycle include, but are not limited to, azetidinyl, azepanyl, aziridinyl, diazepanyl, 1,3-dioxanyl, 1,3-dioxolanyl, 1,3-dithiolanyl, 1,3-dithianyl, imidazolinyl, imidazolidinyl, isothiazolinyl, isothiazolidinyl, isoxazolinyl, isoxazolidinyl, morpholinyl, oxadiazolinyl, oxadiazolidinyl, oxazolinyl, oxazolidinyl, piperazinyl, piperidinyl, pyranyl, pyrazolinyl, pyrazolidinyl, pyrrolinyl, pyrrolidinyl, tetrahydrofuranyl, tetrahydrothienyl, thiadiazolinyl, thiadiazolidinyl, thiazolinyl, thiazolidinyl, thiomorpholinyl, 1,1-dioxidothiomorpholinyl(thiomorpholine sulfone), thiopyranyl, and trithianyl. The bicyclic heterocycle is a monocyclic heterocycle fused to either a phenyl, a monocyclic cycloalkyl, a monocyclic cycloalkenyl, a monocyclic heterocycle, or a monocyclic heteroaryl. The bicyclic heterocycle is connected to the parent molecular moiety through any carbon atom or any nitrogen atom contained within the monocyclic heterocycle portion of the bicyclic ring system. Representative examples of bicyclic heterocyclyls include, but are not limited to, 2,3-dihydrobenzofuran-2-yl, 2,3-dihydrobenzofuran-3-yl, indolin-1-yl, indolin-2-yl, indolin-3-yl, 2,3-dihydrobenzothien-2-yl, decahydroquinolinyl, decahydroisoquinolinyl, octahydro-1H-indolyl, and octahydrobenzofuranyl. Heterocyclyl groups are optionally substituted with one or two groups which are independently oxo or thia. In certain embodiments, the bicyclic heterocyclyl is a 5 or 6 membered monocyclic heterocyclyl ring fused to phenyl ring, a 5 or 6 membered monocyclic cycloalkyl, a 5 or 6 membered monocyclic cycloalkenyl, a 5 or 6 membered monocyclic heterocyclyl, or a 5 or 6 membered monocyclic heteroaryl, wherein the bicyclic heterocyclyl is optionally substituted by one or two groups which are independently oxo or thia.

"Halogen" refers to a chloro, bromo, fluoro or iodo atom radical. The term "halogen" also contemplates terms "halo" or "halide".

The terms "haloalkyl", "haloalkenyl" and "haloalkoxy" refer to an alkyl, alkenyl or alkoxy group, as the case may be, which is substituted with one or more halogen atoms.

"Heteroatom" refers to a non-carbon atom, where boron, nitrogen, oxygen, sulfur and phosphorus are preferred heteroatoms, with nitrogen, oxygen and sulfur being particularly preferred heteroatoms in the compounds of the disclosure.

The term "heteroaryl," as used herein, means a monocyclic heteroaryl or a bicyclic ring system containing at least one heteroaromatic ring. The monocyclic heteroaryl can be a 5 or 6 membered ring. The 5 membered ring consists of two double bonds and one, two, three or four nitrogen atoms and optionally one oxygen or sulfur atom. The 6 membered ring consists of three double bonds and one, two, three or four nitrogen atoms. The 5 or 6 membered heteroaryl is connected to the parent molecular moiety through any carbon atom or any nitrogen atom contained within the heteroaryl. Representative examples of monocyclic heteroaryl include, but are not limited to, furyl, imidazolyl, isoxazolyl, isothiazolyl, oxadiazolyl, oxazolyl, pyridinyl, pyridazinyl, pyrimidinyl, pyrazinyl, pyrazolyl, pyrrolyl, tetrazolyl, thiadiazolyl, thiazolyl, thienyl, triazolyl, and triazinyl. The bicyclic heteroaryl consists of a monocyclic heteroaryl fused to a phenyl, a monocyclic cycloalkyl, a monocyclic cycloalkenyl, a monocyclic heterocyclyl, or a monocyclic heteroaryl. The fused cycloalkyl or heterocyclyl portion of the bicyclic heteroaryl group is optionally substituted with one or two groups which are independently oxo or thia. When the bicyclic heteroaryl contains a fused cycloalkyl, cycloalkenyl, or heterocyclyl ring, then the bicyclic heteroaryl group is connected to the parent molecular moiety through any carbon or nitrogen atom contained within the monocyclic heteroaryl portion of the bicyclic ring system. When the bicyclic heteroaryl is a monocyclic heteroaryl fused to a phenyl ring, then the bicyclic heteroaryl group is connected to the parent molecular moiety through any carbon atom or nitrogen atom within the bicyclic ring system. Representative examples of bicyclic heteroaryl include, but are not limited to, benzimidazolyl, benzofuranyl, benzothienyl, benzoxadiazolyl, benzoxathiadiazolyl, benzothiazolyl, cinnolinyl, 5,6-dihydroquinolin-2-yl, 5,6-dihydroisoquinolin-1-yl, furopyridinyl, indazolyl, indolyl, isoquinolinyl, naphthyridinyl, quinolinyl, purinyl, 5,6,7,8-tetrahydroquinolin-2-yl, 5,6,7,8-tetrahydroquinolin-3-yl, 5,6,7,8-tetrahydroquinolin-4-yl, 5,6,7,8-tetrahydroisoquinolin-1-yl, thienopyridinyl, 4,5,6,7-tetrahydrobenzo[c][1,2,5]oxadiazolyl, and 6,7-dihydrobenzo[c][1,2,5]oxadiazol-4(5H)-onyl. In certain embodiments, the fused bicyclic heteroaryl is a 5 or 6 membered monocyclic heteroaryl ring fused to either a phenyl ring, a 5 or 6 membered monocyclic cycloalkyl, a 5 or 6 membered monocyclic cycloalkenyl, a 5 or 6 membered monocyclic heterocyclyl, or a 5 or 6 membered monocyclic heteroaryl, wherein the fused cycloalkyl, cycloalkenyl, and heterocyclyl groups are optionally substituted with one or two groups which are independently oxo or thia.

"Hydroxyalkyl" refers to a branched or unbranched alkyl group bearing a hydroxy (—OH) group. Examples include hydroxymethyl (—CH$_2$OH, a C1hydroxyalkyl) and 1-hydroxyethyl (—HOHCH$_3$, a C1hydroxyalkyl).

The term "nitro" as used herein, means a —NO$_2$ group.

The term "oxo" as used herein means a =O group.

The term "saturated" as used herein means the referenced chemical structure does not contain any multiple carbon-carbon bonds. For example, a saturated cycloalkyl group as defined herein includes cyclohexyl, cyclopropyl, and the like.

The term "substituted", as used herein, means that a hydrogen radical of the designated moiety is replaced with the radical of a specified substituent, provided that the substitution results in a stable or chemically feasible compound. The term "substitutable", when used in reference to a designated atom, means that attached to the atom is a hydrogen radical, which can be replaced with the radical of a suitable substituent.

The phrase "one or more substituents", as used herein, refers to a number of substituents that equals from one to the maximum number of substituents possible based on the number of available bonding sites, provided that the above conditions of stability and chemical feasibility are met. Unless otherwise indicated, an optionally substituted group may have a substituent at each substitutable position of the group, and the substituents may be either the same or different. As used herein, the term "independently selected" means that the same or different values may be selected for multiple instances of a given variable in a single compound.

Compounds of the disclosure can exist as stereoisomers, wherein asymmetric or chiral centers are present. Stereoisomers are designated (R) or (S) depending on the configuration of substituents around the chiral carbon atom. The terms (R) and (S) used herein are configurations as defined in IUPAC 1974 Recommendations for Section E, Fundamental Stereochemistry, Pure Appl. Chem., (1976), 45: 13-30, hereby incorporated by reference. The disclosure contemplates various stereoisomers and mixtures thereof, which are specifically included within the scope of the disclosure. Stereoisomers include enantiomers, diastereomers, and mixtures of enantiomers or diastereomers. Individual stereoisomers of compounds of the disclosure can be prepared synthetically from commercially available starting materials which contain asymmetric or chiral centers or by preparation of racemic mixtures followed by resolution well-known to those of ordinary skill in the art. These methods of resolution are exemplified by (1) attachment of a mixture of enantiomers to a chiral auxiliary, separation of the resulting mixture of diastereomers by recrystallization or chromatography and liberation of the optically pure product from the auxiliary or (2) direct separation of the mixture of optical enantiomers on chiral chromatographic columns.

Also, moieties disclosed herein which exist in multiple tautomeric forms include all such forms encompassed by a given tautomeric structure.

"Pharmaceutically acceptable" means approved or approvable by a regulatory agency of the Federal or state government or listed in the U.S. Pharmacopoeia or other generally recognized pharmacopoeia for use in animals, and more particularly in humans. It can be material which is not biologically or otherwise undesirable, i.e., the material can be administered to an individual without causing any undesirable biological effects or interacting in a deleterious manner with any of the components of the composition in which it is contained.

The term "pharmaceutically acceptable salt" of a compound means a salt that is pharmaceutically acceptable and that possesses the desired pharmacological activity of the parent compound. Such salts include, for example, acid addition salts and base addition salts.

Pharmaceutical Formulations and Modes of Administration

In various aspects, the disclosure provides a pharmaceutical composition comprising a therapeutically effective amount of a compound of formulae (I), (II), (III), or (IV) and one or more pharmaceutically acceptable diluents, preservatives, solubilizers, emulsifiers, adjuvants, excipients, or carriers.

In certain aspects, the disclosure provides for a pharmaceutical composition comprising the compounds of the disclosure together with one or more pharmaceutically acceptable excipients or vehicles, and optionally other therapeutic and/or prophylactic ingredients. Such excipients include liquids such as water, saline, glycerol, polyethylene glycol, hyaluronic acid, ethanol, and the like.

The term "pharmaceutically acceptable vehicle" refers to a diluent, adjuvant, excipient or carrier with which a compound of the disclosure is administered. The terms "effective amount" or "pharmaceutically effective amount" refer to a nontoxic but sufficient amount of the agent to provide the desired biological result. That result can be reduction and/or alleviation of the signs, symptoms, or causes of a disease, or any other desired alteration of a biological system. An appropriate "effective" amount in any individual case can be determined by one of ordinary skill in the art using routine experimentation.

"Pharmaceutically acceptable carriers" for therapeutic use are well known in the pharmaceutical art, and are described, for example, in Remington's Pharmaceutical Sciences, 18th Edition (Easton, Pa.: Mack Publishing Company, 1990). For example, sterile saline and phosphate-buffered saline at physiological pH can be used. Preservatives, stabilizers, dyes and even flavoring agents can be provided in the pharmaceutical composition. For example, sodium benzoate, sorbic acid and esters of p-hydroxybenzoic acid can be added as preservatives. Id. at 1449. In addition, antioxidants and suspending agents can be used. Id.

Suitable excipients for non-liquid formulations are also known to those of skill in the art. A thorough discussion of pharmaceutically acceptable excipients and salts is available in Remington's Pharmaceutical Sciences, 18th Edition (Easton, Pa.: Mack Publishing Company, 1990).

Additionally, auxiliary substances, such as wetting or emulsifying agents, biological buffering substances, surfactants, and the like, can be present in such vehicles. A biological buffer can be any solution which is pharmacologically acceptable and which provides the formulation with the desired pH, i.e., a pH in the physiologically acceptable range. Examples of buffer solutions include saline, phosphate buffered saline, Tris buffered saline, Hank's buffered saline, and the like.

Depending on the intended mode of administration, the pharmaceutical compositions can be in the form of solid, semi-solid or liquid dosage forms, such as, for example, tablets, suppositories, pills, capsules, powders, liquids, suspensions, creams, ointments, lotions or the like, preferably in unit dosage form suitable for single administration of a precise dosage. The compositions will include an effective amount of the selected drug in combination with a pharmaceutically acceptable carrier and, in addition, can include other pharmaceutical agents, adjuvants, diluents, buffers, and the like.

The disclosure includes a pharmaceutical composition comprising a compound of the disclosure including isomers, racemic or non-racemic mixtures of isomers, or pharmaceutically acceptable salts or solvates thereof together with one or more pharmaceutically acceptable carriers, and optionally other therapeutic and/or prophylactic ingredients.

In general, the compounds of the disclosure will be administered in a therapeutically effective amount by any of the accepted modes of administration. Suitable dosage ranges depend upon numerous factors such as the severity of the disease to be treated, the age and relative health of the subject, the potency of the compound used, the route and form of administration, the indication towards which the administration is directed, and the preferences and experience of the medical practitioner involved. One of ordinary skill in the art of treating such diseases will be able, without undue experimentation and in reliance upon personal knowledge and the disclosure of this application, to ascertain a therapeutically effective amount of the compounds of the disclosure for a given disease.

Thus, the compounds of the disclosure can be administered as pharmaceutical formulations including those suitable for oral (including buccal and sub-lingual), rectal, nasal, topical, pulmonary, or parenteral (including intramuscular, intra-arterial, intrathecal, subcutaneous and intravenous) administration or in a form suitable for administration by inhalation or insufflation. The preferred manner of administration is intravenous or oral using a convenient daily dosage regimen which can be adjusted according to the degree of affliction.

For solid compositions, conventional nontoxic solid carriers include, for example, pharmaceutical grades of mannitol, lactose, starch, magnesium stearate, sodium saccharin, talc, cellulose, glucose, sucrose, magnesium carbonate, and the like. Liquid pharmaceutically administrable compositions can, for example, be prepared by dissolving, dispersing, and the like, an active compound as described herein and optional pharmaceutical adjuvants in an excipient, such as, for example, water, saline, aqueous dextrose, glycerol, ethanol, and the like, to thereby form a solution or suspension. If desired, the pharmaceutical composition to be administered can also contain minor amounts of nontoxic auxiliary substances such as wetting or emulsifying agents, pH buffering agents and the like, for example, sodium acetate, sorbitan monolaurate, triethanolamine sodium acetate, triethanolamine oleate, and the like. Actual methods of preparing such dosage forms are known, or will be apparent, to those skilled in this art; for example, see Remington's Pharmaceutical Sciences, referenced above.

In yet another embodiment is the use of permeation enhancer excipients including polymers such as: polycations (chitosan and its quaternary ammonium derivatives, poly-L-arginine, aminated gelatin); polyanions (N-carboxymethyl chitosan, poly-acrylic acid); and, thiolated polymers (carboxymethyl cellulose-cysteine, polycarbophil-cysteine, chitosan-thiobutylamidine, chitosan-thiogly colic acid, chitosan-glutathione conjugates).

For oral administration, the composition will generally take the form of a tablet, capsule, a softgel capsule or can be an aqueous or nonaqueous solution, suspension or syrup. Tablets and capsules are preferred oral administration forms. Tablets and capsules for oral use can include one or more commonly used carriers such as lactose and corn starch. Lubricating agents, such as magnesium stearate, are also typically added. Typically, the compounds of the disclosure can be combined with an oral, non-toxic, pharmaceutically acceptable, inert carrier such as lactose, starch, sucrose, glucose, methyl cellulose, magnesium stearate, dicalcium phosphate, calcium sulfate, mannitol, sorbitol and the like. Moreover, when desired or necessary, suitable binders, lubricants, disintegrating agents, and coloring agents can also be incorporated into the mixture. Suitable binders include starch, gelatin, natural sugars such as glucose or beta-lactose, corn sweeteners, natural and synthetic gums such as acacia, tragacanth, or sodium alginate, carboxymethylcellulose, polyethylene glycol, waxes, and the like. Lubricants used in these dosage forms include sodium oleate, sodium stearate, magnesium stearate, sodium benzoate, sodium acetate, sodium chloride, and the like. Disintegrators include, without limitation, starch, methyl cellulose, agar, bentonite, xanthan gum, and the like.

Thus, for example, capsules can be prepared by conventional procedures so that the dosage unit is 100 mg of the compounds of the disclosure, 100 mg of cellulose and 10 mg of magnesium stearate. A large number of unit capsules can also prepared by filling standard two-piece hard gelatin capsules each with 100 mg of powdered active ingredient, 150 mg of lactose, 50 mg of cellulose, and 10 mg magnesium stearate. Or, tablets can be prepared by conventional procedures so that the dosage unit is 100 mg of the compounds of the disclosure, 150 mg of lactose, 50 mg of cellulose and 10 mg of magnesium stearate. A large number of tablets can also be prepared by conventional procedures such that the dosage unit was 100 mg of the compounds of the disclosure, and other ingredients can be 0.2 mg of colloidal silicon dioxide, 5 mg of magnesium stearate, 250 mg of microcrystalline cellulose, 10 mg of starch and 100 mg of lactose. Appropriate coatings can be applied to increase palatability or delay absorption.

When liquid suspensions are used, the active agent can be combined with any oral, non-toxic, pharmaceutically acceptable inert carrier such as ethanol, glycerol, water, and the like and with emulsifying and suspending agents. If desired, flavoring, coloring and/or sweetening agents can be added as well. Other optional components for incorporation into an oral formulation herein include, but are not limited to, preservatives, suspending agents, thickening agents, and the like.

Parenteral formulations can be prepared in conventional forms, either as liquid solutions or suspensions, solid forms suitable for solubilization or suspension in liquid prior to injection, or as emulsions. Preferably, sterile injectable suspensions are formulated according to techniques known in the art using suitable carriers, dispersing or wetting agents and suspending agents. The sterile injectable formulation can also be a sterile injectable solution or a suspension in a nontoxic parenterally acceptable diluent or solvent. Among the acceptable vehicles and solvents that can be employed are water, Ringer's solution and isotonic sodium chloride solution. In addition, sterile, fixed oils, fatty esters or polyols are conventionally employed as solvents or suspending media. In addition, parenteral administration can involve the use of a slow release or sustained release system such that a constant level of dosage is maintained.

Parenteral administration includes intraarticular, intravenous, intramuscular, transdermal, intraperitoneal, and subcutaneous routes, and include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. Administration via certain parenteral routes can involve introducing the formulations of the disclosure into the body of a patient through a needle or a catheter, propelled by a sterile syringe or some other mechanical device such as a continuous infusion system. A formulation provided by the disclosure can be administered using a syringe, injector, pump, or any other device recognized in the art for parenteral administration.

Preferably, sterile injectable suspensions are formulated according to techniques known in the art using suitable carriers, dispersing or wetting agents and suspending agents. The sterile injectable formulation can also be a sterile injectable solution or a suspension in a nontoxic parenterally acceptable diluent or solvent. Among the acceptable vehicles and solvents that can be employed are water, Ringer's solution and isotonic sodium chloride solution. In addition, sterile, fixed oils, fatty esters or polyols are conventionally employed as solvents or suspending media. In addition, parenteral administration can involve the use of a slow release or sustained release system such that a constant level of dosage is maintained.

Preparations according to the disclosure for parenteral administration include sterile aqueous or non-aqueous solutions, suspensions, or emulsions. Examples of non-aqueous solvents or vehicles are propylene glycol, polyethylene glycol, vegetable oils, such as olive oil and corn oil, gelatin, and injectable organic esters such as ethyl oleate. Such dosage forms can also contain adjuvants such as preserving, wetting, emulsifying, and dispersing agents. They can be sterilized by, for example, filtration through a bacteria-retaining filter, by incorporating sterilizing agents into the compositions, by irradiating the compositions, or by heating the compositions. They can also be manufactured using sterile water, or some other sterile injectable medium, immediately before use.

The formulations can optionally contain an isotonicity agent. The formulations preferably contain an isotonicity agent, and glycerin is the most preferred isotonicity agent. The concentration of glycerin, when it is used, is in the range known in the art, such as, for example, about 1 mg/mL to about 20 mg/mL.

The pH of the parenteral formulations can be controlled by a buffering agent, such as phosphate, acetate, TRIS or L-arginine. The concentration of the buffering agent is preferably adequate to provide buffering of the pH during storage to maintain the pH at a target pH±0.2 pH unit. The preferred pH is between about 7 and about 8 when measured at room temperature.

Other additives, such as a pharmaceutically acceptable solubilizers like Tween 20® (polyoxyethylene (20) sorbitan monolaurate), Tween 40® (polyoxyethylene (20) sorbitan monopalmitate), Tween 80® (polyoxyethylene (20) sorbitan monooleate), Pluronic F68® (polyoxyethylene polyoxypropylene block copolymers), and PEG (polyethylene glycol) can optionally be added to the formulation, and can be useful if the formulations will contact plastic materials. In addition, the parenteral formulations can contain various antibacterial and antifungal agents, for example, parabens, chlorobutanol, phenol, sorbic acid, thimerosal, and the like.

Sterile injectable solutions are prepared by incorporating one or more of the compounds of the disclosure in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof. Thus, for example, a parenteral composition suitable for administration by injection is prepared by stirring 1.5% by weight of active ingredient in 10% by volume propylene glycol and water. The solution is made isotonic with sodium chloride and sterilized.

Alternatively, the pharmaceutical compositions of the disclosure can be administered in the form of suppositories for rectal administration. These can be prepared by mixing the agent with a suitable nonirritating excipient which is solid at room temperature but liquid at the rectal temperature and therefore will melt in the rectum to release the drug. Such materials include cocoa butter, beeswax and polyethylene glycols.

The pharmaceutical compositions of the disclosure can also be administered by nasal aerosol or inhalation. Such compositions are prepared according to techniques well-known in the art of pharmaceutical formulation and can be prepared as solutions in saline, employing benzyl alcohol or other suitable preservatives, absorption promoters to enhance bioavailability, propellants such as fluorocarbons or nitrogen, and/or other conventional solubilizing or dispersing agents.

Preferred formulations for topical drug delivery are ointments and creams. Ointments are semisolid preparations which are typically based on petrolatum or other petroleum derivatives. Creams containing the selected active agent, are, as known in the art, viscous liquid or semisolid emulsions, either oil-in-water or water-in-oil. Cream bases are water-washable, and contain an oil phase, an emulsifier and an aqueous phase. The oil phase, also sometimes called the "internal" phase, is generally comprised of petrolatum and a fatty alcohol such as cetyl or stearyl alcohol; the aqueous phase usually, although not necessarily, exceeds the oil phase in volume, and generally contains a humectant. The emulsifier in a cream formulation is generally a nonionic, anionic, cationic or amphoteric surfactant. The specific ointment or cream base to be used, as will be appreciated by those skilled in the art, is one that will provide for optimum drug delivery. As with other carriers or vehicles, an ointment base should be inert, stable, nonirritating and nonsensitizing.

Formulations for buccal administration include tablets, lozenges, gels and the like. Alternatively, buccal administration can be affected using a transmucosal delivery system as known to those skilled in the art. The compounds of the disclosure can also be delivered through the skin or muscosal tissue using conventional transdermal drug delivery systems, i.e., transdermal "patches" wherein the agent is typically contained within a laminated structure that serves as a drug delivery device to be affixed to the body surface. In such a structure, the drug composition is typically contained in a layer, or "reservoir," underlying an upper backing layer. The laminated device can contain a single reservoir, or it can contain multiple reservoirs. In one embodiment, the reservoir comprises a polymeric matrix of a pharmaceutically acceptable contact adhesive material that serves to affix the system to the skin during drug delivery. Examples of suitable skin contact adhesive materials include, but are not limited to, polyethylenes, polysiloxanes, polyisobutylenes, polyacrylates, polyurethanes, and the like. Alternatively, the drug-containing reservoir and skin contact adhesive are present as separate and distinct layers, with the adhesive underlying the reservoir which, in this case, can be either a polymeric matrix as described above, or it can be a liquid or gel reservoir, or can take some other form. The backing layer in these laminates, which serves as the upper surface of the device, functions as the primary structural element of the laminated structure and provides the device with much of its flexibility. The material selected for the backing layer should be substantially impermeable to the active agent and any other materials that are present.

The compounds of the disclosure can be formulated for aerosol administration, particularly to the respiratory tract and including intranasal administration. The compound will generally have a small particle size for example of the order of 5 microns or less. Such a particle size can be obtained by means known in the art, for example by micronization. The active ingredient is provided in a pressurized pack with a suitable propellant such as a chlorofluorocarbon (CFC) for example dichlorodifluoromethane, trichlorofluoromethane, or dichlorotetrafluoroethane, carbon dioxide or other suitable gas. The aerosol can conveniently also contain a surfactant such as lecithin. The dose of drug can be controlled by a metered valve. Alternatively, the active ingredients can be provided in a form of a dry powder, for example a powder mix of the compound in a suitable powder base such as lactose, starch, starch derivatives such as hydroxypropylmethyl cellulose and polyvinylpyrrolidine (PVP). The powder carrier will form a gel in the nasal cavity. The powder composition can be presented in unit dose form for example in capsules or cartridges of e.g., gelatin or blister packs from which the powder can be administered by means of an inhaler.

A pharmaceutically or therapeutically effective amount of the composition will be delivered to the subject. The precise effective amount will vary from subject to subject and will depend upon the species, age, the subject's size and health, the nature and extent of the condition being treated, recommendations of the treating physician, and the therapeutics or combination of therapeutics selected for administration. Thus, the effective amount for a given situation can be determined by routine experimentation. For purposes of the disclosure, generally a therapeutic amount will be in the range of about 0.01 mg/kg to about 250 mg/kg body weight, more preferably about 0.1 mg/kg to about 10 mg/kg, in at least one dose. In larger mammals the indicated daily dosage can be from about 1 mg to 300 mg, one or more times per day, more preferably in the range of about 10 mg to 200 mg. The subject can be administered as many doses as is required to reduce and/or alleviate the signs, symptoms, or causes of the disorder in question, or bring about any other desired alteration of a biological system. When desired, formulations can be prepared with enteric coatings adapted for sustained or controlled release administration of the active ingredient.

The pharmaceutical preparations are preferably in unit dosage forms. In such form, the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

Chemical Syntheses

The preparation, purification, and characterization of representative pyrazole and piperazine compounds of the invention is described below.

General

Column chromatography was performed used silica gel 60 (230-400 mesh). Analytical TLC was performed using silica gel 60 F254 precoated on aluminum sheets (0.20 mm thickness). 1H-NMR was recorded using either a Bruker 300 or 500 MHz spectrometer. Chemical shift values are given in ppm and splitting constants measured in Hertz. ESMS was performed using a Bruker Esquire mass spectrometer.

Pyrazole Syntheses

Figure 3:
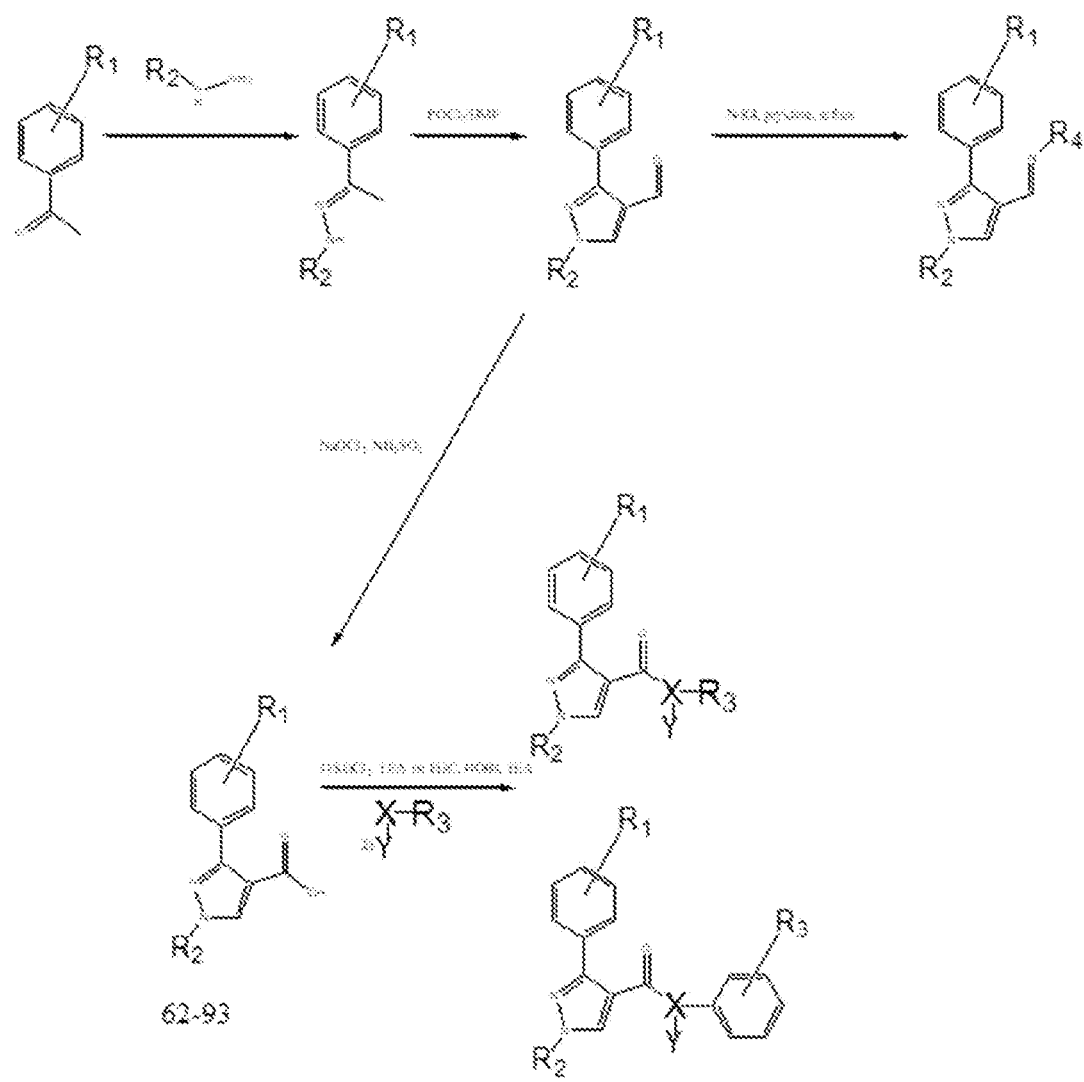
FIG. 3 is a schematic illustration of the preparation of representative pyrazole inhibitors of the invention.

The general synthesis scheme for the preparation of representative pyrazole compounds of the invention is shown in FIG. 3.

Figure 4:
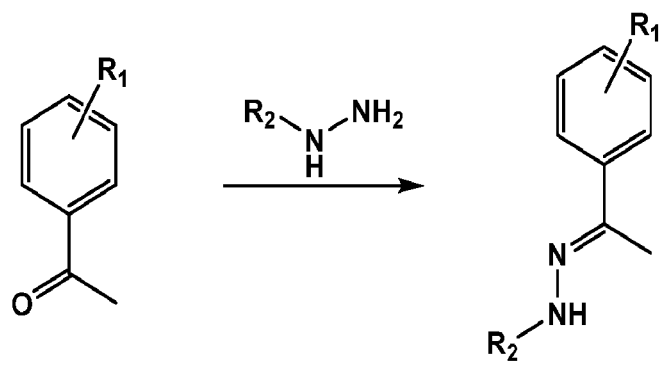
FIG. 4 illustrates step 1 of the preparation of representative pyrazole inhibitors of the invention shown in FIG. 3: hydrazine intermediates.

Step 1 of the synthesis is shown in FIG. 4: hydrazine preparation.

A summary of representative hydrazines useful in the syntheses is shown below.

| Compound | $R^1$ | $R^2$ |
|---|---|---|
| 1 | 4-$NO_2$ | $C_6H_5$ |
| 2 | 4-$CF_3$ | $C_6H_5$ |
| 3 | 4-pyridinyl | $C_6H_5$ |
| 4 | 3,4-F | $C_6H_5$ |
| 5 | 4-CN | $C_6H_5$ |
| 6 | 4-$CO_2CH_3$ | $C_6H_5$ |
| 7 | 4-$SO_2NH_2$ | $C_6H_5$ |
| 8 | 4-Ac | $C_6H_5$ |
| 9 | 4-$SO_3iPr$ | $C_6H_5$ |
| 10 | 4-$SO_2CH_2CH_3$ | $C_6H_5$ |
| 11 | 4-$SO_2CH_3$ | $C_6H_5$ |
| 12 | 4-$SO_2CH_3$ | 2-Chlorophenyl |
| 13 | 4-$SO_2CH_3$ | 4-Fluorophenyl |
| 14 | 4-$SO_2CH_3$ | 3-Chlorophenyl |
| 15 | 4-$SO_2CH_3$ | 2-Fluorophenyl |
| 16 | 4-$SO_2CH_3$ | 3-Fluorophenyl |
| 17 | 4-$SO_2CH_3$ | 4-Trifluoromethoxyphenyl |
| 18 | 4-$SO_2CH_3$ | 4-Cyanophenyl |
| 19 | 4-$SO_2CH_3$ | 4-Trifluoromethylphenyl |
| 20 | 4-$SO_2CH_3$ | 3-Trifluoromethylphenyl |
| 21 | 4-$SO_2CH_3$ | 2-Trifluoromethylphenyl |
| 22 | 4-$SO_2CH_3$ | 3-Cyanophenyl |
| 23 | 4-$SO_2CH_3$ | 4-$H_3CO_2C$phenyl |
| 24 | 4-$SO_2CH_3$ | 4-pyridinyl |
| 25 | 4-$NO_2$ | 4-Cyanophenyl |
| 26 | 4-CN | 4-$CH_3CO_2$phenyl |

The procedures for the preparation of the hydrazine intermediates was adapted from X Li, X Lu, M Xing, et al. Synthesis, biological evaluation, and molecular docking studies of N,1,3-triphenyl-1H-pyrazole-4-carboxamide derivatives as anticancer agents. 2012 Bioorg Med Chem Lett 22(11) 3589-93 and Rector D, Folz S, et al. Structure-Activity Relationships in a Broad-spectrum Anthelmintic Series. Acid Chloride Phenylhydrazones. 1. Aryl Substitutions and Chloride Variations. 1981 J Med Chem 24, 532-8, and as summarized below.

Typical procedure:

(1E)-1-[1-(4-Nitrophenyl)ethylidene]-2-phenylhydrazine (1):

p-Nitroacetophenone (1.0 g, 6.1 mmol) and phenyl hydrazine hydrochloride (0.9 g, 6.1 mmol) were stirred for 20 h in 30 ml anhyd ethanol. The solution rapidly turned to red from the original yellow. The solvent was removed by rotary evaporation and the residue purified by flash chromatography (12:1-8:1 hexane:EtOAc) yielded the hydrazone as a yellow solid (1.2 g, 80%): $R_f$ (3:1 hexane:EtOAc) 0.30; $^1$H-NMR (DMSO 300 MHz) 9.71 (s, 1H, NH), 8.22 (m, 2H), 8.03 (m, 2H), 7.29 (m, 4H), 6.85 (t, 1H, J=6.9), 2.31 (s, 3H, CH3); ESMS 256 (M+H, 100).

(2E)-1-Phenyl-2-{1-[4-(trifluoromethyl)phenyl]ethylidene}hydrazine (2):

4-Trifluoromethylacetophoenone (0.260 g, 1.3 mmol) and phenyl hydrazine hydrochloride (0.210 g, 1.4 mmol) were stirred for 22 h in 10 ml anhyd ethanol. The solvent was removed by rotary evaporation and the residue purified by flash chromatography (8:1-3:1 hexane:EtOAc) yielded the hydrazone as a white solid (0.074 g, 19%): $R_f$ (3:1 hexane:EtOAc) 0.59; $^1$H-NMR (DMSO 300 MHz) 9.51 (s, 1H, NH), 8.00 (m, 2H), 7.71 (m, 3H), 7.57 (m, 1H), 7.25 (m, 1H), 6.80 (m, 1H), 2.28 (s, 3H, $CH_3$).

4-[(1E)-1-(2-Phenylhydrazinylidene)ethyl]pyridine (3): Purified by flash chromatography (1:0-8:1EtOAc:$CH_3$OH) yielded the hydrazone as a brown solid (24%): $R_f$ (3:1 hexane:EtOAc) 0.07; $^1$H-NMR (DMSO 300 MHz) 9.71 (s, 1H, NH), 8.60 (d, 2H), 7.79 (d, 2H), 7.35 (m, 4H), 6.88 (t, 1H), 2.32 (s, 3H, CH3).

(1E)-1-[1-(3,4-Difluorophenyl)ethylidene]-2-phenylhydrazine (4): Purified by flash chromatography (8:1 hexane:EtOAc) yielded the hydrazone as a yellow solid (16%): $R_f$ (3:1 hexane:EtOAc) 0.52; $^1$H-NMR ($CDCl_3$ 300 MHz) 7.59 (m, 1H), 7.38 (m, 1H), 7.23 (m, 2H), 7.07 (m, 2H), 6.84 (t, 1H), 2.14 (s, 3H, CH3).

4-[(1E)-1-(2-Phenylhydrazinylidene)ethyl]benzonitrile (5): Purified by flash chromatography (9:1-3:1 hexane:EtOAc) yielded the hydrazone as a yellow solid (31%): $R_f$ (3:1 hexane:EtOAc) 0.30; $^1$H-NMR ($CDCl_3$ 300 MHz) 7.90 (d, 2H), 7.67 (d, 2H), 7.33 (m, 2H), 7.21 (m, 2H), 6.96 (t, 1H), 2.27 (s, 3H, $CH_3$).

Methyl 4-[(1E)-1-(2-phenylhydrazinylidene)ethyl]benzoate (6):

Step 1: Preparation of methyl 4-acetylbenzoate. To 4-acetylbenzoic acid (0.120 g, 731 umol) in 15 mL DCM was added phosphorous oxychloride. Stir 30 min. Add triethylamine (0.353 ml, 4386 umol) and 3 ml $CH_3OH$. Stir 5 min. Remove the solvent by rotary evaporation and purify the residue by flash chromatography (3:1 hexane:EtOAc) to give the desired product as a yellow solid (46%): $R_f$ (3:1 hexane:EtOAc) 0.52; $^1$H-NMR ($CDCl_3$ 300 MHz) 8.16 (d, 2H), 8.04 (d, 2H), 3.98 (s, 3H), 2.67 (s, 3H).

Step 2: The methyl ester (0.100 g, 56 umol) and phenylhydrazine hydrochloride (0.106 g, 73 umol) were stirred overnight in 10 ml $CH_3OH$. The solvent was removed and the residue purified by flash chromatography (5:1 hexane:EtOAc) to give the desired product as a yellow solid (24%): $R_f$ (3:1 hexane:EtOAc) 0.43; $^1$H-NMR ($CDCl_3$ 300 MHz) 8.06 (d, 2H), 7.88 (d, 2H), 7.31 (m, 4H), 6.94 (t, 1H), 3.96 (s, 3H), 2.29 (s, 3H).

(1E)-1-(1-{4-[amino(dimethylidene)-$\lambda^6$-sulfanyl]phenyl}ethylidene)-2-phenylhydrazine (7): 4-Acetylbenzenesulfanamide (0.100 g, 502 umol) and phenylhydrazine hydrochloride (0.094 g, 652 umol) were stirred overnight in 8 ml $CH_3OH$. The solvent was removed and the residue purified by flash chromatography (2:1-0:1 hexane:EtOAc) to give the desired product as a yellowish solid (17%): (1:1 hexane:EtOAc) 0.39; $^1$H-NMR ($CDCl_3$ 300 MHz) 7.99 (d, 2H), 7.85 (2H), 7.23 (m, 4H), 7.13 (m, 2H), 6.86 (t, 1H), 2.59/2.20 (s, 3H).

1-{4-[(1E)-1-(2-Phenylhydrazinylidene)ethyl]phenyl}ethenone (8):

1,4-Diacetylbenzene (0.150 g, 924 umol) and phenylhydrazine hydrochloride (0.174 g, 1,202 umol) were stirred overnight in 8 ml CH$_3$OH. The solvent was removed and the residue purified by flash chromatography (6:1-0:1 hexane:EtOAc) to give the desired product as an orange solid (78%): R$_f$ (3:1 hexane:EtOAc) 0.45; $^1$H-NMR (CDCl$_3$ 300 MHz) 7.98 (d, 2H), 7.92 (d, 2H), 7.33 (m, 4H), 7.22 (m, 2H), 6.93 (t, 1H), 2.64 (s, 3H), 2.30 (s, 3H).

Propan-2-yl 4-[(1E)-1-(2-phenylhydrazinylidene)ethyl]benzenesulfonate (9):

Propan-2-yl 4-acetylbenzenesulfonate (0.200 g, 825 umol) and phenylhydrazine hydrochloride (0.155 g, 1037 umol) in were stirred overnight in 30 ml CH$_3$OH. The solvent was removed and the residue dried in vacuum (43%): ESMS 333 (M+H, 90%), 291 (M–iPr+H, 100%). Procedure adapted from reference Milstein D, Stille J K, Mild, selective, general method of ketone synthesis from acid chlorides and organotin compounds catalyzed by palladium, 1979 J Org Chem 44(10) 1613-18.

(1E)-1-{1-[4-(Ethylsulfonyl)phenyl]ethylidene}-2-phenylhydrazine (10):

The solvent was removed and the residue purified by flash chromatography (3:1-1:1 hexane:EtOAc) to give the desired product as a yellow solid (28%): R$_f$ (1:1 hexane:EtOAc) 0.56; $^1$H-NMR (CDCl$_3$ 300 MHz) 8.00 (m, 4H), 7.34 (m, 2H), 7.23 (m, 2H), 6.96 (t, 1H), 3.16 (q, 2H), 2.30 (s, 3H), 1.31 (t, 3H).

(1E)-1-{1-[4-(M<ethylsulfonyl)phenyl]ethylidene}-2-phenylhydrazine (11):

The solvent was removed and the residue dried to give the desired product as a yellow solid (100%): R$_f$ (1:1 hexane:EtOAc) 0.61; $^1$H-NMR (CDCl$_3$ 300 MHz) 7.97 (m, 4H), 7.37 (m, 2H), 7.23 (m, 2H), 6.96 (t, 1H), 3.10 (s, 3H), 2.30 (s, 3H).

(2E)-1-(2-Chlorophenyl)-2-{1-[4-(methylsulfonyl)phenyl]ethylidene}hydrazine (12): Flash chromatography (5:1-0:1 hexane:EtOAc) to give the desired product as a yellow solid (88%): R$_f$ (3:1 hexane:EtOAc) 0.21; $^1$H-NMR (CDCl$_3$ 300 MHz) 8.04 (bs, 1H, NH), 7.99 (m, 4H), 7.69 (dd, 1H), 7.33 (m, 2H), 6.88 (dt, 1H), 3.13 (s, 3H), 2.45 (s, 3H).

(2E)-1-(4-Fluorophenyl)-2-{1l-[4-(methylsulfonyl)phenyl]ethylidene}hydrazine (13): Flash chromatography (3:1-0:1 hexane:EtOAc) to give the desired product as a yellow solid (19%): R$_f$(1:1 hexane:EtOAc) 0.70; $^1$H-NMR (CDCl$_3$ 300 MHz) 8.13 (dd, 4H), 7.18 (m, 2H), 6.95 (m, 2H), 3.12 (s, 3H), 2.48 (s, 3H).

(2E)-1-(3-Chlorophenyl)-2-{1-[4-(methylsulfonyl)phenyl]ethylidene}hydrazine (14): Flash chromatography (3:1-0:1 hexane:EtOAc) to give the desired product as a yellow solid (49%): R$_f$(1:1 hexane:EtOAc) 0.03; $^1$H-NMR (CDCl$_3$ 300 MHz) 8.12 (dd, 4H), 7.18 (m, 2H), 6.95 (m, 2H), 3.11 (s, 3H), 2.30 (s, 3H).

(2E)-1-(2-Fluorophenyl)-2-{1-[4-(methylsulfonyl)phenyl]ethylidene}hydrazine (15): Flash chromatography (3:1-0:1 hexane:EtOAc) to give the desired product as a yellow solid (52%): R$_f$(1:1 hexane:EtOAc) 0.72; $^1$H-NMR (CDCl$_3$ 300 MHz) 7.99 (m, 4H), 7.67 (m, 2H), 7.17 (bt, 1H), 7.09 (m, 1H), 6.88 (m, 1H), 3.10 (s, 3H), 2.34 (s, 3H).

(2E)-1-(3-Fluorophenyl)-2-{1-[4-(methylsulfonyl)phenyl]ethylidene}hydrazine (16): Flash chromatography (4:1-0:1 hexane:EtOAc) to give the desired product as a yellow solid (73%): R$_f$(1:1 hexane:EtOAc) 0.39; $^1$H-NMR (CDCl$_3$ 300 MHz) 7.98 (m, 4H), 7.61 (bs, 1H), 7.26 (m, 1H), 7.03 (dt, 1H), 6.90 (dm, 1H), 6.45 (m, 1H), 3.10 (s, 3H), 2.31 (s, 3H).

(2E)-1-(4-Trifluoromethoxyphenyl)-2-{1-[4-(methylsulfonyl)phenyl]ethylidene}-hydrazine (17): Flash chromatography (4:1-0:1 hexane:EtOAc) to give the desired product as a yellow solid (85%): R$_f$ (1:1 hexane:EtOAc) 0.50; $^1$H-NMR (CDCl$_3$ 500 MHz) 7.94 (m, 4H), 7.23 (m, 4H), 3.10 (s, 3H), 2.31 (s, 3H).

(2E)-1-(4-Cyanophenyl)-2-{1-[4-(methylsulfonyl)phenyl]ethylidene}hydrazine (18): Flash chromatography (2:1:0-0:8:1 hexane:EtOAc:CH$_3$OH) to give the desired product as a yellow solid (67%): R$_f$ (1:1 hexane:EtOAc) 0.33; $^1$H-NMR (CDCl$_3$ 300 MHz) 7.99 (s, 4H), 7.79 (bs, 1H), 7.60 (d, 2H), 7.25 (d, 2H), 3.10 (s, 3H), 2.35 (s, 3H).

(2E)-1-(4-Trifluoromethylphenyl)-2-{1-[4-(methylsulfonyl)phenyl]ethylidene}-hydrazine (19): Flash chromatography (4:1-0:1 hexane:EtOAc) to give the desired product as a yellow solid (24%): R$_f$(1:1 hexane:EtOAc) 0.46; $^1$H-NMR (CDCl$_3$ 300 MHz) 7.99 (s, 4H), 7.73 (bs, 1H), 7.57 (d, 2H), 7.27 (d, 2H), 3.10 (s, 3H), 2.33 (s, 3H).

(2E)-1-(3-Trifluoromethylphenyl)-2-{1-[4-(methylsulfonyl)phenyl]ethylidene}-hydrazine (20): Flash chromatography (4:1-0:1 hexane:EtOAc) to give the desired product as a yellow solid (69%): R$_f$(1:1 hexane:EtOAc) 0.57; $^1$H-NMR (CDCl$_3$ 300 MHz) 7.99 (s, 4H), 7.68 (bs, 1H), 7.43 (m, 3H), 7.20 (d, 2H), 3.10 (s, 3H), 2.32 (s, 3H).

(2E)-1-(2-Trifluoromethylphenyl)-2-{1-[4-(methylsulfonyl)phenyl]ethylidene}-hydrazine (21): Flash chromatography (3:1-2:1 hexane:EtOAc) to give the desired product as a yellow solid (90%): R$_f$(1:1 hexane:EtOAc) 0.82; $^1$H-NMR (CDCl$_3$ 300 MHz) 8.11 (bs, 1H), 7.96 (d, 4H), 7.80 (d, 1H), 7.54 (m, 2H), 7.03 (t, 1H), 3.10 (s, 3H), 2.33 (s, 3H).

3-[(2E)-2-{1-[4-(Methylsulfonyl)phenyl]ethylidene}hydrazinyl]benzonitrile (22): Flash chromatography (3:1-0:1 hexane:EtOAc) to give the desired product as a light yellow solid (71%): R$_f$ (1:1 hexane:EtOAc) 0.30; $^1$H-NMR (CDCl$_3$ 500 MHz) 8.00 (s, 4H), 7.65 (s, 1H), 7.54 (s, 1H), 7.41 (m, 2H), 7.23 (m, 1H), 3.12 (s, 3H), 2.34 (s, 3H).

Methyl 4-[(2E)-2-{1-[4-(methylsulfonyl)phenyl]ethylidene}hydrazinyl]benzoate (23): Flash chromatography (2:1-0:1 hexane:EtOAc) to give the desired product as a light yellow solid (25%): R$_f$ (1:1 hexane:EtOAc) 0.39; $^1$H-NMR (CDCl$_3$ 500 MHz) 8.04 (d, 2H), 8.00 (d, 4H), 7.91 (bs, 1H), 7.25 (d, 2H), 3.92 (s, 3H, CO$_2$CH$_3$), 3.11 (s, 3H, SO$_2$CH$_3$), 2.39 (s, 3H).

4-[(2E)-2-{1-[4-(Methylsulfonyl)phenyl]ethylidene}hydrazinyl]pyridine (24): Flash chromatography (0:1-8:1EtOAc:CH$_3$OH) to give the desired product as a light yellow solid (40%): R$_f$ (8:1EtOAc:CH$_3$OH) 0.17; $^1$H-NMR (CDCl$_3$ 500 MHz) 8.44 (m, 1H), 7.99 (s, 3H), 7.29 (s, 3H), 7.11 (m, 1H), 3.10 (s, 3H), 2.34 (s, 3H); ESMS 290 (M+H, 100%).

4-{(2E)-2-[1-(4-Nitrophenyl)ethylidene]hydrazinyl}benzonitrile (25): Flash chromatography (1:1:0-0:8:1 hexane:EtOAc:CH$_3$OH) to give an orange solid (98%): R$_f$(1:1 hexane:EtOAc) 0.47; $^1$H-NMR (CDCl$_3$ 300 MHz) 8.28 (d, 2H), 7.98 (d, 2H), 7.83 (bs, 1H), 7.62 (d, 2H), 7.26 (d, 2H), 2.36 (s, 3H).

Methyl 4-{(E)-[2-(4-cyanophenyl)hydrazinylidene]methyl}benzoate (26): Flash chromatography (3:1-0:1 hexane:EtOAc) to give an yellow solid (91%): R$_f$ (1:1 hexane:EtOAc) 0.76; $^1$H-NMR (CDCl$_3$ 300 MHz) 8.10 (d, 2H), 7.88 (d, 2H), 7.73 (bs, 1H), 7.83 (bs, 1H), 7.60 (d, 2H), 7.23 (d, 2H), 3.97 (s, 3H), 2.34 (s, 3H).

Figure 5:
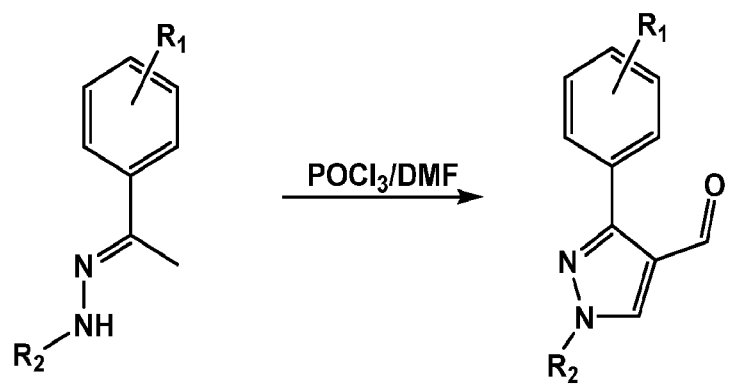
FIG. 5 illustrates step 2 of the preparation of representative pyrazole inhibitors of the invention shown in FIG. 3: pyrazole ring formation.

Step 2 of the synthesis is shown in FIG. 5: pyrazole ring preparation.

A summary of representative pyrazole intermediates useful in the syntheses is shown below.

| Compound | R¹ | R² |
|---|---|---|
| 27 | 4-NO₂ | C₆H₅ |
| 28 | 4-CF₃ | C₆H₅ |
| 29 | 4-pyridinyl | C₆H₅ |
| 30 | 3,4-F | C₆H₅ |
| 31 | 3-CF₃ | C₆H₅ |
| 32 | 4-CN | C₆H₅ |
| 33 | 4-CO₂CH₃ | C₆H₅ |
| 34 | 4-OH | C₆H₅ |
| 35 | 4-OAc | C₆H₅ |
| 36 | 4-Ac | C₆H₅ |
| 37 | 4-CONH₂ | C₆H₅ |
| 38 | 4-SOCH₃ | C₆H₅ |
| 39 | 4-SO₂CH₃ | C₆H₅ |
| 40 | 4-SO₂CH₂CH₃ | C₆H₅ |
| 41 | 4-SO₂CH₃ | 2-Chlorophenyl |
| 42 | 4-SO₂CH₃ | 3-Chlorophenyl |
| 43 | 4-SO₂CH₃ | 3-Fluorophenyl |
| 44 | 4-SO₂CH₃ | 4-Fluorophenyl |
| 45 | 4-SO₂CH₃ | 4-Trifluoromethoxyphenyl |
| 46 | 4-SO₂CH₃ | 4-Cyanophenyl |
| 47 | 4-SO₂CH₃ | 4-Trifluoromethylphenyl |
| 48 | 4-SO₂CH₃ | 3-Trifluoromethylphenyl |
| 49 | 4-SO₂CH₃ | 2-Trifluoromethylphenyl |
| 50 | 4-SO₂CH₃ | 3-Cyanophenyl |
| 51 | 4-SO₂CH₃ | 4-CH₃CO₂phenyl |
| 52 | 4-SO₂CH₃ | 4-Pyridinyl |
| 53 | 4-SO₂CH₃ | 4-Hydroxyphenyl |
| 54 | 4-NO₂ | 4-Cyanophenyl |
| 55 | 4-CN | 4-CH₃CO₂phenyl |
| 56 | 4-CO₂CHCH₂ | C₆H₅ |
| 57 | 4-Br | 4-Cyanophenyl |
| 58 | 4-Ac | C₆H₅ |
| 59 | 4-C(O)CHCl₂ | C₆H₅ |
| 60 | 4-Ac | 4-Cyanophenyl |
| 61 | 4-C(O)CHCl₂ | 4-Cyanophenyl |

The procedures for the preparation of the pyrazole intermediates was adapted from X Li, X Lu, M Xing, et al. Synthesis, biological evaluation, and molecular docking studies of N,1,3-triphenyl-1H-pyrazole-4-carboxamide derivatives as anticancer agents. 2012 Bioorg Med Chem Lett 22(11) 3589-93, and as summarized below.

Typical Procedure:

3-(4-Nitrophenyl)-1-phenyl-1H-pyrazole-4-carbaldehyde (27): To (1E)-1-[1-(4-nitrophenyl)ethylidene]-2-phenylhydrazine (1.151 g, 4.5 mmol) in 25 ml DMF was added phosphorous oxychloride (1.498 ml, 18.0 mmol). Heat the mixture at 60 C for 22 h under Ar. Pour the solution into 30 ml ice water and neutralize with concentrated NaOH (aq) until pH 10. Extract 8×25 ml DCM and wash the combined organics with 20 ml brine. The solvent was removed by rotary evaporation and the residue purified by flash chromatography (6:1-0:1 hexane:EtOAc) yielded the pyrazolealdehyde as a yellow solid (0.533 g, 40%): $R_f$ (3:1 hexane:EtOAc) 0.27; ¹H-NMR (DMSO 300 MHz) 10.04 (s, 1H, CHO), 9.46 (s, 1H, pyrazole-H), 8.36 (dt, 2H), 8.30 (dt, 2H), 8.02 (d, 2H), 7.61 (t, 2H), 7.49 (d, 1H).

3-(4-Trifluoromethylphenyl)-1-phenyl-1H-pyrazole-4-carbaldehyde (28): Brown solid (29%): $R_f$ (3:1 hexane:EtOAc) 0.43; ¹H-NMR (DMSO 300 MHz) 10.02 (s, 1H, CHO), 9.42 (s, 1H, pyrazole-H), 8.20 (d, 2H), 8.03 (d, 2H), 8.02 (d, 2H), 7.89 (d, 2H), 7.61 (t, 2H), 7.48 (t, 1H).

1-Phenyl-3-(pyridin-4-yl)-1H-pyrazole-4-carbaldehyde (29): Black solid (29%): $R_f$ (8:1 EtOAc:CH₃OH) 0.81; ¹H-NMR (DMSO 300 MHz) 10.04 (s, 1H, CHO), 9.43 (s, 1H, pyrazole-H), 8.73 (d, 2H), 7.99 (m, 4H), 7.60 (t, 2H), 7.49 (t, 1H).

3-(3,4-Difluorophenyl)-1-phenyl-1H-pyrazole-4-carbaldehyde (30): Red solid (14%): $R_f$ (3:1 hexane:EtOAc) 0.21; ¹H-NMR (CDCl₃ 300 MHz) 10.07 (s, 1H, CHO), 9.03 (s, 1H, pyrazole-H), 8.41 (s, 1H), 7.70 (d, 2H), 7.66 (m, 2H), 7.41 (m, 1H), 7.39 (m, 2H).

3-(3-Trifluoromethylphenyl)-1-phenyl-1H-pyrazole-4-carbaldehyde (31): Brown liquid (36%): $R_f$ (6:1 hexane:EtOAc) 0.21; ¹H-NMR (CDCl₃ 300 MHz) 10.09 (s, 1H, CHO), 8.59 (s, 1H), 8.21 (s, 1H), 8.12 (d, 1H), 7.84 (d, 2H), 7.75 (d, 1H), 7.64 (m, 1H), 7.54 (t, 2H), 7.45 (t, 1H).

4-(4-Formyl-1-phenyl-1H-pyrazol-3-yl)benzonitrile (32): Light yellow solid (64%): $R_f$ (3:1 hexane:EtOAc) 0.38; ¹H-NMR (CDCl₃ 300 MHz) 10.09 (s, 1H, CHO), 8.59 (s, 1H), 8.11 (d, 1H), 7.80 (m, 4H), 7.59 (t, 2H), 7.48 (t, 1H).

Methyl 4-(4-formyl-1-phenyl-1H-pyrazol-3-yl)benzoate (33): White solid (10%): $R_f$ (3:1 hexane:EtOAc) 0.33; ¹H-NMR (CDCl₃ 300 MHz) 10.01 (s, 1H, CHO), 8.50 (s, 1H), 8.10 (d, 2H), 7.88 (d, 2H), 7.73 (d, 2H), 7.49 (t, 2H), 7.38 (t, 1H), 3.89 (s, 3H).

3-(4-Hydroxyphenyl)-1-phenyl-1H-pyrazole-4-carbaldehyde (34): Orange solid (13%): $R_f$ (3:1 hexane:EtOAc) 0.30; ¹H-NMR (CDCl₃ 300 MHz) 10.06 (s, 1H, CHO), 8.55 (s, 1H), 7.79 (m, 4H), 7.54 (t, 2H), 7.42 (t, 1H), 6.99 (d, 2H).

4-(4-Formyl-1-phenyl-1H-pyrazol-3-yl)phenyl acetate (35):

3-(4-Hydroxyphenyl)-1-phenyl-1H-pyrazole-4-carbaldehyde (5-104) (0.036 g, 136 umol) was stirred overnight with 0.1 ml pyridine and acetic anhydride (0.014 ml, 150 umol). The solvent was removed by rotary evaporation and the residue purified by flash chromatography (5:1-3:1 hexane:ethyl acetate) to provide the product as yellow solid (0.033 g, 79%): $R_f$ (3:1 hexane:EtOAc) 0.32; ¹H-NMR (CDCl₃ 500 MHz) 10.08 (s, 1H, CHO), 8.56 (s, 1H), 7.91 (d, 2H), 7.81 (d, 2H), 7.54 (t, 2H), 7.43 (t, 1H), 7.28 (d, 2H), 2.37 (s, 3H).

3-(4-Acetylphenyl)-1-phenyl-1H-pyrazole-4-carbaldehyde (36): Yellow solid (15%): $R_f$ (3:1 hexane:EtOAc) 0.40; ¹H-NMR (CDCl₃ 300 MHz) 10.30 (s, 1H, CHO), 8.59 (s, 1H), 8.05 (d, 2H), 7.92 (d, 2H), 7.84 (d, 2H), 7.57 (t, 2H), 7.46 (t, 1H), 1.58 (s, 3H). Procedure adapted from Milstein D, Stille J K, Mild, selective, general method of ketone synthesis from acid chlorides and organotin compounds catalyzed by palladium, 1979 J Org Chem 44(10) 1613-18.

4-(4-Formyl-1-phenyl-1H-pyrazol-3-yl)benzamide (37): To methyl 4-(4-formyl-1-phenyl-1H-pyrazol-3-yl)benzoate (5-81, 0.024 mg, 78 umol) in 4 ml THF was added 1 eqv NaOH in 10 ul H₂O. The solution was stirred for 3 h whereupon 2 eqv NaOH (in 30 ul H₂O) were added and the solution stirred for 2 h and then refluxed for an additional 3 h. The solvent was removed by rotary evaporation and the residue dried in high vacuum over night. The residue was suspended in 3 ml toluene and 100 ul DMF. Thionyl chloride (0.057 ml, 783 umol) was added and the reaction refluxed for 2 hrs under dry atmosphere. After cooling to 20 C, 5 ml 0.5 M ammonia in dioxane was added and the reaction stirred for 72 h. The solvent was removed by rotary evaporation and the residue purified by flash chromatography to yield the product as a white solid (4%): $R_f$ (1:1 hexane:EtOAc) 0.15; ¹H-NMR (CDCl₃ 300 MHz) 10.09 (s, 1H, CHO), 8.58 (s, 1H), 7.94 (d, 2H), 7.83 (d, 2H), 7.59 (m, 4H), 7.53 (t, 1H).

3-[4-(Methylsulfinyl)phenyl]-1-phenyl-1H-pyrazole-4-carbaldehyde (38):

3-[4-(Methylsulfanyl)phenyl]-1-phenyl-1H-pyrazole-4-carbaldehyde (0.152 g, 516 umol) in 10 ml of acetone was gently refluxed overnight with predissolved (in 0.5 ml H₂O) sodium chlorite (0.051 g, 568 umol) and sulfamic acid (0.065 g, 671 umol). The solvent was removed by rotary evaporation and the residue purified by flash chromatography (1:1:0-0:8:1 hexane:EtOAc:CH₃OH) to yield the product as a white solid (0.061 g, 38%): $R_f$ (EtOAc) 0.43; ¹H-NMR (CDCl₃ 300 MHz) 10.10 (s, 1H, CHO), 8.59 (s, 1H), 8.11 (d, 2H), 7.94 (d, 2H), 7.82 (m, 4H), 7.57 (t, 2H), 7.48 (t, 1H), 2.82 (s, 3H); ESMS 311 (M+H, 100%).

3-[4-(Methylsulfonyl)phenyl]-1-phenyl-1H-pyrazole-4-carbaldehyde (39):
Purified by flash chromatography (3:1:0-0:8:1 hexane:EtOAc:CH$_3$OH) yielded the pyrazole-aldehyde as a brown-yellow solid (100%): R$_f$ (1:1 hexane:EtOAc) 0.43; $^1$H-NMR (CDCl$_3$ 300 MHz) 10.10 (s, 1H, CHO), 8.61 (s, 1H, pyrazole-H), 8.14 (m, 4H), 7.82 (m, 2H), 7.57 (m, 2H), 7.46 (m, 2H), 3.12 (s, 3H).

3-[4-(Ethylsulfonyl)phenyl]-1-phenyl-1H-pyrazole-4-carbaldehyde (40): Purified by flash chromatography (4:1-0:1 hexane:EtOAc) yielded the pyrazole-aldehyde as a brown-yellow solid (40%): R$_f$ (1:1 hexane:EtOAc) 0.48; $^1$H-NMR (CDCl$_3$ 300 MHz) 10.09 (s, 1H, CHO), 8.60 (s, 1H, pyrazole-H), 8.17 (m, 2H), 8.02 (m, 2H), 7.80 (m, 2H), 7.55 (m, 2H), 7.47 (m, 2H), 3.18 (q, 2H), 1.34 (t, 3H).

1-(2-Chlorophenyl)-3-[4-(methylsulfonyl)phenyl]-1H-pyrazole-4-carbaldehyde (41): Yellow solid (63%): R$_f$ (3:1 hexane:EtOAc) 0.07; $^1$H-NMR (CDCl$_3$ 300 MHz) 10.11 (s, 1H), 8.55 (s, 1H, pyrazole-H), 8.18 (d, 2H), 8.03 (d, 2H), 7.97 (m, 2H), 7.71 (m, 1H), 7.62 (m, 1H), 7.55 (m, 1H), 7.48 (m, 1H), 3.10 (s, 3H).

1-(3-Chlorophenyl)-3-[4-(methylsulfonyl)phenyl]-1H-pyrazole-4-carbaldehyde (42): Yellow solid (54%): R$_f$ (1:1 hexane:EtOAc) 0.50; $^1$H-NMR (CDCl$_3$ 300 MHz) 10.11 (s, 1H), 8.60 (s, 1H, pyrazole-H), 8.15 (dd, 4H), 7.91 (t, 1H), 7.70 (dm, 1H), 7.51 (t, 1H), 7.46 (m, 1H), 3.14 (s, 3H).

1-(3-Fluorophenyl)-3-[4-(methylsulfonyl)phenyl]-1H-pyrazole-4-carbaldehyde (43): Off-white solid (50%): R$_f$ (1:1 hexane:EtOAc) 0.54; $^1$H-NMR (CDCl$_3$ 500 MHz) 10.12 (s, 1H), 8.61 (s, 1H, pyrazole-H), 8.15 (dd, 4H), 7.64 (m, 1H), 7.61 (m, 1H), 7.54 (m, H), 7.29 (dt, 1H), 3.15 (s, 3H).

1-(4-Fluorophenyl)-3-[4-(methylsulfonyl)phenyl]-1H-pyrazole-4-carbaldehyde (44): Off-white solid (17%): R$_f$ (1:1 hexane:EtOAc) 0.67; $^1$H-NMR (CDCl$_3$ 300 MHz) 10.10 (s, 1H), 8.54 (s, 1H, pyrazole-H), 8.13 (dd, 4H), 7.80 (m, 2H), 7.26 (m, 2H), 3.13 (s, 3H).

1-(4-Trifluoromethoxyphenyl)-3-[4-(methylsulfonyl)phenyl]-1H-pyrazole-4-carbaldehyde (45): Off-white solid (61%): R$_f$ (1:1 hexane:EtOAc) 0.81; $^1$H-NMR (CDCl$_3$ 300 MHz) 10.11 (s, 1H), 8.59 (s, 1H, pyrazole-H), 8.14 (dd, 4H), 7.88 (m, 2H), 7.43 (d, 2H), 3.14 (s, 3H).

1-(4-Cyanophenyl)-3-[4-(methylsulfonyl)phenyl]-1H-pyrazole-4-carbaldehyde (46): Yellow solid (23%): R$_f$ (1:1 hexane:EtOAc) 0.33; $^1$H-NMR (CDCl$_3$ 300 MHz) 10.13 (s, 1H), 8.68 (s, 1H, pyrazole-H), 8.14 (dd, 4H), 8.00 (d, 2H), 7.89 (d, 2H), 3.14 (s, 3H).

1-(4-Trifluoromethylphenyl)-3-[4-(methylsulfonyl)phenyl]-1H-pyrazole-4-carbaldehyde (47): Light yellow solid (72%): R$_f$ (1:1 hexane:EtOAc) 0.72; $^1$H-NMR (CDCl$_3$ 300 MHz) 10.13 (s, 1H), 8.68 (s, 1H, pyrazole-H), 8.12 (dd, 4H), 7.80 (dd, 4H), 3.14 (s, 3H).

1-(3-Trifluoromethylphenyl)-3-[4-(methylsulfonyl)phenyl]-1H-pyrazole-4-carbaldehyde (48): Light yellow solid (36%): R$_f$ (1:1 hexane:EtOAc) 0.57; $^1$H-NMR (CDCl$_3$ 500 MHz) 10.14 (s, 1H), 8.68 (s, 1H, pyrazole-H), 8.19 (d, 2H), 8.13 (bs, 1H), 8.07 (d, 2H), 8.04 (m, 1H), 7.73 (m, 2H), 3.15 (s, 3H).

1-(2-Trifluoromethylphenyl)-3-[4-(methylsulfonyl)phenyl]-1H-pyrazole-4-carbaldehyde (49): Light yellow solid (5%): R$_f$ (1:1 hexane:EtOAc) 0.25; $^1$H-NMR (CDCl$_3$ 300 MHz) 10.10 (s, 1H), 8.35 (s, 1H, pyrazole-H), 8.12 (dd, 4H), 7.91 (d, 1H), 7.74 (m, 3H), 3.11 (s, 3H).

1-(3-Cyanophenyl)-3-[4-(methylsulfonyl)phenyl]-1H-pyrazole-4-carbaldehyde (50): Light yellow solid (14%): R$_f$ (1:1 hexane:EtOAc) 0.21; $^1$H-NMR (CDCl$_3$ 300 MHz) 10.03 (s, 1H), 8.55 (s, 1H, pyrazole-H), 8.03 (m, 7H), 7.64 (m, 1H), 3.05 (s, 3H).

Methyl 4-{4-formyl-3-[4-(methylsulfonyl)phenyl]-1H-pyrazol-1-yl}benzoate (51): Yellow solid (55%): R$_f$ (1:1 hexane:EtOAc) 0.50; $^1$H-NMR (CDCl$_3$ 300 MHz) 10.13 (s, 1H), 8.69 (s, 1H), 8.26 (d, 2H), 8.19 (d, 2H), 8.10 (d, 2H), 7.94 (d, 2H), 4.00 (s, 3H), 3.14 (s, 3H).

3-[4-(Methylsulfonyl)phenyl]-1-(pyridin-4-yl)-1H-pyrazole-4-carbaldehyde (52): Yellow solid (23%): R$_f$ (8:1 EtOAc:CH$_3$OH) 0.66; $^1$H-NMR (CDCl$_3$ 300 MHz) 10.13 (s, 1H), 8.74 (s, 1H), 8.16 (m, 4H), 7.80 (m, 4H), 3.13 (s, 3H).

3-(4-Hydroxyphenyl)-1-[4-(methoxycarbonyl)phenyl]-1H-pyrazole-4-carbaldehyde (53): White solid (29%): R$_f$ (1:1 hexane:EtOAc) 0.12; $^1$H-NMR (CDCl$_3$ 500 MHz) 9.02 (s, 1H), 8.70 (s, 1H), 8.24 (m, 2H), 7.82 (m, 4H), 7.41 (m, 2H), 3.99 (s, 3H).

4-[4-Formyl-3-(4-nitrophenyl)-1H-pyrazol-1-yl]benzonitrile (54): Orange solid (62%): R$_f$ (1:1 hexane:EtOAc) 0.60; $^1$H-NMR (CDCl$_3$ 500 MHz) 10.14 (s, 1H), 8.68 (s, 1H), 8.40 (d, 2H), 8.18 (d, 2H), 8.01 (d, 2H), 7.88 (d, 2H).

Methyl 4-[1-(4-cyanophenyl)-4-formyl-1H-pyrazol-3-yl]benzoate (55): Off-white solid (36%): R$_f$ (1:1 hexane:EtOAc) 0.66; $^1$H-NMR (CDCl$_3$ 300 MHz) 10.03 (s, 1H), 8.57 (s, 1H), 8.12 (d, 2H), 7.89 (m, 4H), 7.77 (d, 2H), 3.90 (s, 3H).

3-(4-Acryloylphenyl)-1-phenyl-1H-pyrazole-4-carbaldehyde (56): The starting methyl ester (0.436 g, 1.4 mmol) in 45 ml CH$_3$OH was hydrolyzed to the corresponding carboxylic acid by refluxing with sodium hydroxide (0.068 g, 1.7 mmol) in 1.5 ml H$_2$O overnight. H$_2$O (20 ml) was added and the solution acidified to pH~3 with 1 M HCl (aq), extracted 3×10 ml DCM, 3×10 ml EtOAc. The combined organics was dried with anhyd MgSO$_4$, solvent was removed by rotary evaporation and the residue purified by flash chromatography (1:0-8:1 EtOAc:CH$_3$OH) to yield the carboxylic acid as a yellow solid (0.277 g, 67%): R$_f$(EtOAc) 0.57; $^1$H-NMR (CDCl$_3$ 300 MHz) 10.10 (s, 1H), 8.57 (s, 1H), 8.20 (d, 2H), 8.01 (d, 2H), 7.81 (d, 2H), 7.54 (t, 2H), 7.42 (t, 1H). The carboxylic acid (5-81, 0.058 g, 198 umol) in 8 ml DCM was refluxed with thionyl chloride (29 ul, 397 umol) for 4 hr. After letting cool to room temp, tributylvinyltin (116 ul, 397 umol) and trans-benzyl(chloro)bis(phenylphosphine)palladium(II) (0.015 g, 20 umol) were added and the reaction which slowly turned black was refluxed for 2.5 h. The solution was washed 2×5 ml H$_2$O, dried with anhyd. MgSO$_4$ and then solvent was removed by rotary evaporation and the residue purified by flash chromatography (4:1-0:1 hexane:EtOAc) to yield the vinylketone as a yellow solid (0.031 g, 52%): R$_f$ (1:1 hexane:EtOAc) 0.83; $^1$H-NMR (CDCl$_3$ 500 MHz) 10.09 (s, 1H), 8.57 (s, 1H), 8.05 (dd, 4H), 7.81 (d, 2H), 7.54 (t, 2H), 7.43 (t, 1H), 7.21 (dd, 1H), 6.49 (d, 1H), 5.99 (d, 1H). Procedure adapted reference Milstein D, Stille J K, Mild, selective, general method of ketone synthesis from acid chlorides and organotin compounds catalyzed by palladium, 1979 J Org Chem 44(10) 1613-18.

3-(4-Bromophenyl)-1-(4-cyanophenyl)-1H-pyrazole-4-carbaldehyde (57): Flash chromatography (3:1-1:1 hexane:EtOAc) yielded the pyrazole (86%): R$_f$ (1:1 hexane:EtOAc) 0.80; $^1$H-NMR (CDCl$_3$ 500 MHz) 10.08 (s, 1H), 8.63 (s, 1H), 7.98 (d, 2H), 7.84 (d, 2H), 7.78 (d, 2H), 7.66 (d, 2H).

3-(4-Acetylphenyl)-1-phenyl-1H-pyrazole-4-carbaldehyde (58): To 3-(4-bromophenyl)-1-phenyl-1H-pyrazole-4-carbaldehyde (0.040 g, 122 umol) in 2 ml toluene was added tributyl(1-ethoxy-vinyl)tin (124 ul, 367 umol) and tetrakis(triphenylphosphine)palladium(0) (0.003 g, 2 umol). Reflux for 4 hr under Ar (turns black). Remove the solvent by rotary evaporation, add 8 ml THF and then add 0.5 ml 1 N HCl (aq). Stir for 1 hr. Add 10 ml H$_2$O and basify with sat'd NaHCO$_3$ (aq) so pH ~8. Extract 3×6 ml DCM and purification by flash chromatography (6:1-3:1 hexane:EtOAc) yielded the methyl ketone (65%): R$_f$ (3:1 hexane:EtOAc) 0.50; $^1$H-NMR (CDCl$_3$ 500 MHz) 10.10 (s, 1H), 8.59 (s, 1H), 8.11 (d, 2H), 8.02 (d, 2H), 7.83 (d, 2H), 7.56 (t, 2H), 7.45 (t, 1H), 2.69 (s, 3H). Procedure adapted from Milstein D, Stille J K, Mild, selective, general method of ketone synthesis from acid chlorides and organotin compounds catalyzed by palladium, 1979 J Org Chem 44(10) 1613-18.

3-(4-Dichloroacetylphenyl)-1-phenyl-1H-pyrazole-4-carbaldehyde (59):

Copper (II) chloride (0.208 g, 1550 umol) and lithium chloride (0.066 g, 1550 umol) were stirred for 5 min in 2 ml DMF. Add the methyl ketone (0.045 g, 155 umol) dissolved in 1 ml DMF. The reaction was heated at 88 C for 17.5 h under Argon. The now red solution was diluted with 15 ml DCM, washed 2×10 ml H$_2$O, dried with anhyd MgSO$_4$, filtered, the solvent removed by rotary evaporation and the residue purified by flash chromatography (5:1-3:1 hexane:EtOAc) yielded the dichloromethyl ketone (32%): R$_f$ (3:1 hexane:EtOAc) 0.27; $^1$H-NMR (CDCl$_3$ 500 MHz) 10.13 (s, 1H), 8.60 (s, 1H), 8.24 (d, 2H), 8.11 (d, 2H), 7.84 (d, 2H), 7.57 (t, 2H), 7.46 (t, 1H), 6.74 (s, 1H); ESMS 359 (M+H, 100%).

3-(4-Acetylphenyl)-1-(4-cyanophenyl)-1H-pyrazole-4-carbaldehyde (60): Flash chromatography (3:1-0:1 hexane:EtOAc) yielded the methylketone as a white solid (39%): R$_f$ (1:1 hexane:EtOAc) 0.67; $^1$H-NMR (CDCl$_3$ 500 MHz) 10.14 (s, 1H), 8.68 (s, 1H), 8.13 (d, 2H), 8.01 (m, 4H), 7.88 (d, 2H), 2.71 (s, 3H).

3-(4-Dichloroacetylphenyl)-1-(4-cyanophenyl)-1H-pyrazole-4-carbaldehyde (61): Procedure adapted from Milstein D, Stille J K, Mild, selective, general method of ketone synthesis from acid chlorides and organotin compounds catalyzed by palladium, 1979 J Org Chem 44(10) 1613-18. Flash chromatography (DCM) yielded the dichloromethyl ketone as a white solid (55%): R$_f$ (DCM) 0.25; $^1$H-NMR (CDCl$_3$ 500 MHz) 10.16 (s, 1H), 8.69 (s, 1H), 8.28 (d, 2H), 8.01 (d, 2H), 7.89 (d, 2H), 6.73 (s, 1H); ESMS 384 (M+H, 100%).

Figure 6:
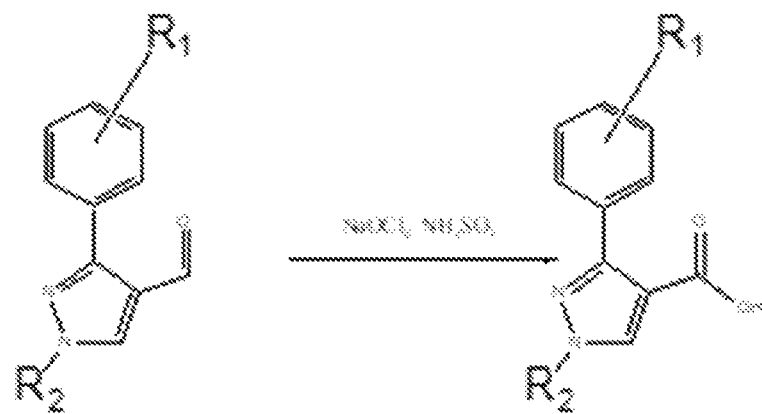
FIG. 6 illustrates step 3 of the preparation of representative pyrazole inhibitors of the invention shown in FIG. 3: pyrazole-carboxylic acid intermediates.

Step 3 of the synthesis is shown in FIG. 6: pyrazole-carboxylic acid preparation.

A summary of representative pyrazole-carboxylic acid intermediates useful in the syntheses is shown below.

| Compound | R$^1$ | R$^2$ |
|---|---|---|
| 62 | 4-NO$_2$ | C$_6$H$_5$ |
| 63 | 3-Cl | C$_6$H$_5$ |
| 64 | 4-CF$_3$ | C$_6$H$_5$ |
| 65 | 4-pyridinyl | C$_6$H$_5$ |
| 66 | 3-CF$_3$ | C$_6$H$_5$ |
| 67 | 4-CN | C$_6$H$_5$ |
| 68 | 4-CO$_2$CH$_3$ | C$_6$H$_5$ |
| 69 | 4-OAc | C$_6$H$_5$ |
| 70 | 4-SCH$_3$ | C$_6$H$_5$ |
| 71 | 4-SO$_2$CH$_3$ | C$_6$H$_5$ |
| 72 | 4-SOCH$_3$ | C$_6$H$_5$ |
| 73 | 4-SO$_2$CH$_2$CH$_3$ | C$_6$H$_5$ |
| 74 | 4-NAc | C$_6$H$_5$ |
| 75 | 4-NBoc | C$_6$H$_5$ |
| 76 | 4-NH$_2$ | C$_6$H$_5$ |
| 77 | 4-SO$_2$CH$_3$ | 2-Chlorophenyl |
| 78 | 4-SO$_2$CH$_3$ | 3-Chlorophenyl |
| 79 | 4-SO$_2$CH$_3$ | 4-Chlorophenyl |
| 80 | 4-SO$_2$CH$_3$ | 3-Fluorophenyl |
| 81 | 4-SO$_2$CH$_3$ | 2-Fluorophenyl |
| 82 | 4-SO$_2$CH$_3$ | 4-Fluorophenyl |
| 83 | 4-SO$_2$CH$_3$ | 4-Trifluoromethoxyphenyl |
| 84 | 4-SO$_2$CH$_3$ | 4-Cyanophenyl |
| 85 | 4-SO$_2$CH$_3$ | 4-Trifluoromethylphenyl |
| 86 | 4-SO$_2$CH$_3$ | 3-Trifluoromethylphenyl |
| 87 | 4-SO$_2$CH$_3$ | 4-CH$_3$CO$_2$phenyl |
| 88 | 4-SO$_2$CH$_3$ | 4-pyridinyl |
| 89 | 4-NO$_2$ | 4-Cyanophenyl |
| 90 | 4-CH$_3$OC(O) | 4-Cyanophenyl |
| 91 | 4-CH$_2$CHCO$_2$ | C$_6$H$_5$ |
| 92 | 4-Cl$_2$CHCO$_2$ | C$_6$H$_5$ |
| 93 | 4-Cl$_2$CHCO$_2$ | 4-Cyanophenyl |

The procedures for the preparation of the pyrazole-carboxylic acid intermediates was adapted from X Li, X Lu, M Xing, et al. Synthesis, biological evaluation, and molecular docking studies of N-1,3-triphenyl-1H-pyrazole-4-carboxamide derivatives as anticancer agents. 2012 Bioorg Med Chem Lett 22(11) 3589-93, and as summarized below.

Typical Procedure:

3-(4-Nitrophenyl)-1-phenyl-1H-pyrazole-4-carboxylic acid (62): To 3-(4-nitrophenyl)-1-phenyl-1H-pyrazole-4-carbaldehyde (0.748 g, 2.6 mmol) in 40 ml acetone was added sulfamic acid (0.322 g, 3.3 mmol) and sodium chlorite (0.254 g, 2.8 mmol) predissolved in 1 ml H$_2$O. The solution was refluxed for 19 h whereupon the solvent was removed by rotary evaporation and the residue purified by flash chromatography (3:1-0:1 hexane:EtOAc) yielded the pyrazole-acid as a yellow solid (0.241 g, 31%): R$_f$ (1:1 hexane:EtOAc) 0.14; $^1$H-NMR (DMSO 300 MHz) 9.45 (s, 1H, pyrazole-H), 8.34 (m, 2H), 8.16 (d, 2H), 8.01 (d, 2H), 7.57 (t, 2H), 7.44 (m, 1H); ESMS 310 (M+H, 100).

3-(3-Chlorophenyl)-1-phenyl-1H-pyrazole-4-carboxylic acid (63): Brown solid (34%): R$_f$ (3:1 hexane:EtOAc) 0.07; $^1$H-NMR (DMSO 300 MHz) 9.08 (s, 1H, pyrazole-H), 7.91 (m, 3H), 7.85 (m, 1H), 7.50 (m, 4H), 7.43 (t, 1H).

3-(4-Trifluoromethylphenyl)-1-phenyl-1H-pyrazole-4-carboxylic acid (64): White solid (75%): R$_f$ (3:1 hexane:EtOAc) 0.07; $^1$H-NMR (CDCl$_3$ 300 MHz) 8.62 (s, 1H, pyrazole-H), 8.07 (d, 2H), 7.81 (d, 2H), 7.73 (d, 2H), 7.54 (t, 2H), 7.43 (t, 1H).

1-Phenyl-3-(pyridin-4-yl)-1H-pyrazole-4-carboxylic acid (65): Light yellow solid (26%): R$_f$ (8:1 EtOAc:CH$_3$OH) 0.17; $^1$H-NMR (DMSO 300 MHz) 9.14 (s, 1H), 8.68 (bs, 2H), 8.00 (d, 2H), 7.88 (s, 2H), 7.57 (t, 2H), 7.43 (t, 1H); ESMS 266 (M+H).

3-(3-Trifluoromethylphenyl)-1-phenyl-1H-pyrazole-4-carboxylic acid (66): Light yellow solid (61%): R$_f$ (3:1 hexane:EtOAc) 0.13; $^1$H-NMR (DMSO 300 MHz) 9.13 (s, 1H, pyrazole-H), 8.22 (s, 1H), 8.17 (d, 2H), 8.00 (d, 2H), 7.80 (d, 1H), 7.71 (t, 2H), 7.56 (t, 2H), 7.42 (t, 1H).

3-(4-Cyanophenyl)-1-phenyl-1H-pyrazole-4-carboxylic acid (67): White solid (55%): R$_f$ (3:1 hexane:EtOAc) 0.12; (DMSO 300 MHz) 9.13 (s, 1H, pyrazole-H), 8.08 (d, 2H), 8.00 (d, 2H), 7.93 (d, 2H), 7.56 (t, 2H), 7.42 (t, 1H).

3-[4-(Methoxycarbonyl)phenyl]-1-phenyl-1H-pyrazole-4-carboxylic acid (68): White solid (33%): R$_f$ (1:1 hexane:EtOAc) 0.33; (CDCl$_3$ 300 MHz) 8.57 (s, 1H, pyrazole-H), 8.10 (d, 2H), 7.97 (d, 2H), 7.76 (d, 2H), 7.50 (t, 2H), 7.38 (t, 1H).

3-[4-(Acetyloxy)phenyl]-1-phenyl-1H-pyrazole-4-carboxylic acid (69): White solid (19%): R$_f$ (3:1 hexane:EtOAc) 0.03; (CDCl$_3$ 300 MHz) 8.61 (s, 1H, pyrazole-H), 7.97 (d, 2H), 7.80 (d, 2H), 7.53 (t, 2H), 7.51 (t, 1H), 7.21 (d, 2H), 2.37 (s, 3H).

3-[4-(Methylsulfanyl)phenyl]-1-phenyl-1H-pyrazole-4-carboxylic acid (70): White solid (14%): R$_f$ (1:1 hexane:EtOAc) 0.03; (CDCl$_3$ 300 MHz) 8.62 (s, 1H, pyrazole-H), 8.13 (d, 2H), 7.84 (m, 4H), 7.56 (m, 2H), 7.43 (t, 1H), 7.38 (m, 2H), 2.81 (s, 3H).

3-[4-(Methylsulfonyl)phenyl]-1-phenyl-1H-pyrazole-4-carboxylic acid (71): White solid (38%): R$_f$ (EtOAc) 0.20; $^1$H-NMR (CDCl$_3$ 300 MHz) 8.64 (s, 1H, pyrazole-H), 8.17 (d, 2H), 8.04 (d, 2H), 7.81 (m, 2H), 7.54 (t, 2H), 7.44 (t, 1H), 3.13 (s, 3H); ESMS 343 (M+H, 100%).

3-[4-(Methylsulfinyl)phenyl]-1-phenyl-1H-pyrazole-4-carboxylic acid (72): White solid (18%): R$_f$ (8:1 EtOAc:CH$_3$OH) 0.07; $^1$H-NMR (CDCl$_3$ 300 MHz) 8.62 (s, 1H, pyrazole-H), 8.13 (d, 2H), 7.79 (m, 4H), 7.81 (m, 2H), 7.55 (t, 2H), 7.43 (t, 1H), 2.81 (s, 3H); ESMS 349 (M+Na, 100%), 328 (M+H, 11%).

3-[4-(Ethylsulfonyl)phenyl]-1-phenyl-1H-pyrazole-4-carboxylic acid (73): White solid (53%): R$_f$ (8:1 EtOAc:CH$_3$OH) 0.48; $^1$H-NMR (CDCl$_3$ 300 MHz) 8.65 (s, 1H, pyrazole-H), 8.17 (d, 2H), 8.00 (d, 2H), 7.81 (m, 2H), 7.54 (t, 2H), 7.45 (t, 1H), 3.17 (q, 2H), 1.34 (t, 3H).

3-[4-(Acetylamino)phenyl]-1-phenyl-1H-pyrazole-4-carboxylic acid (74): 3-(4-Aminophenyl)-1-phenyl-1H-pyrazole-4-carboxylic acid (0.005 g, 19 umol), acetic anhydride (0.002 ml, 21 umol) and triethylamine (0.005 ml, 57 umol) were stirred overnight in 0.5 ml DMF. The solvent was removed by rotary evaporation and the residue purified by flash chromatography (1:1-0:1 hexane:EtOAc) to generate the product as a white solid (15%): R$_f$ (EtOAc) 0.73; $^1$H-NMR (CDCl$_3$ 300 MHz) 8.59 (s, 1H), 7.91 (m, 2H), 7.79 (m, 2H), 7.62 (m, 2H), 7.50 (m, 2H), 7.40 (m, 1H), 2.25 (s, 3H).

3-{4-[(tert-Butoxycarbonyl)amino]phenyl}-1-phenyl-1H-pyrazole-4-carboxylic acid (75): The amine (0.250 g, 0.90 mmol) in 6 ml CH$_3$OH was stirred overnight with di-tert-butyl dicarbonate (0.215 g, 0.98 mmol) and triethylamine (0.293 ml, 2.69 mmol). The solvent was removed by rotary evaporation and the residue purified by flash chromatography (EtOAc) to generate the product as a white solid (100%): R$_f$ (EtOAc) 0.89.

3-(4-Aminophenyl)-1-phenyl-1H-pyrazole-4-carboxylic acid (76): Commercial product.

1-(2-Chlorophenyl)-3-[4-(methylsulfonyl)phenyl]-1H-pyrazole-4-carboxylic acid (77): White solid (28%): R$_f$ (1:1 hexane:EtOAc) 0.07; $^1$H-NMR (CDCl$_3$ 300 MHz) 8.48 (s, 1H, pyrazole-H), 8.01 (dd, 4H), 7.57 (dm, 2H), 7.38 (dd, 1H), 3.02 (s, 3H).

1-(3-Chlorophenyl)-3-[4-(methylsulfonyl)phenyl]-1H-pyrazole-4-carboxylic acid (78): White solid (24%): R$_f$ (1:1 hexane:EtOAc) 0.06; $^1$H-NMR (CDCl$_3$ 300 MHz) 8.62 (s, 1H, pyrazole-H), 8.12 (m, 4H), 8.01 (dd, 4H), 7.88 (s, 1H), 7.70 (m, 1H), 7.49 (t, 1H), 7.43 (m, 1H), 3.13 (s, 3H).

1-(4-Chlorophenyl)-3-[4-(methylsulfonyl)phenyl]-1H-pyrazole-4-carboxylic acid (79): White solid (32%): R$_f$ (1:1 hexane:EtOAc) 0.07; $^1$H-NMR (CDCl$_3$ 300 MHz) 8.60 (s, 1H, pyrazole-H), 8.10 (dd, 4H), 7.64 (dd, 4H), 3.12 (s, 3H).

1-(3-Fluorophenyl)-3-[4-(methylsulfonyl)phenyl]-1H-pyrazole-4-carboxylic acid (80): White solid (28%): R$_f$ (1:1 hexane:EtOAc) 0.11; $^1$H-NMR (CDCl$_3$ 500 MHz) 8.54 (s, 1H, pyrazole-H), 8.02 (dd, 4H), 7.51 (m, 2H), 7.44 (m, 1H), 7.05 (m, 1H), 3.04 (s, 3H).

1-(2-Fluorophenyl)-3-[4-(methylsulfonyl)phenyl]-1H-pyrazole-4-carboxylic acid (81): White solid (47%): R$_f$ (1:1 hexane:EtOAc) 0.14; $^1$H-NMR (CDCl$_3$ 500 MHz) 8.61 (d, 1H, pyrazole-H), 8.02 (dd, 4H), 7.92 (dt, 1H), 7.34 (m, 1H), 7.23 (m, 2H), 3.03 (s, 3H).

1-(4-Fluorophenyl)-3-[4-(methylsulfonyl)phenyl]-1H-pyrazole-4-carboxylic acid (82): White solid (60%): R$_f$ (1:1 hexane:EtOAc) 0.03; $^1$H-NMR (CDCl$_3$ 300 MHz) 8.56 (s, 1H, pyrazole-H), 8.11 (dd, 4H), 7.76 (dd, 2H), 7.26 (dd, 2H), 3.12 (s, 3H).

1-(4-Trifluoromethoxyphenyl)-3-[4-(methylsulfonyl)phenyl]-1H-pyrazole-4-carboxylic acid (83): White solid (54%): R$_f$ (1:1 hexane:EtOAc) 0.06; $^1$H-NMR (CDCl$_3$ 300 MHz) 8.62 (s, 1H, pyrazole-H), 8.10 (dd, 4H), 7.86 (d, 2H), 7.41 (d, 2H), 3.12 (s, 3H).

1-(4-Cyanophenyl)-3-[4-(methylsulfonyl)phenyl]-1H-pyrazole-4-carboxylic acid (84): White solid (24%): R$_f$ (1:1 hexane:EtOAc) 0.08; $^1$H-NMR (CDCl$_3$ 300 MHz) 8.70 (s, 1H, pyrazole-H), 8.11 (dd, 4H), 7.93 (dd, 4H), 3.13 (s, 3H).

1-(4-Trifluoromethylphenyl)-3-[4-(methylsulfonyl)phenyl]-1H-pyrazole-4-carboxylic acid (85): White solid (41%): R$_f$ (1:1 hexane:EtOAc) 0.07; $^1$H-NMR (CDCl$_3$ 300 MHz) 8.70 (s, 1H, pyrazole-H), 8.12 (dd, 4H), 7.90 (d, 2H), 3.13 (s, 3H).

1-(3-Trifluoromethylphenyl)-3-[4-(methylsulfonyl)phenyl]-1H-pyrazole-4-carboxylic acid (86): White solid (86%): R$_f$ (1:1 hexane:EtOAc) 0.11; $^1$H-NMR (CDCl$_3$ 300 MHz) 8.70 (s, 1H, pyrazole-H), 8.18 (d, 2H), 8.11 (m, 1H), 8.07 (d, 2H), 8.02 (m, 1H), 7.04 (m, 2H), 3.13 (s, 3H).

1-[4-(Methoxycarbonyl)phenyl]-3-[4-(methylsulfonyl)phenyl]-1H-pyrazole-4-carboxylic acid (87): White solid (79%): R$_f$ (1:1 hexane:EtOAc) 0.10; $^1$H-NMR (CDCl$_3$ 300 MHz) 8.62 (s, 1H, pyrazole-H), 8.14 (d, 2H), 8.08 (d, 2H), 7.96 (d, 2H), 7.82 (d, 2H), 3.90 (s, 3H), 3.03 (s, 3H).

3-[4-(Methylsulfonyl)phenyl]-1-(pyridin-4-yl)-1H-pyrazole-4-carboxylic acid (88): White solid (68%): R$_f$ (8:1 EtOAc:CH$_3$OH) 0.12; $^1$H-NMR (CD$_3$OD 300 MHz) 9.19 (s, 1H, pyrazole-H), 8.15 (m, 8H), 3.19 (s, 3H).

1-(4-Cyanophenyl)-3-(4-nitrophenyl)-1H-pyrazole-4-carboxylic acid (89): Light orange solid (45%): R$_f$ (1:1 hexane:EtOAc) 0.11; $^1$H-NMR (CDCl$_3$ 300 MHz) 8.70 (s, 1H), 8.36 (m, 2H), 7.90 (m, 6H).

1-(4-Cyanophenyl)-3-[4-(methoxycarbonyl)phenyl]-1H-pyrazole-4-carboxylic acid (90): White solid (95%): R$_f$ (1:1 hexane:EtOAc) 0.10; $^1$H-NMR (CDCl$_3$ 300 MHz) 8.60 (s, 1H), 8.06 (d, 2H), 7.90 (m, 4H), 7.76 (d, 2H), 3.89 (s, 3H).

3-(4-Acryloylphenyl)-1-phenyl-1H-pyrazole-4-carboxylic acid (91): White solid (45%): R$_f$ (1:1 hexane:EtOAc) 0.20; $^1$H-NMR (CDCl$_3$ 500 MHz) 8.60 (s, 1H), 8.04 (m, 4H), 7.79 (d, 2H), 7.51 (m, 2H), 7.41 (m, 1H), 7.20 (dd, 1H), 6.48 (d, 1H), 5.96 (d, 1H).

3-(4-Dichloroacetylphenyl)-1-phenyl-1H-pyrazole-4-carboxylic acid (92): White solid (65%): R$_f$ (3:1 hexane:EtOAc) 0.30; $^1$H-NMR (CDCl$_3$ 500 MHz) 8.56 (s, 1H), 8.01 (m, 4H), 7.72 (d, 2H), 7.39 (m, 3H), 6.63 (s, 1H).

3-(4-Dichloroacetylphenyl)-1-(4-cyanophenyl)-1H-pyrazole-4-carboxylic acid (93): White solid (100%): R$_f$ (1:1 hexane:EtOAc) 0.07; $^1$H-NMR (CDCl$_3$ 500 MHz) 8.72 (s, 1H), 8.22 (2, 2H), 8.13 (d, 2H), 7.99 (d, 2H), 7.87 (d, 2H), 6.74 (m, 2H), 2.73 (s, 1H).

Figure 7:
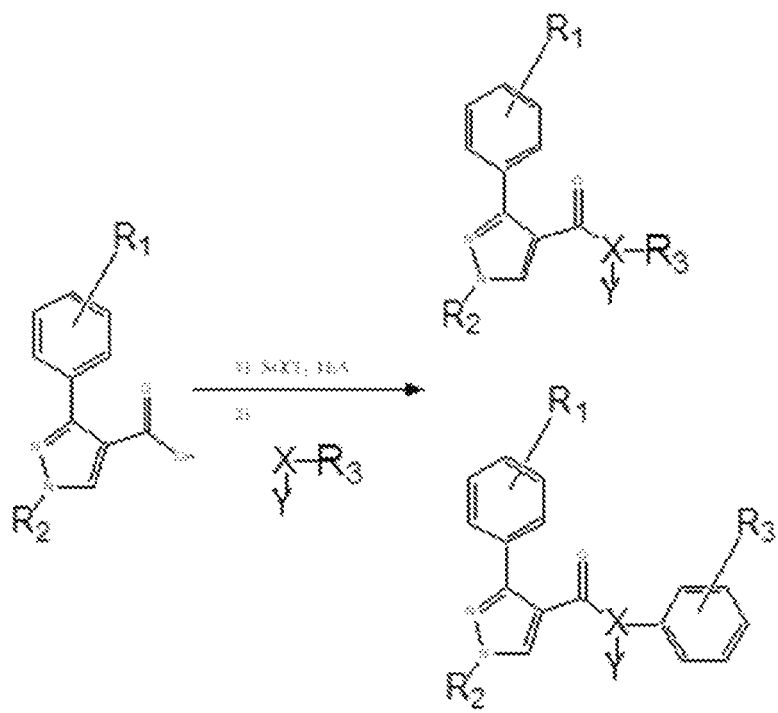
FIG. 7 illustrates step 4 of the preparation of representative pyrazole inhibitors of the invention shown in FIG. 3: general preparation of pyrazole-amides.

Step 4 of the synthesis is shown in FIG. 7: pyrazole-amide preparation.

A summary of representative pyrazole-amides of the invention is shown below.

| Compound | R$^1$ | R$^2$ | R$^3$ | X | Y |
|---|---|---|---|---|---|
| 94 | 4-NO$_2$ | C$_6$H$_5$ | CH$_2$C$_6$H$_5$ | N | H |
| 95 | 4-NO$_2$ | C$_6$H$_5$ | CH$_2$CH$_3$ | N | CH$_2$CH$_3$ |
| 96 | 4-NO$_2$ | C$_6$H$_5$ | C$_6$H$_5$ | N | H |

-continued

| Compound | $R^1$ | $R^2$ | $R^3$ | X | Y |
|---|---|---|---|---|---|
| 97 | 4-$NO_2$ | $C_6H_5$ | N-sBu | N | H |
| 98 | 4-$NO_2$ | $C_6H_5$ | N-iPr | N | H |
| 99 | 4-$NO_2$ | $C_6H_5$ | N-Pr | N | H |
| 100 | 4-$NO_2$ | $C_6H_5$ | $CH_2CH_3$ | N | $CH_3$ |
| 101 | 4-$NO_2$ | $C_6H_5$ | N-tBu | N | H |
| 102 | 4-$NO_2$ | $C_6H_5$ | 2-$OCH_3$ | N | H |
| 103 | 4-$NO_2$ | $C_6H_5$ | 3-$OCH_3$ | N | H |
| 104 | 4-$NO_2$ | $C_6H_5$ | 4-$OCH_3$ | N | H |
| 105 | 4-$NO_2$ | $C_6H_5$ | 2-F | N | H |
| 106 | 4-$NO_2$ | $C_6H_5$ | 3-F | N | H |
| 107 | 4-$NO_2$ | $C_6H_5$ | 4-F | N | H |
| 108 | 4-$NO_2$ | $C_6H_5$ | 2-Cl | N | H |
| 109 | 4-$NO_2$ | $C_6H_5$ | 3-Cl | N | H |
| 110 | 4-$NO_2$ | $C_6H_5$ | 4-Cl | N | H |
| 111 | 4-$NO_2$ | $C_6H_5$ | 2-CN | N | H |
| 112 | 4-$NO_2$ | $C_6H_5$ | 4-CN | N | H |
| 113 | 4-$NO_2$ | $C_6H_5$ | 2-Ac | N | H |
| 114 | 4-$NO_2$ | $C_6H_5$ | 3-Ac | N | H |
| 115 | 4-$NO_2$ | $C_6H_5$ | 4-Ac | N | H |
| 116 | 4-$NO_2$ | $C_6H_5$ | 2-$NHCH_3$ | N | H |
| 117 | 4-$NO_2$ | $C_6H_5$ | 2-$OCH_3$ | N | $CH_3$ |
| 118 | 4-$NO_2$ | $C_6H_5$ | * | N | H |
| 119 | 4-$NO_2$ | $C_6H_5$ | 2,3-F | N | H |
| 120 | 4-$NO_2$ | $C_6H_5$ | 2,5-F | N | H |
| 121 | 4-$NO_2$ | $C_6H_5$ | 3,4-F | N | H |
| 122 | 4-$NO_2$ | $C_6H_5$ | 3,5-F | N | H |
| 123 | 4-$NO_2$ | $CH_3$ | 2-$OCH_3$ | N | H |
| 124 | 4-$NO_2$ | $CH_3$ | 2-F | N | H |
| 125 | 4-$NO_2$ | $C_6H_5$ | 2-$CH_3$ | N | H |
| 126 | 4-$NO_2$ | $C_6H_5$ | 3-$CH_3$ | N | H |
| 127 | 4-$NO_2$ | $C_6H_5$ | 4-$CH_3$ | N | H |
| 128 | 4-F | $C_6H_5$ | 2-$OCH_3$ | N | H |
| 129 | 4-F | $C_6H_5$ | 3-F | N | H |
| 130 | 4-F | $C_6H_5$ | 3,4-F | N | H |
| 131 | 4-F | $C_6H_5$ | 4-$CH_3$ | N | H |
| 132 | 4-Cl | $C_6H_5$ | 2-$OCH_3$ | N | H |
| 133 | 4-Cl | $C_6H_5$ | 3-F | N | H |
| 134 | 4-Cl | $C_6H_5$ | 3,4-F | N | H |
| 135 | 4-Cl | $C_6H_5$ | 4-$CH_3$ | N | H |
| 136 | 4-H | $C_6H_5$ | 2-$OCH_3$ | N | H |
| 137 | 4-H | $C_6H_5$ | 3-F | N | H |
| 138 | 4-H | $C_6H_5$ | 3,4-F | N | H |
| 139 | 4-H | $C_6H_5$ | 4-$CH_3$ | N | H |
| 140 | 4-$CH_3$ | $C_6H_5$ | 2-$OCH_3$ | N | H |
| 141 | 4-$CH_3$ | $C_6H_5$ | 3-F | N | H |
| 142 | 4-$OCH_3$ | $C_6H_5$ | 2-$OCH_3$ | N | H |
| 143 | 4-$OCH_3$ | $C_6H_5$ | 3-F | N | H |
| 144 | 3-$OCH_3$ | $C_6H_5$ | 2-$OCH_3$ | N | H |
| 145 | 3-$OCH_3$ | $C_6H_5$ | 3-F | N | H |
| 146 | 2-$OCH_3$ | $C_6H_5$ | 3-$OCH_3$ | N | H |
| 147 | 2-$OCH_3$ | $C_6H_5$ | 3-F | N | H |
| 148 | 2-$CH_3$ | $C_6H_5$ | 2-$OCH_3$ | N | H |
| 149 | 2-$CH_3$ | $C_6H_5$ | 3-F | N | H |
| 150 | 4-$NO_2$ | $C_6H_5$ | 2-$CF_3$ | N | H |
| 151 | 4-$NO_2$ | $C_6H_5$ | 3-$CF_3$ | N | H |
| 152 | 4-$NO_2$ | $C_6H_5$ | 4-$CF_3$ | N | H |
| 153 | 3-Cl | $C_6H_5$ | 2-$OCH_3$ | N | H |
| 154 | 3-Cl | $C_6H_5$ | 3-F | N | H |
| 155 | 2-$CH_3$ | $C_6H_5$ | 2-$OCH_3$ | N | H |
| 156 | 2-$CH_3$ | $C_6H_5$ | 3-F | N | H |
| 157 | 4-$CF_3$ | $C_6H_5$ | 2-$OCH_3$ | N | H |
| 158 | 4-$CF_3$ | $C_6H_5$ | 3-F | N | H |
| 159 | 3,4-F | $C_6H_5$ | 2-$OCH_3$ | N | H |
| 160 | 3,4-F | $C_6H_5$ | 3-F | N | H |
| 161 | 3-$CF_3$ | $C_6H_5$ | 2-$OCH_3$ | N | H |
| 162 | 3-$CF_3$ | $C_6H_5$ | 3-F | N | H |
| 163 | 4-CN | $C_6H_5$ | 2-$OCH_3$ | N | H |
| 164 | 4-CN | $C_6H_5$ | 3-F | N | H |
| 165 | 4-$NO_2$ | $C_6H_5$ | 2-OH | N | H |
| 166 | 4-$NO_2$ | $C_6H_5$ | 3-OH | N | H |
| 167 | 4-$NO_2$ | $C_6H_5$ | 4-OH | N | H |
| 168 | 4-pryidinyl | $C_6H_5$ | 3-F | N | H |
| 169 | 4-$CO_2CH_3$ | $C_6H_5$ | 3-F | N | H |
| 170 | 4-$CO_2Na$ | $C_6H_5$ | 3-F | N | H |
| 171 | 4-$NO_2$ | $C_6H_5$ | 3-F | O | |
| 172 | 4-$NO_2$ | $C_6H_5$ | 2-$NH_2$ | N | H |
| 173 | 4-$NO_2$ | $C_6H_5$ | 3-$NH_2$ | N | H |
| 174 | 4-OAc | $C_6H_5$ | 3-F | N | H |
| 175 | 4-OH | $C_6H_5$ | 3-F | N | H |
| 176 | 4-$SCH_3$ | $C_6H_5$ | 3-F | N | H |
| 177 | 4-$CONH_2$ | $C_6H_5$ | 3-F | N | H |
| 178 | 4-$SO_2CH_3$ | $C_6H_5$ | 3-F | N | H |
| 179 | 4-$SO_2CH_3$ | $C_6H_5$ | 2-$OCH_3$ | N | H |
| 180 | 4-NHBoc | $C_6H_5$ | 3-F | N | H |
| 181 | 4-pyridylN—O | $C_6H_5$ | 3-F | N | H |
| 182 | 4-$NH_2$ | $C_6H_5$ | 3-F | N | H |
| 183 | 4-NAc | $C_6H_5$ | 3-F | N | H |
| 184 | 4-$NSO_2CH_3$ | $C_6H_5$ | 3-F | N | H |
| 185 | 4-CHO | $C_6H_5$ | 3-F | N | H |
| 186 | 4-$CH_2OH$ | $C_6H_5$ | 3-F | N | H |
| 187 | 4-F | $C_6H_5$ | 4-$CH_3$ | N | H |
| 188 | 4-F | $C_6H_5$ | 2-$CH_3$ | N | H |
| 189 | 4-F | $C_6H_5$ | 3-$OCH_3$ | N | H |
| 190 | 4-F | $C_6H_5$ | 4-$OCH_3$ | N | H |
| 191 | 4-F | $C_6H_5$ | 2-F | N | H |
| 192 | 4-F | $C_6H_5$ | 4-F | N | H |
| 193 | 4-F | $C_6H_5$ | 4-$CF_3$ | N | H |
| 194 | 4-F | $C_6H_5$ | 3-$CF_3$ | N | H |
| 195 | 4-F | $C_6H_5$ | 2-$CF_3$ | N | H |
| 196 | 4-NCHO | $C_6H_5$ | 3-F | N | H |
| 197 | 4-$SOCH_3$ | $C_6H_5$ | 3-F | N | H |
| 198 | 4-$SOCH_3$ | $C_6H_5$ | 4-F | N | H |
| 199 | 4-$SOCH_3$ | $C_6H_5$ | 2-$CH_3$ | N | H |
| 200 | 4-$SOCH_3$ | $C_6H_5$ | 3-$CH_3$ | N | H |
| 201 | 4-$SOCH_3$ | $C_6H_5$ | 4-$CH_3$ | N | H |
| 202 | 4-$SOCH_3$ | $C_6H_5$ | 2-$OCH_3$ | N | H |
| 203 | 4-$SO_2CH_3$ | $C_6H_5$ | 2-F | N | H |
| 204 | 4-$SO_2CH_3$ | $C_6H_5$ | 4-F | N | H |
| 205 | 4-$SO_2CH_3$ | $C_6H_5$ | 4-$CH_3$ | N | H |
| 206 | 4-$SO_2CH_3$ | $C_6H_5$ | 2-$OCH_3$ | N | H |
| 207 | 4-$SO_2CH_3$ | $C_6H_5$ | 3,4-F | N | H |
| 208 | 4-$SO_2CH_3$ | $C_6H_5$ | 3-$CF_3$ | N | H |
| 209 | 4-$SO_2CH_3$ | $C_6H_5$ | 2-OH | N | H |
| 210 | 4-$SO_2CH_3$ | $C_6H_5$ | 2-OAc | N | H |
| 211 | 4-$SO_2CH_3$ | $C_6H_5$ | 3-OH | N | H |
| 212 | 4-$SO_2CH_3$ | $C_6H_5$ | 3-$OCH_3$ | N | H |
| 213 | 4-$SO_2CH_3$ | $C_6H_5$ | 3-$NH_2$ | N | H |
| 214 | 4-$SO_2CH_3$ | $C_6H_5$ | 3-Ac | N | H |
| 215 | 4-$SO_2CH_3$ | $C_6H_5$ | 2-$CH_3$ | N | H |
| 216 | 4-$SO_2CH_3$ | $C_6H_5$ | 3-$CH_3$ | N | H |
| 217 | 4-$SO_2CH_3$ | $C_6H_5$ | 4-$OCH_3$ | N | H |
| 218 | 4-$SO_2CH_3$ | $C_6H_5$ | 2-Cl | N | H |
| 219 | 4-$SO_2CH_3$ | $C_6H_5$ | 3-Cl | N | H |
| 220 | 4-$SO_2CH_3$ | $C_6H_5$ | 4-Cl | N | H |
| 221 | 4-$SO_2CH_3$ | $C_6H_5$ | 4-OH | N | H |
| 222 | 4-$SO_2CH_3$ | $C_6H_5$ | H | N | H |
| 223 | 4-$SO_2CH_2CH_3$ | $C_6H_5$ | 3-F | N | H |
| 224 | 4-$NO_2$ | $C_6H_5$ | OH | N | H |
| 225 | 4-$NO_2$ | $C_6H_5$ | H | N | H |
| 226 | 4-$NO_2$ | $C_6H_5$ | $CH_3$ | N | H |
| 227 | 4-$NO_2$ | $C_6H_5$ | $CH_3$ | N | $CH_3$ |
| 228 | 4-$NO_2$ | $C_6H_5$ | $CH_2CH_3$ | N | H |
| 229 | 4-$NO_2$ | $C_6H_5$ | $CH_3$ | O | |
| 230 | 4-$NO_2$ | $C_6H_5$ | $CH_2CH_3$ | O | |
| 231 | 4-$SO_2CH_3$ | $C_6H_5$ | 2-OH, 3-F | N | H |
| 232 | 4-$SO_2CH_3$ | $C_6H_5$ | $OCH_2CH_3$ | N | H |
| 233 | 4-$SO_2CH_3$ | 4-Cl | 2-OH | N | H |
| 234 | 4-$SO_2CH_3$ | 4-Cl | 3-F | N | H |
| 235 | 4-$SO_2CH_3$ | 2-Cl | 2-OH | N | H |
| 236 | 4-$SO_2CH_3$ | 2-Cl | 3-F | N | H |
| 237 | 4-$SO_2CH_3$ | 2-F | 3-F | N | H |
| 238 | 4-$SO_2CH_3$ | 2-F | 2-OH | N | H |
| 239 | 4-$SO_2CH_3$ | 3-Cl | 3-F | N | H |
| 240 | 4-$SO_2CH_3$ | 3-Cl | 2-OH | N | H |
| 241 | 4-$SO_2CH_3$ | 4-F | 3-F | N | H |
| 242 | 4-$SO_2CH_3$ | 4-F | 2-OH | N | H |
| 243 | 4-$SO_2CH_3$ | 3-F | 2-OH | N | H |
| 244 | 4-$SO_2CH_3$ | 3-F | 2-$NH_2$ | O | |
| 245 | 4-$SO_2CH_3$ | 3-F | 3-F | N | H |
| 246 | 4-$SO_2CH_3$ | 4-$OCF_3$ | 3-F | N | H |
| 247 | 4-$SO_2CH_3$ | 4-$OCF_3$ | 3-OH | N | H |
| 248 | 4-$SO_2CH_3$ | 4-$CF_3$ | 3-F | N | H |

-continued

| Compound | R¹ | R² | R³ | X | Y |
|---|---|---|---|---|---|
| 249 | 4-SO₂CH₃ | 4-CN | 3-F | N | H |
| 250 | 4-SO₂CH₃ | 3-CF₃ | 3-F | N | H |
| 251 | 4-SO₂CH₃ | 2-CF₃ | 3-F | N | H |
| 252 | 4-SO₂CH₃ | C₆H₅ | 2-pyridyl | N | H |
| 253 | 4-SO₂CH₃ | C₆H₅ | 3-pyridyl | N | H |
| 254 | 4-SO₂CH₃ | C₆H₅ | CH₃ | O | |
| 255 | 4-SO₂CH₃ | 4-F | 3,4-diF | N | H |
| 256 | 4-SO₂CH₃ | 4-F | 3-CF₃ | N | H |
| 257 | 4-SO₂CH₃ | 4-F | CH₃ | O | |
| 258 | 4-SO₂CH₃ | 4-OCF₃ | 3-F | N | H |
| 259 | 4-SO₂CH₃ | 4-OCF₃ | 3-CF₃ | N | H |
| 260 | 4-SO₂CH₃ | 4-OCF₃ | CH₃ | O | |
| 261 | 4-SO₂CH₃ | 4-CN | 3,4-diF | N | H |
| 262 | 4-SO₂CH₃ | 4-CN | 3-CF₃ | N | H |
| 263 | 4-SO₂CH₃ | 4-CN | CH₃ | O | |
| 264 | 4-SO₂CH₃ | 3-F | 3-F | N | H |
| 265 | 4-SO₂CH₃ | 3-F | 3,4-diF | N | H |
| 266 | 4-SO₂CH₃ | 3-F | 3-CF₃ | N | H |
| 267 | 4-SO₂CH₃ | 3-F | CH₃ | O | |
| 268 | 4-SO₂CH₃ | 3-CN | 3-F | N | H |
| 269 | 4-SO₂CH₃ | 3-CN | 3,4-diF | N | H |
| 270 | 4-SO₂CH₃ | 3-CN | 3-CF₃ | N | H |
| 271 | 4-SO₂CH₃ | 3-CN | CH₃ | O | |
| 272 | 4-SO₂CH₃ | 4-OCF₃ | 3,4-diF | N | H |
| 273 | 4-SO₂CH₃ | 4-CH₃O₂C | 3-F | N | H |
| 274 | 4-SO₂CH₃ | 4-CH₃O₂C | 2-NH₂ | O | |
| 275 | 4-SO₂CH₃ | 4-CH₃O₂C | 2-OH | N | H |
| 276 | 4-SO₂CH₃ | 4-HO₂C | 3-F | N | H |
| 277 | 4-SO₂CH₃ | 4-CH₃O₂C | 2-OH | N | H |
| 278 | 4-SO₂CH₃ | 4-pyridyl | 2-NH₂ | N | H |
| 279 | 4-NHC(O)CHCl₂ | C₆H₅ | 3-F | N | H |
| 280 | 4-SO₂CH₃ | 4-CN | 3-F | N | H |
| 281 | 4-SO₂CH₃ | 4-HC(NOH) | 3-F | N | H |
| 282 | 4-SO₂CH₃ | 4-H₂NC(O) | 3-F | N | H |
| 283 | 4-SO₂CH₃ | 4-HONC(O) | 3-F | N | H |
| 284 | 4-SO₂CH₃ | 4-HNCH₃C(O) | 3-F | N | H |
| 285 | 4-SO₂CH₃ | 4-(CH₃)₂NC(O) | 3-F | N | H |
| 286 | 4-NO₂ | 4-CN | 3-F | N | H |
| 287 | 4-CO₂CH₃ | 4-CN | 3-F | N | H |
| 288 | 4-CH₂OH | 4-CN | 3-F | N | H |
| 289 | 4-CH₂Cl | 4-CN | 3-F | N | H |
| 290 | 4-SO₂CH₃ | 3-Cl | 2-OC(O)CH₃ | N | H |
| 291 | 4-SO₂CH₃ | 3-Cl | 2-NC(O)CH₃ | O | |
| 292 | 4-SO₂CH₃ | 4-F | 2-OC(O)CH₃ | N | H |
| 293 | 4-NHC(O)CH₂Cl | C₆H₅ | 3-F | N | H |
| 294 | 4-CO₂H | 4-CN | 3-F | N | O |
| 295 | 4-C(O)NCH₃OCH₃ | 4-CN | 3-F | N | H |
| 296 | 4-SO₂CH₃ | 4-CH₃OC(O) | 2-OC(O)CH₃ | N | H |
| 297 | 4-SO₂CH₃ | 4-CH₃OC(O) | 2-NC(O)CH₃ | O | |
| 298 | 4-SO₂CHCH₂ | C₆H₅ | 3-F | N | O |
| 299 | 3-Cl | C₆H₅ | 2-CH₃ | N | O |
| 300 | 3-Cl | C₆H₅ | 3-CH₃ | N | O |
| 301 | 3-Cl | C₆H₅ | 4-CH₃ | N | O |
| 302 | 3-Cl | C₆H₅ | H | N | O |
| 303 | 3-Cl | C₆H₅ | 2-F | N | O |
| 304 | 3-Cl | C₆H₅ | 4-F | N | O |
| 305 | 4-OH | 4-CH₃OC(O) | 2-OH | N | O |
| 306 | 4-OH | 4-HO₂C | 3-F | N | O |
| 307 | 4-OH | 4-HO₂C | 2-OH | N | O |
| 308 | 4-NC(O)oxirane | C₆H₅ | 3-F | N | O |
| 309 | 4-C(O)CHCH₂ | C₆H₅ | 3-F | N | O |
| 310 | 4-C(O)CHCl₂ | 4-CNC₆H₅ | 3-F | N | O |
| 311 | 4-C(CH₂)CO₂CH₃ | C₆H₅ | 3-F | N | O |
| 312 | 4-C(CH₂)CO₂CH₃ | 4-CNC₆H₅ | 3-F | N | O |
| 313 | 4-NC(O)C₃H₅ | C₆H₅ | 3-F | N | O |
| 314 | 4-NC(O)CHCH₂ | C₆H₅ | 3-F | N | O |
| 315 | 4-NC(O)CH₂OH | C₆H₅ | 3-F | N | O |
| 316 | 4-C(O)CH₃ | 4-CNC₆H₅ | 3-F | N | O |
| 316a | 4-NC(O)CHCl₂ | 4-CNC₆H₅ | 3-F | N | O |

* 2,3-dihydro-1,4-benzodioxin

The procedures for the preparation of the pyrazole-amides was adapted from M. Bratenko, V. Chornous, M. Vovk 4-Functionally Substituted 3-Heterylpyrazoles: III. 3-Aryl (heteryl)pyrazole-4-carboxylic Acids and Their Derivatives 2001 Russian J Org Chem 37(4) 552-5, and as summarized below.

Typical Procedure:

To carboxylic acid (0.020 g, 65 umol) in about 20 ml toluene and 4 drops DMF (for solubility) was added thionyl chloride (0.024 ml, 323 umol). The reaction was refluxed for 2 h. After cooling to ambient triethylamine (0.052 ml, 646 umol) and amine (9 eqv, 581 umol) was added the reaction allowed to stir at least 30 mins. The solvent was removed by rotary evaporation and the residue purified by flash chromatography to yield the desired compounds.

Alternate procedure: Stir starting carboxylic acid overnight with EDC (1.1 eqv), HOBt (1.1 eqv), TEA (2 eqv) and aniline (1 eqv) in 1 ml DMF. Add 5 ml CH2CL2, wash 2×5 ml sat'd NaHCO3 (aq), 1×5 ml brine, dry with anhyd MgSO4, filter, dry by rotary evaporation and the residue purified by flash chromatography to yield the desired compounds.

N-Benzyl-3-(4-nitrophenyl)-1-phenyl-1H-pyrazole-4-carboxamide (94): 3:1-0:1 Hexane:EtOAc, yellow solid (0.026 g, 100%): $R_f$ (1:1 hexane:EtOAc) 0.26; ¹H-NMR (DMSO 500 MHz) 8.89 (s, 1H, pyrazole-H), 8.34 (d, 2H), 7.98 (m, 4H), 7.57 (t, 2H), 7.58 (t, 2H), 7.41 (t, 1H), 7.28 (m, 3H), 6.86 (1H, NH), 4.22 (d, 2H, CH2).

N,N-Diethyl-3-(4-nitrophenyl)-1-phenyl-1H-pyrazole-4-carboxamide (95): 3:1-0:1 hexane:EtOAc, yellow solid (33%): $R_f$(1:1 hexane:EtOAc) 0.52; ¹H-NMR (CDCl₃ 500 MHz) 8.19 (d, 2H), 8.01 (s, 1H, pyrazole-H), 7.95 (d, 2H), 7.70 (d, 2H), 7.45 (t, 2H), 7.58 (t, 2H), 7.41 (t, 1H), 3.53 (bs, 2H, CH2), 3.13 (bs, 2H, CH2), 1.19 (bs, 6H, CH₃); ESMS 365 (M+H, 100).

3-(4-Nitrophenyl)-N,1-diphenyl-1H-pyrazole-4-carboxamide (96): 1:1-0:1 Hexane:EtOAc, yellow solid (15%): $R_f$ (1:1 hexane:EtOAc) 0.93; ¹H-NMR (CDCl₃ 500 MHz) 8.44 (s, 1H, pyrazole-H), 8.26 (d, 2H), 8.01 (d, 2H), 7.72 (d, 2H), 7.45 (t, 2H), 7.39 (d, 2H), 7.34 (t, 1H), 7.28 (t, 2H), 7.09 (t, 1H); ESMS 385 (M+H, 100).

N-(Butan-2-yl)-3-(4-nitrophenyl)-1-phenyl-1H-pyrazole-4-carboxamide (97): 1:1-0:1 Hexane:EtOAc, yellow solid (42%): $R_f$(1:1 hexane:EtOAc) 0.74; ¹H-NMR (CDCl₃ 500 MHz) 8.28 (s, 1H, pyrazole-H), 8.26 (d, 2H), 7.97 (d, 2H), 7.68 (d, 2H), 7.43 (t, 2H), 7.31 (d, 2H), 5.36 (bd, 1H, NH), 4.02 (m, 1H), 1.41 (m, 2H), 1.08 (d, 3H), 0.84 (t, 3H); ESMS 365 (M+H, 100).

3-(4-Nitrophenyl)-1-phenyl-N-(propan-2-yl)-1H-pyrazole-4-carboxamide (98): 1:1-0:1 Hexane:EtOAc, yellow solid (42%): $R_f$(1:1 hexane:EtOAc) 0.17; ¹H-NMR (CDCl₃ 500 MHz) 8.26 (s, 1H, pyrazole-H), 8.25 (d, 2H), 7.97 (d, 2H), 7.69 (d, 2H), 7.44 (t, 2H), 7.33 (d, 2H), 5.38 (bd, 1H, NH), 4.19 (m, 1H), 1.10 (d, 6H); ESMS 351 (M+H, 100).

3-(4-Nitrophenyl)-1-phenyl-N-propyl-1H-pyrazole-4-carboxamide (99): 1:1-0:1 Hexane:EtOAc, yellow solid (75%): $R_f$(1:1 hexane:EtOAc) 0.55; ¹H-NMR (CDCl₃ 500 MHz) 8.30 (s, 1H, pyrazole-H), 8.25 (d, 2H), 7.97 (d, 2H), 7.68 (d, 2H), 7.44 (t, 2H), 7.32 (d, 2H), 5.60 (bt, 1H, NH), 3.29 (m, 2H), 1.48 (m, 2H), 0.85 (t, 3H); ESMS 365 (M+H, 100).

N-Ethyl-N-methyl-3-(4-nitrophenyl)-1-phenyl-1H-pyrazole-4-carboxamide (100): 1:1-0:1 Hexane:EtOAc, yellow solid (25%): $R_f$(1:1 hexane:EtOAc) 0.35; ¹H-NMR (CDCl₃ 500 MHz) mixture of rotomers 8.30 (d, 2H), 8.15 and 8.11 (s, 1H, pyrazole-H), 8.03 (d, 2H), 7.80 (d, 2H), 7.54 (t, 2H), 7.41 (t, 1H), 3.64 and 3.26 (bt, CH2), 3.10 and 2.82 (s, 3H, CH₃), 1.28 (bt, 3H); ESMS 351 (M+H, 100).

N-tert-Butyl-3-(4-nitrophenyl)-1-phenyl-1H-pyrazole-4-carboxamide (101): 1:1-0:1 Hexane:EtOAc, yellow solid (55%): R$_f$ (1:1 hexane:EtOAc) 0.84; $^1$H-NMR (CDCl$_3$ 500 MHz) 8.25 (m, 3H), 7.96 (d, 2H), 7.68 (d, 2H), 7.44 (t, 2H), 7.31 (t, 1H), 5.42 (s, NH), 1.32 (s, 9H); ESMS 365 (M+H, 100).

N-(2-Methoxyphenyl)-3-(4-nitrophenyl)-1-phenyl-1H-pyrazole-4-carboxylate (102): 1:1-0:1 Hexane:EtOAc, yellow solid (77%): R$_f$ (1:1hexane:EtOAc) 0.88; $^1$H-NMR (CDCl$_3$ 500 MHz) 8.70 (s, 1H, pyrazole-H), 8.18 (m, 4H), 7.77 (d, 2H), 7.49 (t, 2H), 7.36 (t, 1H), 7.18 (m, 1H), 7.06 (m, 1H), 6.95 (m, 2H), 3.78 (s, 3H); ESMS 416 (M+H, 100).

N-(3-Methoxyphenyl)-3-(4-nitrophenyl)-1-phenyl-1H-pyrazole-4-carboxamide (103): 3:1-0:1 Hexane:EtOAc, red solid (56%): R$_f$ (3:1 hexane:EtOAc) 0.16; $^1$H-NMR (CDCl$_3$ 500 MHz) 8.51 (s, 1H, pyrazole-H), 8.36 (d, 2H), 8.10 (d, 2H), 7.81 (d, 2H), 7.56 (t, 2H), 7.37 (t, 1H), 7.29 (t, 1H), 7.09 (t, 1H), 6.88 (d, 1H), 6.73 (m, 1H), 3.80 (s, 3H).

N-(4-Methoxyphenyl)-3-(4-nitrophenyl)-1-phenyl-1H-pyrazole-4-carboxamide (104): 3:1-0:1 Hexane:EtOAc, orange solid (89%): R$_f$ (3:1 hexane:EtOAc) 0.19; $^1$H-NMR (CDCl$_3$ 500 MHz) 8.55 (s, 1H, pyrazole-H), 8.36 (d, 2H), 8.11 (d, 2H), 7.81 (d, 2H), 7.55 (t, 2H), 7.45 (m, 3H), 6.87 (bt, 2H), 6.73 (m, 1H), 3.80 (s, 3H).

N-(2-Fluorophenyl)-3-(4-nitrophenyl)-1-phenyl-1H-pyrazole-4-carboxamide (105): 3:1-0:1 Hexane:EtOAc, red solid (56%): R$_f$ (3:1 hexane:EtOAc) 0.44; $^1$H-NMR (CDCl$_3$ 500 MHz) 8.56 (s, 1H, pyrazole-H), 8.38 (d, 2H), 8.07 (d, 2H), 7.80 (d, 2H), 7.64 (bs, 1H), 7.55 (t, 2H), 7.46 (t, 1H), 7.20 (m, 1H), 7.08 (m, 2H).

N-(3-fluorophenyl)-3-(4-nitrophenyl)-1-phenyl-1H-pyrazole-4-carboxamide (106): 3:1-0:1 Hexane:EtOAc, yellow solid (33%): R$_f$ (3:1 hexane:EtOAc) 0.31; $^1$H-NMR (CDCl$_3$ 500 MHz) 8.54 (s, 1H, pyrazole-H), 8.38 (d, 2H), 8.09 (d, 2H), 7.81 (d, 2H), 7.55 (m, 3H), 7.45 (t, 1H), 7.31 (t, 1H), 7.02 (d, 1H), 6.88 (t, 1H).

N-(4-Fluorophenyl)-3-(4-nitrophenyl)-1-phenyl-1H-pyrazole-4-carboxamide (107): 3:1-0:1 Hexane:EtOAc, yellow solid (66%): R$_f$ (3:1 hexane:EtOAc) 0.25; $^1$H-NMR (CDCl$_3$ 500 MHz) 8.54 (s, 1H, pyrazole-H), 8.38 (d, 2H), 8.09 (d, 2H), 7.81 (d, 2H), 7.55 (t, 2H), 7.44 (t, 2H), 7.38 (t, 1H), 7.07 (t, 2H).

N-(2-Chlorophenyl)-3-(4-nitrophenyl)-1-phenyl-1H-pyrazole-4-carboxamide (108): 3:1-0:1 Hexane:EtOAc, yellow solid (30%): R$_f$ (3:1 hexane:EtOAc) 0.25; $^1$H-NMR (CDCl$_3$ 500 MHz) 8.56 (s, 1H, pyrazole-H), 8.37 (d, 2H), 8.06 (d, 2H), 7.81 (d, 2H), 7.55 (m, 3H), 7.44 (t, 1H), 7.36 (t, 2H), 7.09 (t, 1H).

N-(3-Chlorophenyl)-3-(4-nitrophenyl)-1-phenyl-1H-pyrazole-4-carboxamide (109): 3:1-0:1 Hexane:EtOAc, light red solid (50%): R$_f$ (3:1 hexane:EtOAc) 0.25; $^1$H-NMR (CDCl$_3$ 500 MHz) 8.48 (s, 1H, pyrazole-H), 8.28 (d, 2H), 7.99 (d, 2H), 7.72 (d, 2H), 7.60 (bs, 0.5H), 7.47 (t, 2H), 7.41 (bs, 0.5H), 7.35 (t, 2H), 7.18 (m, 2H), 7.06 (m, 1H).

N-(4-Chlorophenyl)-3-(4-nitrophenyl)-1-phenyl-1H-pyrazole-4-carboxamide (110): 3:1-0:1 Hexane:EtOAc, tan solid (80%): R$_f$ (3:1 hexane:EtOAc) 0.27; $^1$H-NMR (CDCl$_3$ 500 MHz) 8.53 (s, 1H, pyrazole-H), 8.38 (d, 2H), 8.09 (d, 2H), 7.81 (d, 2H), 7.57 (t, 2H), 7.45 (m, 3H), 7.35 (m, 3H).

N-(2-Cyanophenyl)-3-(4-nitrophenyl)-1-phenyl-1H-pyrazole-4-carboxamide (111): 1:1-0:1 Hexane:EtOAc, tan solid (55%): R$_f$ (1:1 hexane:EtOAc) 0.21; $^1$H-NMR (CDCl$_3$ 500 MHz) 8.31 (d, 2H), 8.15 (s, 1H, pyrazole-H), 8.00 (d, 2H), 7.78 (d, 2H), 7.64 (bs, 1H), 7.62 (dt, 1H), 7.54 (t, 2H), 7.45 (m, 2H), 7.43 (t, 1H), 7.08 (bs, NH).

N-(3-Cyanophenyl)-3-(4-nitrophenyl)-1-phenyl-1H-pyrazole-4-carboxamide (112): 1:1-0:1 Hexane:EtOAc, yellow solid (45%): R$_f$ (1:1 hexane:EtOAc) 0.21; $^1$H-NMR (CDCl$_3$ 500 MHz) 8.31 (d, 2H), 8.15 (s, 1H, pyrazole-H), 8.00 (d, 2H), 7.78 (d, 2H), 7.64 (d, 1H), 7.54 (d, 2H), 7.43 (m, 3H).

N-(2-Acetylphenyl)-3-(4-nitrophenyl)-1-phenyl-1H-pyrazole-4-carboxamide (113): 5:1-3:1 Hexane:EtOAc, yellow solid (17%): R$_f$ (1:1 hexane:EtOAc) 0.72; $^1$H-NMR (CDCl$_3$ 500 MHz) 8.87 (d, 2H), 8.60 (s, 1H, pyrazole-H), 8.35 (d, 2H), 8.15 (d, 2H), 7.97 (d, 1H), 7.87 (d, 1H), 7.64 (t, 1H), 7.58 (t, 2H), 7.45 (t, 1H), 7.20 (t, 1H), 2.67 (s, 3H).

N-(3-Acetylphenyl)-3-(4-nitrophenyl)-1-phenyl-1H-pyrazole-4-carboxamide (114): 7:1-0:1 Hexane:EtOAc, orange solid (67%): R$_f$ (1:1 hexane:EtOAc) 0.40; $^1$H-NMR (CDCl$_3$ 500 MHz) 8.55 (s, 1H, pyrazole-H), 8.34 (d, 2H), 8.10 (d, 2H), 8.03 (s, 1H), 7.79 (m, 3H), 7.54 (t, 2H), 7.46 (t, 1H), 7.44 (t, 1H), 7.35 (d, 1H).

N-(4-Acetylphenyl)-3-(4-nitrophenyl)-1-phenyl-1H-pyrazole-4-carboxamide (115): 2:1-0:1 Hexane:EtOAc, orange solid (17%): R$_f$ (1:1 hexane:EtOAc) 0.86; $^1$H-NMR (CDCl$_3$ 500 MHz) 8.57 (s, 1H, pyrazole-H), 8.39 (d, 2H), 8.09 (d, 2H), 7.99 (m, 4H), 7.83 (d, 2H), 7.58 (t, 2H), 7.58 (t, 2H), 7.46 (t, 1H).

N-[2-(Methylamino)phenyl]-3-(4-nitrophenyl)-1-phenyl-1H-pyrazole-4-carboxamide (116): 4:1-0:1 Hexane:EtOAc, orange solid (16%): R$_f$ (1:1 hexane:EtOAc) 0.38; $^1$H-NMR (CDCl$_3$ 500 MHz) 8.32 (d, 2H), 8.03 (d, 2H), 7.63 (s, 1H, pyrazole-H), 7.48 (t, 2H), 7.45 (t, 2H), 7.34 (t, 1H), 7.14 (t, 1H), 6.90 (d, 1H), 6.77 (d, 1H), 6.70 (t, 1H), 3.40 (s, 3H).

N-(2-Methoxyphenyl)-N-methyl-3-(4-nitrophenyl)-1-phenyl-1H-pyrazole-4-carboxamide (117): 8:1-6:1 Hexane:EtOAc, yellow solid (7%): R$_f$ (3:1 hexane:EtOAc) 0.50; $^1$H-NMR (CDCl$_3$ 500 MHz, mixture of amide rotomers) 8.95 (s, 1H), 8.41 (d, 2H), 7.86 (m, 4H), 7.56 (t, 2H), 7.45 (t, 2H), 7.24 (1H), 6.96 (m, 3H), 3.93 and 3.40 (s, 3H), 2.94 (s, 3H).

N-(2,3-Dihydro-1,4-benzodioxin-6-yl)-3-(4-nitrophenyl)-1-phenyl-1H-pyrazole-4-carboxamide (118): 3:1-0:1 Hexane:EtOAc, light yellow solid (20%): R$_f$ (1:1 hexane:EtOAc) 0.38; $^1$H-NMR (CDCl$_3$ 500 MHz) 8.31 (d, 2H), 8.16 (s, 1H), 8.01 (d, 2H), 7.78 (d, 2H), 7.53 (t, 2H), 7.42 (t, 2H), 7.17 (m, 1H), 6.86 (t, 1H), 6.71 (d, 1H), 3.93 and 4.30 (m, 4H, OCH2).

N-(2,3-Difluorophenyl)-3-(4-nitrophenyl)-1-phenyl-1H-pyrazole-4-carboxamide (119): 3:1-0:1 Hexane:EtOAc, light yellow solid (22%): R$_f$ (3:1 hexane:EtOAc) 0.39; $^1$H-NMR (CDCl$_3$ 300 MHz) 8.56 (s, 1H), 8.39 (d, 2H), 8.06 (d, 2H), 7.81 (d, 2H), 7.58 (m, 2H), 7.46 (m, 1H), 7.13 (m, 2H), 6.95 (m, 1H).

N-(2,5-Difluorophenyl)-3-(4-nitrophenyl)-1-phenyl-1H-pyrazole-4-carboxamide (120): 3:1-0:1 Hexane:EtOAc, light yellow solid (33%): R$_f$ (3:1 hexane:EtOAc) 0.42; $^1$H-NMR (CDCl$_3$ 300 MHz) 8.48 (s, 1H), 8.30 (d, 2H), 8.19 (m, 1H), 7.96 (d, 2H), 7.72 (d, 2H), 7.54 (bt, 1H, NH), 7.48 (t, 2H), 7.36 (t, 1H), 6.94 (m, 1H), 6.70 (m, 1H).

N-(3,4-Difluorophenyl)-3-(4-nitrophenyl)-1-phenyl-1H-pyrazole-4-carboxamide (121): 3:1-0:1 Hexane:EtOAc, light yellow solid (56%): R$_f$ (3:1 hexane:EtOAc) 0.28; $^1$H-NMR (CDCl$_3$ 300 MHz) 8.53 (s, 1H), 8.40 (d, 2H), 8.08 (d, 2H), 7.82 (d, 2H), 7.66 (m, 1H), 7.57 (t, 2H), 7.45 (t, 1H), 7.33 (bs, 1H, NH), 7.13 (m, 1H), 6.93 (m, 1H).

N-(3,5-Difluorophenyl)-3-(4-nitrophenyl)-1-phenyl-1H-pyrazole-4-carboxamide (122): 3:1-0:1 Hexane:EtOAc, light yellow solid (44%): R$_f$ (3:1 hexane:EtOAc) 0.40; $^1$H-NMR (CDCl$_3$ 300 MHz) 8.52 (s, 1H), 8.40 (d, 2H), 8.09 (m, 1H), 7.80 (d, 2H), 7.55 (m, 2H), 7.43 (t, 3H), 7.01 (m, 1H).

N-(2-Methoxyphenyl)-1-methyl-3-(4-nitrophenyl)-1H-pyrazole-4-carboxamide (123): 5:1-0:1 Hexane:EtOAc, light yellow solid (44%): R*f* (EtOAc) 0.62; ¹H-NMR (CDCl₃ 300 MHz) 8.44 (dd, 1H), 8.32 (d, 2H), 7.97 (m, 3H), 7.02 (m, 2H), 6.81 (d, 1H), 4.04 (s, 3H, NCH₃), 3.63 (s, 3H, OCH₃).

N-(3-Fluorophenyl)-1-methyl-3-(4-nitrophenyl)-1H-pyrazole-4-carboxamide (124): 3:1-0:1 Hexane:EtOAc, white solid (39%): R*f* (EtOAc) 0.57; ¹H-NMR (CDCl₃ 300 MHz) 8.34 (1H), 7.98 (m, 3H), 7.47 (m, 1H), 7.38 (m, 2H), 6.96 (m, 1H), 6.85 (m, 1H), 4.04 (s, 3H).

N-(2-Methylphenyl)-3-(4-nitrophenyl)-1-phenyl-1H-pyrazole-4-carboxamide (125): 3:1-0:1 Hexane:EtOAc, tan solid (50%): R*f* (3:1 hexane:EtOAc) 0.36; ¹H-NMR (CDCl₃ 500 MHz) 8.43 (s, 1H), 8.26 (d, 2H), 8.00 (d, 2H), 7.71 (d, 2H), 7.44 (t, 2H), 7.34 (t, 1H), 7.05 (m, 4H), 1.92 (s, 3H, CH₃).

N-(3-Methylphenyl)-3-(4-nitrophenyl)-1-phenyl-1H-pyrazole-4-carboxamide (126): 3:1-0:1 Hexane:EtOAc, tan solid (25%): R*f* (3:1 hexane:EtOAc) 0.33; ¹H-NMR (CDCl₃ 500 MHz) 8.51 (s, 1H), 8.36 (d, 2H), 8.11 (d, 2H), 7.82 (d, 2H), 7.56 (t, 2H), 7.43 (t, 1H), 7.36 (bs, 2H), 7.22 (m, 1H), 6.99 (d, 1H), 2.43 (s, 3H, CH₃).

N-(4-methylphenyl)-3-(4-nitrophenyl)-1-phenyl-1H-pyrazole-4-carboxamide (127): 3:1-0:1 Hexane:EtOAc, tan solid (25%): R*f* (3:1 hexane:EtOAc) 0.34; ¹H-NMR (CDCl₃ 500 MHz) 8.50 (s, 1H), 8.36 (d, 2H), 8.10 (d, 2H), 7.80 (d, 2H), 7.55 (t, 2H), 7.46 (t, 1H), 7.34 (m, 3H), 7.17 (d, 1H), 2.35 (s, 3H, CH₃).

3-(4-Fluorophenyl)-N-(2-methoxyphenyl)-1-phenyl-1H-pyrazole-4-carboxamide (128): 3:1-0:1 Hexane:EtOAc, white solid (92%): R*f* (3:1 hexane:EtOAc) 0.33; ¹H-NMR (CDCl₃ 300 MHz) 8.62 (s, 1H), 7.77 (m, 4H), 7.52 (t, 2H), 7.36 (t, 1H), 7.24 (t, 2H), 7.01 (m, 2H), 6.80 (m, 2H). 3.59 (s, 3H).

N-(3-Fluorophenyl)-3-(4-fluorophenyl)-1-phenyl-1H-pyrazole-4-carboxamide (129): 3:1-0:1 Hexane:EtOAc, white solid (83%): R*f* (3:1 hexane:EtOAc) 0.43; ¹H-NMR (CDCl₃ 300 MHz) 8.60 (s, 1H), 7.77 (m, 4H), 7.45 (m, 5H), 7.25 (m, 3H), 7.08 (m, 1H), 6.87 (m, 2H).

N-(3,4-Difluorophenyl)-3-(4-fluorophenyl)-1-phenyl-1H-pyrazole-4-carboxamide (130): 3:1-0:1 Hexane:EtOAc, white solid (83%): R*f* (3:1 hexane:EtOAc) 0.43; ¹H-NMR (CDCl₃ 300 MHz) 8.60 (s, 1H), 7.77 (m, 4H), 7.55 (m, 3H), 7.41 (t, 1H), 7.38 (m, 3H), 7.08 (m, 1H), 6.78 (m, 1H).

3-(4-Fluorophenyl)-N-(4-methylphenyl)-1-phenyl-1H-pyrazole-4-carboxamide (131): 3:1-0:1 Hexane:EtOAc, white solid (25%): R*f* (3:1 hexane:EtOAc) 0.50; ¹H-NMR (CDCl₃ 300 MHz) 8.58 (s, 1H), 7.78 (m, 3H), 7.53 (t, 2H), 7.42 (t, 1H), 7.27 (m, 6H), 7.13 (d, 2H), 2.32 (s, 3H, CH₃).

3-(4-Chlorophenyl)-N-(2-methoxyphenyl)-1-phenyl-1H-pyrazole-4-carboxamide (132): 6:1-3:1 Hexane:EtOAc, white solid (90%): R*f* (3:1 hexane:EtOAc) 0.34; ¹H-NMR (CDCl₃ 500 MHz) 8.51 (s, 1H), 7.70 (d, 2H), 7.63 (d, 2H), 7.42 (m, 3H), 7.29 (t, 1H), 6.95 (m, 1H), 6.89 (m, 1H), 6.71 (m, 1H), 3.50 (s, 3H).

3-(4-Chlorophenyl)-N-(3-fluorophenyl)-1-phenyl-1H-pyrazole-4-carboxamide (133): 6:1-3:1 Hexane:EtOAc, white solid (40%): R*f* (3:1 hexane:EtOAc) 0.29; ¹H-NMR (CDCl₃ 500 MHz) 8.60 (s, 1H), 7.80 (d, 2H), 7.76 (d, 2H), 7.48 (dt, 1H), 7.46 (m, 2H), 7.27 (t, 1H), 6.88 (m, 1H), 6.84 (dt, 1H).

3-(4-Chlorophenyl)-N-(3,4-difluorophenyl)-1-phenyl-1H-pyrazole-4-carboxamide (134): 6:1-3:1 Hexane:EtOAc, white solid (67%): R*f* (3:1 hexane:EtOAc) 0.45; ¹H-NMR (CDCl₃ 500 MHz) 8.59 (s, 1H), 7.79 (d, 2H), 7.74 (d, 2H), 7.57 (m, 5H), 7.43 (t, 1H), 7.34 (bs, 1H), 7.10 (m, 1H), 6.82 (m, 1H).

3-(4-Chlorophenyl)-N-(4-methylphenyl)-1-phenyl-1H-pyrazole-4-carboxamide (135): 6:1-3:1 Hexane:EtOAc, white solid (44%): R*f* (3:1 hexane:EtOAc) 0.37; ¹H-NMR (CDCl₃ 500 MHz) 8.57 (s, 1H), 7.78 (m, 4H), 7.52 (m, 4H), 7.41 (t, 1H), 7.27 (2H), 7.15 (d, 2H), 2.34 (s, 3H).

N-(2-Methoxyphenyl)-1,3-diphenyl-1H-pyrazole-4-carboxamide (136): 6:1-3:1 Hexane:EtOAc, white solid (55%): R*f* (3:1 hexane:EtOAc) 0.39; ¹H-NMR (CDCl₃ 500 MHz) 8.65 (s, 1H), 8.54 (d, 1H), 8.17 (bs, 1H), 7.81 (m, 4H), 7.55 (m, 4H), 7.39 (t, 1H), 7.00 (m, 2H), 6.79 (d, 1H), 3.51 (s, 3H).

N-(3-Fluorophenyl)-1,3-diphenyl-1H-pyrazole-4-carboxamide (137): 6:1-3:1 Hexane:EtOAc, white solid (73%): R*f* (3:1 hexane:EtOAc) 0.30; ¹H-NMR (CDCl₃ 500 MHz) 8.65 (s, 1H), 7.82 (m, 2H), 7.76 (m, 2H), 7.62 (m, 2H), 7.52 (t, 2H), 7.49 (bs, 1H), 7.38 (m, 2H), 6.81 (m, 1H).

N-(3,4-Difluorophenyl)-1,3-diphenyl-1H-pyrazole-4-carboxamide (138): 6:1-3:1 Hexane:EtOAc, white solid (64%): R*f* (3:1 hexane:EtOAc) 0.33; ¹H-NMR (CDCl₃ 500 MHz) 8.64 (s, 1H), 7.81 (m, 2H), 7.76 (m, 2H), 7.62 (m, 2H), 7.54 (m, 3H), 7.42 (m, 2H), 7.05 (m, 1H), 6.75 (m, 1H).

N-(4-Methylphenyl)-1,3-diphenyl-1H-pyrazole-4-carboxamide (139): 6:1-3:1 Hexane:EtOAc, white solid (82%): R*f* (3:1 hexane:EtOAc) 0.33; ¹H-NMR (CDCl₃ 500 MHz) 8.63 (s, 1H), 7.81 (m, 4H), 7.59 (m, 3H), 7.53 (m, 2H), 7.41 (m, 2H), 7.22 (d, 2H), 7.10 (d, 2H), 7.00 (d, 0.5H), 6.67 (d, 0.5H), 2.32 (s, 3H).

N-(2-Methoxyphenyl)-3-(4-methylphenyl)-1-phenyl-1H-pyrazole-4-carboxamide (140): 6:1-3:1 Hexane:EtOAc, white solid (57%): R*f* (3:1 hexane:EtOAc) 0.45; ¹H-NMR (CDCl₃ 300 MHz) 8.64 (s, 1H), 8.53 (dd, 1H), 8.20 (bs, 1H), 7.80 (m, 2H) 7.64 (m, 2H), 7.51 (m, 2H), 7.38 (m, 3H), 7.00 (m, 2H), 6.77 (m, 1H), 3.52 (s, 3H), 2.49 (s, 3H).

N-(3-Fluorophenyl)-3-(4-methylphenyl)-1-phenyl-1H-pyrazole-4-carboxamide (141): 6:1-3:1 Hexane:EtOAc, white solid (71%): R*f* (3:1 hexane:EtOAc) 0.52; ¹H-NMR (CDCl₃ 300 MHz) 8.64 (s, 1H), 7.81 (m, 2H) 7.63 (m, 2H), 7.52 (m, 3H), 7.42 (m, 4H), 7.26 (m, 1H), 6.85 (m, 1H), 2.51 (s, 3H).

N-(2-Methoxyphenyl)-3-(4-methoxyphenyl)-1-phenyl-1H-pyrazole-4-carboxamide (142): 6:1-3:1 Hexane:EtOAc, white solid (57%): R*f* (3:1 hexane:EtOAc) 0.31; ¹H-NMR (CDCl₃ 500 MHz) 8.63 (s, 1H), 8.55 (dd, 1H), 8.21 (bs, 1H), 7.80 (m, 2H) 7.68 (m, 2H), 7.52 (m, 2H), 7.39 (m, 1H), 7.09 (m, 2H), 7.01 (m, 2H), 6.78 (m, 1H), 3.92 (s, 3H), 3.55 (s, 3H).

N-(3-Fluorophenyl)-3-(4-methoxyphenyl)-1-phenyl-1H-pyrazole-4-carboxamide (143): 6:1-3:1 Hexane:EtOAc, white solid (14%): R*f* (3:1 hexane:EtOAc) 0.32; ¹H-NMR (CDCl₃ 500 MHz) 8.64 (s, 1H), 7.81 (d, 2H) 7.70 (d, 2H), 7.53 (m, 3H), 7.40 (m, 2H), 7.23 (m, 1H), 7.12 (d, 2H), 6.86 (d, 1H), 6.80 (t, 1H), 3.95 (s, 3H).

N-(2-Methoxyphenyl)-3-(3-methoxyphenyl)-1-phenyl-1H-pyrazole-4-carboxamide (144): 6:1-3:1 Hexane:EtOAc, white solid (29%): R*f* (3:1 hexane:EtOAc) 0.33; ¹H-NMR (CDCl₃ 500 MHz) 8.65 (s, 1H), 8.56 (bd, 1H), 8.15 (bs, 1H), 7.81 (d, 2H) 7.62 (d, 1H), 7.51 (m, 3H), 7.37 (m, 1H), 7.19 (t, 1H), 7.06 (d, 1H), 6.99 (m, 2H), 6.77 (d, 1H), 3.75 (s, 3H), 3.53 (s, 3H).

N-(3-Fluorophenyl)-3-(3-methoxyphenyl)-1-phenyl-1H-pyrazole-4-carboxamide (145): 6:1-3:1 Hexane:EtOAc, white solid (14%): R*f* (3:1 hexane:EtOAc) 0.27; ¹H-NMR (CDCl₃ 500 MHz) 8.64 (s, 1H), 7.80 (m, 3H) 7.60 (m, 2H), 7.52 (t, 2H), 7.36 (t, 1H), 7.33 (d, 1H), 7.22 (m, 2H), 7.14 (d, 1H), 6.80 (m, 2H), 3.83 (s, 3H).

N-(2-Methoxyphenyl)-3-(2-methoxyphenyl)-1-phenyl-1H-pyrazole-4-carboxamide (146): 6:1-3:1 Hexane:EtOAc, white solid (100%): $R_f$ (3:1 hexane:EtOAc) 0.52; $^1$H-NMR (CDCl$_3$ 300 MHz) 8.72 (s, 1H), 8.51 (bd, 1H), 7.98 (bs, 1H), 7.80 (d, 2H) 7.51 (m, 5H), 7.39 (m, 3H), 6.92 (m, 3H), 4.98 (s, 3H), 2.31 (s, 3H).

N-(3-Fluorophenyl)-3-(2-methoxyphenyl)-1-phenyl-1H-pyrazole-4-carboxamide (147): 6:1-3:1 Hexane:EtOAc, white solid (14%): $R_f$ (3:1 hexane:EtOAc) 0.60; $^1$H-NMR (CDCl$_3$ 300 MHz) 8.63 (s, 1H), 7.72 (d, 2H) 7.44 (m, 6H), 7.33 (t, 1H), 7.16 (dt, 1H), 7.03 (m, 1H), 6.68 (m, 1H), 6.51 (m, 1H), 2.23 (s, 3H).

N-(2-Methoxyphenyl)-3-(2-methylphenyl)-1-phenyl-1H-pyrazole-4-carboxamide (148): 6:1-3:1 Hexane:EtOAc, white solid (38%): $R_f$ (3:1 hexane:EtOAc) 0.24; $^1$H-NMR (CDCl$_3$ 300 MHz) 8.65 (s, 1H), 8.56 (bd, 1H), 8.21 (bs, 1H), 7.81 (d, 2H) 7.52 (m, 5H), 7.44 (t, 2H), 7.40 (m, 2H), 7.01 (m, 2H), 6.79 (d, 1H), 3.52 (s, 3H), 2.46 (s, 3H).

N-(3-Fluorophenyl)-3-(2-methylphenyl)-1-phenyl-1H-pyrazole-4-carboxamide (149): 6:1-3:1 Hexane:EtOAc, white solid (13%): $R_f$ (3:1 hexane:EtOAc) 0.37; $^1$H-NMR (CDCl$_3$ 300 MHz) 8.66 (s, 1H), 7.81 (d, 2H) 7.51 (m, 8H), 7.40 (t, 1H), 7.35 (m, 1H), 7.25 (m, 1H), 6.82 (m, 2H), 2.49 (s, 3H).

3-(4-Nitrophenyl)-1-phenyl-N-[2-(trifluoromethyl)phenyl]-1H-pyrazole-4-carboxamide (150): 6:1-3:1 Hexane:EtOAc, white solid (13%): $R_f$ (3:1 hexane:EtOAc) 0.29; $^1$H-NMR (CDCl$_3$ 300 MHz) 8.49 (s, 1H), 8.35 (d, 2H) 8.08 (d, 2H), 7.81 (d, 2H), 7.70-7.45 (m, 7H).

3-(4-Nitrophenyl)-1-phenyl-N-[3-(trifluoromethyl)phenyl]-1H-pyrazole-4-carboxamide (151): 6:1-3:1 Hexane:EtOAc, white solid (88%): $R_f$ (3:1 hexane:EtOAc) 0.25; $^1$H-NMR (CDCl$_3$ 300 MHz) 8.44 (s, 1H), 8.29 (d, 2H) 8.00 (d, 2H), 7.77 (s, 1H), 7.71 (d, 2H), 7.50-7.36 (m, 6H).

3-(4-Nitrophenyl)-1-phenyl-N-[4-(trifluoromethyl)phenyl]-1H-pyrazole-4-carboxamide (152): 6:1-3:1 hexane:EtOAc, white solid (50%): $R_f$ (3:1 hexane:EtOAc) 0.22; $^1$H-NMR (CDCl$_3$ 300 MHz) 8.46 (s, 1H), 8.29 (d, 2H) 8.00 (d, 2H), 7.71 (d, 2H), 7.52-7.36 (m, 7H).

3-(3-Chlorophenyl)-N-(2-methoxyphenyl)-1-phenyl-1H-pyrazole-4-carboxamide (153): 6:1-4:1 Hexane:EtOAc, white solid (40%): $R_f$ (3:1 hexane:EtOAc) 0.44; $^1$H-NMR (CDCl$_3$ 300 MHz) 8.52 (s, 1H), 8.43 (dd, 1H) 8.00 (bs, 1H), 7.70 (m, 3H), 7.56 (dt, 1H), 7.46-7.28 (m, 5H), 6.94 (m, 2H), 6.70 (dd, 1H), 3.51 (s, 3H).

3-(3-Chlorophenyl)-N-(3-fluorophenyl)-1-phenyl-1H-pyrazole-4-carboxamide (154): 6:1-4:1 hexane:EtOAc, white solid (100%): $R_f$ (3:1 hexane:EtOAc) 0.40; $^1$H-NMR (CDCl$_3$ 300 MHz) 8.52 (s, 1H), 7.71 (m, 2H), 7.57 (m, 1H), 7.45 (m, 3H), 7.35 (m, 3H), 7.15 (m, 1H), 6.82 (m, 1H), 6.77 (m, 1H).

3-(2-Methylphenyl)-N-(2-methoxyphenyl)-1-phenyl-1H-pyrazole-4-carboxamide (155): 6:1-3:1 hexane:EtOAc, white solid (71%): $R_f$ (3:1 hexane:EtOAc) 0.37; $^1$H-NMR (CDCl$_3$ 300 MHz) 8.63 (s, 1H), 8.42 (dd, 1H) 7.89 (bs, 1H), 7.72 (d, 2H), 7.42 (m, 4H), 7.31 (m, 3H), 6.88 (m, 2H), 6.64 (dd, 1H), 3.40 (s, 3H), 2.23 (s, 3H).

3-(2-Methylphenyl)-N-(3-fluorophenyl)-1-phenyl-1H-pyrazole-4-carboxamide (156): 6:1-3:1 hexane:EtOAc, white solid (100%): $R_f$ (3:1 hexane:EtOAc) 0.61; $^1$H-NMR (CDCl$_3$ 300 MHz) 8.72 (s, 1H), 7.83 (d, 2H), 7.53 (m, 7H), 7.40 (m, 1H), 7.20 (m, 2H), 6.75 (dt, 1H), 6.61 (d, 1H), 6.53 (m, 1H), 2.33 (s, 3H).

3-(4-Trifluoromethylphenyl)-N-(2-methoxyphenyl)-1-phenyl-1H-pyrazole-4-carboxamide (157): 6:1-3:1 hexane:EtOAc, white solid (100%): $R_f$ (3:1 hexane:EtOAc) 0.48; $^1$H-NMR (CDCl$_3$ 300 MHz) 8.52 (s, 1H), 8.43 (dd, 1H), 7.94 (bs, 1H), 7.85 (d, 2H), 7.70 (m, 4H), 7.44 (t, 2H), 7.32 (m, 1H), 6.94 (m, 2H), 6.71 (dd, 1H), 3.45 (s, 3H).

3-(4-Trifluoromethylphenyl)-N-(3-fluorophenyl)-1-phenyl-1H-pyrazole-4-carboxamide (158): 6:1-3:1 hexane:EtOAc, white solid (100%): $R_f$ (3:1 hexane:EtOAc) 0.36; $^1$H-NMR (CDCl$_3$ 300 MHz) 8.57 (s, 1H), 7.96 (d, 2H), 7.80 (m, 4H), 7.53 (m, 3H), 7.45 (t, 1H), 7.42 (m, 2H), 7.25 (m, 1H), 6.82 (m, 2H).

3-(3,4-Difluorophenyl)-N-(2-methoxyphenyl)-1-phenyl-1H-pyrazole-4-carboxamide (159): 6:1-3:1 hexane:EtOAc, off-white solid (50%): $R_f$ (3:1 hexane:EtOAc) 0.44; $^1$H-NMR (CDCl$_3$ 300 MHz) 8.48 (s, 1H), 8.41 (d, 1H), 7.97 (s, 1H), 7.69 (d, 2H), 7.58 (m, 1H), 7.44 (m, 4H), 7.29-7.22 (m, 2H), 6.94 (m, 1H), 6.75 (d, 1H), 3.58 (s, 3H).

3-(3,4-Difluorophenyl)-N-(3-fluorophenyl)-1-phenyl-1H-pyrazole-4-carboxamide (160): 6:1-3:1 hexane:EtOAc, off-white solid (33%): $R_f$ (3:1 hexane:EtOAc) 0.41; $^1$H-NMR (CDCl$_3$ 300 MHz) 8.55 (s, 1H), 7.78 (d, 2H), 7.71 (m, 1H), 7.54 (m, 4H), 7.44 (m, 2H), 7.26 (m, 1H), 6.95 (m, 1H), 6.85 (m, 1H).

3-(3-Trifluoromethylphenyl)-N-(2-methoxyphenyl)-1-phenyl-1H-pyrazole-4-carboxamide (161): 6:1-4:1 hexane:EtOAc, white solid (31%): $R_f$ (3:1 hexane:EtOAc) 0.38; $^1$H-NMR (CDCl$_3$ 300 MHz) 8.51 (s, 1H), 8.42 (dd, 1H), 8.01 (s, 1H), 7.89 (d, 2H), 7.70 (m, 4H), 7.56 (t, 2H), 7.45 (t, 2H), 7.31 (t, 1H), 6.93 (m, 2H), 6.70 (m, 1H), 3.44 (s, 3H).

3-(3-Trifluoromethylphenyl)-N-(3-fluorophenyl)-1-phenyl-1H-pyrazole-4-carboxamide (162): 6:1-4:1 hexane:EtOAc, white solid (42%): $R_f$ (3:1 hexane:EtOAc) 0.48; $^1$H-NMR (CDCl$_3$ 300 MHz) 8.60 (s, 1H), 8.12 (s, 1H), 8.00 (d, 2H), 7.80 (m, 2H), 7.67 (t, 2H), 7.55 (t, 2H), 7.40 (m, 3H), 7.24 (m, 1H), 6.84 (m, 2H).

3-(4-Cyanophenyl)-N-(3-methoxy phenyl)-1-phenyl-1H-pyrazole-4-carboxamide (163): 6:1-3:1 hexane:EtOAc, yellow solid (44%): $R_f$ (3:1 hexane:EtOAc) 0.34; $^1$H-NMR (CDCl$_3$ 300 MHz) 8.55 (s, 1H), 8.51 (m, 1H), 7.98 (m, 3H), 7.80 (m, 3H), 7.55 (m, 2H), 7.42 (t, 1H), 7.04 (m, 2H), 6.87 (m, 1H), 3.67 (s, 3H).

3-(4-Cyanophenyl)-N-(3-fluorophenyl)-1-phenyl-1H-pyrazole-4-carboxamide (164): 6:1-3:1 hexane:EtOAc, yellow solid (44%): $R_f$ (3:1 hexane:EtOAc) 0.29; $^1$H-NMR (CDCl$_3$ 300 MHz) 8.56 (s, 1H), 7.99 (m, 2H), 7.81 (m, 4H), 7.53 (m, 3H), 7.41 (m, 1H), 7.26 (m, 1H), 6.95 (m, 1H), 6.87 (m, 1H).

N-(2-Hydroxyphenyl)-3-(4-nitrophenyl)-1-phenyl-1H-pyrazole-4-carboxamide (165): 6:1-0:1 hexane:EtOAc, off-white solid (18%): $R_f$ (3:1 hexane:EtOAc) 0.25; $^1$H-NMR (CDCl$_3$ 300 MHz) 8.60 (s, 1H), 8.42 (m, 2H), 8.08 (d, 2H), 7.81 (d, 2H), 7.66 (bs, 1H), 7.57 (t, 2H), 7.45 (t, 1H), 7.15 (m, 1H), 7.02 (m, 2H), 6.91 (m, 1H).

N-(3-Hydroxyphenyl)-3-(4-nitrophenyl)-1-phenyl-1H-pyrazole-4-carboxamide (166): 6:1-0:1 hexane:EtOAc, light red solid (91%): $R_f$ (3:1 hexane:EtOAc) 0.09; $^1$H-NMR (CDCl$_3$ 300 MHz) 8.54 (s, 1H), 8.38 (d, 2H), 8.08 (d, 2H), 7.53 (m, 1H), 7.43 (m, 3H), 7.20 (m, 1H), 7.03 (m, 1H), 6.67 (m, 2H).

N-(4-Hydroxyphenyl)-3-(4-nitrophenyl)-1-phenyl-1H-pyrazole-4-carboxamide (167): 6:1-0:1 hexane:EtOAc, off-white solid (36%): $R_f$ (3:1 hexane:EtOAc) 0.10; $^1$H-NMR (CDCl$_3$ 300 MHz) 8.42 (m, 2H), 8.15 (s, 1H), 8.01 (d, 2H), 7.77 (d, 2H), 7.55 (m, 3H), 7.00 (m, 1H), 6.82 (m, 2H), 6.68 (m, 2H).

N-(3-Fluorophenyl)-1-phenyl-3-(pyridin-4-yl)-1H-pyrazole-4-carboxamide (168): 6:1-0:1 hexane:EtOAc, off-white solid (6%): $R_f$ (1:1 hexane:EtOAc) 0.55; $^1$H-NMR (DMSO 300 MHz) 8.30 (s, 1H), 7.58 (m, 3H), 7.37 (m, 4H), 7.12 (m, 1H), 7.02 (m, 2H), 6.93 (m, 1H).

Methyl 4-{4-[(3-fluorophenyl)carbamoyl]-1-phenyl-1H-pyrazol-3-yl}benzoate (169): 3:1-0:1 hexane:EtOAc, white solid (100%): $R_f$ (3:1 hexane:EtOAc) 0.52; $^1$H-NMR (CDCl$_3$ 300 MHz) 8.53 (s, 1H), 8.01 (m, 2H), 7.79 (m, 4H), 7.53 (m, 3H), 7.40 (m, 1H), 7.27 (m, 1H), 6.93 (m, 1H), 6.89 (m, 1H), 3.89 (s, 3H).

Sodium 4-{4-[(3-fluorophenyl)carbamoyl]-1-phenyl-1H-pyrazol-3-yl}benzoate (170): To the methyl ester in 1 ml THF was added 1 equivalent of sodium hydroxide dissolved in 5 ul H$_2$O. The reaction was stirred for 4.5 h whereupon TLC showed no starting material. The solvent was removed by rotary evaporation and the white residue dried in vacuum (100%): $^1$H-NMR (DMSO 300 MHz) 8.28 (s, 1H), 8.15 (m, 2H), 7.67 (m, 4H), 7.23 (m, 4H), 6.68 (m, 2H), 6.14 (m, 1H 3-Fluorophenyl 3-(4-nitrophenyl)-1-phenyl-1H-pyrazole-4-carboxylate (171): 5:1-3:1 hexane:EtOAc, white solid (100%): $R_f$ (3:1 hexane:EtOAc) 0.54; $^1$H-NMR (CDCl$_3$ 300 MHz) 8.67 (s, 1H), 8.23 (d, 2H), 8.11 (d, 2H), 7.75 (d, 2H), 7.49 (t, 2H), 7.34 (m, 2H), 6.91 (m, 3H).

N-(2-Aminophenyl)-3-(4-nitrophenyl)-1-phenyl-1H-pyrazole-4-carboxamide (172): 2:1-1:1 hexane:EtOAc, off-white solid (50%): $R_f$ (1:1 hexane:EtOAc) 0.58; $^1$H-NMR (CDCl$_3$ 300 MHz) 8.53 (bs, 1H), 8.35 (d, 2H), 8.13 (d, 2H), 7.80 (d, 2H), 7.58 (t, 2H), 7.43 (t, 1H), 7.27 (s, 1H), 7.19 (m, 1H), 6.86 (m, 2H).

N-(3-Aminophenyl)-3-(4-nitrophenyl)-1-phenyl-1H-pyrazole-4-carboxamide (173): 2:1-1:1 hexane:EtOAc, off-white solid (50%): $R_f$ (1:1 hexane:EtOAc) 0.41; $^1$H-NMR (CDCl$_3$ 300 MHz) 8.49 (s, 1H), 8.35 (d, 2H), 8.08 (d, 2H), 7.80 (d, 2H), 7.55 (t, 2H), 7.44 (t, 1H), 7.31 (bs, 1H), 7.17 (bs, 1H), 7.11 (t, 1H), 6.95 (t, 1H), 6.56 (dd, 1H), 6.49 (dd, 1H), 6.14 (dd, 1H), 6.07 (t, 1H).

4-{4-[(3-Fluorophenyl)carbamoyl]-1-phenyl-1H-pyrazol-3-yl}phenyl acetate (174): 5:1-0:1 hexane:EtOAc, white solid (13%): $R_f$ (3:1 hexane:EtOAc) 0.33; $^1$H-NMR (CDCl$_3$ 300 MHz) 8.54 (s, 1H), 7.70 (m, 4H), 7.44 (t, 2H), 7.31 (m, 2H), 7.24 (d, 2H), 7.13 (m, 1H), 6.74 (m, 2H), 2.30 (s, 3H).

N-(3-Fluorophenyl)-3-(4-hydroxyphenyl)-1-phenyl-1H-pyrazole-4-carboxamide (175): To 4-{4-[(3-fluorophenyl)carbamoyl]-1-phenyl-1H-pyrazol-3-yl}phenyl acetate (2 mg, 5 umol) in 5 ml THF was added 11 eqv NaOH (in 22 ul H$_2$O). After stirring overnight the solvent was removed by rotary evaporation and the residue purified by flash chromatography (3:1 hexane:EtOAc) to give the product as a white solid (50%): $R_f$ (3:1 hexane:EtOAc) 0.23; $^1$H-NMR (CDCl$_3$ 300 MHz) 8.63 (s, 1H), 7.72 (d, 2H), 7.65 (d, 2H), 7.50 (t, 2H), 7.41 (m, 2H), 7.25 (m, 2H), 7.14 (m, 2H), 6.85 (m, 2H).

N-(3-Fluorophenyl)-3-[4-(methylsulfanyl)phenyl]-1-phenyl-1H-pyrazole-4-carboxamide (176): 1:1 hexane:EtOAc, white solid (13%): $R_f$ (1:1 hexane:EtOAc) 0.31; $^1$H-NMR (CDCl$_3$ 300 MHz) 8.42 (s, 1H), 7.86 (d, 2H), 7.75 (m, 4H), 7.46 (t, 2H), 7.31 (m, 2H), 6.90 (m, 2H), 2.72 (s, 3H).

3-(4-Carbamoylphenyl)-N-(3-fluorophenyl)-1-phenyl-1H-pyrazole-4-carboxamide (177): To methyl 4-{4-[(3-fluorophenyl)carbamoyl]-1-phenyl-1H-pyrazol-3-yl}benzoate (0.008 g, 19 umol) in 5 ml THF was added 10 eqv sodium hydroxide in 320 ul H$_2$O. After stirring overnight and additional 10 eqv NaOH was added and the reaction stirred for 6 h whereupon the solution was refluxed for 20 min. After cooling to 20° C. 3 ml H$_2$O was added and the solution acidified with 3 ml 1 M HCl (aq). The mixture was extracted 3×5 ml CH$_2$Cl$_2$ and the combined organics washed with 5 ml brine and then dried with anhyd MgSO$_4$, filtered and then the solvent evaporated. The residue was dissolved in 3 ml toluene and 50 ul DMF and refluxed with thionyl chloride (0.0058 ul, 80 umol) for 2 h. After cooling to 20° C., 0.8 ml of 0.5 M ammonia in dioxane was added and the solution stirred for 10 min. The solvent was removed by rotary evaporation and the residue purified by flash chromatography (3:1 hexane:EtOAc) to give the desired product as a white solid (0.005 g, 63%): $R_f$ (3:1 hexane:EtOAc) 0.301; $^1$H-NMR (CDCl$_3$ 300 MHz) 8.63 (s, 1H), 8.22 (d, 2H), 7.90 (d, 2H), 7.80 (t, 2H), 7.51 (m, 2H), 7.49 (m, 3H), 7.27 (m, 1H), 6.84 (m, 1H).

3-(4-(Methylsulfonyl)phenyl)-N-(3-fluorophenyl)-1-phenyl-1H-pyrazole-4-carboxamide (178): 5:1-0:1 hexane:EtOAc, off-white solid (27%): $R_f$ (3:1 hexane:EtOAc) 0.07; $^1$H-NMR (CDCl$_3$ 300 MHz) 8.60 (s, 1H), 8.08 (m, 3H), 7.81 (m, 2H), 7.55 (m, 2H), 7.43 (m, 1H), 7.31 (m, 2H), 7.04 (m, 1H), 6.87 (m, 1H), 3.12 (s, 3H).

3-(4-(Methylsulfonyl)phenyl)-N-(2-methoxy phenyl)-1-phenyl-1H-pyrazole-4-carboxamide (179): 5:1-0:1 hexane:EtOAc, off-white solid (53%): $R_f$ (3:1 hexane:EtOAc) 0.10; $^1$H-NMR (CDCl$_3$ 300 MHz) 8.58 (s, 1H), 8.48 (d, 1H), 8.06 (m, 4H), 7.79 (d, 2H), 7.54 (t, 2H), 7.43 (t, 1H), 7.04 (m, 2H), 6.83 (dd, 1H), 3.64 (s, 3H, OCH$_3$), 3.13 (s, 3H, SO$_2$CH$_3$).

3-(4-N-t-Butylcarbomylphenyl)-N-(3-fluorophenyl)-1-phenyl-1H-pyrazole-4-carboxamide (180): 6:1-0:1 hexane:EtOAc, white solid (4%): $R_f$ (3:1 hexane:EtOAc) 0.30; $^1$H-NMR (CDCl$_3$ 300 MHz) 8.53 (s, 1H), 7.71 (d, 2H), 7.60 (d, 2H), 7.45 (m, 4H), 7.32 (m, 1H), 7.14 (m, 1H), 6.79 (m, 1H), 6.72 (m, 1H), 6.60 (bs, 1H), 1.49 (s, 9H).

N-(3-Fluorophenyl)-1-phenyl-3-(pyridin-4-yl-oxide)-1H-pyrazole-4-carboxamide (181): The pyridine compound (0.005 g, 14 umol) and methyltrioxorhenium(VII) (0.001 g, 0.4 umol) in 3 ml CH$_2$Cl$_2$ was stirred for 6 hrs with 0.5 ml 30% hydrogen peroxide. Manganese (IV) oxide (0.001 g, 12 umol) was added and the solution stirred overnight. The precipitate was removed, layers separated and the aqueous extracted 4×3 ml CH$_2$Cl$_2$. The organics were dried with MgSO$_4$, filtered, rotovapped and the residue dried under vacuum. NMR and ESMS showed that this was a mixture of starting pyridine and desired pyridine N-oxide. The isolated white residue was dried was the desired product (0.001 g, 20%) as determined by NMR (DMSO, 300 MHz): 10.51 (s, 1H), 9.21 (s, 1H), 7.97 (m, 4H), 7.70 (m, 1H), 7.61 (m, 2H), 7.44 (m, 3H), 6.95 (m, 1H); ESMS 375 (M+H, 100) Procedure adapted from C. Coperet, H. Adolfsson, T. Khuong, A. Yudin, K. Barry Sharpless A Simple and Efficient Method for the Preparation of Pyridine N-Oxides 1998 J Org Chem 63, 1740-1.

3-(4-Aminophenyl)-N-(3-fluorophenyl)-1-phenyl-1H-pyrazole-4-carboxamide (182): To the corresponding nitro (0.051 g, 127 umol) in 20 ml EtOH and 5 ml H$_2$O was added sodium hydrosulfite. The reaction was heated to 50° C. for 4 h whereupon the solvent was removed by rotary evaporation and the residue purified by flash chromatography (3:1:0-0:8:1 hexane:EtOAc:CH$_3$OH) to give the desired product as a white solid (0.011 g, 23%): $R_f$ (8:1 EtOAc:CH$_3$OH) 0.11; $^1$H-NMR (DMSO 300 MHz) 10.40 (s, 1H), 9.04 (s, 1H), 8.13 (s, 1H), 7.96 (d, 2H), 7.70 (d, 1H), 7.59 (m, 3H), 7.41 (m, 2H), 7.08 (d, 2H), 6.94 (m, 1H); ESMS 373 (M+H, 100).

3-(4-Acetoaminophenyl)-N-(3-fluorophenyl)-1-phenyl-1H-pyrazole-4-carboxamide (183): The starting amine (0.015 g, 40 umol) was stirred overnight in 2 ml DMF with triethylamine (0.013 ml, 161 umol) and acetic anhydride (0.005 ml, 48 umol). The solvent was removed by rotary evaporation and the residue purified by flash chromatography (1:0-8:1 EtOAc:CH$_3$OH) to give the desired product as a white solid (0.012 g, 71%): $R_f$ (8:1 EtOAc:CH$_3$OH) 0.13; $^1$H-NMR (DMSO 300 MHz) 10.40 (s, 1H), 9.04 (s, 1H), 8.13 (s, 1H), 7.95 (d, 2H), 7.70 (d, 1H), 7.59 (m, 4H), 7.44 (m, 2H), 7.08 (d, 2H), 6.94 (m, 1H), 2.01 (s, 3H).

3-(4-Methylsulfonylaminophenyl)-N-(3-fluorophenyl)-1-phenyl-1H-pyrazole-4-carboxamide (184): The starting amine (0.039 g, 105 umol) was stirred overnight in 2 ml DMF with pyridine (0.15 ml) and methanesulfonyl chloride (0.010 ml, 126 umol). The solvent was removed by rotary evaporation and the residue purified by flash chromatography (1:1:0-0:8:1 hexane:EtOAc:CH$_3$OH) to give the desired product as a red solid (0.016 g, 34%): R$_f$ (8:1 EtOAc:CH$_3$OH) 0.68; $^1$H-NMR (CDCl$_3$ 300 MHz) 8.63 (s, 1H), 7.78 (m, 3H), 7.53 (m, 4H), 7.40 (m, 2H), 7.25 (m, 1H), 6.91 (m, 3H), 6.80 (m, 1H), 2.91 (s, 3H).

N-(3-Fluorophenyl)-3-(4-formylphenyl)-1-phenyl-1H-pyrazole-4-carboxamide (185): To the starting nitrile (0.015 g, 39 umol) in 10 ml dry THF at 0° C. was added 1 M diisobutylaluminum hydride in hexane (86 ul, 86 umol). The reaction was stirred for 1 hr at 0° C. whereupon 2 ml 1 M H$_2$SO$_4$ (aq) was added and the reaction refluxed for 1 hour. After cooling to room temperature 5 ml 5% NaHCO$_3$ (aq) and 20 ml H$_2$O were added slowly. The mixture was extracted 3×10 ml CH$_2$Cl$_2$ and the combined organics dried with anhyd. MgSO$_4$, filtered and solvent removed by rotary evaporation and the residue purified by flash chromatography (6:1-3:1 hexane:EtOAc) to give the desired product as a white solid (0.010 g, 67%): R$_f$ (3:1 hexane:EtOAc) 0.20; $^1$H-NMR (CDCl$_3$ 300 MHz) 10.10 (s, 1H), 8.59 (s, 1H), 8.11 (m, 3H), 8.00 (d, 2H), 7.83 (m, 3H), 7.59 (m, 2H), 7.49 (m, 1H), 6.96 (m, 1H), 6.87 (m, 1H).

N-(3-Fluorophenyl)-3-[4-(hydroxymethyl)phenyl]-1-phenyl-1H-pyrazole-4-carboxamide (186): To the starting aldehyde (0.005 g, 13 umol) in 8 ml CH$_3$OH and 4 ml CH$_2$Cl$_2$ was added sodium borohydride (0.002 g, 39 umol). After stirring for 5 hr 100 ul 1 M H$_2$SO$_4$ (aq) was added and stirring continued for 5 min. The solvent was removed by rotary evaporation and the residue purified by flash chromatography (3:1-0:1 hexane:EtOAc) to give the desired product as a white solid (0.005 g, 100%): R$_f$ (1:1 hexane:EtOAc) 0.61; $^1$H-NMR (CDCl$_3$ 300 MHz) 8.44 (s, 1H), 8.00 (m, 2H), 7.94 (d, 2H), 7.69 (m, 4H), 7.45 (m, 3H), 7.29 (m, 1H), 6.87 (m, 1H), 6.79 (m, 1H), 4.73 (s, 2H).

3-(4-Fluorophenyl)-N-(4-methylphenyl)-1-phenyl-1H-pyrazole-4-carboxamide (187): 6:1-3:1 hexane:EtOAc, white solid (75%): R$_f$ (3:1 hexane:EtOAc) 0.41; $^1$H-NMR (CDCl$_3$ 300 MHz) 8.49 (s, 1H), 7.68 (m, 4H), 7.43 (m, 2H), 7.30 (m, 2H), 7.19 (m, 1H), 7.08 (m, 2H), 6.98 (d, 1H), 6.85 (d, 1H), 2.25 (s, 3H).

3-(4-Fluorophenyl)-N-(2-methylphenyl)-1-phenyl-1H-pyrazole-4-carboxamide (188): 6:1-3:1 hexane:EtOAc, white solid (75%): R$_f$ (3:1 hexane:EtOAc) 0.33; $^1$H-NMR (CDCl$_3$ 300 MHz) 8.62 (s, 1H), 8.11 (d, 1H), 7.76 (m, 4H), 7.52 (t, 2H), 7.40 (t, 2H), 7.25 (m, 2H), 7.09 (m, 2H), 1.77 (s, 3H).

3-(4-Fluorophenyl)-N-(3-methoxyphenyl)-1-phenyl-1H-pyrazole-4-carboxamide (189): 5:1-3:1 hexane:EtOAc, white solid (67%): R$_f$ (3:1 hexane:EtOAc) 0.19; $^1$H-NMR (CDCl$_3$ 300 MHz) 8.60 (s, 1H), 7.78 (m, 4H), 7.55 (t, 2H), 7.39 (t, 2H), 7.25 (m, 3H), 6.70 (m, 2H), 3.82 (s, 3H).

3-(4-Fluorophenyl)-N-(4-methoxyphenyl)-1-phenyl-1H-pyrazole-4-carboxamide (190): 5:1-3:1 hexane:EtOAc, white solid (80%): R$_f$ (3:1 hexane:EtOAc) 0.28; $^1$H-NMR (CDCl$_3$ 300 MHz) 8.58 (s, 1H), 7.77 (m, 4H), 7.52 (t, 2H), 7.39 (m, 1H), 7.31 (m, 2H), 7.25 (m, 2H), 6.86 (m, 2H), 3.81 (s, 3H).

3-(4-Fluorophenyl)-N-(2-fluorophenyl)-1-phenyl-1H-pyrazole-4-carboxamide (191): 6:1-3:1 hexane:EtOAc, white solid (47%): R$_f$ (3:1 hexane:EtOAc) 0.37; $^1$H-NMR (CDCl$_3$ 300 MHz) 8.53 (s, 1H), 8.34 (dt, 1H), 7.69 (m, 4H), 7.58 (bs, 1H), 7.44 (t, 2H), 7.32 (m, 1H), 7.17 (m, 2H), 7.06 (m, 1H), 6.95 (m, 2H).

3-(4-Fluorophenyl)-N-(4-fluorophenyl)-1-phenyl-1H-pyrazole-4-carboxamide (192): 6:1-3:1 hexane:EtOAc, white solid (35%): R$_f$ (3:1 hexane:EtOAc) 0.39; $^1$H-NMR (CDCl$_3$ 300 MHz) 8.50 (s, 1H), 8.34 (dt, 1H), 7.67 (m, 4H), 7.43 (t, 2H), 7.25 (m, 5H), 6.93 (m, 2H).

3-(4-Fluorophenyl)-N-(4-trifluoromethyphenyl)-1-phenyl-1H-pyrazole-4-carboxamide (193): 6:1-3:1 hexane:EtOAc, white solid (21%): R$_f$ (3:1 hexane:EtOAc) 0.47; $^1$H-NMR (CDCl$_3$ 300 MHz) 8.63 (s, 1H), 7.79 (m, 5H), 7.59-7.42 (m, 9H).

3-(4-Fluorophenyl)-N-(3-trifluoromethyphenyl)-1-phenyl-1H-pyrazole-4-carboxamide (194): 6:1-3:1 hexane:EtOAc, white solid (100%): R$_f$ (3:1 hexane:EtOAc) 0.50; $^1$H-NMR (CDCl$_3$ 300 MHz) 8.61 (s, 1H), 7.78 (m, 5H), 7.59-7.38 (m, 7H), 7.29 (m, 2H).

3-(4-Fluorophenyl)-N-(2-trifluoromethyphenyl)-1-phenyl-1H-pyrazole-4-carboxamide (195): 6:1-3:1 hexane:EtOAc, white solid (70%): R$_f$ (3:1 hexane:EtOAc) 0.46; $^1$H-NMR (CDCl$_3$ 300 MHz) 8.23 (s, 1H), 7.79 (m, 2H), 7.67 (m, 3H), 7.45 (m, 3H), 7.34 (m, 1H), 7.03 (m, 2H).

N-(3-Fluorophenyl)-3-[4-(formylamino)phenyl]-1-phenyl-1H-pyrazole-4-carboxamide (196): N-(3-fluorophenyl)-3-[4-aminophenyl]-1-phenyl-1H-pyrazole-4-carboxamide (0.009 g, 24 umol) was stirred over the weekend in 5 ml THF with 2,2,2-trifluoroethylformate (0.012 ml, 121 umol). The solvent was removed by rotary evaporation and the residue purified by flash chromatography (1:1:0-0:8:1 hexane:EtOAc:CH$_3$OH) to give the desired formamide as a off-white solid (0.001 g, 10%): R$_f$ (1:1 hexane:EtOAc) 0.76; $^1$H-NMR (CDCl$_3$ 300 MHz) 8.52 (s, 1H), 8.50 (s, 1H), 7.70 (m, 4H), 7.45-7.30 (m, 6H), 7.18 (m, 1H), 6.81 (m, 2H). Procedure taken from D. Hill, C Hsiao, R Kurukulasuriya, S. Wittenberger 2,2,2-Trifluoroethyl Formate: A Versatile and Selective Reagent for the Formylation of Alcohols, Amines, and N-Hydroxylamines. 2002 Organic Lett 4(1) 111-3.

N-(3-Fluorophenyl)-3-[4-(methylsulfinyl)phenyl]-1-phenyl-1H-pyrazole-4-carboxamide (197): 6:1-3:1 hexane:EtOAc, white solid (7%): R$_f$ (3:1 hexane:EtOAc) 0.45; $^1$H-NMR (CDCl$_3$ 300 MHz) 8.52 (s, 1H), 7.94 (m, 2H), 7.80 (m, 2H), 7.70 (m, 4H), 7.34 (m, 3H), 7.03 (m, 2H), 2.56 (s, 3H), 2.54 (s, 3H).

N-(4-Fluorophenyl)-3-[4-(methylsulfinyl)phenyl]-1-phenyl-1H-pyrazole-4-carboxamide (198): 6:1-3:1 hexane:EtOAc, white solid (9%): R$_f$ (3:1 hexane:EtOAc) 0.31; $^1$H-NMR (CDCl$_3$ 300 MHz) 8.51 (s, 1H), 7.94 (m, 2H), 7.81 (m, 2H), 7.71 (m, 4H), 7.53 (m, 2H), 7.44 (m, 1H), 6.93 (m, 2H), 2.56 (s, 3H), 2.54 (s, 3H).

N-(2-Methylphenyl)-3-[4-(methylsulfinyl)phenyl]-1-phenyl-1H-pyrazole-4-carboxamide (199): 6:1-3:1 hexane:EtOAc, white solid (7%): R$_f$ (3:1 hexane:EtOAc) 0.46; $^1$H-NMR (CDCl$_3$ 300 MHz) 8.10 (s, 1H), 7.90 (m, 2H), 7.75 (m, 4H), 7.53 (m, 2H), 7.45 (m, 1H), 7.32 (m, 1H), 6.95 (m, 2H), 2.51 (s, 3H), 2.49 (s, 3H).

N-(3-Methylphenyl)-3-[4-(methylsulfinyl)phenyl]-1-phenyl-1H-pyrazole-4-carboxamide (200): 6:1-3:1 hexane:EtOAc, white solid (13%): R$_f$ (3:1 hexane:EtOAc) 0.46; $^1$H-NMR (CDCl$_3$ 300 MHz) 8.41 (s, 1H), 7.95 (m, 2H), 7.81 (m, 2H), 7.71 (m, 4H), 7.44 (m, 3H), 7.06 (m, 2H), 2.75 (s, 3H), 2.29 (s, 3H).

N-(4-Methylphenyl)-3-[4-(methylsulfinyl)phenyl]-1-phenyl-1H-pyrazole-4-carboxamide (201): 6:1-3:1 hexane:EtOAc, white solid (7%): R$_f$ (3:1 hexane:EtOAc) 0.33;

¹H-NMR (CDCl₃ 300 MHz) 8.41 (s, 1H), 7.91 (m, 2H), 7.71 (m, 4H), 7.44 (m, 5H), 7.03 (m, 2H), 2.69 (s, 3H), 2.48 (s, 3H).

N-(2-Methoxyphenyl)-3-[4-(methylsulfinyl)phenyl]-1-phenyl-1H-pyrazole-4-carboxamide (202): 6:1-3:1 hexane:EtOAc, white solid (5%): $R_f$ (3:1 hexane:EtOAc) 0.50; ¹H-NMR (CDCl₃ 300 MHz) 8.54 (s, 1H), 7.72 (m, 4H), 7.46 (m, 5H), 6.84 (m, 2H), 3.81 (s, 3H), 2.99 (s, 3H).

3-(4-(Methylsulfonyl)phenyl)-N-(2-fluorophenyl)-1-phenyl-1H-pyrazole-4-carboxamide (203): 5:1-0:1 hexane:EtOAc, off-white solid (86%): $R_f$ (3:1 hexane:EtOAc) 0.11; ¹H-NMR (CDCl₃ 300 MHz) 8.58 (s, 1H), 8.41 (t, 1H), 8.09 (m, 4H), 7.83 (m, 2H), 7.56 (m, 3H), 7.44 (m, 1H), 7.19 (m, 1H), 7.09 (m, 1H), 3.13 (s, 3H).

3-(4-(Methylsulfonyl)phenyl)-N-(4-fluorophenyl)-1-phenyl-1H-pyrazole-4-carboxamide (204): 5:1-0:1 hexane:EtOAc, off-white solid (86%): $R_f$ (3:1 hexane:EtOAc) 0.09; ¹H-NMR (CDCl₃ 300 MHz) 8.55 (s, 1H), 8.07 (m, 4H), 7.81 (m, 2H), 7.55 (m, 3H), 7.44 (m, 2H), 7.06 (m, 2H), 3.12 (s, 3H).

3-(4-(Methylsulfonyl)phenyl)-N-(4-methylphenyl)-1-phenyl-1H-pyrazole-4-carboxamide (205): 5:1-0:1 hexane:EtOAc, off-white solid (43%): $R_f$ (3:1 hexane:EtOAc) 0.07; ¹H-NMR (CDCl₃ 300 MHz) 8.53 (s, 1H), 8.08 (m, 4H), 7.80 (m, 2H), 7.54 (m, 2H), 7.48 (bs, 1H), 7.44 (m, 1H), 7.35 (m, 2H), 7.16 (m, 2H), 3.11 (s, 3H), 2.35 (s, 3H).

3-(4-(Methylsulfonyl)phenyl)-N-(2-methoxyphenyl)-1-phenyl-1H-pyrazole-4-carboxamide (206): 5:1-0:1 hexane:EtOAc, off-white solid (100%): $R_f$ (3:1 hexane:EtOAc) 0.10; ¹H-NMR (CDCl₃ 300 MHz) 8.48 (s, 1H), 8.39 (bd, 1H), 8.01 (m, 5H), 7.71 (m, 2H), 7.44 (m, 2H), 7.44 (m, 1H), 6.95 (m, 2H), 6.75 (m, 1H), 3.54 (s, 3H), 3.03 (s, 3H).

3-(4-(Methylsulfonyl)phenyl)-N-(3,4-difluorophenyl)-1-phenyl-1H-pyrazole-4-carboxamide (207): 3:1-1:1 hexane:EtOAc, off-white solid (10%): $R_f$ (3:1 hexane:EtOAc) 0.07; ¹H-NMR (CDCl₃ 300 MHz) 8.56 (s, 1H), 8.08 (bs, 4H), 7.81 (m, 2H), 7.67 (m, 1H), 7.56 (m, 2H), 7.44 (m, 1H), 7.13 (m, 1H), 6.97 (m, 1H), 3.13 (s, 3H).

3-(4-(Methylsulfonyl)phenyl)-N-(3-trifluoromethylphenyl)-1-phenyl-1H-pyrazole-4-carboxamide (208): 3:1-1:1 hexane:EtOAc, off-white solid (40%): $R_f$ (3:1 hexane:EtOAc) 0.10; ¹H-NMR (CDCl₃ 300 MHz) 8.60 (s, 1H), 8.06 (m, 4H), 7.84 (m, 4H), 7.66 (m, 1H), 7.50 (m, 5H), 3.12 (s, 3H).

3-(4-(Methylsulfonyl)phenyl)-N-(2-hydroxyphenyl)-1-phenyl-1H-pyrazole-4-carboxamide (209): 3:1-1:1 hexane:EtOAc, off-white solid (33%): $R_f$ (3:1 hexane:EtOAc) 0.10; ¹H-NMR (CDCl₃ 500 MHz) 8.65 (s, 1H), 8.07 (m, 4H), 7.92 (bs, 1H), 7.81 (d, 2H), 7.55 (t, 2H), 7.43 (t, 1H), 7.12 (m, 2H), 7.01 (d, 1H), 6.88 (t, 1H), 3.13 (s, 3H).

N-(2-Acetoxyphenyl)-3-[4-(methylsulfonyl)phenyl]-1-phenyl-1H-pyrazole-4-carboxamide (210): The starting phenol (0.013 g, 30 umol) was stirred 48 h with acetic anhydride (12 ul, 130 umol) and DMAP (0.001 g, 1 umol) purified by flash chromatography (3:1-0:1 hexane:EtOAc) to generate the product as a white solid (93%): $R_f$ (1:1 hexane:EtOAc) 0.68; ¹H-NMR (CDCl₃ 300 MHz, 2 rotamers) 8.64 (s, 0.5H), 8.54 (s, 0.5H), 8.05 (m, 4H), 7.81 (t, 1H), 7.61-7.12 (m, 7H), 3.11 (s, 3H), 2.45 (s, 1.5H), 2.28 (s, 1.5H).

3-(4-(Methylsulfonyl)phenyl)-N-(3-hydroxyphenyl)-1-phenyl-1H-pyrazole-4-carboxamide (211): 3:1-1:1 hexane:EtOAc, off-white solid (44%): $R_f$ (1:1 hexane:EtOAc) 0.44; ¹H-NMR (CDCl₃ 500 MHz) 8.59 (s, 1H), 8.07 (m, 4H), 7.81 (d, 2H), 7.54 (t, 2H), 7.44 (m, 2H), 7.17 (t, 1H), 6.67 (t, 2H), 3.12 (s, 3H).

3-(4-(Methylsulfonyl)phenyl)-N-(3-methoxyphenyl)-1-phenyl-1H-pyrazole-4-carboxamide (212): 3:1-1:1 hexane:EtOAc, off-white solid (20%): $R_f$ (1:1 hexane:EtOAc) 0.36; ¹H-NMR (CDCl₃ 500 MHz) 8.53 (s, 1H), 8.07 (m, 4H), 7.80 (d, 2H), 7.54 (m, 3H), 7.42 (t, 1H), 7.25 (m, 2H), 6.90 (d, 1H), 6.71 (d, 1H), 3.83 (s, 3H), 3.11 (s, 3H).

3-(4-(Methylsulfonyl)phenyl)-N-(3-aminophenyl)-1-phenyl-1H-pyrazole-4-carboxamide (213): 3:1-1:1 hexane:EtOAc, off-white solid (78%): $R_f$ (1:1 hexane:EtOAc) 0.15; ¹H-NMR (CDCl₃ 500 MHz) 8.49 (s, 1H), 8.06 (m, 4H), 7.79 (d, 2H), 7.54 (m, 2H), 7.40 (m, 1H), 7.10 (m, 1H), 6.96 (t, 1H), 6.59 (m, 1H), 6.48 (m, 1H), 3.11 (s, 3H).

3-(4-(Methylsulfonyl)phenyl)-N-(3-acetylphenyl)-1-phenyl-1H-pyrazole-4-carboxamide (214): 4:1-0:1 hexane:EtOAc, off-white solid (22%): $R_f$ (1:1 hexane:EtOAc) 0.43; ¹H-NMR (CDCl₃ 300 MHz) 8.70 (s, 1H), 8.08 (m, 4H), 7.92 (m, 2H), 7.79 (d, 2H), 7.50 (m, 6H), 3.15 (s, 3H), 2.62 (s, 3H).

3-(4-(Methylsulfonyl)phenyl)-N-(2-methylphenyl)-1-phenyl-1H-pyrazole-4-carboxamide (215): 4:1-0:1 hexane:EtOAc, white solid (71%): $R_f$ (1:1 hexane:EtOAc) 0.43; ¹H-NMR (CDCl₃ 300 MHz) 8.54 (s, 1H), 8.07 (m, 4H), 7.95 (bd, 1H), 7.79 (d, 2H), 7.54 (t, 2H), 7.42 (m, 1H), 7.25 (m, 1H), 7.12 (m, 2H), 3.09 (s, 3H), 1.96 (s, 3H).

3-(4-(Methylsulfonyl)phenyl)-N-(3-methylphenyl)-1-phenyl-1H-pyrazole-4-carboxamide (216): 2:1-0:1 hexane:EtOAc, white solid (93%): $R_f$ (1:1 hexane:EtOAc) 0.62; ¹H-NMR (CDCl₃ 300 MHz) 8.48 (s, 1H), 8.04 (m, 4H), 7.77 (d, 2H), 7.67 (bs, 1H), 7.53 (t, 2H), 7.42 (m, 1H), 7.38 (m, 1H), 7.25 (m, 1H), 6.99 (m, 1H), 3.09 (s, 3H), 2.36 (s, 3H).

3-(4-(Methylsulfonyl)phenyl)-N-(4-methoxyphenyl)-1-phenyl-1H-pyrazole-4-carboxamide (217): 2:1-0:1 hexane:EtOAc, white solid (67%): $R_f$ (1:1 hexane:EtOAc) 0.41; ¹H-NMR (CDCl₃ 300 MHz) 8.47 (s, 1H), 8.04 (m, 4H), 7.77 (d, 2H), 7.64 (bs, 1H), 7.53 (t, 2H), 7.41 (m, 2H), 6.89 (m, 2H), 3.82 (s, 3H), 3.09 (s, 3H).

3-(4-(Methylsulfonyl)phenyl)-N-(2-chlorophenyl)-1-phenyl-1H-pyrazole-4-carboxamide (218): 2:1-0:1 hexane:EtOAc, white solid (33%): $R_f$ (1:1 hexane:EtOAc) 0.69; ¹H-NMR (CDCl₃ 300 MHz) 8.59 (s, 1H), 8.53 (d, 1H), 8.07 (m, 4H), 7.89 (bs, 1H), 7.81 (d, 2H), 7.56 (t, 2H), 7.44 (t, 1H), 7.33 (m, 2H), 7.07 (m, 1H), 3.12 (s, 3H).

3-(4-(Methylsulfonyl)phenyl)-N-(3-chlorophenyl)-1-phenyl-1H-pyrazole-4-carboxamide (219): 2:1-0:1 hexane:EtOAc, white solid (80%): $R_f$ (1:1 hexane:EtOAc) 0.66; ¹H-NMR (CDCl₃ 300 MHz) 8.52 (s, 1H), 8.06 (m, 4H), 7.89 (bs, 1H), 7.81 (d, 2H), 7.69 (bs, 1H), 7.65 (bs, 1H), 7.55 (t, 2H), 7.44 (t, 1H), 7.26 (m, 1H), 7.14 (m, 1H), 3.12 (s, 3H).

3-(4-(Methylsulfonyl)phenyl)-N-(4-chlorophenyl)-1-phenyl-1H-pyrazole-4-carboxamide (220): 2:1-0:1 hexane:EtOAc, white solid (33%): $R_f$ (1:1 hexane:EtOAc) 0.68; ¹H-NMR (CDCl₃ 300 MHz) 8.54 (s, 1H), 8.06 (m, 4H), 7.80 (d, 2H), 7.69 (bs, 1H), 7.55 (m, 3H), 7.45 (m, 2H), 7.32 (m, 2H), 3.12 (s, 3H).

3-(4-(Methylsulfonyl)phenyl)-N-(4-hydroxyphenyl)-1-phenyl-1H-pyrazole-4-carboxamide (221): 2:1-0:1 hexane:EtOAc, white solid (40%): $R_f$ (1:1 hexane:EtOAc) 0.23; ¹H-NMR (CDCl₃ 300 MHz) 8.52 (s, 1H), 8.10 (m, 4H), 7.80 (d, 2H), 7.55 (m, 3H), 7.43 (m, 1H), 6.99 (m, 1H), 6.83 (m, 2H), 3.13 (s, 3H).

3-(4-(Methylsulfonyl)phenyl)-N-phenyl-1-phenyl-1H-pyrazole-4-carboxamide (222): 4:1-0:1 hexane:EtOAc, white solid (29%): $R_f$ (1:1 hexane:EtOAc) 0.43; ¹H-NMR (CDCl₃ 300 MHz) 8.52 (s, 1H), 8.08 (m, 4H), 7.80 (d, 2H), 7.55 (t, 2H), 7.45 (m, 2H), 7.37 (t, 2H), 7.17 (t, 1H), 3.12 (s, 3H).

3-(4-(Ethylsulfonyl)phenyl)-N-(3-fluorophenyl)-1-phenyl-1H-pyrazole-4-carboxamide (223): 2:1-0:1 hexane:EtOAc, white solid (77%): $R_f$ (1:1 hexane:EtOAc) 0.67;

¹H-NMR (CDCl₃ 300 MHz) 8.40 (s, 1H), 8.08 (m, 4H), 7.94 (m, 2H), 7.84 (d, 2H), 7.78 (bs, 1H), 7.70 (m, 2H), 7.45 (m, 3H), 7.35 (m, 1H), 7.19 (t, 1H), 6.98 (m, 1H), 6.76 (m, 1H), 3.07 (q, 2H), 1.23 (t, 3H).

N-Hydroxy-3-(4-nitrophenyl)-1-phenyl-1H-pyrazole-4-carboxamide (224): 1:0-8:1 EtOAc:CH₃OH, off-white solid (83%): R_f (8:1 hexane:EtOAc) 0.62; ¹H-NMR (CDCl₃ 300 MHz) 8.17 (m, 2H), 7.95 (m, 3H), 7.67 (m, 2H), 7.41 (m, 2H), 7.31 (m, 1H).

3-(4-Nitrophenyl)-1-phenyl-1H-pyrazole-4-carboxamide (225): 2:1-0:1 hexane:EtOAc, white solid (28%): R_f (1:1 hexane:EtOAc) 0.10; ¹H-NMR (CDCl₃ 300 MHz) 8.22 (d, 2H), 8.06 (s, 1H), 7.91 (d, 2H), 7.69 (d, 2H), 7.45 (t, 2H), 7.31 (t, 1H).

N-Methyl-3-(4-nitrophenyl)-1-phenyl-1H-pyrazole-4-carboxamide (226): 2:1-0:1 hexane:EtOAc, white solid (60%): R_f (1:1 hexane:EtOAc) 0.20; ¹H-NMR (CDCl₃ 300 MHz) 8.38 (s, 1H), 8.33 (d, 2H), 8.07 (d, 2H), 7.77 (d, 2H), 7.53 (t, 2H), 7.41 (t, 1H), 5.71 (bs, 1H), 2.97 (d, 3H).

N,N-Dimethyl-3-(4-nitrophenyl)-1-phenyl-1H-pyrazole-4-carboxamide (227): 2:1-0:1 hexane:EtOAc, white solid (60%): R_f (1:1 hexane:EtOAc) 0.43; ¹H-NMR (CDCl₃ 300 MHz) 8.38 (s, 1H), 8.33 (d, 2H), 8.07 (d, 2H), 7.77 (d, 2H), 7.53 (t, 2H), 7.41 (t, 1H), 3.23 (d, 6H).

N-Ethyl-3-(4-nitrophenyl)-1-phenyl-1H-pyrazole-4-carboxamide (228): 2:1-0:1 hexane:EtOAc, white solid (14%): R_f (1:1 hexane:EtOAc) 0.40; ¹H-NMR (CDCl₃ 300 MHz) 8.35 (m, 3H), 8.06 (d, 2H), 7.76 (d, 2H), 7.52 (t, 2H), 7.40 (t, 1H), 5.65 (bs, NH), 3.45 (m, 2H), 1.19 (t, 3H).

Methyl 3-(4-nitrophenyl)-1-phenyl-1H-pyrazole-4-carboxylate (229): 2:1-0:1 hexane:EtOAc, white solid (14%): R_f (1:1 hexane:EtOAc) 0.83; ¹H-NMR (CDCl₃ 300 MHz) 8.56 (s, 1H), 8.32 (d, 2H), 8.15 (d, 2H), 7.54 (t, 2H), 7.43 (t, 1H), 3.88 (s, 3H).

Ethyl 3-(4-nitrophenyl)-1-phenyl-1H-pyrazole-4-carboxylate (230): 2:1-0:1 hexane:EtOAc, white solid (14%): R_f (1:1 hexane:EtOAc) 0.87; ¹H-NMR (CDCl₃ 300 MHz) 8.56 (s, 1H), 8.31 (d, 2H), 8.15 (d, 2H), 7.81 (m, 2H), 7.54 (t, 2H), 7.42 (t, 1H), 4.34 (q, 2H), 1.37 (t, 3H).

N-(3-Fluoro-2-hydroxyphenyl)-3-[4-(methylsulfonyl)phenyl]-1-phenyl-1H-pyrazole-4-carboxamide (231): 3:1-0:1 hexane:EtOAc), white solid (20%): R_f (1:1 hexane:EtOAc) 0.31; ¹H-NMR (CDCl₃ 300 MHz) 8.82 (s, 0.5H), 8.62 (s, 0.5H), 8.21 (d, 2H), 8.04 (m, 2H), 7.81 (m, 3H), 7.55 (m, 2H), 7.48 (t, 1H), 6.95 (m, 2H), 6.62 (m, 1H), 3.43 (s, 3H).

Ethyl 3-[4-(methylsulfonyl)phenyl]-1-phenyl-1H-pyrazole-4-carboxylate (232): 3:1-1:1 hexane:EtOAc, white solid (25%): R_f (1:1 hexane:EtOAc) 0.68; ¹H-NMR (CDCl₃ 300 MHz) 8.56 (s, 1H), 8.16 (d, 2H), 8.04 (d, 2H), 7.81 (m, 2H), 7.54 (t, 2H), 7.44 (t, 1H), 4.34 (q, 2H), 3.11 (s, 3H), 1.37 (t, 3H).

N-(2-Hydroxyphenyl)-3-[4-(methylsulfonyl)phenyl]-1-(4-chloropheny)-1H-pyrazole-4-carboxamide (233): 4:1-1:1 hexane:EtOAc, white solid (16%): R_f (1:1 hexane:EtOAc) 0.48; ¹H-NMR (CDCl₃ 500 MHz) 8.49 (s, 1H), 8.13 (d, 1H), 7.97 (d, 4H), 7.77 (bs, 1H), 7.66 (d, 1H), 7.42 (m, 2H), 7.17 (m, 1H), 7.02 (t, 1H), 6.93 (d, 1H), 6.80 (t, 1H), 3.04 (s, 3H).

N-(3-Fluorophenyl)-3-[4-(methylsulfonyl)phenyl]-1-(4-chloropheny)-1H-pyrazole-4-carboxamide (234): 4:1-0:1 hexane:EtOAc, white solid (17%): R_f (1:1 hexane:EtOAc) 0.85; ¹H-NMR (CDCl₃ 300 MHz) 8.41 (s, H), 7.98 (s, 4H), 7.68 (d, 2H), 7.44 (d, 2H), 7.39 (d, 1H), 7.19 (m, 1H), 6.89 (m, 1H), 6.78 (m, 1), 3.04 (s, 3H).

N-(2-Hydroxyphenyl)-3-[4-(methylsulfonyl)phenyl]-1-(2-chloropheny)-1H-pyrazole-4-carboxamide (235): 4:1-0:1 hexane:EtOAc white solid (8%): R_f (1:1 hexane:EtOAc) 0.42; ¹H-NMR (CDCl₃ 500 MHz) 8.65 (s, 1H), 8.12 (d, 2H), 7.95 (dd, 4H), 7.63 (m, 2H), 7.53 (m, 2H), 7.04 (m, 2H), 6.80 (m, 2H), 2.99 (s, 3H).

N-(3-Fluorophenyl)-3-[4-(methylsulfonyl)phenyl]-1-(2-chloropheny)-1H-pyrazole-4-carboxamide (236): 4:1-0:1 hexane:EtOAc, white solid (67%): R_f (1:1 hexane:EtOAc) 0.55; ¹H-NMR (CDCl₃ 300 MHz) 8.45 (s, 1H), 8.08 (m, 4H), 7.68 (m, 1H), 7.61 (m, 1H), 7.50 (m, 4H), 7.02 (m, 1H), 6.87 (m, 1H), 3.11 (s, 3H).

N-(3-Fluorophenyl)-3-[4-(methylsulfonyl)phenyl]-1-(2-fluoropheny)-1H-pyrazole-4-carboxamide (237): 3.5:1-1.5:1 hexane:EtOAc, white solid (100%): R_f (1:1 hexane:EtOAc) 0.71; ¹H-NMR (CDCl₃ 300 MHz) 8.59 (s, 1H), 8.01 (m, 7H), 7.40 (m, 3H), 7.04 (m, 1H), 6.89 (m, 1H), 6. 3.13 (s, 3H).

N-(2-Hydroxphenyl)-3-[4-(methylsulfonyl)phenyl]-1-(2-fluoropheny)-1H-pyrazole-4-carboxamide (238): 3.5:1-1.5:1 hexane:EtOAc, white solid (40%): R_f (1:1 hexane:EtOAc) 0.85; ¹H-NMR (CDCl₃ 300 MHz) 8.57 (s, 1H), 8.01 (m, 7H), 7.61 (bs, 1H), 7.28 (m, 2H), 7.03 (m, 2H), 6.92 (m, 1H), 6.81 (m, 1H), 3.05 (s, 3H).

N-(3-Fluorophenyl)-3-[4-(methylsulfonyl)phenyl]-1-(3-chloropheny)-1H-pyrazole-4-carboxamide (239): 3.5:1-0:1 hexane:EtOAc, white solid (77%): R_f (1:1 hexane:EtOAc) 0.77; ¹H-NMR (CDCl₃ 300 MHz) 8.44 (s, 1H), 8.05 (dd, 4H), 8.02 (s, 4H), 7.79 (m, 1H), 7.59 (m, 1H), 7.39 (m, 3H), 6.88 (m, 1H), 6.79 (m, 1H), 3.04 (s, 3H).

N-(2-Hydroxyphenyl)-3-[4-(methylsulfonyl)phenyl]-1-(3-chlorophenyl)-1H-pyrazole-4-carboxamide (240): 4:1-1:1 hexane:EtOAc, white solid (8%): R_f (1:1 hexane:EtOAc) 0.69; ¹H-NMR (CDCl₃ 300 MHz) 8.63 (s, 1H), 8.22 (d, 1H), 8.10 (dd, 4H), 8.02 (d, 1H), 7.91 (d, 1H), 7.83 (bs, 1H), 7.68 (m, 1H), 7.46 (m, 2H), 7.25 (d, 1H), 7.11 (m, 1H), 6.99 (d 1H), 6.93 (t, 1H), 3.15 (s, 3H).

N-(3-Fluorophenyl)-3-[4-(methylsulfonyl)phenyl]-1-(4-fluorophenyl)-1H-pyrazole-4-carboxamide (241): 4:1-1:1 hexane:EtOAc, white solid (3%): R_f (1:1 hexane:EtOAc) 0.76; ¹H-NMR (CDCl₃ 500 MHz) 8.37 (s, 1H), 7.96 (s, 4H), 7.69 (m, 2H), 7.48 (bs, 1H), 7.42 (m, 1H), 7.19 (m, 2H), 7.15 (m, 2H), 6.92 (d 1H), 6.77 (dt, 1H), 3.03 (s, 3H).

N-(2-Hydroxyphenyl)-3-[4-(methylsulfonyl)phenyl]-1-(4-fluorophenyl)-1H-pyrazole-4-carboxamide (242): 3.5-0:1 hexane:EtOAc, white solid (2%): R_f (1:1 hexane:EtOAc) 0.79; ¹H-NMR (CDCl₃ 500 MHz) rotamers 8.76/8.54 (s, 1H), 8.20 (m, 2H), 8.08 (dd, 4H), 8.03 (bs, 1H), 8.02 (d, 2H), 7.90 (bs, 1H), 7.84/7.80 (m, 1H), 7.26/7.11 (m, 1H), 6.99 (dd, 1H), 6.90 (dt, 1H), 3.14/3.09 (s, 3H).

N-(2-Hydroxyphenyl)-3-[4-(methylsulfonyl)phenyl]-1-(3-fluorophenyl)-1H-pyrazole-4-carboxamide (243): 3.5-0:1 hexane:EtOAc, white solid (23%): R_f (1:1 hexane:EtOAc) 0.73; ¹H-NMR (CDCl₃ 300 MHz) rotamers 8.82/8.63 (s, 1H), 8.22 (m, 2H), 8.05 (dd, 4H), 8.01 (d, 2H), 7.67/7.63 (m, 1H), 7.58/7.52 (m, 1H), 7.25 (dd, 1H), 7.10 (m, 1H), 7.10 (dd, 1H), 6.88 (m, 1H), 3.14/3.09 (s, 3H).

2-Aminophenyl 1-(3-fluorophenyl)-3-[4-(methylsulfonyl)phenyl]-1H-pyrazole-4-carboxylate (244): 3.5-0:1 hexane:EtOAc, white solid (38%): R_f (1:1 hexane:EtOAc) 0.30; ¹H-NMR (CDCl₃ 300 MHz) rotamers 8.68/8.38 (s, 1H), 8.04 (m, 2H), 7.89 (m, 5H), 7.62 (m, 1H), 7.51 (m, 2H), 7.32 (m, 1H), 7.27 (m, 2H), 7.14 (dd, 1H), 3.07/3.04 (s, 3H).

N-(3-Fluorophenyl)-3-[4-(methylsulfonyl)phenyl]-1-(3-fluorophenyl)-1H-pyrazole-4-carboxamide (245): 3.5:1-0:1 hexane:EtOAc, white solid (8%): R_f (1:1 hexane:EtOAc) 0.24; ¹H-NMR (CDCl₃ 500 MHz) rotamers 8.55 (s, 1H), 8.10 (m, 4H), 7.60 (m, 2H), 7.53 (m, 2H), 7.42 (bs, 1H), 7.14 (m, 1H), 6.98 (m, 1H), 6.89 (m, 1H), 3.15 (s, 3H).

N-(4-Trifluoromethoxyphenyl)-3-[4-(methylsulfonyl)phenyl]-1-(3-fluorophenyl)-1H-pyrazole-4-carboxamide (246): 3:1-0:1 hexane:EtOAc, white solid (75%): $R_f$ (1:1 hexane:EtOAc) 0.71; $^1$H-NMR (CDCl$_3$ 300 MHz) 8.50 (s, 1H), 8.06 (s, 4H), 7.85 (d, 2H), 7.51 (m, 2H), 7.40 (d, 2H), 7.14 (m, 1H), 7.00 (m, 1H), 6.88 (m, 1H), 3.13 (s, 3H).

N-(4-Trifluoromethoxyphenyl)-3-[4-(methylsulfonyl)phenyl]-1-(2-hydroxyphenyl)-1H-pyrazole-4-carboxamide (247): 3.5:1-0:1 hexane:EtOAc, white solid (83%): $R_f$ (1:1 hexane:EtOAc) 0.50; $^1$H-NMR (CDCl$_3$ 300 MHz) 8.52 (s, 1H), 8.12 (m, 1H), (7.99, dd, 4H), 7.77 (m, 2H), 7.33 (m, 2H), 7.16 (d, 1H), 7.01 (m, 1H), 6.89 (m, 1H), 6.80 (t, 1H), 3.05 (s, 3H).

N-(4-Trifluoromethylphenyl)-3-[4-(methylsulfonyl)phenyl]-1-(3-fluorophenyl)-1H-pyrazole-4-carboxamide (248): 2:1-0:1 hexane:EtOA (15%): $R_f$ (1:1 hexane:EtOAc) 0.90; $^1$H-NMR (CDCl$_3$ 500 MHz) 8.53 (s, 1H), 8.01 (dd, 4H), 7.87 (d, 2H), 7.74 (d, 2H), 7.45 (m, 1H), 7.37 (bs, 1H), 6.88 (m, 1H), 6.79 (dt, 1H), 3.05 (s, 3H).

N-(4-Cyanophenyl)-3-[4-(methylsulfonyl)phenyl]-1-(3-fluorophenyl)-1H-pyrazole-4-carboxamide (249): 3:1-0:1 hexane:EtOAc, white solid (75%): $R_f$ (1:1 hexane:EtOAc) 0.71; $^1$H-NMR (CDCl$_3$ 300 MHz) 8.62 (s, 1H), 8.09 (dd, 4H), 7.92 (dd, 4H), 7.52 (m, 1H), 7.44 (m, 1H), 6.97 (m, 1H), 6.90 (m, 1H), 3.14 (s, 3H).

N-(3-Trifluoromethyphenyl)-3-[4-(methylsulfonyl)phenyl]-1-(3-fluorophenyl)-1H-pyrazole-4-carboxamide (250): 3:1-1:1 hexane:EtOAc, white solid (47%): $R_f$ (1:1 hexane:EtOAc) 0.57; $^1$H-NMR (CDCl$_3$ 300 MHz) 9.08 (s, 1H), 8.61 (s, 1H), 8.08 (s, 4H), 7.69 (m, 2H), 7.61 (m, 1H), 7.56 (m, 1H), 7.52 (m, 1H), 7.48 (m, 1H), 7.05 (m, 1H), 6.88 (m, 1H), 3.13 (s, 3H).

N-(2-Trifluoromethyphenyl)-3-[4-(methylsulfonyl)phenyl]-1-(3-fluorophenyl)-1H-pyrazole-4-carboxamide (251): 2:1-0:1 hexane:EtOAc, light yellow solid (47%): $R_f$ (1:1 hexane:EtOAc) 0.43; $^1$H-NMR (CDCl$_3$ 300 MHz) 8.27 (s, 1H), 8.05 (s, 4H), 7.90 (dm, 1H), 7.69 (m, 2H), 7.80-7.63 (m, 4H), 7.52 (dt, 1H), 7.29 (m, 1H), 7.03 (dm, 1H), 6.85 (m, 1H), 3.10 (s, 3H).

3-[4-(Methylsulfonyl)phenyl]-1-phenyl-N-(pyridin-2-yl)-1H-pyrazole-4-carboxamide (252): 2:1-0:1 hexane:EtOAc, light white solid (28%): $R_f$ (1:1 hexane:EtOAc) 0.71; $^1$H-NMR (CDCl$_3$ 300 MHz) 9.00 (s, 1H), 8.18 (m, 2H), 8.13 (dt, 1H), 8.08 (t, 1H), 8.02 (m, 2H), 7.88 (m, 2H), 7.80 (m, 1H), 7.60 (m, 2H), 7.52 (m, 3H), 3.08 (s, 3H).

3-[4-(Methylsulfonyl)phenyl]-1-phenyl-N-(pyridin-3-yl)-1H-pyrazole-4-carboxamide (253): 1:1-0:1 hexane:EtOAc, light white solid (28%): $R_f$ (1:1 hexane:EtOAc) 0.71; $^1$H-NMR (CDCl$_3$ 300 MHz) 9.00 (s, 1H), 8.18 (m, 2H), 8.13 (dt, 1H), 8.08 (t, 1H), 8.02 (m, 2H), 7.88 (m, 2H), 7.80 (m, 1H), 7.60 (m, 2H), 7.52 (m, 3H), 3.08 (s, 3H).

Methyl 3-[4-(methylsulfonyl)phenyl]-1-phenyl-1H-pyrazole-4-carboxylate (254): 3:1-1:1 hexane:EtOAc, white solid (91%): $R_f$ (1:1 hexane:EtOAc) 0.77; $^1$H-NMR (CDCl$_3$ 500 MHz) 8.57 (s, 1H), 8.17 (d, 2H), 8.05 (d, 2H), 7.81 (d, 2H), 7.55 (t, 2H), 7.43 (t, 1H), 3.88 (s, 3H), 3.12 (s, 3H).

N-(3,4-Difluorophenyl)-1-(4-fluorophenyl)-3-[4-(methylsulfonyl)phenyl]-1H-pyrazole-4-carboxamide (255): 3:1-2:1 hexane:EtOAc, white solid (80%): $R_f$ (1:1 hexane:EtOAc) 0.61; $^1$H-NMR (CDCl$_3$ 500 MHz) 8.52 (s, 1H), 8.07 (bs, 2H), 7.96 (bs, 2H), 7.93 (bs, 2H), 7.80 (bs, 2H), 7.68 (bt, 1H), 7.56 (m, 2H), 7.25 (t, 2H), 7.13 (m, 1H), 6.98 (m, 1H), 3.14 (s, 3H).

N-(3-Trifluoromethylphenyl)-1-(4-fluorophenyl)-3-[4-(methylsulfonyl)phenyl]-1H-pyrazole-4-carboxamide (256): 3:1-2:1 hexane:EtOAc, white solid (36%): $R_f$ (1:1 hexane:EtOAc) 0.73; $^1$H-NMR (CDCl$_3$ 500 MHz) 8.51 (s, 1H), 8.06 (bs, 2H), 8.01 (d, 2H), 7.90 (s, 1H), 7.80 (m, 2H), 7.68 (d, 2H), 7.49 (t, 1H), 7.42 (d, 1H), 7.26 (t, 2H), 3.12 (s, 3H).

Methyl 1-(4-fluorophenyl)-3-[4-(methylsulfonyl)phenyl]-1H-pyrazole-4-carboxylate (257): 2:1-1:1 hexane:EtOAc, white solid (30%): $R_f$ (1:1 hexane:EtOAc) 0.58; $^1$H-NMR (CDCl$_3$ 500 MHz) 8.52 (s, 1H), 8.05 (d, 2H), 7.95 (d, 2H), 7.68 (m, 2H), 7.68 (d, 2H), 7.14 (t, 1H), 3.78 (s, 3H), 3.02 (s, 3H).

N-(3-Fluorophenyl)-1-(4-trifluoromethoxypheny)-3-[4-(methylsulfonyl)phenyl]-1H-pyrazole-4-carboxamide (258): 3:1-1:1 hexane:EtOAc, white solid (33%): $R_f$ (1:1 hexane:EtOAc) 0.79; $^1$H-NMR (CDCl$_3$ 500 MHz) 8.41 (s, 1H), 8.08 (s, 4H), 7.86 (d, 2H), 7.54 (d, 1H), 7.50 (bs, 1H), 7.42 (d, 2H), 7.30 (m, 1H), 7.01 (bd, 1H), 6.89 (m, 1H), 3.14 (s, 3H).

N-(3-Trifluoromethylphenyl)-1-(4-trifluoromethoxypheny)-3-[4-(methylsulfonyl)phenyl]-1H-pyrazole-4-carboxamide (259): 2:1 hexane:EtOAc, white solid (85%): $R_f$ (1:1 hexane:EtOAc) 0.81; $^1$H-NMR (CDCl$_3$ 500 MHz) 8.51 (s, 1H), 8.05 (d, 4H), 7.97 (d, 2H), 7.91 (s, 1H), 7.86 (d, 2H), 7.70 (d, 1H), 7.49 (t, 1H), 7.43 (t, 3H), 3.12 (s, 3H).

Methyl 3-[4-(methylsulfonyl)phenyl]-1-[4-(trifluoromethoxy)phenyl]-1H-pyrazole-4-carboxylate (260): 2:1 hexane:EtOAc, white solid (67%): $R_f$ (1:1 hexane:EtOAc) 0.66; $^1$H-NMR (CDCl$_3$ 500 MHz) 8.56 (s, 1H), 8.15 (d, 2H), 8.05 (d, 2H), 7.86 (d, 2H), 7.41 (d, 2H), 3.89 (s, 3H), 3.12 (s, 3H).

1-(4-Cyanophenyl)-N-(3,4-difluorophenyl)-3-[4-(methylsulfonyl)phenyl]-1H-pyrazole-4-carboxamide (261): 3:1-1:1 hexane:EtOAc, white solid (69%): $R_f$ (1:1 hexane:EtOAc) 0.67; $^1$H-NMR (CDCl$_3$ 500 MHz) 8.03 (m, 4H), 7.96 (d, 2H), 7.87 (d, 2H), 7.84 (d, 1H), 7.23 (d, 2H), 6.86 (d, 1H), 3.03 (s, 3H).

1-(4-Cyanophenyl)-N-(3-trifluoromethylphenyl)-3-[4-(methylsulfonyl)phenyl]-1H-pyrazole-4-carboxamide (262): 3:1-1:1 hexane:EtOAc, white solid (29%): $R_f$ (1:1 hexane:EtOAc) 0.70; $^1$H-NMR (CDCl$_3$ 500 MHz) 8.60 (s, 1H), 8.14 (m, 1H), 8.06 (s, 4H), 7.99 (d, 2H), 7.88 (d, 2H), 7.70 (d, 1H), 7.63 (d, 1H), 7.50 (t, 1H), 7.46 (d, 1H), 3.14 (s, 3H).

Methyl 1-(4-cyanophenyl)-3-[4-(methylsulfonyl)phenyl]-1H-pyrazole-4-carboxylate (263): 2:1-1:1 hexane:EtOAc, white solid (62%): $R_f$ (1:1 hexane:EtOAc) 0.47; $^1$H-NMR (CDCl$_3$ 500 MHz) 8.66 (s, 1H), 8.15 (d, 2H), 8.07 (d, 2H), 7.97 (d, 2H), 7.65 (d, 2H), 3.90 (s, 3H), 3.13 (s, 3H).

1-(3-Fluorophenyl)-N-(3-fluorophenyl)-3-[4-(methylsulfonyl)phenyl]-1H-pyrazole-4-carboxamide (264): 3:1-0:1 hexane:EtOAc, white solid (21%): $R_f$ (1:1 hexane:EtOAc) 0.53; $^1$H-NMR (CDCl$_3$ 500 MHz) 8.54 (s, 1H), 8.11 (bs, 4H), 7.61 (m, 2H), 7.53 (m, 2H), 7.40 (bs, 1H), 7.15 (m, 1H), 6.98 (m, 1H), 6.89 (m, 1H), 3.15 (s, 3H).

1-(3-Fluorophenyl)-N-(3,4-difluorophenyl)-3-[4-(methylsulfonyl)phenyl]-1H-pyrazole-4-carboxamide (265): 2:1-1:1 hexane:EtOAc, white solid (50%): $R_f$ (1:1 hexane:EtOAc) 0.41; $^1$H-NMR (CDCl$_3$ 500 MHz) 8.54 (s, 1H), 8.08 (s, 4H), 7.68 (m, 1H), 7.61 (m, 1H), 7.55 (m, 2H), 7.14 (m, 2H), 6.98 (m, 1H), 3.14 (s, 3H).

1-(3-Fluorophenyl)-N-(3-trifluoromethylphenyl)-3-[4-(methylsulfonyl)phenyl]-1H-pyrazole-4-carboxamide (266): 2:1-1:1 hexane:EtOAc, white solid (66%): $R_f$ (1:1 hexane:EtOAc) 0.46; $^1$H-NMR (CDCl$_3$ 500 MHz) 8.48 (s, 1H), 8.04 (d, 2H), 7.98 (d, 2H), 7.91 (d, 2H), 7.68 (d, 1H), 7.61 (m, 2H), 7.52 (m, 2H), 7.43 (d, 1H), 7.15 (bt, 1H), 3.12 (s, 3H).

Methyl 1-(3-fluorophenyl)-3-[4-(methylsulfonyl)phenyl]-1H-pyrazole-4-carboxylate (267): 1:1 hexane:EtOAc, white solid (62%): R$_f$ (1:1 hexane:EtOAc) 0.42; $^1$H-NMR (CDCl$_3$ 500 MHz) 8.57 (s, 1H), 8.16 (d, 2H), 8.05 (d, 2H), 7.60 (bt, 2H), 7.51 (m, 1H), 7.14 (bt, 1H), 3.89 (s, 3H), 3.14 (s, 3H).

1-(3-Cyanophenyl)-N-(3-fluorophenyl)-3-[4-(methylsulfonyl)phenyl]-1H-pyrazole-4-carboxamide (268): 2:1-1:1 hexane:EtOAc, white solid (82%): R$_f$ (1:1 hexane:EtOAc) 0.33; $^1$H-NMR (CDCl$_3$ 300 MHz) 8.59 (s, 1H), 8.10 (m, 9H), 7.69 (m, 3H), 6.95 (d, 1H), 3.13 (s, 3H).

1-(3-Cyanophenyl)-N-(3,4-difluorophenyl)-3-[4-(methylsulfonyl)phenyl]-1H-pyrazole-4-carboxamide (269): 3:1-1:1 hexane:EtOAc, white solid (91%): R$_f$ (1:1 hexane:EtOAc) 0.24; $^1$H-NMR (CDCl$_3$ 300 MHz) 8.61 (s, 1H), 8.10 (m, 8H), 7.65 (m, 1H), 7.64 (m, 1H), 6.94 (d, 1H), 3.13 (s, 3H).

1-(3-Cyanophenyl)-N-(3-trifluoromethylphenyl)-3-[4-(methylsulfonyl)phenyl]-1H-pyrazole-4-carboxamide (270): 2:1-1:1 hexane:EtOAc, white solid (24%): R$_f$ (1:1 hexane:EtOAc) 0.50; $^1$H-NMR (CDCl$_3$ 300 MHz) 8.59 (s, 1H), 8.19 (m, 1H), 8.05 (d, 4H), 7.88 (bs, 2H), 7.70 (m, 2H), 7.48 (m, 2H), 3.13 (s, 3H).

Methyl 1-(3-cyanophenyl)-3-[4-(methylsulfonyl)phenyl]-1H-pyrazole-4-carboxylate (271): 2:1-1:1 hexane:EtOAc, white solid (100%): R$_f$ (1:1 hexane:EtOAc) 0.60; $^1$H-NMR (CDCl$_3$ 300 MHz) 8.62 (s, 1H), 8.15 (d, 2H), 8.06 (d, 2H), 7.00 (m, 2H), 3.89 (s, 3H), 3.13 (s, 3H).

N-(3,4-Difluorophenyl)-3-[4-(methylsulfonyl)phenyl]-1-[4-trifluoromethoxy)phenyl]-1H-pyrazole-4-carboxamide (272): flash chromatography (3:1-2:1 hexane:EtOAc) to generate the product as a white solid (40%): R$_f$ (3:1 hexane:EtOAc) 0.78; $^1$H-NMR (CDCl$_3$ 300 MHz) 8.28 (s, 1H), 8.09 (bs, 1H), 7.85 (d, 2H), 7.74 (m, 3H), 7.61 (m, 1H), 7.32 (m, 2H), 7.04 (m, 2H), 2.99 (s, 3H).

Methyl 4-{4-[(3-fluorophenyl)carbamoyl]-3-[4-(methylsulfonyl)phenyl]-1H-pyrazol-1-yl} benzoate (273): flash chromatography (5:1-1:1 hexane:EtOAc) to generate the product as a white solid (40%): R$_f$ (1:1 hexane:EtOAc) 0.57; $^1$H-NMR (CDCl$_3$ 300 MHz) 8.62 (s, 1H), 8.24 (d, 2H), 8.11 (s, 4H), 7.91 (d, 2H), 7.53 (m, 1H), 7.25 (m, 1H), 6.92 (m, 2H), 4.00 (s, 3H), 3.14 (s, 3H).

Methyl 4-{4-[(2-hydroxyphenyl)carbamoyl]-[4-(methylsulfonyl)phenyl]-1H-pyrazol-1-yl} benzoate (274): flash chromatography (5:1-0:1 hexane:EtOAc) to generate the product as a white solid (47%): R$_f$ (1:1 hexane:EtOAc) 0.17; $^1$H-NMR (CDCl$_3$ 300 MHz) 8.75 (s, 1H), 8.48 (s, 1H), 8.22 (m, 4H), 8.05 (m, 2H), 7.92 (m, 5H), 4.00 (s, 3H), 3.07 (s, 3H).

2-Aminophenyl 1-[4-(methoxycarbonyl)phenyl]-3-[4-(methylsulfonyl)phenyl]-1H-pyrazole-4-carboxylate (275): flash chromatography (5:1-0:1 hexane:EtOAc) to generate the product as a yellow solid (36%): R$_f$ (1:1 hexane:EtOAc) 0.50; $^1$H-NMR (CDCl$_3$ 300 MHz) 8.68 (s, 1H), 8.38 (bs, 1H), 8.20 (m, 3H), 8.03 (m, 5H), 7.89 (m, 2H), 7.55 (d, 1H), 7.09 (m, 1H), 6.96 (m, 1H), 6.88 (m, 1H), 3.98 (s, 3H), 3.10 (s, 3H).

4-{4-[(3-Fluorophenyl)carbamoyl]-[4-(methylsulfonyl)phenyl]-1H-pyrazol-1-yl}benzoic acid (276): flash chromatography (1:0-8:1 EtOAc:CH$_3$OH) to generate the product as a white solid (94%): R$_f$ (EtOAc) 0.18; $^1$H-NMR (DMSO/CD$_3$OD 300 MHz) 9.11 (s, 1H), 8.11 (dd, 8H), 7.65 (m, 1H), 7.36 (m, 2H), 6.87 (m, 1H), 3.19 (s, 3H).

4-{4-[(2-Hydroxyphenyl)carbamoyl]-[4-(methylsulfonyl)phenyl]-1H-pyrazol-1-yl}benzoic acid (277): flash chromatography (1:0-8:1 EtOAc:CH$_3$OH) to generate the product as a white solid (37%): R$_f$ (EtOAc) 0.18; $^1$H-NMR (CDCl$_3$ 300 MHz) 8.57 (s, 1H), 8.17 (d, 2H), 8.07 (d, 2H), 7.97 (d, 2H), 7.85 (d, 2H), 7.63 (m, 1H), 7.44 (m, 2H), 3.04 (s, 3H).

N-(2-Aminophenyl)-3-[4-(methylsulfonyl)phenyl]-1-(pyridin-4-yl)-1H-pyrazole-4-carboxamide (278): flash chromatography (1:1-0:1 hexane:EtOAc) to generate the product as a white solid (19%): R$_f$ (8:1 EtOAc:CH$_3$OH) 0.70; $^1$H-NMR (CD$_3$OD 300 MHz) 9.21 (s, 1H), 8.72 (d, 2H), 8.26 (d, 1H), 8.17 (d, 2H), 8.07 (d, 4H), 8.03 (dd, 1H), 7.23 (dd, 1H), 7.64 (dd, 1H), 3.21 (s, 3H).

3-{4-[(Difluoroacetyl)amino]phenyl}-1-(4-cyanophenyl)-N-(3-fluorophenyl)-1H-pyrazole-4-carboxamide (279): Amine material (0.012 g, 32 umol) in 2 ml DMF was stirred overnight with triethylamine (7.0 ul, 64 umol) and difluoroacetyl chloride (4.0 ul, 35 umol). The solvent was removed by rotary evaporation and the residue purified by flash chromatography (3:1-0:1 hexane:EtOAc) to yield the target as a white solid (44%): R$_f$ (1:1 hexane:EtOAc) 0.50; $^1$H-NMR (CDCl$_3$ 300 MHz) 8.54 (s, 1H), 8.21 (bs, 1H), 7.72 (m, 6H), 7.40 (m, 6H), 7.18 (m, 1H), 6.78 (m, 3H), 6.032 (s, 1H); ESMS 505 (M+Na), 100%), 483 (M+H, 33%); HRMS C24H18FN4O2Cl2 calc 483.0785 found 452.483.0770.

1-(4-Formylphenyl)-3-[4-(methylsulfonyl)phenyl]-N-(3-fluorophenyl)-1H-pyrazole-4-carboxamide (280): The nitrile (0.100 g, 217 umol) suspended in 25 ml THF (freshly distilled over LiAlH4) was stirred with 1 M diisobutylaluminm hydride (5.0 ml) for 1.5 h. The now red solution was quenched with 3 ml 1:1 CH$_3$OH: 1 M H$_2$SO$_4$ was added and the solution refluxed for 30 min. Water (10 ml) was added and the reaction neutralized with ~25 ml sat'd NaHCO$_3$ (aq), extracted 4×10 ml DCM. The solvent was removed by rotary evaporation and the residue purified by flash chromatography (3:1-0:1 hexane:EtOAc) to generate the product as a white solid (7%): R$_f$ (1:1 hexane:EtOAc) 0.51; $^1$H-NMR (CDCl$_3$ 300 MHz) 9.96 (s, 1H), 8.06 (s, 1H), 7.90 (m, 8H), 7.08 (m, 1H), 6.37 (m, 3H), 3.01 (s, 3H); ESMS 462 (M–H, 100%).

1-{4-[(E)-(Hydroxyimino)methyl]phenyl}-N,3-diphenyl-1H-pyrazole-4-carboxamide (281): The aldehyde (0.005 g, 11 umol) in 5 ml pyridine was refluxed overnight with hydroxylamine hydrochloride (0.004 g, 65 umol). The solvent was removed by rotary evaporation and the residue purified by flash chromatography (2:1-1:1 hexane:EtOAc) to generate the product as a white solid (100%): R$_f$ (1:1 hexane:EtOAc) 0.50; $^1$H-NMR (CDCl$_3$ 300 MHz) 8.18 (s, 1H), 8.12 (m, 5H), 7.78 (m, 4H), 7.21 (m, 1H), 6.46 (m, 3H), 3.08 (s, 3H).

1-(4-Hydroxymethylphenyl)-3-[4-(methylsulfonyl)phenyl]-N-(3-fluorophenyl)-1H-pyrazole-4-carboxamide (282): The aldehyde (0.008 g, 17 umol) was stirred overnight with sodium borohydride (0.001 g, 35 umol) in 1.5 ml THF. The solvent was removed by rotary evaporation and the residue purified by flash chromatography (2:1-0:1 hexane:EtOAc) to generate the product as a white solid (75%): R$_f$ (1:1 hexane:EtOAc) 0.25; $^1$H-NMR (CDCl$_3$ 300 MHz) 7.97 (s, 1H), 7.94 (m, 4H), 7.65 (d, 2H), 7.40 (d, 2H), 7.08 (m, 1H), 6.38 (m, 3H), 4.30 (s, 2H), 3.02 (s, 3H).

1-(4-Carbomylphenyl)-3-[4-(methylsulfonyl)phenyl]-N-(3-fluorophenyl)-1H-pyrazole-4-carboxamide (283): The carboxylic acid (0.006 g, 13 umol) in 0.4 ml DMF was stirred overnight with EDCI (2 eqv), HOBt (2 eqv), TEA (2 eqv) and 100 ul 0.5 M ammonia in dioxane whereupon 1 ml 1 M HCl and 5 ml H$_2$O were added, the solution extracted 2×5 ml DCM, the solvent removed by rotary evaporation and the residue purified by flash chromatography (1:1-0:1 hexane:EtOAc) to generate the product as a white solid (83%): R$_f$ (EtOAc) 0.52; $^1$H-NMR (CDCl$_3$ 300 MHz) 8.12 (s, 1H), 8.09 (d, 1H), 8.04 (s, 4H), 8.00 (m, 5H), 7.88 (m, 4H), 3.12 (s, 3H).

1-(4-Hydroxycarbomylphenyl)-3-[4-(methylsulfonyl)phenyl]-N-(3-fluorophenyl)-1H-pyrazole-4-carboxamide (284): The carboxylic acid (0.006 g, 13 umol) in 0.4 ml DMF was stirred overnight with EDCI (2 eqv), HOBt (2 eqv), TEA (2 eqv) and hydroxylamine hydrochloride (0.010 g, 144 umol) whereupon 1 ml 1 M HCl and 5 ml H$_2$O were added, the solution extracted 2×5 ml DCM, the solvent removed by rotary evaporation and the residue purified by flash chromatography (1:1-0:1 hexane:EtOAc) to generate the product as a white solid (33%): R$_f$ (EtOAc) 0.63; $^1$H-NMR (CDCl$_3$ 500 MHz) 8.00 (m, 5H), 7.45 (m, 2H), 7.29 (m, 2H), 7.06 (m, 1H), 6.75 (m, 3H), 3.04 (s, 3H).

1-(4-Methylcarbomylphenyl)-3-[4-(methylsulfonyl)phenyl]-N-(3-fluorophenyl)-1H-pyrazole-4-carboxamide (285): The carboxylic acid (0.006 g, 13 umol) in 0.4 ml DMF was stirred overnight with EDCI (2 eqv), HOBt (2 eqv), TEA (2 eqv) and 100 ul 2.0 M methylamine in THF whereupon 1 ml 1 M HCl and 5 ml H$_2$O were added, the solution extracted 2×5 ml DCM, the solvent removed by rotary evaporation and the residue purified by flash chromatography (1:1-0:1 hexane:EtOAc) to generate the product as a white solid (33%): R$_f$ (EtOAc) 0.50; $^1$H-NMR (CDCl$_3$ 300 MHz) 8.09 (s, 1H), 8.04 (m, 5H), 7.89 (m, 4H), 7.35 (m, 1H), 6.50 (d, 1H), 6.19 (m, 2H), 3.12 (s, 3H), 3.07 (d, 3H).

1-(4-Dimethylcarbomylphenyl)-3-[4-(methylsulfonyl)phenyl]-N-(3-fluorophenyl)-1H-pyrazole-4-carboxamide (286): The carboxylic acid (0.006 g, 13 umol) in 0.4 ml DMF was stirred overnight with EDCI (2 eqv), HOBt (2 eqv), TEA (2 eqv) and 100 ul 2.0 M dimethylamine in THF whereupon 1 ml 1 M HCl and 5 ml H$_2$O were added, the solution extracted 2×5 ml DCM, the solvent removed by rotary evaporation and the residue purified by flash chromatography (1:1-0:1 hexane:EtOAc) to generate the product as a white solid (50%): R$_f$ (EtOAc) 0.50; $^1$H-NMR (CDCl$_3$ 300 MHz) 8.09 (s, 1H), 7.95 (m, 6H), 7.73 (d, 2H), 7.51 (d, 2H), 7.24 (m, 1H), 7.16 (m, 1H), 6.41 (m, 2H), 3.02 (s, 9H).

1-(4-Cyanophenyl)-N-(3-fluorophenyl)-3-(4-nitrophenyl)-1H-pyrazole-4-carboxamide (287): flash chromatography (3:1-1:1 hexane:EtOAc) to generate the product as a yellow solid (9%): R$_f$ (1:1 hexane:EtOAc) 0.71; $^1$H-NMR (CDCl$_3$ 300 MHz) 8.64 (s, 1H), 8.39 (m, 5H), 8.07 (m, 2H), 7.91 (m, 5H).

Methyl 4-{1-(4-cyanophenyl)-4-[(3-fluorophenyl)carbamoyl]-1H-pyrazol-3-yl}benzoate (288): flash chromatography (3:1-0:1 hexane:EtOAc) to generate the product as a off-white solid (52%): R$_f$ (1:1 hexane:EtOAc) 0.72; $^1$H-NMR (CDCl$_3$ 300 MHz) 8.69 (s, 1H), 8.26 (d, 2H), 7.97 (d, 2H), 7.86 (m, 4H), 7.45 (m, 1H), 7.37 (m, 1H), 6.86 (m, 2H), 4.01 (s, 3H).

1-(4-Cyanophenyl)-N-(3-fluorophenyl)-3-[4-(hydroxymethyl)phenyl]-1H-pyrazole-4-carboxamide (289): The corresponding methyl ester (0.026 g, 54 umol) in 5 mL 4:1 THF:CH$_3$OH was stirred overnight with NaBH$_4$ (0.034 g, 910 umol). The reaction was quenched by adding slowly adding 1 M HCl (aq) until bubbling stopped whereupon the solvent was removed by rotary evaporation and the residue purified by flash chromatography (2:1-1:1 hexane:EtOAc) to generate the product as a off-white solid (33%): R$_f$ (1:1 hexane:EtOAc) 0.45; $^1$H-NMR (CDCl$_3$ 300 MHz) 8.71 (s, 1H), 8.20 (m, 1H), 7.95 (d, 2H), 7.88 (m, 1H), 7.85 (m, 3H), 7.76 (d, 2H), 7.62 (d, 2H), 7.48 (bs, 1H), 7.38 (m, 1H), 7.23 (m, 1H), 6.84 (m, 2H), 4.88 (s, 2H).

3-[4-(Chloromethyl)phenyl]-1-(4-cyanophenyl)-N-(3-fluorophenyl)-1H-pyrazole-4-carboxamide (290): The benzyl alcohol (0.005 g, 11 umol) was stirred overnight with POCl$_3$ (1.8 ul, 22 umol) in 0.5 ml DCM whereupon another 20 ul reagent was added and the reaction refluxed for 1.5 h. The solvent was removed by rotary evaporation and the residue purified by flash chromatography (3:1-1:1 hexane:EtOAc) to generate the product as a white solid (40%): R$_f$ (1:1 hexane:EtOAc) 0.87; $^1$H-NMR (CDCl$_3$ 300 MHz) 8.70 (s, 1H), 7.96 (m, 2H), 7.82 (m, 4H), 7.63 (d, 2H), 7.35 (m, 3H), 6.83 (m, 2H), 4.72 (s, 2H).

2-(Acetyloxy)phenyl 1-(3-chlorophenyl)-3-[4-(methylsulfonyl)phenyl]-1H-pyrazole-4-carboxylate (291): The phenol (0.013 g, 29 umol) was stirred overnight in 5 ml DCM with acetic anhydride (5.4 ul, 58 umol), 50 ul pyridine and 0.001 mg DMAP. The solvent was removed and the residue purified by flash chromatography (3:1:-1:1 hexane:EtOAc) to generate the product as a white solid (43%): R$_f$ (1:1 hexane:EtOAc) 0.43; $^1$H-NMR (CDCl$_3$ 300 MHz) 8.63 (s, 1H), 8.13 (m, 2H), 8.04 (m, 5H), 7.70 (m, 2H), 7.52 (m, 1H), 7.45 (m, 3H), 7.13 (m, 1H), 3.23 (s, 3H), 2.43 (s, 3H).

2-(Acetylamino)phenyl 1-(3-chlorophenyl)-3-[4-(methylsulfonyl)phenyl]-1H-pyrazole-4-carboxylate (292): The arylamine (0.006 g, 13 umol) was stirred overnight in 3 ml DCM with acetic anhydride (3.0 ul, 26 umol), 50 ul pyridine and 0.001 mg DMAP. The solvent was removed and the residue purified by flash chromatography (2:1-0:1 hexane:EtOAc) to generate the product as a white solid (14%): R$_f$ (1:1 hexane:EtOAc) 0.14; $^1$H-NMR (CDCl$_3$ 300 MHz) 8.60 (s, 1H), 8.13 (m, 2H), 8.00 (m, 2H), 7.95 (s, 4H), 7.81 (m, 1H), 7.61 (m, 1H), 7.40 (m, 6H), 3.06 (s, 3H), 2.35 (s, 3H).

2-(Acetyloxy)phenyl 1-(4-fluorophenyl)-3-[4-(methylsulfonyl)phenyl]-1H-pyrazole-4-carboxylate (293): The phenol (0.046 g, 102 umol) was stirred overnight in 5 ml DCM with acetic anhydride (100 ul), 1 ml pyridine and 0.001 mg DMAP. The solvent was removed and the residue purified by flash chromatography (3:1:-0:1 hexane:EtOAc) to generate the product as a white solid (74%): R$_f$ (1:1 hexane:EtOAc) 0.28; $^1$H-NMR (CDCl$_3$ 500 MHz) 8.03 (m, 4H), 7.93 (s, 1H), 7.58 (m, 2H), 7.42 (m, 1H), 7.26 (m, 2H), 7.16 (m, 3H), 3.12 (s, 3H), 2.29 (s, 3H).

3-{4-[(Chloroacetyl)amino]phenyl}-N-(3-fluorophenyl)-1-phenyl-1H-pyrazole-4-carboxamide (294): The starting amine (0.020 g, 49 umol) was stirred overnight in 1 ml DMF with chloroacetyl chloride (4.3 ul, 54 umol) and triethylamine (11.2 ul, 103 umol). H$_2$O (5 ml) and 1 ml 1M HCl (aq) were added and the mixture extracted with 5 ml DCM. The organics was washed 2×5 ml H$_2$O, 5 ml brine and dried with anhyd MgSO4, filtered and the solvent was removed by rotary evaporation and the residue by flash chromatography (3:1-1:1 hexane:EtOAc) to yield the target as a white solid (23%): R$_f$ (3:1 hexane:EtOAc) 0.33; $^1$H-NMR (CDCl$_3$ 300 MHz) 8.59 (s, 1H), 8.42 (bs, 1H), 7.77 (m, 6H), 7.53 (m, 3H), 7.40 (m, 2H), 7.22 (m, 1H), 6.88 (m, 1H), 6.80 (m, 1H), 4.26 (s, 2H).

4-{1-(4-Cyanophenyl)-4-[(3-fluorophenyl)carbamoyl]-1H-pyrazol-3-yl}benzoic acid (295): The methyl ester (0.171 g, 388 umol) was refluxed overnight in 25 ml CH$_3$OH, 3 ml DCM and sodium hydroxide (0.033 g, 815 umol) dissolved 1.6 ml H$_2$O. The reaction was acidified with 3 ml 1 M HCl (aq), diluted with 25 ml H$_2$O and the solvent partially removed by rotary evaporation. The remaining ~17 ml solution was extracted 3×10 ml DCM and 3×10 ml EtOAc. The combined organics were dried with anhyd MgSO$_4$, filtered, the solvent was removed by rotary evaporation and the residue purified by flash chromatography (2:1-0:1 hexane:EtOAc) to yield the target as a off-white solid (33%): R$_f$ (EtOAc) 0.07; $^1$H-NMR (DMSO 300 MHz)

9.32 (s, 1H), 8.18 (d, 2H), 8.09 (d, 2H), 8.01 (m, 5H), 7.68 (d, 2H), 7.42 (m, 3H), 6.96 (m, 1H); ESMS 426 (M–H, 100%).

1-(4-Cyanophenyl)-N-(3-fluorophenyl)-3-[4-(methoxy (methyl)carbamoyl]phenyl}]-1H-pyrazole-4-carboxamide (296): Starting carboxylic acid (0.054 g, 15 umol) was reacted with EDC as described to yield after flash chromatography (2:1-0:1 hexane:EtOAc) to yield the target as a white solid (100%): $R_f$ (1:1 hexane:EtOAc) 0.43; $^1$H-NMR (CDCl$_3$ 300 MHz) 8.70 (s, 1H), 7.79 (m, 8H), 7.44 (m, 4H), 7.23 (m, 1H), 7.00 (d, 1H), 6.82 (m, 1H), 3.60 (s, 3H), 3.43 (s, 3H); ESMS 470 (100%, M+H), 492 (67%, M+Na); $C_{26}H_{21}FN_5O_3$ calc 470.1623, found 470.1620.

Methyl 4-{4-[(2-acetoxyphenyl)carbamoyl]-3-[4-(methylsulfonyl)phenyl]-1H-pyrazol-1-yl}benzoate (297): The starting phenol (0.010 g, 20 umol) in 2 ml 1:1 pyridine:DCM was stirred with acetic anhydride (150 ul) and DMAP (0.001 g) overnight. The solvent was removed by rotary evaporation and the residue purified by flash chromatography (2:1-1:1 hexane:EtOAc) to yield the target as a white solid (100%): $R_f$ (1:1 hexane:EtOAc) 0.48; $^1$H-NMR (CDCl$_3$ 300 MHz) 8.15 (d, 2H), 8.09 (s, 1H), 8.06 (m, 5H), 7.70 (d, 2H), 7.43 (m, 1H), 7.24 (m, 1H), 7.15 (m, 1H), 3.98 (s, 3H), 3.12 (s, 3H), 2.43 (s, 3H).

2-(Acetylamino)phenyl 1-[4-(methoxycarbonyl)phenyl]-3-[4-(methylsulfonyl)phenyl]-1H-pyrazole-4-carboxylate (298): The aromatic amine (0.015 g, 31 umol) in 4 ml 1:1 DCM:pyridine was stirred overnight with acetic anhydride (0.150 ml) and DMAP (0.001 g). Flash chromatography (2:1-0:1 hexane:EtOAc) generated the product as a white solid (33%): $R_f$(1:1 hexane:EtOAc) 0.06; $^1$H-NMR (CDCl$_3$ 300 MHz) 8.72 (s, 1H), 8.20 (d, 2H), 8.10 (m, 5H), 7.85 (d, 2H), 7.50 (m, 1H), 7.36 (m, 1H), 7.25 (m, 1H), 3.98 (s, 3H), 3.08 (s, 3H), 3.04 (s, 3H).

3-(3-Chlorophenyl)-N-(2-methylphenyl)-1-phenyl-1H-pyrazole-4-carboxamide (299): flash chromatography (6:1-4:1 hexane:EtOAc) to generate the product as a white solid (78%): $R_f$ (3:1 hexane:EtOAc) 0.62; $^1$H-NMR (CDCl$_3$ 500 MHz) 8.62 (s, 1H), 8.07 (bd, 1H), 7.81 (m, 3H), 7.67 (d, 1H), 7.54 (m, 5H), 7.41 (t, 1H), 7.27 (m, 2H), 7.11 (dd, 2H), 1.84 (s, 3H).

3-(3-Chlorophenyl)-N-(3-methylphenyl)-1-phenyl-1H-pyrazole-4-carboxamide (300): flash chromatography (6:1-4:1 hexane:EtOAc) to generate the product as a white solid (78%): $R_f$ (3:1 hexane:EtOAc) 0.60; $^1$H-NMR (CDCl$_3$ 500 MHz) 8.58 (s, 1H), 7.85 (s, 1H), 7.79 (d, 2H), 7.69 (d, 1H), 7.52 (m, 5H), 7.42 (m, 2H), 7.29 (bs, 1H), 7.23 (m, 1H), 7.14 (m, 1H), 6.96 (d, 1H), 2.40 (s, 3H).

3-(3-Chlorophenyl)-N-(4-methylphenyl)-1-phenyl-1H-pyrazole-4-carboxamide (301): flash chromatography (6:1-4:1 hexane:EtOAc) to generate the product as a white solid (94%): $R_f$ (3:1 hexane:EtOAc) 0.60; $^1$H-NMR (CDCl$_3$ 500 MHz) 8.58 (s, 1H), 7.85 (s, 1H), 7.79 (d, 2H), 7.69 (d, 1H), 7.51 (m, 4H), 7.40 (m, 2H), 7.28 (d, 1H), 7.13 (d, 2H), 2.34 (s, 3H).

3-(3-Chlorophenyl)-N-phenyl-1-phenyl-1H-pyrazole-4-carboxamide (302): flash chromatography (6:1-4:1 hexane:EtOAc) to generate the product as a white solid (76%): $R_f$ (3:1 hexane:EtOAc) 0.59; $^1$H-NMR (CDCl$_3$ 500 MHz) 8.59 (s, 1H), 7.85 (s, 1H), 7.79 (d, 2H), 7.69 (d, 1H), 7.53 (m, 4H), 7.46 (s, 1H), 7.41 (m, 3H), 7.34 (t, 2H), 7.14 (t, 1H).

3-(3-Chlorophenyl)-N-(2-fluorophenyl)-1-phenyl-1H-pyrazole-4-carboxamide (303): flash chromatography (6:1-4:1 hexane:EtOAc) to generate the product as a white solid (22%): $R_f$ (3:1 hexane:EtOAc) 0.59; $^1$H-NMR (CDCl$_3$ 500 MHz) 8.96 (s, 1H), 8.12 (d, 1H), 7.99 (m, 1H), 7.88 (m, 3H), 7.58 (m, 2H), 7.52 (m, 2H), 7.46 (m, 2H).

3-(3-Chlorophenyl)-N-(4-fluorophenyl)-1-phenyl-1H-pyrazole-4-carboxamide (304): flash chromatography (6:1-4:1 hexane:EtOAc) to generate the product as a white solid (67%): $R_f$(3:1 hexane:EtOAc) 0.57; $^1$H-NMR (CDCl$_3$ 500 MHz) 8.58 (s, 1H), 7.83 (m, 1H), 7.77 (m, 2H), 7.67 (dt, 1H), 7.51 (m, 4H), 7.48-33 (m, 3H), 7.02 (t, 2H).

Methyl 4-{4-[(2-hydroxyphenyl)carbamoyl]-3-[4-(methylsulfonyl)phenyl]-1H-pyrazol-1-yl}benzoate (305): flash chromatography (1:1-0:1 hexane:EtOAc) to generate the product as a white solid (29%): $R_f$(1:1 hexane:EtOAc) 0.50; $^1$H-NMR (CDCl$_3$ 300 MHz) 8.58 (s, 1H), 8.17 (dd, 2H), 7.90 (dd, 2H), 7.77 (m, 3H), 7.46 (d, 1H), 7.19 (m, 1H), 7.07 (m, 1H), 6.80 (d, 1H), 6.57 (d, 1H), 3.96 (s, 3H).

4-{4-[(3-Fluorophenyl)carbamoyl]-3-(4-hydroxyphenyl)-1H-pyrazol-1-yl}benzoic acid (306): flash chromatography (2:1-0:1 hexane:EtOAc) to generate the product as a white solid (100%): $R_f$ (1:1 hexane:EtOAc) 0.07; $^1$H-NMR (CDCl$_3$ 300 MHz) 8.53 (s, 1H), 8.07 (m, 6H), 7.79 (m, 4H), 7.60 (m, 2H), 7.45 (m, 1H), 6.80 (d, 1H), 3.04 (s, 3H).

4-{3-(4-Hydroxyphenyl)-4-[(2-hydroxyphenyl)carbamoyl]-1H-pyrazol-1-yl}benzoic acid (307): flash chromatography (2:1-0:1 hexane:EtOAc) to generate the product as a white solid (100%): $R_f$(1:1 hexane:EtOAc) 0.07; $^1$H-NMR (CDCl$_3$ 300 MHz) 9.19 (bs, 1H), 8.65 (s, 1H), 8.11 (m, 2H), 7.80 (m, 2H), 7.67 (bs, 1H), 7.56 (m, 2H), 7.00 (m, 4H), 6.72 (m, 1H), 6.43 (m, 1H).

N-(3-Fluorophenyl)-3-[4-(oxiran-2-ylcarbonyl)phenyl]-1-phenyl-1H-pyrazole-4-carboxamide (308): flash chromatography (3:1-0:1 hexane:EtOAc) generated the product as a white solid (24%): $R_f$ (1:1 hexane:EtOAc) 0.46; $^1$H-NMR (CDCl$_3$ 300 MHz) 8.59 (s, 1H), 8.01 (bs, 1H), 7.80 (m, 4H), 7.50 (m, 3H) 7.38 (m, 2H), 7.29 (m, 1H), 6.90 (m, 2H), 6.78 (m, 1H), 3.99 (t, 1H), 3.81 (d, 2H).

3-(4-Acryloylphenyl)-1-phenyl-1H-pyrazole-4-carbaldehyde (309): The starting methyl ester (0.436 g, 1.4 mmol) in 45 ml CH$_3$OH was hydrolyzed to the corresponding carboxylic acid by refluxing with sodium hydroxide (0.068 g, 1.7 mmol) in 1.5 ml H$_2$O overnight. H$_2$O (20 ml) was added and the solution acidified to pH~3 with 1 M HCl (aq), extracted 3×10 ml DCM, 3×10 ml EtOAc. The combined organics was dried with anhyd MgSO$_4$, solvent was removed by rotary evaporation and the residue purified by flash chromatography (1:0-8:1 EtOAc:CH$_3$OH) to yield the carboxylic acid as a yellow solid (0.277 g, 67%): $R_f$(EtOAc) 0.57; $^1$H-NMR (CDCl$_3$ 300 MHz) 10.10 (s, 1H), 8.57 (s, 1H), 8.20 (d, 2H), 8.01 (d, 2H), 7.81 (d, 2H), 7.54 (t, 2H), 7.42 (t, 1H). The carboxylic acid (5-81, 0.058 g, 198 umol) in 8 ml DCM was refluxed with thionyl chloride (29 ul, 397 umol) for 4 hr. After letting cool to room temp, tributylvinyltin (116 ul, 397 umol) and trans-benzyl(chloro)bis(phenylphosphine)palladium(II) (0.015 g, 20 umol) were added and the reaction which slowly turned black was refluxed for 2.5 h. The solution was washed 2×5 ml H$_2$O, dried with anhyd. MgSO$_4$ and then solvent was removed by rotary evaporation and the residue purified by flash chromatography (4:1-0:1 hexane:EtOAc) to yield the vinylketone as a yellow solid (0.031 g, 52%): $R_f$ (1:1 hexane:EtOAc) 0.83; $^1$H-NMR (CDCl$_3$ 500 MHz) 10.09 (s, 1H), 8.57 (s, 1H), 8.05 (dd, 4H), 7.81 (d, 2H), 7.54 (t, 2H), 7.43 (t, 1H), 7.21 (dd, 1H), 6.49 (d, 1H), 5.99 (d, 1H). Procedure adapted from Milstein D, Stille J K, Mild, selective, general method of ketone synthesis from acid chlorides and organotin compounds catalyzed by palladium. 1979 J Org Chem 44(10) 1613-18.

3-{4-[(Dichloroacetyl)amino]phenyl}-1-(4-cyanophenyl)-N-(3-fluorophenyl)-1H-pyrazole-4-carboxamide (310): The carboxylic acid was coupled in DMF with 3-fluoroaniline (2 eqv) using HATU (1.1 eqv) and DIPEA (1.1 eqv) overnight whereupon the solution was diluted with water, acidified with 1 M HCl (aq) and extracted 3×DCM. The DCM extracts were washed with water and brine and then dried using anhyd MgSO4, filtered and the solvent removed by rotary evaporation. The residue was purified by flash chromatography (5:1-3:1 hexane:EtOAc) to provide the product as a white solid (43%): $R_f$ (3:1 hexane:EtOAc) 0.38; $^1$H-NMR (CDCl$_3$ 500 MHz) 8.58 (s, 1H), 8.28 (d, 2H), 8.03 (d, 2H), 7.83 (d, 2H), 7.57 (t, 2H), 7.55 (d, 1H), 7.43 (t, 1H), 7.39 (bs, 1H), 7.26 (q, 1H), 6.96 (d, 1H), 6.86 (dt, 1H), 6.72 (s, 1H), 4.00 (s, 2H); ESMS 469 (M+1, 100%), HRMS C$_{24}$H$_{17}$FCl$_2$N$_3$O$_2$ calc 468.0676, found 468.0673.

Methyl 2-(4-{4-[(3-fluorophenyl)carbamoyl]-1-phenyl-1H-pyrazol-3-yl}phenyl)prop-2-enoate (311): The starting bromide (107 mg, 245 umol) was refluxed in 25 ml toluene under Ar with 2-(tributylstannyl)acrylic acid methyl ester (0.138 g, 368 umol) and tetrakis(triphenylphosphoryl)palladium(0). The now black solution was removed by rotary evaporation and the residue dissolved in 30 ml THF. 1 M HCl (aq) was added and the mix stirred for 30 min whereupon 30 ml H$_2$O was added and the solution basified so pH~8 with sat'd NaHCO$_3$ (aq). The solution was extracted 3×10 ml DCM and the combined organics dried with anhyd MgSO4, filter and flashed (5:1 hexane:EtOAc) to provide the target as a white solid (14%): $R_f$ (3:1 hexane:EtOAc) 0.41; $^1$H-NMR (CDCl$_3$ 500 MHz) 8.63 (s, 1H), 7.79 (m, 4H), 7.64 (d, 2H), 7.53 (m, 3H), 7.41 (m, 1H), 7.26 (q, 1H), 6.93 (d, 1H), 6.81 (dt, 1H), 6.52 (s, 1H), 6.04 (s, 1H), 3.90 (s, 3H); ESMS 465 (M+Na, 100%).

Methyl 2-(4-{4-[(3-fluorophenyl)carbamoyl]-1-4-cyanophenyl-1H-pyrazol-3-yl}phenyl)prop-2-enoate (312): Procedure was identical to that of compound 311: flashed (5:1-3:1 hexane:EtOAc) to provide the target as a white solid (14%): $R_f$ (3:1 hexane:EtOAc) 0.26; $^1$H-NMR (CDCl$_3$ 500 MHz) 8.72 (s, 1H), 7.98 (d, 2H), 7.85 (d, 2H), 7.77 (d, 2H), 7.68 (d, 2H), 7.47 (t, 1H), 7.38 (bs, 1H), 7.26 (q, 1H), 6.91 (d, 1H), 6.84 (m, 1H), 6.54 (s, 1H), 6.06 (s, 1H), 3.91 (s, 3H); ESMS 354 (M+H, 100%).

3-{4-[(Cyclopropylcarbonyl)amino]phenyl}-N-(3-fluorophenyl)-1-methyl-1H-pyrazole-4-carboxamide (313): flash chromatography (6:1-0:1hexane:EtOAc) generated the product as a white solid (56%): $R_f$ (3:1 hexane:EtOAc) 0.20; $^1$H-NMR (CDCl$_3$ 500 MHz) 8.56 (s, 1H), 7.90 (bs, 1H), 7.74 (d, 2H), 7.69 (m, 6H), 7.48 (t, 2H), 7.49 (m, 1H), 7.36 (m, 1H), 7.19 (m, 1H), 6.88 (d, 1H), 6.77 (m, 1H), 1.12 (m, 2H), 1.04 (m, 1H), 0.88 (m, 2H).

3-[4-(Acryloylamino)phenyl]-N-(3-fluorophenyl)-1-phenyl-1H-pyrazole-4-carboxamide (314): flash chromatography (3:1-2:1 hexane:EtOAc) generated the product as a white solid (13%): $R_f$ (1:1 hexane:EtOAc) 0.63; $^1$H-NMR (CDCl$_3$ 500 MHz) 8.54 (s, 1H), 7.72 (m, 7H), 7.48 (t, 2H), 7.43 (d, 1H), 7.35 (t, 1H), 7.20 (m, 1H), 6.89 (d, 1H), 6.77 (m, 1H), 6.48 (d, 1H), 6.30 (dd, 1H), 5.78 (d, 1H).

3-[4-(Hydroxyacetyl)amino)phenyl]-N-(3-fluorophenyl)-1-phenyl-1H-pyrazole-4-carboxamide (315): Starting amine (0.105 g, 282 umol) was refluxed overnight with methyl hydroxyacetate (0.295 g, 3254 umol) and triethylamine (1 ml). The solvent was removed by rotary evaporation and the residue purified by flash chromatography (3:1-0:1 hexane:EtOAc) to provide the product as a white solid (20%): $R_f$ (1:1 hexane:EtOAc) 0.75; $^1$H-NMR (CDCl$_3$ 500 MHz) 8.61 (s, 1H), 7.78 (m, 4H), 7.52 (m, 5H), 7.42 (d, 1H), 7.36 (t, 1H), 7.22 (q, 1H), 6.91 (d, 1H), 6.85 (d, 2H), 6.79 (t, 1H), 4.00 (s, 2H).

3-(4-Acetylphenyl)-N-(3-fluorophenyl)-1-(4-cyanophenyl)-1H-pyrazole-4-carboxamide (316): To the bromide (0.094 g, 213 umol) in 50 ml toluene was refluxed under Ar for 4 hours with tributyl(1-ethoxyvinyl)tin (216 ul, 640 umol) and tetrakis(triphenylphosphine)palladium(0) (0.013 g, 11 umol). Procedure then follows that of compound 311: flashed (5:1-3:1 hexane:EtOAc) to provide the target as a white solid (87%): $R_f$ (1:1 hexane:EtOAc) 0.69; $^1$H-NMR (CDCl$_3$ 500 MHz) 8.69 (s, 1H), 8.17 (d, 2H), 7.98 (d, 2H), 7.93 (d, 2H), 7.86 (d, 2H), 7.46 (d, 1H), 7.38 (bs, 1H), 7.26 (q, 1H), 6.88 (m, 2H), 2.73 (s, 3H).

3-(4-Dichloroacetamidophenyl)-N-(3-fluorophenyl)-1-(4-cyanophenyl)-1H-pyrazole-4-carboxamide (316a): To the amine (0.094 g, 213 umol) in 2 ml DMF was stirred overnight with TEA (12 ul, 113 umol) and dichloroacetylchloride (4 ul, 42 umol). The reaction was quenched with 8 ml acidic H$_2$O and extracted 3×5 ml DCM. The combined organic phases were washed 2×5 ml H$_2$O, dried with anhyd MgSO$_4$, filtered and the solvent removed by rotary evaporation. Flash chromatography of the residue (2:1-1:1 hexane:EtOAc) generated the product as a white solid (37%): $R_f$ (1:1 hexane:EtOAc) 0.82; $^1$H-NMR (CDCl$_3$ 500 MHz) 8.69 (s, 1H), 8.41 (d, 2H), 7.95 (m, 3H), 7.82 (m, 5H), 7.46 (m, 2H), 6.90 (m, 1H), 6.13 (s, 1H).

The following pyrazole compounds were prepared by the methods described above.

3-{4-Dichloroacetyl-N-methyl-aminophenyl}-N-(3-fluorophenyl)-1-phenyl-1H-pyrazole-4-carboxamide (7-239)

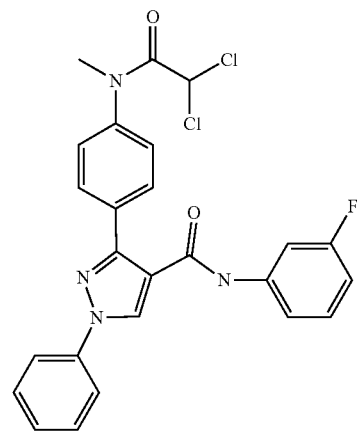

7-239

The starting methylphenylamine (0.004 g, 10 umol) in 2 ml DCM and 2 ml CH$_3$OH was refluxed for 2 hrs with DIPEA (100 ul, 574 umol) and dichloroacetic acid methyl ester (500 ul, 4830 umol). The solvent was removed by rotary evaporation and the residue purified by flash chromatography (4:1-3:1 hexane:EtOAc) to provide a white solid (80%): $R_f$ (3:1 hexane:EtOAc) 0.29; $^1$H-NMR (CD$_3$Cl 500 MHz) 8.54 (s, 1H), 7.70 (d, 2H), 7.67 (bs, 1H), 7.48 (d, 1H), 7.40 (t, 1H), 7.29 (m, 2H), 7.13 (q, 1H), 6.82 (d, 1H), 6.69 (m, 2H), 3.26 (s, 3H).

N-(3-Fluorophenyl)-3-(2-benzyloxyethyl)-1-phenyl-1H-pyrazole-4-carboxamide (7-240)

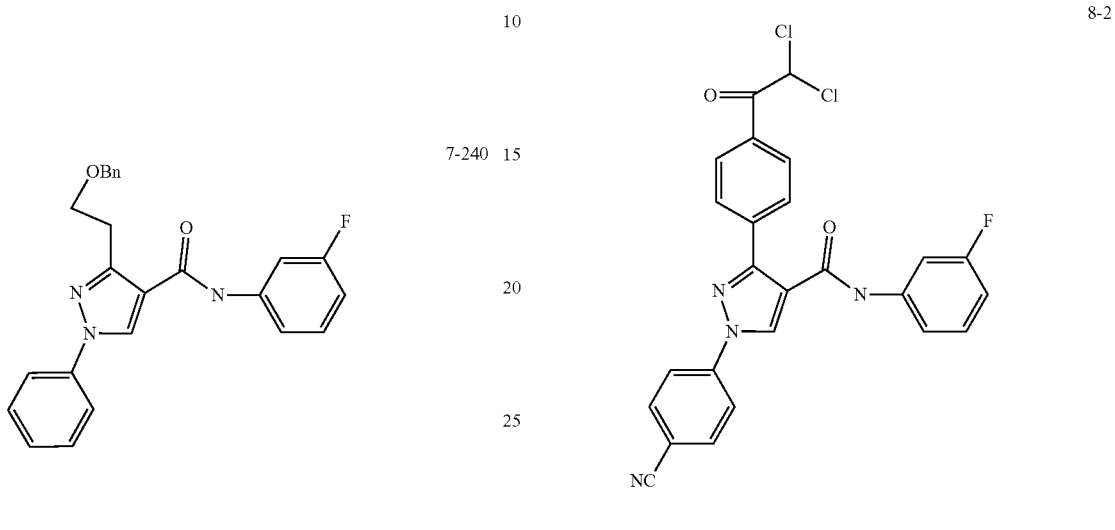

Step 1: Ethyl 5-(benzyloxy)-3-oxopentanoate (1987 J Org Chem 52, 192) (0.7 g, 2.8 mmol) was stirred overnight with N,N-dimethylformamide dimethyl acetal (0.446 ml, 3.4 mmol). The now orange solution was purified by flash chromatography to provide the desired compound (36%): $R_f$ (3:1 hexane:EtOAc) 0.20; $^1$H-NMR (CD$_3$Cl 500 MHz) 7.69 (s, 1H), 7.34 (m, 5H), 4.53 (s, 2H), 4.23 (q, 2H), 3.84 (t, 2H), 3.3-2.8 (bs, 6H), 3.06 (t, 2H), 1.33 (t, 3H).

Step 2: Ethyl 3-[2-(benzyloxy)ethyl]-1-phenyl-1H-pyrazole-4-carboxylate: The above material (0.068 g, 223 umol) in 5 ml Et$_2$O at 0 C was stirred overnight warming to room temp with phenylhydrazine (26 ul, 267 umol). The even more orange solution was purified by flash chromatography to provide the pyrazole compound (28%): $R_f$ (3:1 hexane:EtOAc) 0.52; $^1$H-NMR (CD$_3$Cl 300 MHz) 8.07 (s, 1H), 7.47 (m, 5H), 7.31 (m, 3H), 7.21 (m, 2H), 4.44 (s, 2H), 4.34 (q, 2H), 3.77 (t, 2H), 3.28 (t, 2H), 1.38 (t, 2H).

Step 3: 3-[2-(Benzyloxy)ethyl]-1-phenyl-1H-pyrazole-4-carboxylic acid: The ethyl ester (0.054 g, 154 umol) in 5 ml ethanol with palladium on carbon 10% by weight (0.008 g) was allowed to uptake H$_2$(g) overnight. The solution was purified by flash chromatography to provide the carboxylic acid (100%): $R_f$ (1:1 hexane:EtOAc) 0.20; $^1$H-NMR (CD$_3$Cl 500 MHz) 8.16 (s, 1H), 7.59 (m, 5H), 7.30 (m, 3H), 7.22 (m, 2H), 4.64 (s, 2H), 3.80 (t, 2H), 3.30 (t, 2H); ESMS 324 (100%, M+H).

Step 4: (7-240): HATU/DIPEA coupling (10%): $R_f$ (1:1 hexane:EtOAc) 0.64; $^1$H-NMR (CD$_3$Cl 500 MHz) 9.22 (bs, 1H), 8.01 (s, 1H), 7.36 (m, 3H), 7.30 (dt, 1H), 7.22 (m, 2H), 7.18 (m, 2H), 7.12 (m, 2H), 7.02 (m, 1H), 6.69 (m, 1H), 4.47 (s, 2H), 3.57 (t, 2H), 3.10 (t, 2H); ESMS 416 (100%, M+H).

3-[4-(Dichloroacetyl)phenyl]-N-(3-fluorophenyl)-1-phenyl-1H-pyrazole-4-carboxamide (8-2):

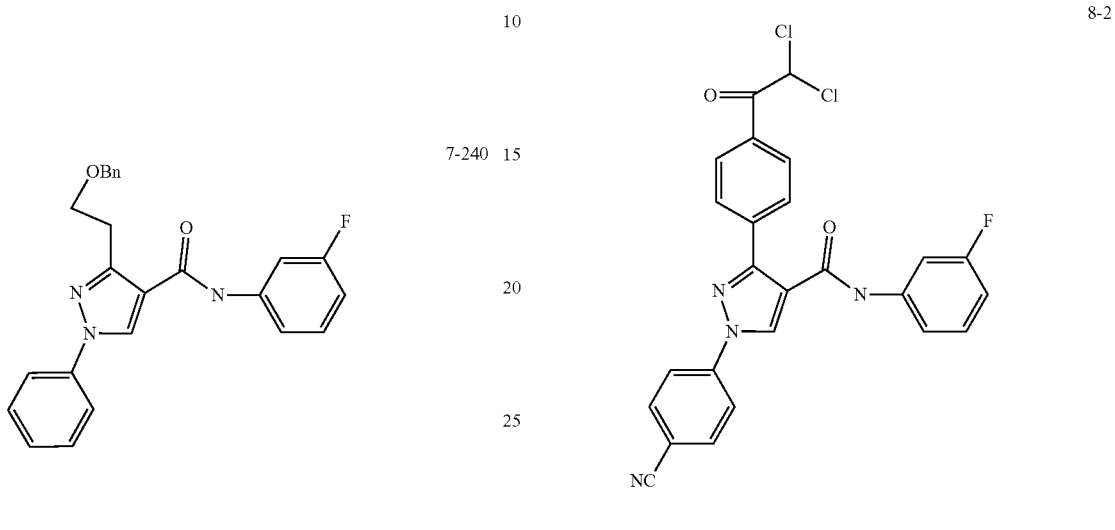

$R_f$ (6:1 hexane:EtOAc) 0.83; $^1$H-NMR (DMSO 300 MHz) 10.59 (s, 1H), 9.35 (s, 1H), 8.13 (m, 6H), 7.93 (s, 1H), 7.68 (d, 1H), 7.44 (m, 2H), 6.95 (m, 1H), ESMS 494 (100%, M+H.

3-[4-(Bromomethyl)phenyl]-N-(3-fluorophenyl)-1-phenyl-1H-pyrazole-4-carboxamide (8-44):

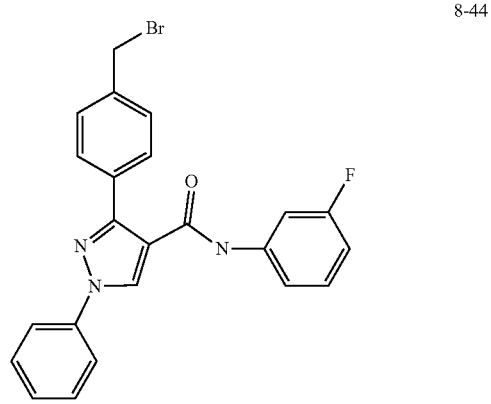 [SMILES: O=C(Nc1cccc(F)c1)c1cn(-c2ccccc2)nc1-c1ccc(CBr)cc1]

$R_f$ (6:1 hexane:EtOAc) 0.83; $^1$H-NMR (CD$_3$Cl 300 MHz) 8.62 (s, 1H), 7.85 (m, 4H), 7.61 (m, 2H), 7.54 (t, 2H), 7.39 (m, 2H), 7.24 (m, 1H), 6.83 (m, 1H), 4.62 (s, 2H); ESMS 450 (100%, M+H).

Ethyl 3-{[(dichloroacetyl)(ethyl)amino]methyl}-1-phenyl-1H-pyrazole-4-carboxylate (8-51):

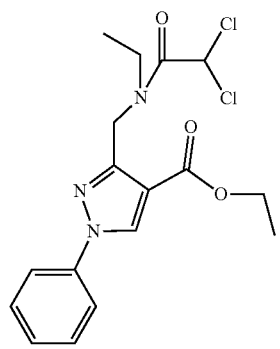

8-51

$R_f$ (3:1 hexane:EtOAc) 0.33; $^1$H-NMR (CD$_3$Cl 300 MHz, mixture of rotomers) 8.09 (s, 1H), 7.85 (m, 4H), 7.58 (m, 1H), 7.47 (m, 2H), 7.38 (m, 2H), 6.19/5.97 (s, 1H), 5.25/4.85 (s, 1H), 4.36 (q, 2H), 3.21/3.11 (q, 2H), 1.38 (t, 3H), 1.11/0.82 (t, 3H)

3-{[(Dichloroacetyl)(ethyl)amino]methyl}-N-(3-fluorophenyl)-1-phenyl-1H-pyrazole-4-carboxamide (8-54):

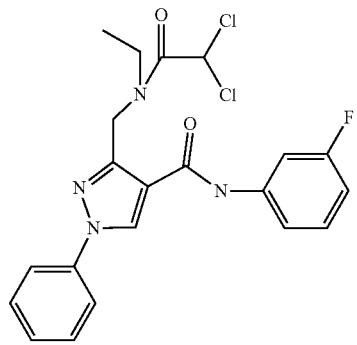

8-54

$R_f$ (3:1 hexane:EtOAc) 0.21; $^1$H-NMR (CD$_3$Cl 300 MHz) 8.45 (s, 1H), 8.13 (d, 1H), 7.50 (m, 13H), 5.99 (s, 1H), 5.08 (s, 2H), 3.31 (q, 2H), 1.13 (t, 3H)

3-(4-{[(Dichloroacetyl)amino]methyl}phenyl)-N-(3-fluorophenyl)-1-phenyl-1H-pyrazole-4-carboxamide (8-64):

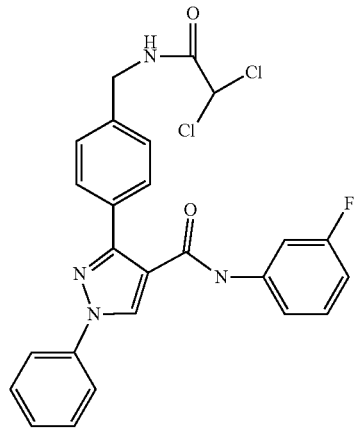

8-64

$R_f$ (1:1 hexane:EtOAc) 0.93; $^1$H-NMR (CD$_3$Cl 500 MHz) 8.63 (s, 1H), 7.80 (m, 3H), 7.47 (m, 7H), 7.25 (m, 1H), 6.85 (m, 2H), 6.36/6.04 (s, 1H), 4.67 (d, 2H).

3-{[(Dichloroacetyl)amino]methyl}-N-(3-fluorophenyl)-1-phenyl-1H-pyrazole-4-carboxamide (8-66):

8-66

$R_f$ (3:1 hexane:EtOAc) 0.10; $^1$H-NMR (CD$_3$Cl 300 MHz) 8.43 (t, 1H), 8.01 (s, 1H), 7.55 (m, 12H), 7.30 (m, 2H), 6.91 (m, 2H), 5.93 (s, 1H), 4.72 (d, 2H).

Inhibitory Activity of Representative Pyrazole Compounds

The inhibition of ALDH1A1 (IC$_{50}$), ALDH1A2 (IC$_{50}$), ALDH2 (IC$_{50}$), and ALDH1A1/ALDH1A2 (EC$_{50}$) of representative pyrazole compounds of the invention is summarized in Table 1. The inhibition activities were determined by the screening assay described herein.

TABLE 1

| Pyrazole Compound Inhibition of ALDH1A1, ALDH1A2, and ALDH2. | | | | |
|---|---|---|---|---|
| | IC50 (uM) | IC50 (uM) | IC50 (uM) | EC50 (uM) | |
| Cmpd | ALDH1A1 | ALDH1A2 | ALDH2 | ALDH1A1 | ALDH1A2 |
| 33 | | 0.198 | 0.077 | | |
| 34 | | 1.726 | 18.2 | 0.469 | 0.798 |
| 35 | | | | 3.38 | 0.952 |
| 103 | | 0.62 | 313.3 | | |
| 106 | | 0.07 | 145.9 | | |
| 131 | 0.388 | 3.02 | 18.79 | | |
| 147 | 0.230 | 1.35 | 3.21 | | |

TABLE 1-continued

Pyrazole Compound Inhibition of ALDH1A1, ALDH1A2, and ALDH2.

| Cmpd | IC50 (uM) ALDH1A1 | IC50 (uM) ALDH1A2 | IC50 (uM) ALDH2 | EC50 (uM) ALDH1A1 | EC50 (uM) ALDH1A2 |
|---|---|---|---|---|---|
| 149 | 0.601 | 2.15 | 4.6 | | |
| 150 | | 0.170 | 12.99 | | |
| 151 | | 0.822 | 24.65 | | |
| 165 | | 0.211 | 23.26 | | |
| 166 | | 0.779 | 95.22 | | |
| 167 | | 0.397 | 16.86 | | |
| 173 | | 0.383 | 73.68 | | |
| 178 | | 0.192 | 20.85 | 5.5 | 0.065 |
| 196 | 1.218 | 0.890 | 6.92 | | |
| 207 | | 0.010 | 10.3 | | |
| 208 | | 0.010 | 145.1 | | |
| 210 | | 0.032 | 112.4 | | |
| 211 | | 0.081 | 15.47 | 2 | 0.12 |
| 219 | | 0.606 | >25 | >20 | 0.11 |
| 223 | | 0.208 | 133.5 | 1.3 | 0.088 |
| 229 | | 0.217 | 15.25 | | |
| 231 | | 0.323 | 67.34 | >20 | 0.069 |
| 232 | | >5 | | 0.723 | 0.317 |
| 233 | | 0.795 | 87.23 | 13.23 | 0.055 |
| 238 | | 0.05/0.985 | 40.85 | | |
| 239 | | 0.271 | 9.603 | | |
| 240 | | 0.036 | 14.25 | | <0.5 |
| 241 | | 0.092 | 16.56 | 10.9 | 0.056 |
| 242 | | 0.045 | 6.32 | | <0.5 |
| 243 | | 0.076 | 62.02 | | |
| 246 | | 0.119 | 61.19 | | |
| 249 | | 0.038 | 35.9 | | |
| 250 | | 0.291 | 85.78 | | |
| 253 | | 0.059 | 10 | | |
| 256 | | 0.112 | 25 | 46 | 0.011 |
| 258 | | 0.112 | 100 | 26.4 | 0.051 |
| 262 | | 0.352 | 16.65 | >20 | 0.016 |
| 266 | | 0.029 | 100 | >20 | 0.354 |
| 268 | | 0.840 | 83.74 | 2.427 | 0.026 |
| 269 | | 0.238 | 67.66 | 3.56 | 0.045 |
| 270 | | 0.346 | 91.74 | | |
| 273 | | 0.179 | | 5.63 | 0.045 |
| 274 | | 0.131 | | 2.228 | 0.008 |
| 279 | 0.029 | 0.61 | | 0.056 | 0.017 |
| 280 | | >5 | | >20 | 0.3 |
| 281 | | | | 15.8 | 0.14 |
| 282 | | | | >20 | 0.24 |
| 283 | | | | 18.4 | 0.4 |
| 284 | | | | 1.93 | 0.04 |
| 285 | | | | 0.81 | 0.25 |
| 286 | | | | >20 | 0.11 |
| 291 | | | | >20 | 0.042 |
| 293 | | | | >20 | 0.07 |
| 294 | 0.003 | 0.025 | 24.4 | <0.005 | <0.005 |
| 296 | 9.44 | 0.150 | | 0.542 | 0.023 |
| 306 | | | | 9.62 | 0.15 |
| 307 | | | | >20 | 0.25 |
| 309 | 0.005 | 0.005 | >0.16 | 0.73 | 0.87 |
| 310 | 0.009 | 0.065 | | 0.14 | 0.245 |
| 312 | 3.61 | 1.2 | | 0.251 | 12.5 |
| 316 | 10.2 | 0.6 | | 0.28 | 0.123 |
| 316a | 0.249 | 0.037 | 4.0 | 0.18 | 0.013 |
| 8-2 | 0.04 | 0.0002 | | | |
| 8-44 | 3.9 | 0.72 | | | |
| 8-54 | 0.092 | 3.9 | | | |
| 8-64 | 2 | 0.015 | | | |

Piperazine Syntheses

The general synthesis schemes for the preparation of representative piperazine compounds of the invention are shown in FIGS. 9, 10, 13, 15, and 16. Representative genera of representative piperazine compounds of the invention are shown in FIGS. 8, 11, 12, 14, 17, 18, and 19.

The chemical syntheses of representative piperazine compounds of the invention are and described below.

Figure 8:
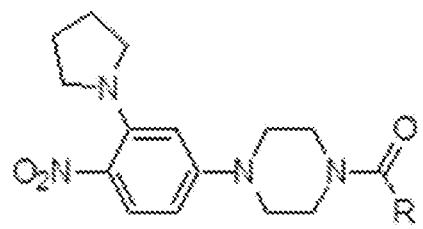
FIG. 8 illustrates a representative genus of piperazine compounds of the invention.

The structure of piperazines 317-320 is shown in FIG. 8 and their preparation is described below.

4-[4-Nitro-3-(pyrrolidin-1-yl)phenyl]piperazin-1-yl}(3-methylthiophen-2-yl)methanone (317): To 1-(4-nitro-3-pyrrolidin-1-ylphenyl)piperazine hydrochloride salt (0.007 g, 22 umol) in 2 ml dry DMF was added triethylamine (15 ml, 44 umol) and then 3-methylthiophen-2-carbonyl chloride (5.4 ul, 44 umol). The reaction was allowed to sit for at least 30 min. The solvent was removed by rotary evaporation and the residue purified by flash chromatography (3:1-0:1 hexane:EtOAc) to yield the product as a yellow solid (0.008 g, 100%): $R_f$ (3:1 hexane:EtOAc) 0.11; $^1$H-NMR (CDCl$_3$ 300 MHz) 7.84 (d, 1H, J=9.3), 7.32 (d, 1H, J=5.0), 6.88 (d, 1H, J=5.0), 6.29 (dd, 1H, J=2.5, 9.3), 6.15 (d, 1H, 2.5), 3.8 (m, 4H), 3.37 (m, 4H), 3.25 (m, 4H), 2.32 (s, 3H), 1.99 (m, 4H).

{4-[4-Nitro-3-(pyrrolidin-1-yl)phenyl]piperazin-1-yl}(4-methylthiophen-2-yl)methanone (318): As above but add 4-methylthiophen-2-carbonyl chloride (5.4 ul, 44 umol) and obtain a yellow solid (0.008 g, 100%): $R_f$ (3:1 hexane:EtOAc) 0.11; $^1$H-NMR (CDCl$_3$ 300 MHz) 7.85 (d, 1H, J=9.2), 7.17 (s, 1H) 7.08 (s, 1H), 6.28 (dd, 1H, J=2.5, 9.2), 6.13 (bs, 1H), 3.92 (m, 4H), 3.49 (m, 4H), 3.24 (m, 4H), 2.29 (s, 3H), 1.99 (m, 4H).

{4-[4-Nitro-3-(pyrrolidin-1-yl)phenyl]piperazin-1-yl}(5-methylthiophen-2-yl)methanone (319): As above but add 5-methylthiophen-2-carbonyl chloride (5.4 ul, 44 umol). Yield the product as a yellow solid (0.008 g, 100%): $R_f$ (3:1 hexane:EtOAc) 0.11; $^1$H-NMR (CDCl$_3$ 300 MHz) 7.86 (d, 1H, J=9.3), 7.18 (d, 1H, J=3.6) 6.75 (d, 1H, J=3.6), 6.28 (dd, 1H, J=2.5, 9.3), 6.13 (bs, 1H), 3.94 (m, 4H), 3.42 (m, 4H), 3.25 (m, 4H), 2.53 (s, 3H), 1.99 (m, 4H).

{4-[4-Nitro-3-(pyrrolidin-1-yl)phenyl]piperazin-1-yl}(thiophen-3-yl)methanone (320): As above but add thiophen-3-carbonyl chloride (5.4 ul, 44 umol) to yield the product as a yellow solid (0.001 g, 11%): $R_f$ (3:1 hexane:EtOAc) 0.11; $^1$H-NMR (CDCl$_3$ 300 MHz) 8.40 (s, 1H), 7.83 (m, 3H, J=9.2), 6.28 (d, 1H), 6.18 (bs, 1H), 3.92 (m, 4H), 3.49 (m, 4H), 3.24 (m, 4H), 1.99 (m, 4H).

Figure 9:
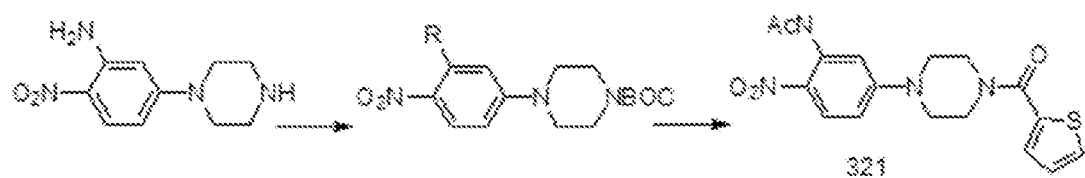
FIG. 9 is a schematic illustration of the preparation of a representative piperazine compound of the invention.

The synthesis of piperazine 321 is shown in FIG. 9 and described below.

N-{2-nitro-5-[4-(thiophen-2-ylcarbonyl)piperazin-1-yl]phenyl}acetamide (321):

Step 1: tert-Butyl 4-(3-amino-4-nitrophenyl)piperazine-1-carboxylate (4-72).

2-Nitro-5-(1-piperazinyl)aniline (0.100 g, 450 mmol) in 5 ml CH$_3$OH was reacted with triethylamine (0.043 ml, 540 umol) and di-tert-butyldicarbonate (0.108 g, 495 mmol) overnight. The solvent was removed by rotary evaporation and the residue purified by flash chromatography (3:1-0:1 hexane:EtOAc) to yield the product as a yellow solid (0.124 g, 86%): $R_f$ (1:1 hexane:EtOAc) 0.82; $^1$H-NMR (CDCl$_3$ 300 MHz) 8.05 (d, 1H), 6.28 (dd, 1H), 6.17 (bs, 2H), 5.95 (d, 1H), 3.59 (t, 4H), 3.38 (t, 4H), 1.51 (s, 9H).

Step 2: tert-Butyl 4-[3-(acetylamino)-4-nitrophenyl]piperazine-1-carboxylate (5-82). The above material 4-72 (0.024 g, 74 umol) was refluxed with acetic anhydride (0.2 ml) and sodium acetate (0.050 g) in 3 ml CHCl$_3$ for 2 h and then stirred at room temperature for 72 h. The solvent was removed by rotary evaporation and the residue purified by flash chromatography (5:1-1:1 hexane:EtOAc) to yield the product as a yellow solid (0.024 g, 89%): $R_f$ (1:1 hexane:EtOAc) 0.74; $^1$H-NMR (CDCl$_3$ 300 MHz) 10.90 (bs, 1H), 8.25 (d, 1H), 8.09 (d, 1H), 6.44 (dd, 1H), 3.51 (t, 4H), 3.43 (t, 4H), 2.21 (s, 3H), 1.41 (s, 9H).

Step 3: To the above t-butylcarbamate (0.006 g, 15 umol) in 3 ml DCM was added 1 ml trifluoroacetic acid. The reaction was stirred for 45 min and the solvent removed by rotary evaporation. The residue was trice rinsed with 3 ml DCM and evaporated. Finally, 3 ml CHCl₃, triethylamine (0.012 ml, 148 umol) and 2-thiophenecarbonyl chloride (0.003 ml, 30 umol) were added and the reaction stirred for 30 min. The solvent was removed by rotary evaporation and the residue purified by flash chromatography (3:1-0:1 hexane:EtOAc) to yield the product as a yellow solid (0.002 g, 33%): $R_f$ (1:1 hexane:EtOAc) 0.43; $^1$H-NMR (CDCl₃ 300 MHz) 10.99 (bs, 1H), 8.38 (d, 1H), 8.21 (d, 1H), 7.53 (d, 1H), 7.38 (d, 1H), 7.11 (t, 1H), 6.56 (dd, 1H), 3.97 (t, 4H), 3.62 (t, 4H), 2.31 (s, 3H).

Figure 10:
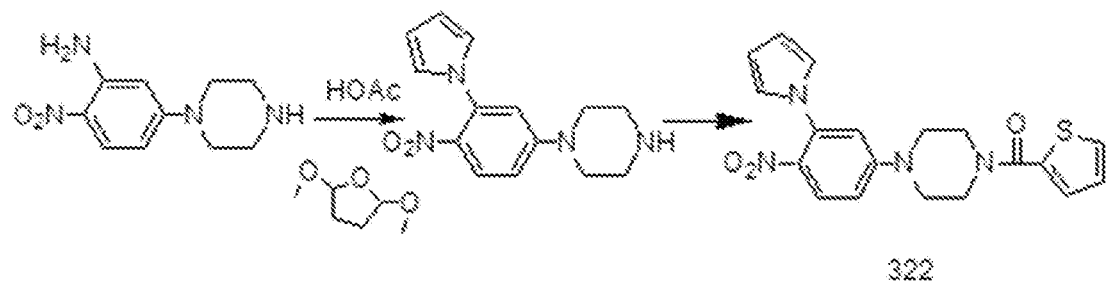
FIG. 10 is a schematic illustration of the preparation of a representative piperazine compound of the invention.

The synthesis of piperazine 322 is shown in FIG. 10 and described below.

{4-[4-nitro-3-(1H-pyrrol-1-yl)phenyl]piperazin-1-yl}(thiophen-2-yl)methanone (322):

2-Nitro-5-(1-piperazinyl)aniline (0.102 g, 459 umol) was refluxed with 2,5-dimethoxytetrahydrofuran (0.059 ml, 459 umol) in 3 ml glacial acetic acid for 30 min. The solvent was removed from the now dark red solution by rotary evaporation: $^1$H-NMR (DMSO 300 MHz) 7.97 (d, 1H), 6.98 (dd, 1H), 6.91 (t, 2H), 6.82 (d, 1H), 6.21 (t, 2H), 5.75 (s, 1H), 3.38 (t, 4H), 2.81 (t, 4H). The red residue was dissolved in 5 ml DCM and stirred for 30 min with 1 ml triethylamine and 2-thiophenecarbonyl chloride (0.098 ml, 910 umol). The solvent was removed by rotary evaporation and the residue purified by flash chromatography (3:1-0:1 hexane:EtOAc) to yield the product as a yellow solid (0.045 g, 26%): $R_f$ (1:1 hexane:EtOAc) 0.46; $^1$H-NMR (CDCl₃ 300 MHz) 8.04 (d, 1H), 7.52 (t, 1H), 7.39 (m, 3H), 7.29 (m, 1H), 7.11 (m, 1H), 6.80 (m, 3H), 6.38 (t, 1H), 3.98 (m, 4H), 3.54 (m, 4H).

Figure 11:
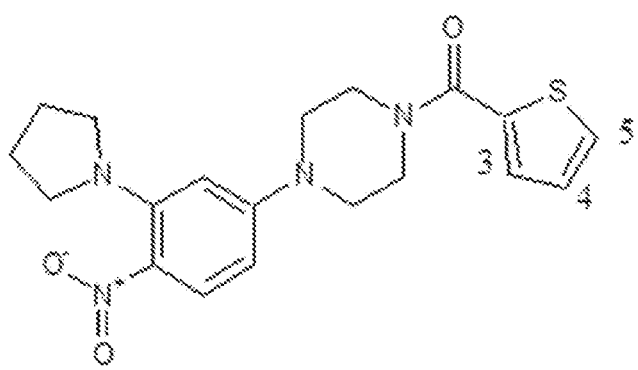
FIG. 11 illustrates a representative genus of piperazine compounds of the invention.

The structure of piperazines 323-335 is shown in FIG. 11 and their preparation is described below.

{4-[4-Nitro-3-(pyrrolidin-1-yl)phenyl]piperazin-1-yl}(5-ethylthiophen-2-yl)methanone (323): 5-Ethyl-thiophene-2-carboxylic acid (0.005 g, 32 umol) was refluxed with thionyl chloride (0.007 ml, 96 umol) in 0.75 ml toluene for 1.5 h. After cooling to room temperature, triethylamine (0.018 ml, 224 umol) and 1-(4-nitro-3-pyrrolidin-1-ylphenyl)piperazine hydrochloride salt (0.010 g, 32 umol) in 0.3 ml dry DMF was added After stirring for 30 min the solvent was removed by rotary evaporation and the residue purified by flash chromatography (3:1-0:1 hexane:EtOAc) to yield the product as a yellow solid (0.004 g, 31%): $R_f$ (3:1 hexane:EtOAc) 0.07; $^1$H-NMR (CDCl₃ 300 MHz) 7.86 (d, 1H), 7.21 (d, 1H), 6.78 (d, 1H), 6.30 (dd, 1H), 6.16 (d, 1H), 3.95 (m, 4H), 3.43 (m, 4H), 3.26 (m, 4H), 2.89 (q, 2H), 2.00 (m, 4H), 1.36 (t, 3H).

{4-[4-Nitro-3-(pyrrolidin-1-yl)phenyl]piperazin-1-yl}(3-chlorothiophen-2-yl)methanone (324): 3-Chloro-thiophene-2-carboxylic acid (0.005 g, 31 umol) was refluxed with thionyl chloride (0.007 ml, 92 umol) in 0.75 ml toluene for 1.5 h. After cooling to room temperature, triethylamine (0.017 ml, 215 umol) and 1-(4-nitro-3-pyrrolidin-1-ylphenyl)piperazine hydrochloride salt (0.010 g, 31 umol) in 0.3 ml dry DMF was added After stirring for 30 min the solvent was removed by rotary evaporation and the residue purified by flash chromatography (3:1-0:1 hexane:EtOAc) to yield the product as a yellow solid (0.004 g, 23%): $R_f$ (3:1 hexane:EtOAc) 0.10; $^1$H-NMR (CDCl₃ 300 MHz) 7.77 (d, 1H), 7.35 (d, 1H), 6.87 (d, 1H), 6.21 (dd, 1H), 6.09 (d, 1H), 3.71 (m, 4H), 3.34 (m, 4H), 3.16 (m, 4H), 1.90 (m, 4H), 1.36 (t, 3H).

{4-[4-Nitro-3-(pyrrolidin-1-yl)phenyl]piperazin-1-yl}(5-chlorothiophen-2-yl)methanone (325): 5-Chlorothiophene-2-carboxylic acid (0.006 g, 35 umol) in 1 ml toluene was refluxed with thionyl chloride (0.007 ml, 96 umol) for 1.5 h under dry conditions. After cooling to ambient triethylamine (0.018 ml, 224 umol) and 1-(4-nitro-3-pyrrolidin-1-ylphenyl)piperazine hydrochloride salt (0.010 g, 32 umol) were added. After stirring for 30 min the solvent was removed by rotary evaporation and the residue purified by flash chromatography (3:1-0:1 hexane:EtOAc) to yield the product as a yellow solid (0.006 g, 46%): $R_f$ (3:1 hexane:EtOAc) 0.13; $^1$H-NMR (CDCl₃ 300 MHz) 7.86 (d, 1H), 7.16 (d, 1H), 6.92 (d, 1H), 6.29 (dd, 1H), 6.15 (d, 1H), 3.93 (m, 4H), 3.43 (m, 4H), 3.26 (m, 4H), 2.00 (m, 4H).

{4-[4-Nitro-3-(pyrrolidin-1-yl)phenyl]piperazin-1-yl}(3-ethoxythiophen-2-yl)methanone (326): 3-Ethoxythiophene-2-carboxylic acid (0.003 g, 16 umol), hydroxbenzotriazole (0.003 g, 18 umol), triethylamine (0.003 ml, 32 umol), 1-Ethyl-3-(3-dimethylaminopropyl)carbodiimide (0.003 g, 18 umol) and 1-(4-nitro-3-pyrrolidin-1-ylphenyl)piperazine hydrochloride salt (0.005 g, 16 umol) were stirred overnight in 1 ml DMF. The solvent was removed by rotary evaporation and the residue purified by flash chromatography (3:1-1:1 hexane:EtOAc) to yield the product as a yellow solid (0.007 g, 100%): $R_f$ (1:1 hexane:EtOAc) 0.45; $^1$H-NMR (CDCl₃ 300 MHz) 7.78 (d, 1H), 7.30 (d, 1H), 6.70 (d, 1H), 6.22 (dd, 1H), 6.08 (d, 1H), 4.07 (q, 2H), 3.71 (m, 4H), 3.33 (m, 4H), 3.17 (m, 4H), 1.90 (m, 4H), 1.34 (t, 3H).

{4-[4-Nitro-3-(pyrrolidin-1-yl)phenyl]piperazin-1-yl}(4,5-dimethylthiophen-2-yl)methanone (327): As above but use 4,5-dimethylthiophen-2-carboxylic acid: yellow solid (0.005 g, 86%): $R_f$ (1:1 hexane:EtOAc) 0.53; $^1$H-NMR (CDCl₃ 300 MHz) 7.87 (d, 1H), 7.10 (s, 1H), 6.30 (dd, 1H), 6.16 (bs, 1H), 3.94 (m, 4H), 3.42 (m, 4H), 3.26 (m, 4H), 2.39 (s, 3H), 2.16 (s, 3H), 2.01 (m, 4H).

{4-[4-Nitro-3-(pyrrolidin-1-yl)phenyl]piperazin-1-yl}(5-carboxythiophen-2-yl)methanone (328): As above but use thiophen-2,5-dicarboxylic acid: yellow solid (48%): $R_f$ (EtOAc) 0.57; $^1$H-NMR (CDCl₃ 300 MHz) 7.87 (d, 1H), 7.30 (d, 2H), 6.31 (dd, 1H), 6.20 (bs, 1H), 3.93 (m, 4H), 3.43 (m, 4H), 3.26 (m, 4H), 2.01 (m, 4H).

{4-[4-Nitro-3-(pyrrolidin-1-yl)phenyl]piperazin-1-yl}(3-methoxythiophen-2-yl)methanone (329): As above but use 3-methoxythiophen-2-carboxylic acid: yellow solid (0.006 g, 83%): $R_f$ (1:1 hexane:EtOAc) 0.34; $^1$H-NMR (CDCl₃ 300 MHz) 7.87 (d, 1H), 7.41 (d, 1H), 6.83 (d, 1H), 6.32 (dd, 1H), 6.19 (bs, 1H), 3.93 (s, 3H), 3.81 (m, 4H), 3.42 (m, 4H), 3.26 (m, 4H), 2.62 (s, 3H), 2.00 (m, 4H).

{4-[4-Nitro-3-(pyrrolidin-1-yl)phenyl]piperazin-1-yl}(3-N-t-butylcarbomylthiophen-2-yl)methanone (330): As above but use 3-N-t-butylcarbomylthiophen-2-carboxylic acid: yellow solid (0.011 g, 85%): $R_f$ (3:1 hexane:EtOAc) 0.24; $^1$H-NMR (CDCl₃ 300 MHz) 9.45 (s, 1H, NH), 7.91 (d, 1H), 7.87 (d, 1H), 7.40 (d, 1H), 6.83 (d, 1H), 6.30 (dd, 1H), 6.18 (bs, 1H), 4.00 (m, 4H), 3.47 (m, 4H), 3.26 (m, 4H), 2.01 (m, 4H), 1.52 (s, 9H).

{4-[4-Nitro-3-(pyrrolidin-1-yl)phenyl]piperazin-1-yl}(3-aminothiophen-2-yl)methanone hydrochloride (331): Stir {4-[4-nitro-3-(pyrrolidin-1-yl)phenyl]piperazin-1-yl}(3-N-t-butylcarbomylthiophen-2-yl)methanone (330) in 4 ml CH₃OH with 0.1 ml 6 M HCl (aq) for 2.5 h. The solvent was removed by rotary evaporation and the yellow residue dried in vacuum (100%): $^1$H-NMR (DMSO 300 MHz) 7.53 (d, 1H), 7.49 (d, 1H), 7.40 (d, 1H), 6.63 (d, 1H), 6.43 (dd, 1H), 6.18 (bs, 1H), 3.72 (m, 4H), 3.55 (m, 4H), 3.30 (m, 4H), 1.90 (m, 4H).

{4-[4-Nitro-3-(pyrrolidin-1-yl)phenyl]piperazin-1-yl}(3-N-acetylthiophen-2-yl)methanone (332): Stir {4-[4-nitro-3-(pyrrolidin-1-yl)phenyl]piperazin-1-yl}(3-aminothiophen-2-yl)methanone hydrochloride (331) (2 mg, 8 umol) in 0.5 ml DMF with triethylamine (0.004 ml, 48 umol), acetic anhydride (0.004 ml, 40 umol) and N,N-dimethylaminopyridine (0.001 g, 8 umol) overnight. The solvent was removed by rotary evaporation and the yellow residue purified by flash chromatography to give the desired product as a yellow solid (0.002 g, 50%): $R_f$(1:1 hexane:EtOAc) 0.15; $^1$H-NMR (CDCl$_3$ 300 MHz) 10.38 (bs, 1H, NH), 8.12 (d, 1H), 7.88 (d, 1H), 7.44 (d, 1H), 6.30 (dd, 1H), 6.17 (d, 1H), 4.03 (m, 4H), 3.49 (m, 4H), 3.27 (m, 4H), 2.22 (s, 3H), 2.00 (m, 4H).

{4-[4-Nitro-3-(pyrrolidin-1-yl)phenyl]piperazin-1-yl}(5-trifluoromethylthiophen-2-yl)methanone (333): Use 5-trifluoromethylthiophen-2-carboxylic acid: yellow solid (67%): $R_f$ (3:1 hexane:EtOAc) 0.10; $^1$H-NMR (CDCl$_3$ 300 MHz) 7.85 (d, 1H), 7.42 (m, 1H), 7.30 (m, 1H), 6.30 (dd, 1H), 6.17 (d, 1H), 3.93 (m, 4H), 3.43 (m, 4H), 3.26 (m, 4H), 2.01 (m, 4H).

{4-[4-Nitro-3-(pyrrolidin-1-yl)phenyl]piperazin-1-yl}(5-fluorothiophen-2-yl)methanone (334): Use 5-fluorothiophen-2-carboxylic acid: yellow solid (100%): $R_f$(3:1 hexane:EtOAc) 0.12; $^1$H-NMR (CDCl$_3$ 300 MHz) 7.86 (d, 1H), 7.05 (t, 1H), 6.50 (dd, 1H), 6.29 (dd, 1H), 6.15 (d, 1H), 3.95 (m, 4H), 3.44 (m, 4H), 3.25 (m, 4H), 2.00 (m, 4H).

4-[4-Nitro-3-(pyrrolidin-1-yl)phenyl]piperazin-1-yl](5-hydroxythiophen-2-yl)methanone (335): Use 5-hydroxythiophen-2-carboxylic acid: yellow solid (64%): $R_f$ (1:1 hexane:EtOAc) 0.74; $^1$H-NMR (CDCl$_3$ 300 MHz) 7.87 (d, 1H), 7.39 (d, 1H), 6.84 (d, 1H), 6.29 (dd, 1H), 6.18 (d, 1H), 4.07 (m, 4H), 3.53 (m, 4H), 3.27 (m, 4H), 2.02 (m, 4H).

Figure 12:
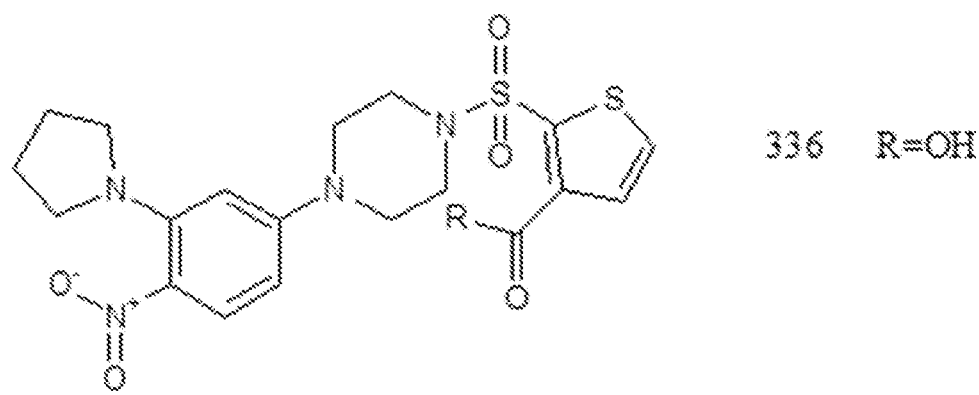
FIG. 12 illustrates a representative piperazine compound of the invention.

The structure of piperazine 336 is shown in FIG. 12 and its preparation is described below.

1-[4-Nitro-3-(pyrrolidin-1-yl)phenyl-4-sulfonyl]thiophene-3-carboxylic acid (336): 1-[4-nitro-3-(pyrrolidin-1-yl)phenyl]-4-(thiophen-2-ylsulfonyl-3-methylcarboxy)piperazine (0.002 g, 4 umol) in 2 ml CH$_3$OH and 2 ml DCM was stirred for 1 hr with 10 equivalents of sodium hydroxide in 0.1 ml H$_2$O. The solution was acidified with 1 M HCl (aq) so pH ~3 and then extracted 3×5 ml DCM. The combined organics were dried to provide the final product as a yellow solid (100%): $^1$H-NMR (CDCl$_3$ 300 MHz) 7.69 (d, 1H), 7.60 (d, 2H), 7.35 (d, 1H), 6.12 (dd, 1H), 6.02 (d, 1H), 3.32 (bs, 4H), 3.24 (bs, 4H), 3.13 (m, 4H), 1.90 (m, 4H).

Figure 13:
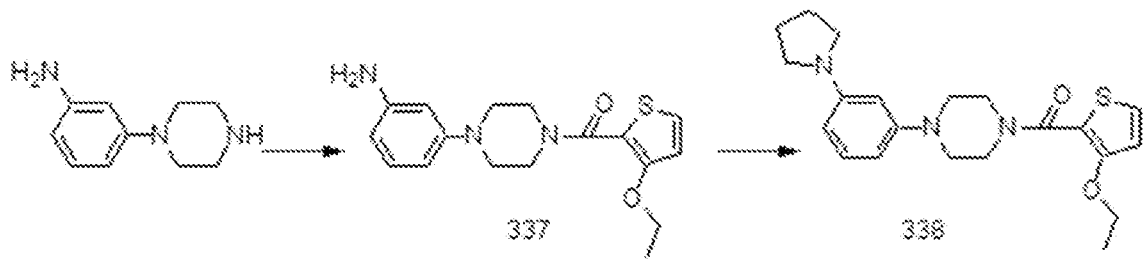
FIG. 13 is a schematic illustration of the preparation of a representative piperazine compound of the invention.

The synthesis of piperazines 337 and 338 is shown in FIG. 13 and described below.

(3-Ethoxythiophen-2-yl){4-[3-(pyrrolidin-1-yl)phenyl]piperazin-1-yl}methanone (338)

Step 1: [4-(3-Aminophenyl)piperazin-1-yl](3-ethoxythiophen-2-yl)methanone (337): 3-(1-Piperazinyl)-benzamine (0.005 g, 19 umol), hydroxybenzotriazole (0.003 g, 21 umol), triethylamine (0.003 ml, 37 umol), 1-ethyl-3-(3-dimethylaminopropyl)carbodiimide (0.004 g, 21 umol) and 3-ethoxythiophen-2-carboxylic acid (0.003 g, 19 umol) were stirred overnight in 1.0 ml DMF. The solvent was removed by rotary evaporation and the residue purified by flash chromatography (3:1-0:1 hexane:EtOAc) to yield the product as a yellow solid (100%): $R_f$(1:1 exane:EtOAc) 0.17; $^1$H-NMR (CDCl$_3$ 300 MHz) 7.28 (d, 1H), 7.02 (t, 1H), 6.69 (d, 1H), 6.32 (d, 1H), 6.25 (bs, 1H), 6.21 (d, 1H), 4.06 (q, 2H), 3.72 (bs, 4H), 3.16 (t, 4H), 1.32 (t, 3H); ESMS 332 (M+H).

Step 2: Aniline derivative (0.006 g, 18 umol), K$_2$CO$_3$ (0.010 g, 72 umol) and 1,4-dibromobutane (0.0024 ml, 20 umol) were combined in 1 ml 9:1 DMF:NMP and heated at 110 C for 21 h under Ar. After cooling to 20 C, 10 ml H$_2$O was added and the mixture extracted 2×6 ml EtOAc and 1×6 ml DCM. The combined organics were washed with 6 ml brine, the solvent removed by rotary evaporation and the residue purified by flash chromatography (3:1-1:1 hexane:EtOAc) to yield the product as a yellow solid (0.001 g, 15%): $R_f$ (1:1 hexane:EtOAc) 0.68; $^1$H-NMR (CDCl$_3$ 500 MHz) 7.28 (d, 1H), 7.19 (d, 1H), 7.07 (bs, 1H), 6.69 (d, 1H), 6.23 (bs, 1H), 6.08 (d, 1H), 4.07 (q, 2H), 3.72 (bs, 4H), 3.22 (bs, 4H), 3.17 (bs, 4H), 1.93 (bs, 4H), 1.32 (t, 3H).

Figure 14:
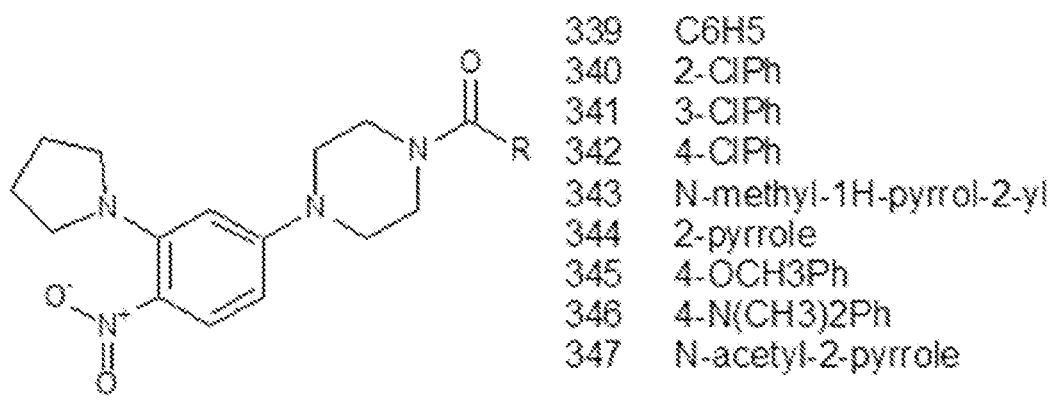
FIG. 14 illustrates a representative genus of piperazine compounds of the invention.

The structure of piperazines 339-347 is shown in FIG. 14 and their preparation is described below.

Phenyl-1-{4-[4-nitro-3-(pyrrolidin-1-yl)phenyl]piperazin-1-yl}methanone (339): 1-(4-nitro-3-(pyrrolidin-1-ylphenyl)piperazine hydrochloride (0.006 g, 19 umol), hydroxbenzotriazole (0.003 g, 21 umol), triethylamine (0.003 ml, 38 umol), 1-ethyl-3-(3-dimethylaminopropyl) carbodiimide (0.004 g, 21 umol) and benzoic acid (0.002 g, 19 umol) were stirred overnight in 0.3 ml DMF. The solvent was removed by rotary evaporation and the residue purified by flash chromatography (2:1-0:1 hexane:EtOAc) to yield the product as a yellow solid (86%): $R_f$(1:1 hexane:EtOAc) 0.33; $^1$H-NMR (CDCl$_3$ 300 MHz) 7.86 (d, 1H), 7.46 (s, 5H), 6.30 (dd, 1H), 6.20 (bs, 1H), 3.93 (bs, 2H), 3.66 (bs, 2H), 3.38 (bs, 4H), 3.28 (m, 4H), 2.00 (m, 4H).

2-Chlorophenyl-1-{4-[4-nitro-3-(pyrrolidin-1-yl)phenyl]piperazin-1-yl}methanone (340): 1-(4-nitro-3-(pyrrolidin-1-ylphenyl)piperazine hydrochloride (0.006 g, 19 umol), hydroxbenzotriazole (0.003 g, 21 umol), triethylamine (0.003 ml, 38 umol), 1-ethyl-3-(3-dimethylaminopropyl) carbodiimide (0.004 g, 21 umol) and 2-chlorobenzoic acid (0.003 g, 19 umol) were stirred overnight in 0.3 ml DMF. The solvent was removed by rotary evaporation and the residue purified by flash chromatography (2:1-0:1 hexane: EtOAc) to yield the product as a yellow solid (75%): $R_f$(1:1 hexane:EtOAc) 0.57; $^1$H-NMR (CDCl$_3$ 300 MHz) 7.86 (d, 1H), 7.45-7.33 (m, 4H), 6.29 (dd, 1H), 6.19 (bs, 1H), 4.06 (m, 1H), 3.95 (m, 1H), 3.47 (t, 4H), 3.38 (m, 2H), 3.25 (m, 4H), 2.00 (m, 4H).

3-Chlorophenyl-1-{4-[4-nitro-3-(pyrrolidin-1-yl)phenyl]piperazin-1-yl}methanone (341): 1-(4-Nitro-3-(pyrrolidin-1-ylphenyl)piperazine hydrochloride (0.006 g, 19 umol), hydroxbenzotriazole (0.003 g, 21 umol), triethylamine (0.003 ml, 38 umol), 1-ethyl-3-(3-dimethylaminopropyl) carbodiimide (0.004 g, 21 umol) and 3-chlorobenzoic acid (0.003 g, 19 umol) were stirred overnight in 0.3 ml DMF. The solvent was removed by rotary evaporation and the residue purified by flash chromatography (2:1-0:1 hexane: EtOAc) to yield the product as a yellow solid (100%): $R_f$ (1:1 hexane:EtOAc) 0.50; $^1$H-NMR (CDCl$_3$ 300 MHz) 7.86 (d, 1H), 7.47-7.28 (m, 4H), 6.30 (dd, 1H), 6.20 (bs, 1H), 3.93 (bs, 2H), 3.64 (bs, 2H), 3.38 (bs, 4H), 3.25 (m, 4H), 2.00 (m, 4H).

4-Chlorophenyl-1-{4-[4-nitro-3-(pyrrolidin-1-yl)phenyl]piperazin-1-yl}methanone (342): 1-(4-Nitro-3-(pyrrolidin-1-ylphenyl)piperazine hydrochloride (0.006 g, 19 umol), hydroxbenzotriazole (0.003 g, 21 umol), triethylamine (0.003 ml, 38 umol), 1-ethyl-3-(3-dimethylaminopropyl) carbodiimide (0.004 g, 21 umol) and 4-chlorobenzoic acid (0.003 g, 19 umol) were stirred overnight in 0.3 ml DMF. The solvent was removed by rotary evaporation and the residue purified by flash chromatography (2:1-0:1 hexane: EtOAc) to yield the product as a yellow solid (88%): $R_f$(1:1 hexane:EtOAc) 0.47; $^1$H-NMR (CDCl$_3$ 300 MHz) 7.77 (d, 1H), 7.34 (d, 4H), 6.21 (dd, 1H), 6.11 (bs, 1H), 3.81 (bs, 2H), 3.60 (bs, 2H), 3.29 (bs, 4H), 3.16 (m, 4H), 1.92 (m, 4H).

[4-(4-Nitro-3-(pyrrolidin-1-yl)phenyl)piperazin-1-yl](1-methyl-1H-pyrrol-2-yl)methanone (343): 1-(4-Nitro-3-(pyrrolidin-1-ylphenyl)piperazine hydrochloride (0.006 g, 19 umol), hydroxybenzotriazole (0.003 g, 21 umol), triethylamine (0.003 ml, 38 umol), 1-ethyl-3-(3-dimethylaminopropyl) carbodiimide (0.004 g, 21 umol) and 1-methyl-2-pyrrolecarboxylic acid (0.002 g, 19 umol) were stirred overnight in 0.3 ml DMF. The solvent was removed by rotary evaporation and the residue purified by flash chromatography (2:1-

0:1 hexane:EtOAc) to yield the product as a yellow solid (43%): R$_f$ (1:1 hexane:EtOAc) 0.34; $^1$H-NMR (CDCl$_3$ 300 MHz) 7.86 (d, 1H), 7.01 (t, 1H), 6.75 (bs, 1H), 6.40 (m, 1H), 6.31 (dd, 1H), 6.20 (s, 1H), 6.12 (bs, 1H), 3.94 (t, 4H), 3.83 (s, 3H), 3.41 (t, 4H), 3.26 (t, 4H), 2.01 (m, 4H).

{4-[4-Nitro-3-(pyrrolidin-1-yl)phenyl]piperazin-1-yl}(1H-pyrrol-2-yl)methanone (344): Step 1: Methyl N-Boc-2-pyrrolecarboxylate (0.150 ml, 697 umol) was refluxed overnight in 10 ml CH$_3$OH with 800 ul of concentrated NaOH (aq). After cooling, 10 ml H$_2$O was added and the acidity adjusted to pH 4 with 1 M HCl (aq). The solution was extracted 4×5 ml DCM. The solvent was removed by rotary evaporation and the white residue dried in vacuum (18 mg, 12%) to generate an about 2:1 mix of Boc protected:Boc deprotected carboxylic acid.

Step 2: The pyrrolecarboxylate from the previous step was stirred overnight with 1-(4-nitro-3-(pyrrolidin-1-ylphenyl)piperazine hydrochloride (0.013 g, 43 umol), hydroxybenzotriazole (0.007 g, 47 umol), triethylamine (0.010 ml, 128 umol) and 1-ethyl-3-(3-dimethylaminopropyl)carbodiimide (0.009 g, 47 umol) in 1 ml DMF. The solvent was removed by rotary evaporation and the residue purified by flash chromatography (3:1-0:1 hexane:EtOAc) to yield the product as a yellow solid (60%): R$_f$ (1:1 hexane:EtOAc) 0.36; $^1$H-NMR (CDCl$_3$ 300 MHz) 10.01 (bs, 0.8H, NH), 9.51 (bs, 0.2H, NH) 7.87 (d, 1H), 7.00 (m, 1H), 6.61 (m, 1H), 6.32 (m, 2H), 6.20 (s, 1H), 6.10 (m, 1H), 4.06 (bt, 4H), 3.49 (t, 4H), 3.25 (t, 4H), 2.01 (m, 4H).

4-Methoxyphenyl-1-{4-[4-nitro-3-(pyrrolidin-1-yl)phenyl]piperazin-1-yl}methanone (345): Purified by flash chromatography (3:1-0:1 hexane:EtOAc) to yield the product as a yellow solid (100%): R$_f$ (1:1 hexane:EtOAc) 0.25; $^1$H-NMR (CDCl$_3$ 300 MHz) 7.84 (d, 1H), 7.43 (d, 2H), 6.94 (d, 2H), 6.28 (dd, 1H), 6.14 (d, 1H), 3.86 (s, 3H), 3.78 (bs, 4H), 3.36 (bt, 4H), 3.24 (t, 4H), 1.98 (m, 4H).

4-Dimethylaminophenyl-1-{4-[4-nitro-3-(pyrrolidin-1-yl)phenyl]piperazin-1-yl}methanone (346): Purified by flash chromatography (2:1-0:1 hexane:EtOAc) to yield the product as a yellow solid (100%): R$_f$ (1:1 hexane:EtOAc) 0.25; $^1$H-NMR (CDCl$_3$ 300 MHz) 7.85 (d, 1H), 7.41 (d, 2H), 6.70 (d, 2H), 6.30 (dd, 1H), 6.14 (d, 1H), 3.81 (bs, 4H), 3.47 (bt, 4H), 3.24 (t, 4H), 3.03 (s, 6H), 1.98 (m, 4H).

{4-[4-Nitro-3-(pyrrolidin-1-yl)phenyl]piperazin-1-yl}(1-acetyl-pyrrol-2yl)methanone (347): {4-[4-Nitro-3-(pyrrolidin-1-yl)phenyl]piperazin-1-yl}(1H-pyrrol-2-yl)methanone (6-122, 0.012 g, 32 umol) was stirred for 3 hr with N,N-dimethylaminopyridine (0.004 g, 32 umol) and acetic anhydride (0.012 ul, 130 umol) in 1 ml pyridine and 5 ml DCM. The solvent was removed by rotary evaporation and the residue purified by flash chromatography (2:1-0:1 hexane:EtOAc) to yield the product as a yellow solid (69%): R$_f$ (1:1 hexane:EtOAc) 0.41; $^1$H-NMR (CDCl$_3$ 300 MHz) 7.87 (d, 1H), 7.00 (m, 1H), 6.60 (m, 1H), 6.30 (m, 2H), 6.12 (d, 1H), 4.06 (t, 4H), 3.50 (t, 4H), 3.26 (t, 4H), 2.00 (m, 7H).

Figure 15:
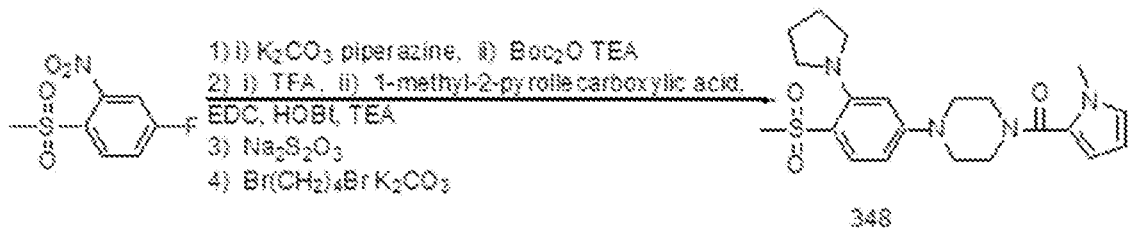
FIG. 15 is a schematic illustration of the preparation of a representative piperazine compound of the invention.

The synthesis of piperazine 348 is shown in FIG. 15 and described below.

4-[3-Pyrrolidin-1-yl)-4-(methylsulfonyl)phenyl]piperazin-1-yl}(1-methyl-1H-pyrrol-2-yl)methanone (348): Step 1: tert-Butyl 4-[4-(methylsulfonyl)-3-nitrophenyl]piperazine-1-carboxylate: 4-Fluoro-1-methanesulfonyl-2-nitrobenzene (0.075 g, 342 umol), piperazine (0.035 g, 411 umol) and potassium carbonate (0.076 g, 547 umol) were refluxed overnight in 10 ml acetonitrile. After cooling to room temperature, 400 mg Boc$_2$O and 500 ul triethylamine were added. The solution was stirred for 1.5 h whereupon the solvent was removed by rotary evaporation and residue purified using flash chromatography (2:1-0:1 hexane: EtOAc) to give the final product as a yellow solid (0.131 g, 100%): R$_f$ (3:1 hexane:EtOAc) 0.12; $^1$H-NMR (CDCl$_3$ 300 MHz) 7.98 (d, 1H), 7.28 (d, 1H), 7.00 (dd, 1H), 3.63 (t, 4H), 3.45 (t, 4H), 3.39 (s, 3H), 1.54 (s, 9H).

Step 2: (1-Methyl-1H-pyrrol-2-yl){4-[4-(methylsulfonyl)-3-nitrophenyl]piperazin-1-yl}methanone: The carbamate (0.065 g, 169 umol) was stirred overnight in 3 ml DCM with 3 ml trifluoroacetic. The solvent was removed by rotary evaporation and EDC (0.065 g, 336 umol), HOBt (0.052 g, 336 umol), 1-methyl-2-pyroolecarboxylic acid (0.042 g, 336 umol), TEA (0.183 ml, 1682 umol) were added in 1.5 ml DMF and stirred overnight. After adding 5 ml DCM the solution was washed twice with 3 ml 5% NaHCO$_3$ (aq) and once with 3 ml brine. The organics were dried with anhyd. MgSO$_4$, filtered and the solvent was removed by rotary evaporation and residue purified using flash chromatography (3:1-0:1 hexane:EtOAc) to give the final product as a yellow solid (0.018 g, 41%): R$_f$ (8:1 EtOAc:CH$_3$OH) 0.11; $^1$H-NMR (CDCl$_3$ 300 MHz) 7.99 (d, 1H), 7.17 (d, 1H), 7.02 (dd, 1H), 6.78 (t, 1H), 6.42 (dd, 1H), 6.14 (dd, 1H), 3.97 (t, 4H), 3.83 (s, 3H), 3.54 (t, 4H), 3.39 (s, 3H, NCH$_3$).

Step 3: {4-[3-Amino-4-(methylsulfonyl)phenyl]piperazin-1-yl}(1-methyl-1H-pyrrol-2-yl)methanone: The nitro (0.656 g, 1.7 mmol) was refluxed overnight in 50 ml ethanol with sodium hydrosulfite (1.455 g, 8.4 mmol) predissolved in 3 ml H$_2$O whereupon 5 ml 1 M HCl (aq) was added and the solution stirred an additional 30 min. An additional 50 ml H$_2$O was added and sat'd NaHCO$_3$ (aq) was added until pH ~8. The solution was extracted 7×10 ml DCM and the combined organics washed 2×20 ml brine, dried with anhyd MgSO4, filtered and the solvent was removed by rotary evaporation and residue purified using flash chromatography (1:0-8:1 EtOAc:CH$_3$OH) to give the final product as a white solid (0.400 g, 66%): R$_f$ (8:1 EtOAc:CH$_3$OH) 0.87; $^1$H-NMR (CDCl$_3$ 500 MHz) 7.51 (d, 1H), 6.66 (s, 1H), 6.29 (m, 2H), 6.04 (m, 2H), 3.83 (t, 4H), 3.74 (s, 3H), 3.28 (t, 4H), 3.95 (s, 3H, NCH$_3$); ESMS 363 (M+H, 100%).

Step 4: {4-[3-Pyrrolidin-1-yl)-4-(methylsulfonyl)phenyl]piperazin-1-yl}(1-methyl-1H-pyrrol-2-yl)methanone: The amine (0.308 g, 0.85 mmol), potassium carbonate (0.470 g, 3.40 mmol) and 1,4-dibromobutane were heated at 120 C for 21 h under Ar in 12 ml 1:1 NMP:DMF whereupon 30 ml H$_2$O was added and the solution extracted 6×10 ml DCM. The combined organics were washed 3×10 ml H$_2$O and 3×10 ml brine and the solvent was removed by rotary evaporation and residue purified using flash chromatography (3:1-1:1 hexane:EtOAc) to give the final product as a white solid (0.004 g, 1%): R$_f$ (1:1 hexane:EtOAc) 0.93; $^1$H-NMR (CDCl$_3$ 500 MHz) 8.09 (s, 1H), 6.96 (dd, 2H), 6.18 (m, 2H), 6.14 (m, 1H), 3.95 (s, 3H), 3.48 (m, 15H), 1.95 (m, 4H).

Figure 16:
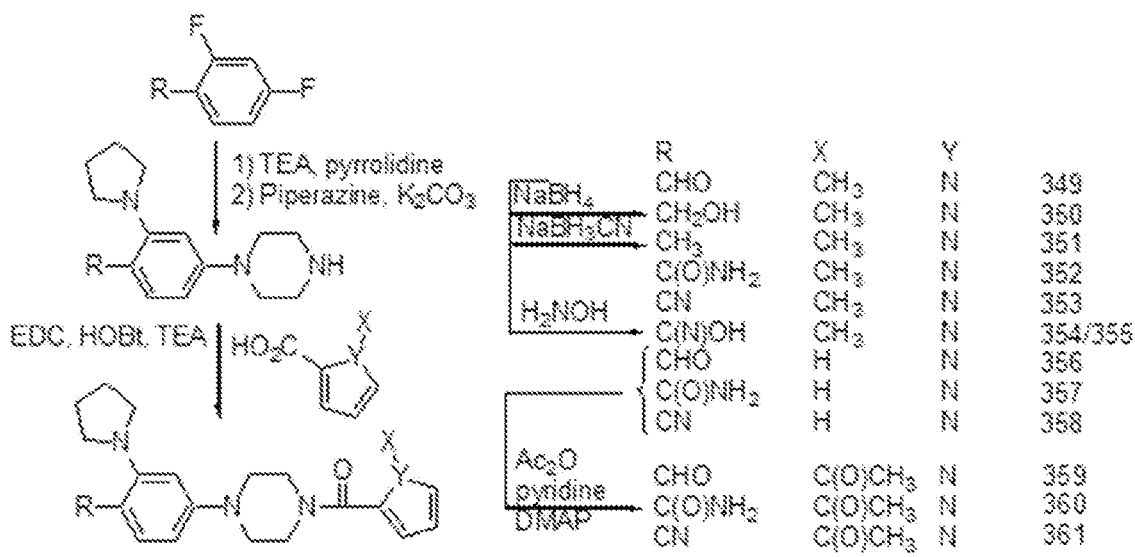
FIG. 16 is a schematic illustration of the preparation of representative piperazine compounds of the invention.

The synthesis of piperazines 349-361 is shown in FIG. 16 and described below.

General Procedure to Add o-substitute Pyrrolidine 2,4-Difluorobenzene derivative was reacted with 1.1 eqv triethylamine and 0.9 eqv pyrrolidine at 80 C in p-dioxane (1 g per 20 ml solvent) for 16 h under Ar. Upon cooling the solution was diluted 50% with DCM and then washed three times with water and 1 time with brine, dried with anhyd MgSO$_4$, filtered and the solvent was removed by rotary evaporation and residue purified using flash chromatography.

General procedure to Add Piperazine

The fluorobenzaldehyde (0.062 g, 321 umol), piperazine (0.041 g, 481 umol) and potassium carbonate (0.133 g, 963 umol) were heated at 112 C overnight under Ar for 16.5 h in 5 ml DMF. After cooling 50 ml H$_2$O was added and the solution extracted 4×12 ml DCM. The combine organics were washed 6×15 ml H₂O, 2×15 ml brine, dried with anhyd MgSO₄, filtered and the solvent was removed by rotary evaporation and residue purified using flash chromatography.

General Procedure to Couple N-methylpyrrole-2-carboxylic Acid or pyrrole-2-Carboxylic Acid The piperazine derivative (0.037 g, 143 umol), EDC (0.055 g, 285 umol), HOBt (0.044 g, 285 umol), pyrrole carboxylic acid derivative (0.036 g, 285 umol), TEA (0.062 ml, 571 umol) were stirred overnight in 8 ml DMF. After adding 20 ml H₂O the solution was extracted 4×10 ml DCM. The combined organics were washed with 2×10 ml H₂O (pH ~5) and 2×10 ml saturated NaHCO₃ (aq), dried with anhydrous MgSO₄, filtered and the solvent was removed by rotary evaporation and residue purified using flash chromatography General Procedure to Acetylate Pyrrole Pyrrole (1.0) eqv overnight in 5 ml pyridine with acetic anhydride (1.1 eqv) and DMAP (0.1 eqv). The solvent was removed by rotary evaporation and the residue purified by flash chromatography.

2-(Pyrollidino-1-yl)-4-{4-[(1-methyl-1H-pyrrol-2-yl)carbonyl]piperazin-1-yl}benzaldehyde (349): 4:1-0:1 hexane: EtOAc to give the final product as a yellow solid (0.024 g, 46%): R$_f$ (1:1 hexane:EtOAc) 0.26; ¹H-NMR (CDCl₃ 300 MHz) 9.89 (s, 1H), 7.66 (d, 1H), 6.74 (t, 1H), 6.40 (m, 2H), 6.12 (m, 2H), 3.93 (m, 4H), 3.83 (s, 3H), 3.43 (m, 8H), 2.01 (t, 4H).

{4-[3-(Pyrrolidin-1-yl)-4-methylphenyl]piperazin-1-yl}(1-methyl-1H-pyrrol-2-yl)methanone (350): The benzaldehyde (0.050 g, 136 umol) in 3 mL THF was stirred overnight with NaBH₄ (0.021 g, 546 umol). The solvent was removed by rotary evaporation and residue purified using flash chromatography (1:1-0:1 hexane:EtOAc) to give the final product as a white solid (0.023 g, 46%): R$_f$ (EtOAc) 0.47; ¹H-NMR (CDCl₃ 300 MHz) 7.13 (d, 1H), 6.74 (t, 1H), 6.64 (d, 1H), 6.55 (dd, 1H), 6.39 (dd, 1H), 6.12 (dd, 1H), 4.74 (s, 2H), 3.95 (t, 4H), 3.82 (s, 3H, NCH₃), 3.20 (m, 8H), 2.00 (m, 4H).

{4-[3-(Pyrrolidin-1-yl)-4-methylphenyl]piperazin-1-yl}(1-methyl-1H-pyrrol-2-yl)methanone (351): The benzaldehyde (0.213 g, 581 umol) in 5 mL methanol was stirred overnight with NaBH₃CN (0.128 g, 2034 umol). The solvent was removed by rotary evaporation and residue purified using flash chromatography (1:1-0:1 hexane:EtOAc) to give the final product as a white solid (0.100 g, 47%): R$_f$(EtOAc) 0.83; ¹H-NMR (CDCl₃ 300 MHz) 7.04 (d, 1H), 6.73 (t, 1H), 6.57 (d, 1H), 6.48 (dd, 1H), 6.42 (m, 1H), 6.12 (m, 1H), 3.96 (t, 4H), 3.85 (s, 3H, NCH₃), 3.24 (m, 8H), 2.31 (s, 3H), 1.98 (m, 4H); ESMS 353 (M+1, 100%). Similar complete reduction of benzaldehyde to toluene has been reported in reference 62.

2-(Pyrrolidino-1-yl)-4-{4-[(1-methyl-1H-pyrrol-2-yl)carbonyl]piperazin-1-yl}benzamide (352): 4:1-0:8:1 hexane: EtOAc:CH₃OH to give the final product as a yellow solid (22%): R$_f$(EtOAc) 0.07; ¹H-NMR (CDCl₃ 300 MHz) 7.76 (d, 1H), 6.65 (m, 1H), 6.50 (m, 2H), 6.31 (m, 1H), 6.03 (m, 1H), 5.72 (bs, 1H), 3.85 (m, 4H), 3.75 (s, 3H), 3.28 (m, 4H), 3.16 (m, 4H), 1.87 (m, 4H).

2-(Pyrrolidino-1-yl)-4-{4-[(1-methyl-1H-pyrrol-2-yl)carbonyl]piperazin-1-yl}benzonitrile (353): 2:1-0:1 hexane:EtOAc to give the final product as a yellow solid (70%): R$_f$ (1:1 hexane:EtOAc) 0.43; ¹H-NMR (CDCl₃ 300 MHz) 7.32 (d, 1H), 6.73 (m, 1H), 6.38 (m, 1H), 6.26 (dd, 1H), 6.11 (m, 1H), 5.96 (m, 1H), 3.91 (t, 4H), 3.82 (s, 3H), 3.60 (t, 4H), 3.34 (t, 4H), 2.00 (m, 4H).

(4-{3-(Pyrrolidin-1-yl)-4-[(E)-(hydroxyimino)methyl]phenyl}piperazin-1-yl)(1-methyl-1H-pyrrol-2-yl)methanone (354) and (4-{3-(pyrrolidin-1-yl)-4-[(Z)-(hydroxyimino)methyl]phenyl}piperazin-1-yl)(1-methyl-1H-pyrrol-2-yl)methanone (355): Aldehyde (0.047 g, 128 umol) was refluxed overnight in 10 ml ethanol with 269 ul pyridine and hydroxylamine hydrochloride (0.067 g, 962 umol). The solvent was removed by rotary evaporation and the residue dissolved in 5 ml H₂O and extracted with 15 ml EtOAc and 3×15 ml DCM. The combined organics were dried with anhyd. MgSO₄, filtered and solvent was removed by rotary evaporation and residue purified using flash chromatography (4:1:0-0:8:1 hexane:EtOAc:CH₃OH) to give the final products as a white solid:

E product: (0.026 g, 53%): R$_f$ (1:1 hexane:EtOAc) 0.47; ¹H-NMR (CDCl₃ 500 MHz) 8.39 (s, 1H), 7.52 (d, 1H), 6.74 (s, 1H), 6.48 (dd, 1H), 6.42 (s, 1H), 6.40 (m, 1H), 6.13 (t, 1H), 3.94 (t, 4H), 3.85 (s, 3H), 3.31 (t, 8H), 1.98 (t, 4H).

Z product: (0.002 g, 4%): R$_f$ (1:1 hexane:EtOAc) 0.34; ¹H-NMR (CDCl₃ 500 MHz) 7.63 (s, 1H), 7.37 (d, 1H), 6.65 (s, 1H), 6.51 (m, 1H), 6.48 (s, 1H), 6.31 (m, 1H), 6.03 (t, 1H), 3.85 (t, 4H), 3.72 (s, 3H), 3.24 (m, 4H), 3.09 (m, 4H), 1.93 (t, 4H).

2-(Pyrrolidino-1-yl)-4-{4-[(1H-pyrrol-2-yl)carbonyl]piperazin-1-yl}benzaldehyde (356): 3:1-0:1 hexane:EtOAc to give the final product as a yellow solid (67%): R$_f$ (1:1 hexane:EtOAc) 0.10; ¹H-NMR (CDCl₃ 300 MHz) 9.88 (s, 1H), 9.47 (bs, 1H), 7.69 (d, 1H), 6.98 (s, 1H), 6.60 (s, 1H), 6.47 (bs, 1H), 6.31 (m, 1H), 4.06 (bs, 4H), 3.55 (bs, 4H), 3.40 (bs, 4H), 2.09 (bs, 4H).

2-(Pyrrolidino-1-yl)-4-{4-[(1H-pyrrol-2-yl)carbonyl]piperazin-1-yl}benzamide (357): 1:1:0-0:8:1 hexane:EtOAc: CH₃OH to give the product as a white solid (32%): R$_f$ (EtOAc) 0.07; ¹H-NMR (CDCl₃ 300 MHz) 9.84 (bs, 1H), 7.97 (bs, 1H), 7.84 (d, 1H), 6.98 (m, 1H), 6.55 (m, 3H), 6.29 (m, 1H), 5.94 (bs, 1H), 4.04 (t, 4H), 3.40 (t, 4H), 3.20 (m, 4H), 1.98 (m, 4H).

2-(Pyrrolidino-1-yl)-4-{4-[(1H-pyrrol-2-yl)carbonyl]piperazin-1-yl}benzonitrile (358): 3:1-0:1 hexane:EtOAc to give the product as a white solid (90%): R$_f$ (EtOAc) 0.73; ¹H-NMR (CDCl₃ 300 MHz) 9.51 (bs, 1H), 7.36 (d, 1H), 6.99 (m, 1H), 6.59 (m, 2H), 6.30 (m, 1H), 6.03 (bs, 1H), 4.03 (m, 4H), 3.62 (m, 4H), 3.43 (t, 4H), 2.05 (m, 4H).

2-(Pyrrolidino-1-yl)-4-{4-[(N-acetylpyrrol-2-yl)carbonyl]piperazin-1-yl}benzaldehyde (359): 2:1-0:1 hexane:EtOAc to provide a white solid (60%): R$_f$ (EtOAc) 0.39; ¹H-NMR (CDCl₃ 300 MHz) 9.79 (s, 1H), 7.56 (d, 1H), 7.07 (m, 1H), 6.27 (m, 3H), 6.03 (s, 1H), 3.84 (m, 2H), 3.35 (m, 10H), 2.48 (s, 3H), 1.94 (m, 4H).

2-(Pyrrolidino-1-yl)-4-{4-[(N-acetylpyrrol-2-yl)carbonyl]piperazin-1-yl}benzamide (360): 1:1:0-0:8:1 hexane: EtOAc:CH₃OH to provide a white solid (100%): R$_f$(EtOAc) 0.07; ¹H-NMR (CDCl₃ 300 MHz) 8.03 (bs, 1H), 7.80 (d, 1H), 7.15 (m, 1H), 6.52 (m, 2H), 6.32 (m, 3H), 3.92 (m, 2H), 3.53 (m, 2H), 3.38 (m, 2H), 3.18 (m, 6H), 2.26 (s, 3H), 1.95 (m, 4H).

2-(Pyrollidino-1-yl)-4-{4-[(N-acetylpyrrol-2-yl)carbonyl]piperazin-1-yl}benzonitrile (361): 2:1-1:2 hexane: EtOAc to provide a white solid (73%): R$_f$ (EtOAc) 0.53; ¹H-NMR (CDCl₃ 300 MHz) 7.25 (d, 1H), 7.12 (m, 1H), 6.31 (m, 1H), 6.25 (m, 1H), 6.19 (dd, 1H), 5.90 (d, 1H), 3.85 (m, 2H), 3.53 (t, 4H), 3.47 (m, 2H), 3.35 (m, 2H), 3.20 (m, 2H), 2.51 (s, 3H), 1.94 (t, 4H).

Figure 17:
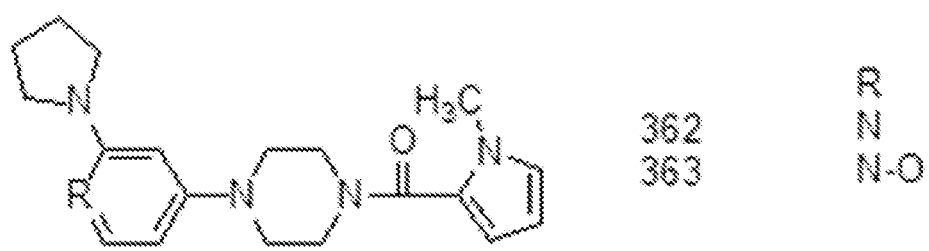
FIG. 17 illustrates representative piperazine compounds of the invention.

The structure of piperazines 362 and 363 are shown in FIG. 17 and their preparation is described below.

(1-Methyl-1H-pyrrol-2-yl){4-[2-(pyrrolidin-1-yl)pyridin-4-yl]piperazin-1-yl}methanone (362): Step 1: 1-(2-nitropyridin-4-yl)piperazine: 4-Chloro-3-nitropyridine (0.791 g, 4.99 mmol) was heated at 110 C overnight in 20 ml DMSO under Ar with piperazine (0.433 g, 4.99 mmol) and potassium carbonate (0.758 g, 5.49 mmol) upon which 50 ml H$_2$O was added and the solution extracted 5×10 ml DCM. The combined organics were washed 2×20 ml H$_2$O, 20 ml brine and then dried with anhyd. MgSO$_4$. The solvent was removed by rotary evaporation and the residue flash chromatography (1:1-0:1 hexane:EtOAc) purified to yield a yellow solid (9%): R$_f$ (EtOAc) 0.07; $^1$H-NMR (CDCl$_3$ 300 MHz) 8.83 (s, 1H), 8.37 (d, 1H), 6.87 (d, 1H), 3.22 (m 4H), 3.03 (m, 4H).

Step 2: (1-Methyl-1H-pyrrol-2-yl)[4-(2-nitropyridin-4-yl)piperazin-1-yl]methanone: EDCI coupling, 1:1-0:1 hexane:EtOAc, yellow solid (40%): R$_f$ (EtOAc) 0.22; $^1$H-NMR (CDCl$_3$ 300 MHz) 8.91 (bs, 1H), 8.43 (d, 1H), 8.08 (d, 1H), 6.90 (d, 1H), 6.74 (bs, 1H), 6.11 (m, 1H), 3.99 (m, 4H), 3.83 (s, 3H), 3.34 (m, 4H).

Step 3: [4-(2-Aminopyridin-4-yl)piperazin-1-yl](1-methyl-1H-pyrrol-2-yl)methanone:sodium hydrosulfite reduction: 0:1-8:1 EtOAc:CH$_3$OH, white solid (17%): R$_f$ (8:1 EtOAc:CH$_3$OH) 0.33; $^1$H-NMR (CDCl$_3$ 300 MHz) 8.11 (bs, 1H), 8.03 (bd, 1H), 6.82 (d, 1H), 6.75 (t, 1H), 6.39 (dd, 1H), 6.12 (dd, 1H), 3.94 (m, 4H), 3.83 (s, 3H), 3.06 (m, 4H), 2.25 (bs, 2H).

Step 4: K$_2$CO$_3$/Br(CH$_2$)$_4$Br coupling: 1:1-0-0:8:1 hexane:EtOAc:CH$_3$OH, brown solid (43%): R$_f$ (EtOAc) 0.17; $^1$H-NMR (CDCl$_3$ 300 MHz) 8.14 (s, 1H), 6.75 (m, 1H), 6.36 (m, 2H), 6.13 (m, 1H), 5.15 (m, 1H), 3.81 (s, 3H), 3.76 (m, 8H), 3.44 (m, 4H), 2.89 (m, 2H), 2.37 (m, 2H).

(1-Methyl-1H-pyrrol-2-yl){4-[2-(pyrrolidin-1-yl)pyridine-N-oxide-4-yl]piperazin-1-yl}methanone (363): Pyridine compound (0.004 g, 1.1 umol), methyltrioxorhenium (VI) (0.001 g) in 3 ml DCM was treated with 0.5 ml 30% H$_2$O$_2$ (aq) for 5 h whereupon MnO$_2$ (0.001 g) was added and the solution stirred overnight. The 115iperidin were removed and the solution extracted 4×3 ml CH$_2$Cl$_2$ and purified 1:0-8:1 EtOAc:CH$_3$OH, to give a white solid (25%): R$_f$ (EtOAc) 0.06; $^1$H-NMR (CDCl$_3$ 500 MHz) 7.31 (m, 2H), 7.10 (m, 1H), 6.75 (m, 1H), 6.38 (m, 1H), 6.07 (m, 1H), 3.95 (m, 2H), 3.78 (m, 2H), 3.70 (m, 2H), 3.60 (m, 2H), 3.39 (s, 3H), 2.25 (m, 2H), 1.95 (m, 2H).

Figure 18:
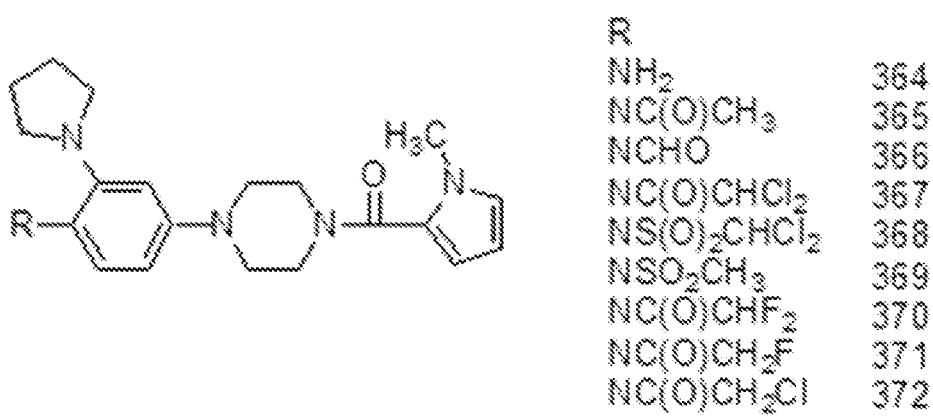
FIG. 18 illustrates a representative genus of piperazine compounds of the invention.

The structures of piperazines 364-372 are shown in FIG. 18 and their preparation is described below.

1-[4-(4-Amino-3-(pyrrolidin-1-yl)phenyl]piperazin-1-yl](1-methyl-1H-pyrrol-2-yl)methanone (364): The nitro compound (1.329 g, 3.5 mmol) in 40 ml EtOH was reduced by refluxing overnight with sodium thiosulfate (2.414 g, 13.9 mmol, pre-dissolved in 10 ml H$_2$O). The reaction was quenched with 1 ml 1 M HCl (aq), stirred for about 40 min, basify so about pH 9 with saturated NaHCO$_3$ (aq), extracted 6×10 ml DCM, the organic solvent removed by rotary evaporation and residue purified by flash chromatography (2:1-0:1 hexane:EtOAc) to provide the amine as an off-white solid (20%): R$_f$(1:1 hexane:EtOAc) 0.16; $^1$H-NMR (CDCl$_3$ 300 MHz) 6.63 (m, 2H), 6.60 (s, 1H), 6.48 (dd 1H), 6.29 (dd, 1H), 6.03 (dd, 1H), 3.84 (m, 4H), 3.73 (s, 3H), 3.03 (m, 4H), 2.98 (m, 4H), 1.90 (m, 4H); ESMS 354 (M+H, 100%).

1-[4-(4-N-Acetyl-3-(pyrrolidin-1-yl)phenyl]piperazin-1-yl](1-methyl-1H-pyrrol-2-yl)methanone (365): The amino compound (0.018 g, 51 umol) in 0.5 ml pyridine was stirred over the weekend with acetic anhydride (9.6 ul, 102 umol) and DMAP (0.001 g). Purified by flash chromatography (1:1-0:1 hexane:EtOAc) to provide the acetamide as an off-white solid (75%): R$_f$ (EtOAc) 0.29; $^1$H-NMR (CDCl$_3$ 300 MHz) 7.75 (bs, 1H), 6.73 (m, 1H), 6.68 (m, 1H), 6.62 (dd, 1H), 6.38 (m, 2H), 6.11 (m, 1H), 3.92 (m, 4H), 3.81 (s, 3H), 3.12 (m, 8H), 2.20 (s, 3H), 1.97 (m, 4H).

1-[4-(4-N-Formyl-3-(pyrrolidin-1-yl)phenyl]piperazin-1-yl](1-methyl-1H-pyrrol-2-yl)methanone (366): The amino compound (0.015 g, 42 umol) in 1 ml DCM was stirred over the weekend with 2,2,2-trifluoroethyl formate (20.6 ul, 212 umol). Purified by flash chromatography (1:1-0:1 hexane:EtOAc) to provide the acetamide as an off-white solid (88%): R$_f$ (EtOAc) 0.47; $^1$H-NMR (CDCl$_3$ 300 MHz) 8.49 (d, 1H), 8.08 (d, 1H), 6.75 (m, 2H), 6.66 (dd, 1H), 6.57 (d, 1H), 6.54 (dd, 1H), 6.11 (m, 1H), 3.93 (m, 4H), 3.82 (s, 3H), 3.19 (m, 8H), 1.96 (m, 4H).

1-[4-(4-N-Dichloroacetyl-3-(pyrrolidin-1-yl)phenyl]piperazin-1-yl](1-methyl-1H-pyrrol-2-yl)methanone (367): The amino compound (0.013 g, 37 umol) in 1 ml DCM was stirred overnight with dichloroacetyl chloride (3.9 ul, 40 umol) and triethylamine (8.0 ul, 74 umol). Purified by flash chromatography (1:1-0:1 hexane:EtOAc) to provide the acetamide as an off-white solid (100%): R$_f$ (EtOAc) 0.87; $^1$H-NMR (CDCl$_3$ 300 MHz) 9.07 (bs, 1H), 8.01 (d, 1H), 6.75 (m, 3H), 6.68 (dd, 1H), 6.39 (dd, 1H), 6.12 (dd, 1H), 6.08 (s, 1H), 3.94 (m, 4H), 3.82 (s, 3H), 3.21 (m, 4H), 3.10 (m, 4H), 2.00 (m, 4H).

1-[4-(4-N-Dichloromethylsulfonamide-3-(pyrrolidin-1-yl)phenyl]piperazin-1-yl](1-methyl-1H-pyrrol-2-yl)methanone (368): The amino compound (0.018 g, 51 umol) in 1 ml DCM was stirred overnight with dichloromethanesulfonyl chloride (10.2 ul, 102 umol) and triethylamine (16.6 ul, 153 umol). Purified by flash chromatography (1:1-0:0:8:1 hexane:EtOAc:CH$_3$OH) to provide the sulfonamide as an off-white solid (42%): R$_f$ (EtOAc) 0.86; $^1$H-NMR (CDCl$_3$ 300 MHz) 7.32 (d, 1H), 6.44 (bs, 1H), 6.59 (d, 1H), 6.50 (dd, 1H), 6.29 (m, 1H), 6.24 (s, 1H), 6.03 (m, 1H), 3.84 (m, 4H), 3.73 (s, 3H), 3.11 (m, 8H), 1.91 (m, 4H).

1-[4-(4-N-Methylsulfonamide-3-(pyrrolidin-1-yl)phenyl]piperazin-1-yl](1-methyl-1H-pyrrol-2-yl)methanone (369): The amino compound (0.011 g, 31 umol) in 3 ml DCM was stirred overnight with methanesulfonyl chloride (2.6 ul, 34 umol) and triethylamine (6.8 ul, 62 umol). Purified by flash chromatography (1:0-0:1 hexane:EtOAc) to provide the sulfonamide as an off-white solid (46%): R$_f$ (EtOAc) 0.72; $^1$H-NMR (CDCl$_3$ 300 MHz) 7.29 (d, 1H), 6.65 (m, 2H), 6.55 (dd, 1H), 6.30 (dd, 1H), 6.03 (dd 1H), 3.84 (m, 4H), 3.73 (s, 3H), 3.08 (m, 8H), 2.91 (s, 3H), 1.90 (m, 4H).

1-[4-(4-N-Fluoroacetyl-3-(pyrrolidin-1-yl)phenyl]piperazin-1-yl](1-methyl-1H-pyrrol-2-yl)methanone (370): EDC coupling: Purified by flash chromatography (1:1 hexane:EtOAc) to yield difluoroacetamide as a light brown solid (58%): R$_f$(1:1 hexane:EtOAc) 0.27; $^1$H-NMR (CDCl$_3$ 300 MHz) 8.74 (bs, 1H), 8.05 (s, 1H), 6.74 (m, 2H), 6.68 (bd, 1H), 6.40 (m, 1H), 6.12 (m, 1H), 3.92 (m, 4H), 3.83 (s, 3H), 3.20 (m, 4H), 3.09 (m, 4H), 2.00 (m, 4H).

1-[4-(4-N-Fluoroacetyl-3-(pyrrolidin-1-yl)phenyl]piperazin-1-yl](1-methyl-1H-pyrrol-2-yl)methanone (371): EDC coupling: Purified by flash chromatography (2:1-1:1 hexane:EtOAc) to fluoroacetamide as a yellow solid (61%): R$_f$(1:1 hexane:EtOAc) 0.16; $^1$H-NMR (CDCl$_3$ 300 MHz) 8.60 (bs, 1H), 8.00 (m, 1H), 6.71 (s, 2H), 6.63 (m, 1H), 6.36 (m, 1H), 6.09 (m, 1H), 4.93 (d, 2H), 3.91 (m, 4H), 3.79 (s, 3H), 3.17 (m, 4H), 3.08 (m, 4H), 1.95 (m, 4H).

1-[4-(4-N-Chloroacetyl-3-(pyrrolidin-1-yl)phenyl]piperazin-1-yl](1-methyl-1H-pyrrol-2-yl)methanone (372): Chloroacetyl chloride (5.5 ul, 68 umol), triethylamine (7.5 ul, 68 umol) was added to the amine (0.022 g, 62 umol) dissolved in 0.8 ml DMF. The reaction was stirred for 72 hrs whereupon 8 ml H$_2$O was added and the mixture extracted 2×4 ml CH$_2$Cl$_2$. The combined organics were washed 2×3 ml H$_2$O, dried with anhyd MgSO$_4$, the solvent removed and the residue purified by flash chromatography (3:1-1:1 hexane:EtOAc) to yield a brown solid (30%): R$_f$ (1:1 hexane:EtOAc) 0.18; $^1$H-NMR (CDCl$_3$ 300 MHz) 8.03 (s, 1H), 7.68 (d, 1H), 7.04 (m, 2H), 6.71 (s, 1H), 6.38 (m, 1H), 6.09 (m, 1H), 4.81 (bs, 2H), 4.38 (m, 2H), 4.22 (m, 2H), 3.91 (m, 4H), 3.79 (s, 3H), 3.26 (m, 4H), 2.53 (m, 2H), 2.25 (m, 2H).

Figure 19:
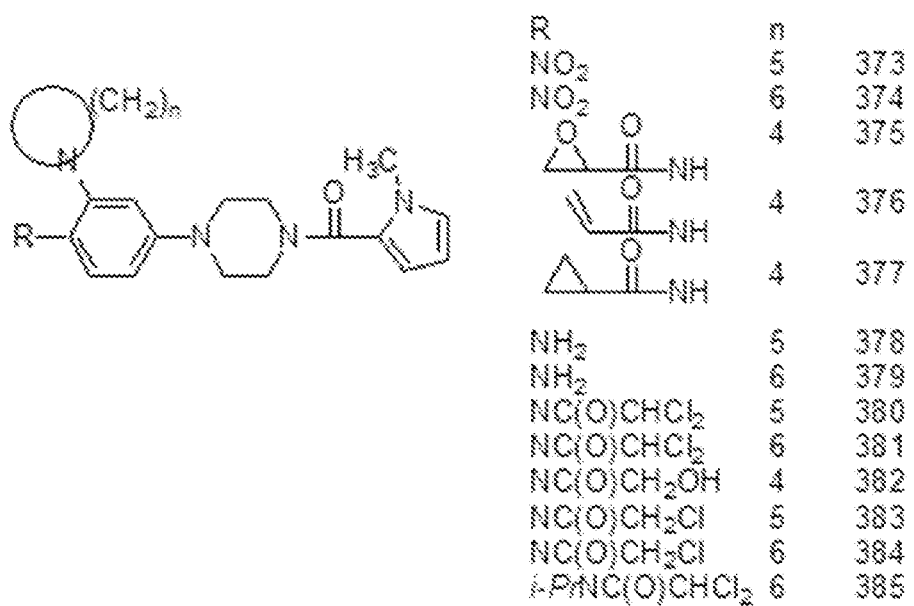
FIG. 19 illustrates a representative genus of piperazine compounds of the invention.

The structures of piperazines 373-385 are shown in FIG. 19 and their preparation is described below.

1-[4-(4-Nitrophenyl)-3-(piperidin-1-yl)phenyl]piperazin-1-yl](1-methyl-1H-pyrrol-2-yl)methanone (373): Step 1: 1-(5-Fluoro-2-nitrophenyl)piperidine: 2,4-dinitrobenzene (0.500 g, 3.14 mmol) was refluxed overnight in 23 ml p-dioxane with piperidine (0.268 g, 3.14 mmol) and triethylamine (0.349 g, 3.45 mmol) under Ar. The solvent was removed by rotary evaporation and the residue purified by flash chromatography (6:1 hexane:EtOAc) to provide the target as a yellow liquid (67%): R$_f$ (6:1 hexane:EtOAc) 0.74; $^1$H-NMR (CDCl$_3$ 300 MHz) 7.85 (dd, 1H), 6.73 (dd, 1H), 6.60 (m, 1H), 3.03 (m, 4H), 1.72 (m, 4H), 1.62 (m, 2H).

Step 2: 1-[4-Nitro-3-(piperidin-1-yl)phenyl]piperazine: Aryl fluoride (0.470 g, 2.1 mmol), potassium carbonate (0.435 g, 3.1 mmol) and piperazine (0.545 g, 6.3 mmol) were heated at ~100 C in 25 ml DMF overnight under Ar. Water (50 ml) was added and the solution extracted 4×20 ml DCM. The combined organics were washed 3×15 ml H$_2$O and 15 ml brine, dried with MgSO$_4$ and the solvent removed by rotary evaporation and the residue purified by flash chromatography (short column) 1:0-8:1 EtOAc:MeOH to provide the target as orange gum (74%): R$_f$ (8:1 EtOAc:MeOH) 0.06; $^1$H-NMR (CDCl$_3$ 300 MHz) 7.99 (d, 1H), 6.39 (d, 1H), 6.31 (d, 1H), 3.32 (m, 4H), 3.01 (m, 8H), 1.75 (m, 4H), 1.60 (m, 2H).

Step 3: The amine (0.452 g, 1.6 mmol), EDC (0.895 g, 4.7 mmol), HOBt (0.477 g, 3.1 mmol), N-methyl-pyrazole-2-carboxylic acid (0.584 g, 4.7 mmol) and TEA (0.473 g, 4.7 mmol) were stirred overnight in 50 ml DCM. The solution was washed 2×20 ml H$_2$O (+1 ml 1 M HCl (aq)), 20 ml sat'd NaHCO$_3$ (aq) and the solvent removed by rotary evaporation and the residue purified by flash chromatography 2:1-1:1 hexane:EtOAc to provide the target as a yellow solid (87%): R$_f$ (1:1 hexane:EtOAc) 0.48; $^1$H-NMR (CDCl$_3$ 300 MHz) 7.99 (d, 1H), 6.73 (s, 1H), 6.39 (m, 3H), 6.11 (dd, 1H), 3.92 (m, 4H), 3.81 (s, 3H), 3.42 (t, 4H), 3.03 (t, 4H), 1.76 (m, 4H), 1.61 (m, 2H).

1-[4-(4-Nitrophenyl)-3-(azepan-1-yl)phenyl]piperazin-1-yl](1-methyl-1H-pyrrol-2-yl)methanone (374): Step 1: 1-(5-Fluoro-2-nitrophenyl)azepane: 2,4-dinitrobenzene (0.500 g, 3.14 mmol) was refluxed overnight in 15 ml p-dioxane with hexamethylene imine (0.312 g, 3.14 mmol) and triethylamine (0.350 g, 3.46 mmol) under Ar. The solvent was removed by rotary evaporation and the residue purified by flash chromatography (6:1 hexane:EtOAc) to provide the target as a yellow liquid (91%): R$_f$ (6:1 hexane:EtOAc) 0.58; $^1$H-NMR (CDCl$_3$ 300 MHz) 7.74 (dd, 1H), 6.69 (dd, 1H), 6.43 (m, 1H), 3.27 (m, 4H), 1.80 (m, 4H), 1.60 (m, 4H).

Step 2: 1-[4-Nitro-3-(piperidine-1-yl)phenyl]azepane: Aryl fluoride (0.680 g, 2.9 mmol), potassium carbonate (0.592 g, 4.3 mmol) and piperazine (0.743 g, 8.6 mmol) were heated at about 100° C. in 25 ml DMF overnight under Ar. Water (50 ml) was added and the solution extracted 4×20 ml DCM. The combined organics were washed 3×15 ml H$_2$O and 15 ml brine, dried with MgSO$_4$ and the solvent removed by rotary evaporation and the residue purified by flash chromatography (short column) 1:0-8:1 EtOAc:MeOH to provide the target as orange gum (67%): R$_f$ (8:1 EtOAc:MeOH) 0.06; $^1$H-NMR (CDCl$_3$ 300 MHz) 7.81 (d, 1H), 6.29 (m, 2H), 3.28 (m, 8H), 3.00 (m, 4H), 1.79 (m, 4H), 1.62 (m, 4H).

Step 3: The amine (0.580 g, 1.9 mmol), EDC (1.096 g, 5.7 mmol), HOBt (0.584 g, 3.8 mmol), N-methyl-pyrazole-2-carboxylic acid (0.715 g, 5.7 mmol) and TEA (0.578 g, 5.7 mmol) were stirred overnight in 50 ml DCM. The solution was washed 2×20 ml H$_2$O (+1 ml 1 M HCl (aq)), 20 ml sat'd NaHCO$_3$ (aq) and the solvent removed by rotary evaporation and the residue purified by flash chromatography 2:1-1:1 hexane:EtOAc to provide the target as a yellow solid (85%): R$_f$ (1:1 hexane:EtOAc) 0.41; $^1$H-NMR (CDCl$_3$ 300 MHz) 7.84 (d, 1H), 6.73 (s, 1H), 6.33 (m, 3H), 6.10 (dd, 1H), 3.92 (m, 4H), 3.81 (s, 3H), 3.38 (m, 8H), 1.85 (m, 4H), 1.63 (m, 4H).

(3-Pyrrolidin-1yl)-N-4-{4-[(1-methyl-1H-pyrrol-2-yl)carbonyl]piperazin-1-yl}phenyl)oxirane-2-carboxamide (375): To EDC (0.018 g, 94 umol), HOBt (0.010, 63 umol) and potassium oxirane-2-carboxylate (0.012 g, 94 umol) in 0.5 ml DMF was added 24 ul of 4 M HCl (in dioxane). After stirring for 20 min, amine (0.012 g, 31 umol) was added and the reaction stirred overnight. The solvent was removed by rotary evaporation and the residue purified by flash chromatography 3:1:0-0:8:1 hexane:EtOAc:MeOH to provide the target as a yellowish solid (8%): R$_f$ (8:1 EtOAc:MeOH) 0.10; $^1$H-NMR (CDCl$_3$ 500 MHz) 7.54 (d, 1H), 6.96 (d, 1H), 6.79 (s, 1H), 6.72 (s, 1H), 6.37 (s, 1H), 6.10 (bt, 1H), 4.07 (t, 2H), 3.94 (m, 4H), 3.80 (s, 3H), 3.19 (m, 4H), 3.38 (m, 4H), 2.98 (d, 1H) 1.95 (m, 4H).

3-Pyrrolidin-1yl-N-{4-[4-(pyrrolidin-2-ylcarbonyl)piperazin-1-yl]phenyl}prop-2-enamide (376): Amine (0.028 g, 73 umol), EDC (0.042 g, 219 umol), HOBt (0.022 g, 146 umol), prop-2-enoic acid (0.021 g, 292 umol) were stirred in 6 ml DMF for 1 h. Add TEA (0.022 g, 219 umol) and stir overnight. Add 10 ml H$_2$O and 1 ml 1 M HCl. Extract 5×5 ml DCM. Wash combined organics 2×5 ml brine. The solvent was removed by rotary evaporation and the residue purified by flash chromatography 3:1-0:1 hexane:EtOAc to provide the target as a yellowish solid (34%): R$_f$ (8:1 EtOAc:MeOH) 0.76; $^1$H-NMR (CDCl$_3$ 500 MHz) 8.11 (d, 1H), 7.96 (s, 1H), 6.72 (s, 2H), 6.65 (d, 1H), 6.36 (m, 2H), 6.26 (m, 1H), 6.10 (s, 1H), 5.73 (d, 1H), 3.91 (s, 4H), 3.80 (s, 3H), 3.16 (s, 4H), 3.05 (s, 4H), 1.96 (s, 4H).

1-[4-(4-Cyclopropanecarboxamidyl)-3-(pyrrolidin-1-yl)phenyl]piperazin-1-yl](1-methyl-1H-pyrrol-2-yl)methanone (377): Amine (0.053 g, 138 umol), EDC (0.079 g, 414 umol), HOBt (0.042 g, 276 umol), cyclopropane carboxylic acid (0.054 g, 690 umol) were stirred in 2 ml DMF for 1 h. Add TEA (0.098 g, 966 umol) and stir overnight. Add 20 ml H$_2$O, extract 4×5 ml DCM. Wash combined organics 2×5 ml brine 2×5 ml sat'd NaHCO$_3$ (aq), dry with MgSO$_4$. The solvent was removed by rotary evaporation and the residue purified by flash chromatography 3:1-0:1 hexane:EtOAc to provide the target as a yellowish solid (88%): R$_f$ (1:1 hexane:EtOAc) 0.76; $^1$H-NMR (CDCl$_3$ 500 MHz) 7.95 (d, 1H), 6.69 (m, 2H), 6.59 (d, 1H), 6.35 (m, 1H), 6.09 (dd, 1H), 3.89 (m, 4H), 3.79 (s, 3H), 3.14 (s, 4H), 3.08 (s, 4H), 1.96 (s, 4H), 1.54 (m, 1H), 1.06 (m, 2H), 0.81 (m, 2H).

{4-[4-Amino-3-(piperidin-1-yl)phenyl]piperazin-1-yl}(1-methyl-1H-pyrrol-2-yl)methanone (378): To nitro compound (0.109 g, 0.274 mmol) in 20 ml 3:1 EtOH:H$_2$O was added sodium hydrosulfite (0.191 g, 1.097 mmol). The reaction was refluxed overnight whereupon 1 ml 1 M HCl (aq) was added and mixture stirred for 40 min. Sat'd NaHCO$_3$ (aq) was added until about pH 9 and then extracted 5×5 ml DCM. The solvent was removed by rotary evaporation and the residue purified by flash chromatography 3:1-0:1 hexane:EtOAc to provide the target as a yellowish solid (29%): $R_f$(EtOAc) 0.64; $^1$H-NMR (CDCl$_3$ 500 MHz) 6.71 (m, 3H), 6.59 (m, 1H), 6.36 (m, 1H), 6.09 (m, 1H), 3.91 (m, 4H), 3.80 (s, 3H), 3.06 (m, 4H), 2.87 (m, 3H, NH3+), 1.73 (m, 4H), 1.56 (m, 6H).

{4-[4-Amino-3-(azepan-1-yl)phenyl]piperazin-1-yl}(1-methyl-1H-pyrrol-2-yl)methanone (379): To nitro compound (0.116 g, 0.282 mmol) in 20 ml 3:1 EtOH:H$_2$O was added sodium hydrosulfite (0.196 g, 1.128 mmol). The reaction was refluxed overnight whereupon 1 ml 1 M HCl (aq) was added and mixture stirred for 40 min. Sat'd NaHCO$_3$ (aq) was added until pH was ~9 and then extracted 5×5 ml DCM. The solvent was removed by rotary evaporation and the residue purified by flash chromatography 3:1-0:1 hexane:EtOAc to provide the target as a yellowish solid (26%): $R_f$(1:1 hexane:EtOAc) 0.27; $^1$H-NMR (CDCl$_3$ 300 MHz) 6.68 (m, 4H), 6.36 (m, 1H), 6.09 (m, 1H), 3.91 (m, 4H), 3.80 (s, 3H), 3.05 (m, 8H), 1.74 (m, 4H), 1.54 (m, 6H).

{4-[4-Dichloroacetamido-3-(piperidin-1-yl)phenyl]piperazin-1-yl}(1-methyl-1H-pyrrol-2-yl)methanone (380): Treat amine (0.029 g, 77 umol) in 2 ml DCM with dichloroacetylchloride (0.023 g, 154 umol) and triethylamine (0.023 g, 231 umol). Stir overnight after which the solvent was removed by rotary evaporation and the residue purified by flash chromatography 1:1-0:1 hexane:EtOAc to provide the target as a yellowish solid (58%): $R_f$(EtOAc) 0.89; $^1$H-NMR (CDCl$_3$ 300 MHz) 9.56 (bs, 1H), 8.19 (d, 1H), 6.73 (m, 3H), 6.36 (m, 1H), 6.09 (m, 1H), 6.05 (s, 1H), 3.91 (m, 4H), 3.80 (s, 3H), 3.18 (m, 4H), 2.83 (m, 4H), 1.75 (m, 4H), 1.61 (m, 2H).

{4-[4-Dichloroacetamido-3-(azepan-1-yl)phenyl]piperazin-1-yl}(1-methyl-1H-pyrrol-2-yl)methanone (381): Treat amine (0.032 g, 84 umol) in 2 ml DCM with dichloroacetylchloride (0.025 g, 168 umol) and triethylamine (0.025 g, 252 umol). Stir overnight after which the solvent was removed by rotary evaporation and the residue purified by flash chromatography 1:1 hexane:EtOAc to provide the target as a yellowish solid (44%): $R_f$(EtOAc) 0.87; $^1$H-NMR (CDCl$_3$ 300 MHz) 9.78 (bs, 1H), 8.20 (d, 1H), 6.81 (m, 1H), 6.73 (m, 1H), 6.71 (m, 1H), 6.37 (m, 1H), 6.09 (m, 1H), 6.04 (s, 1H), 3.91 (m, 4H), 3.80 (s, 3H), 3.16 (m, 4H), 3.02 (m, 4H), 1.79 (m, 8H).

{4-[4-2-Hydroxy-N-3-(piperidin-1-yl)phenyl]piperazin-1-yl}(1-methyl-1H-pyrrol-2-yl)methanone (382): Arylamine (0.114 g, 323 umol), triethylamine (1 ml) and methyl hydroxyacetate (0.293 g, 3.26 mmol) in 7.5 ml CH$_3$OH was refluxed overnight. The solvent was removed by rotary evaporation and the residue purified by flash chromatography 4:1-0:1 hexane:EtOAc to provide the target as a yellowish solid (20%): $R_f$(1:1 hexane:EtOAc) 0.10; $^1$H-NMR (CDCl$_3$ 500 MHz) 8.40 (bs, 1H), 8.12 (d, 1H), 6.74 (m, 4H), 6.40 (m, 1H), 6.17 (m, 1H), 4.05 (s, 2H), 3.95 (m, 4H), 3.83 (s, 3H), 3.20 (m, 4H), 3.11 (m, 4H), 2.00 (m, 4H).

2-Chloro-N-(4-{4-[(1-methyl-1H-pyrrol-2-yl)carbonyl]piperadin-1-yl}phenyl)acetamide (383): From the starting amine (378)(0.035 g, 95 umol) in 5 ml DCM was stirred overnight with chloroacetyl chloride (15.1 ul, 190 umol) and TEA (39.7 ul, 285 umol). The solvent was removed by rotary evaporation and the residue purified by flash chromatography 1:1-0:1 hexane:EtOAc to provide the target as a yellowish solid (79%): $R_f$(EtOAc) 0.81; $^1$H-NMR (CDCl$_3$ 500 MHz) 9.63 (bs, 1H), 8.29 (d, 1H), 6.81 (d, 1H), 6.74 (m, 2H), 6.40 (m, 1H), 6.12 (m, 1H), 4.24 (s, 2H), 3.94 (m, 4H), 3.83 (s, 3H), 3.19 (m, 4H), 2.84 (m, 4H), 1.79 (m, 4H), 1.62 (bs, 2H); ESMS 445 (M+H, 100%); HRMS C$_{23}$H$_{31}$ClN$_5$O$_2$ calc 444.2161, found 444.2165.

2-Chloro-N-(4-{4-[(1-methyl-1H-pyrrol-2-yl)carbonyl]-3-(azepan-1-yl)piperazin-1-yl}phenyl)acetamide (384): From the starting amine (379)(0.018 g, 47 umol) in 3 ml DCM was stirred overnight with chloroacetyl chloride (15.1 ul, 190 umol) and TEA (39.7 ul, 285 umol). The solvent was removed by rotary evaporation and the residue purified by flash chromatography 1:1-0:1 hexane:EtOAc to provide the target as a yellowish solid (50%): $R_f$(EtOAc) 0.81; $^1$H-NMR (CDCl$_3$ 500 MHz) 9.77 (bs, 1H), 8.29 (d, 1H), 6.83 (d, 1H), 6.73 (m, 2H), 6.40 (m, 1H), 6.13 (m, 1H), 4.24 (s, 2H), 3.94 (m, 4H), 3.83 (s, 3H), 3.19 (m, 4H), 3.03 (m, 4H), 1.79 (m, 10H); ESMS 481 (M+Na, 100%); HRMS C$_{24}$H$_{33}$ClN$_5$O$_2$ calc 458.2317, found 458.2317.

2,2-Dichloro-N-isopropyl-(4-{4-[(1-methyl-1H-pyrrol-2-yl)carbonyl]-3-(piperadin-1-yl)piperazin-1-yl}phenyl)acetamide (385): From the starting amine (0.012 g, 28 umol) in 2 ml DCM was stirred overnight with dichloroacetyl chloride (5 ul, 56 umol) and TEA (12 ul, 84 umol). The solvent was removed by rotary evaporation and the residue purified by flash chromatography 2:1-1:1 hexane:EtOAc to provide the target as a yellowish solid (33%): $R_f$ (1:1 hexane:EtOAc) 0.62; $^1$H-NMR (CDCl$_3$ 300 MHz) 6.95 (d, 1H), 6.75 (m, 1H), 6.62 (d, 1H), 6.50 (dd, 1H), 6.40 (dd, 1H), 6.12 (dd, 1H), 5.94 (s, 1H), 4.50 (m, 1H), 3.95 (m, 4H), 3.83 (s, 3H), 3.28 (m, 4H), 3.20 (m, 4H), 1.68 (m, 8H), 1.29 (d, 3H), 1.09 (d, 3H); ESMS 535 (M+H, 100%); HRMS C$_{27}$H$_{38}$Cl$_2$N$_5$O$_2$ calc 534.2397, found 534.2403.

The following piperazine compounds were prepared by the methods described above.

1-[4-(4-Nitrophenyl)-3-(pyrrolidin-1-yl)phenyl]-1,4-diazepan-1-yl](1-methyl-1H-pyrrol-2-yl)methanone (N102):

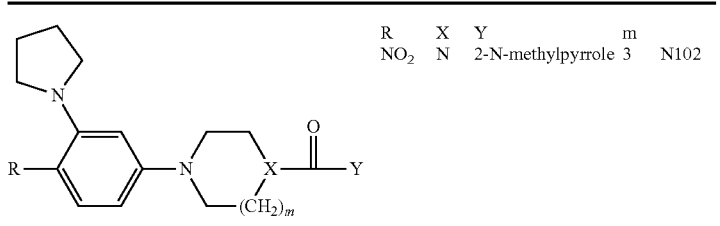

| R | X | Y | m | |
|---|---|---|---|---|
| NO$_2$ | N | 2-N-methylpyrrole | 3 | N102 |

$R_f$ (EtOAc) 0.58; $^1$H-NMR (CDCl$_3$ 500 MHz) 7.82 (d, 1H), 6.62 (bs, 1H), 6.29 (bs, 1H), 6.11 (bd, 1H), 6.04 (t, 1H), 5.82 (bs, 1H), 4.02 (bs, 2H), 3.72 (t, 2H), 3.67 (m, 4H), 3.14 (bs, 4H), 2.06 (bs, 2H), 1.95 (bs, 4H).

1-[4-(4-Dichloroacetamido-N-methyl-phenyl)-3-(azepan-1-yl)]piperazin-1-yl](1-methyl-1H-pyrrol-2-yl)methanone (7-220):

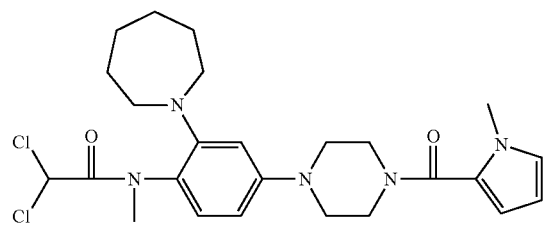

$R_f$ (1:1 hexane EtOAc) 0.48; $^1$H-NMR (CDCl$_3$ 500 MHz) 7.05 (d, 1H), 6.76 (t, 1H), 6.63 (d, 1H), 6.54 (dd, 1H), 6.41 (dd, 1H), 6.14 (dd, 1H), 6.04 (s, 1H), 3.96 (t, 4H), 3.84 (s, 3H), 3.32 (s, 3H), 3.29 (t, 4H), 3.19 (t, 4H), 1.76 (m, 4H), 1.68 (m, 4H), 1.61 (m, 2H); ESMS 508 (100%, M+H).

1-[4-(4-Nitrophenyl)-3-(azocan-1-yl)]piperazin-1-yl](1-methyl-1H-pyrrol-2-yl)methanone (N104):

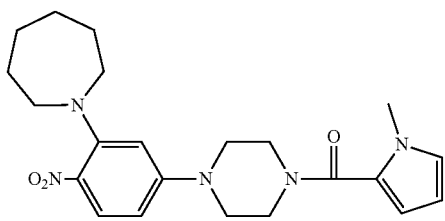

$R_f$ (1:1 hexane EtOAc) 0.48; $^1$H-NMR (CDCl$_3$ 500 MHz) 7.75 (d, 1H), 6.75 (s, 1H), 6.41 (s, 2H), 6.33 (d, 1H), 6.12 (s, 1H), 3.93 (bs, 4H), 3.83 (s, 3H), 3.37 (m, 8H), 1.76 (m, 4H), 1.58 (m, 6H).

1-[4-(4-Nitro-3methylphenyl)-3-(piperidin-1-yl)]piperazin-1-yl](1-methyl-1H-pyrrol-2-yl)methanone (8-32) and 1-[4-(4-amino-3-methylphenyl)-3-(piperidin-1-yl)]piperazin-1-yl](1-methyl-1H-pyrrol-2-yl)methanone (8-34):

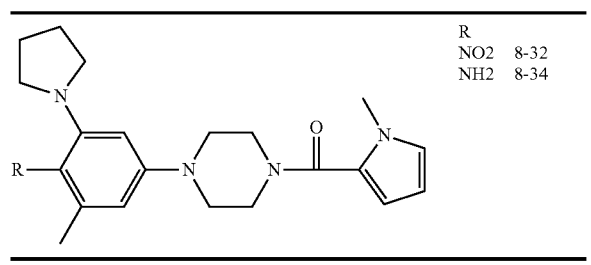

| R | |
|---|---|
| NO2 | 8-32 |
| NH2 | 8-34 |

8-32: $R_f$ (1:1 hexane:EtOAc) 0.45; $^1$H-NMR (CDCl$_3$ 300 MHz) 6.73 (t, 1H), 6.38 (dd, 1H), 6.14 (d, 1H), 6.11 (dd, 1H), 6.08 (d, 1H), 3.92 (t, 4H), 3.81 (s, 3H), 3.30 (t, 4H), 3.23 (t, 4H), 2.30 (s, 3H), 1.95 (m, 4H).

(8-34): flash chromatography (2:1-1:1 hexane:EtOAc) to provide the product as a yellow solid (34%): $R_f$ (1:1 hexane:EtOAc) 0.20; $^1$H-NMR (CDCl$_3$ 300 MHz) 6.72 (dd, 1H), 6.66 (d, 1H), 6.51 (d, 1H), 6.38 (dd, 1H), 6.11 (dd, 1H), 3.92 (t, 4H), 3.82 (s, 3H), 3.05 (m, 8H), 2.20 (s, 3H), 1.95 (m, 4H); ESMS 368 (100%, M+H).

1-[4-(4-Nitrophenyl)-3-(piperidin-1-yl)-2-methylphenyl]piperazin-1-yl](1-methyl-1H-pyrrol-2-yl)methanone (8-33), 1-[4-(4-amino-2-methylphenyl)-3-(piperidin-1-yl)]piperazin-1-yl](1-methyl-1H-pyrrol-2-yl)methanone (8-83), and 1-{4-[4-dichloroacetamido-2-methylphenyl]piperazin-1-yl}(1-methyl-1H-pyrrol-2-yl)methanone (8-85):

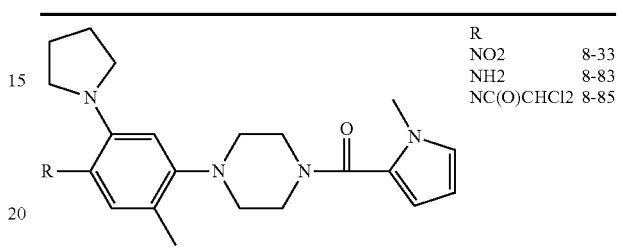

| R | |
|---|---|
| NO2 | 8-33 |
| NH2 | 8-83 |
| NC(O)CHCl2 | 8-85 |

(8-33): $R_f$ (1:1 hexane:EtOAc) 0.64; $^1$H-NMR (CDCl$_3$ 300 MHz) 7.70 (s, 1H), 6.74 (t, 1H), 6.43 (s, 1H), 6.40 (dd, 1H), 6.12 (dd, 1H), 3.95 (t, 4H), 3.82 (s, 3H), 3.23 (t, 4H), 3.02 (t, 4H), 2.26 (s, 3H), 2.02 (m, 4H).

(8-83): $R_f$ (1:1 hexane:EtOAc) 0.27; $^1$H-NMR (CDCl$_3$ 500 MHz) 6.77 (s, 1H), 6.73 (s, 1H), 6.62 (s, 1H), 6.40 (s, 1H), 6.12 (s, 1H), 3.90 (s, 4H), 3.84 (s, 3H), 3.05 (4H), 2.89 (4H), 2.26 (s, 3H), 1.94 (m, 4H); ESMS 368 (100%, M+H).

(8-85): $R_f$ (1:1 hexane:EtOAc) 0.59; $^1$H-NMR (CDCl$_3$ 500 MHz) 9.33 (bs, 1H), 8.01 (s, 1H), 6.87 (s, 1H), 6.74 (s, 1H), 6.40 (s, 1H), 6.13 (s, 1H), 6.10 (s, 1H), 3.93 (4H), 3.84 (3H), 3.08 (4H), 2.93 (4H), 2.34 (3H), 2.01 (4H).

Inhibitory Activity of Representative Pipirazine Compounds

The inhibition of ALDH1A1 (IC$_{50}$), ALDH1A2 (IC$_{50}$), ALDH2 (IC$_{50}$), and ALDH1A1/ALDH1A2 (EC$_{50}$) of representative piperazine compounds of the invention is summarized in Table 2. The inhibition activities were determined by the screening assay described herein.

TABLE 2

Piperazine Compound Inhibition of ALDH1A1, ALDH1A2, and ALDH2.

| Cmpd | IC50 (uM) ALDH1A1 | IC50 (uM) ALDH1A2 | IC50 (uM) ALDH2 | EC50 (uM) ALDH1A1 | EC50 (uM) ALDH1A2 |
|---|---|---|---|---|---|
| 323 | | 0.103 | 52 | 0.195 | 0.457 |
| 324 | | 0.142 | 5.22 | | |
| 326 | | 0.058 | 97.3 | 0.44 | 0.11 |
| 327 | | 0.313 | 79.83 | >0.5 | 0.862 |
| 329 | | 0.079 | 86.36 | <0.5 | <0.5 |
| 330 | | 0.053 | 10.15 | | |
| 331 | | 0.062 | 24.93 | 0.088 | 0.121 |
| 332 | | 0.388 | 58.29 | 0.413 | 0.437 |
| 334 | | 1.326 | >100 | 0.260 | 0.377 |
| 335 | | 0.342 | 2.067 | | |
| 339 | 0.675 | 0.837 | 48.14 | 0.333 | 0.293 |
| 341 | 1.65 | 1.447 | >100 | <0.5 | 0.505 |
| 342 | | 4.561 | >100 | 0.468 | 0.966 |
| 343 | | 1.943 | 97.52 | <0.5 | <0.5 |
| 344 | 0.453 | 0.264 | 48.58 | <0.5 | <0.5 |
| 345 | | 3.991 | >100 | <0.5 | 1.19 |
| 346 | | 5.692 | >100 | <0.5 | 1.42 |
| 347 | 1.07 | 0.042 | 61.61 | 0.33 | 0.35 |
| 367 | 0.23 | 2.3 | >80 | 0.244 | >5 |
| 372 | 0.3 | 3.6 | 3.5 | 0.069 | 0.7 |

TABLE 2-continued

Piperazine Compound Inhibition of ALDH1A1, ALDH1A2, and ALDH2.

| | IC50 (uM) | IC50 (uM) | IC50 (uM) | EC50 (uM) | |
|---|---|---|---|---|---|
| Cmpd | ALDH1A1 | ALDH1A2 | ALDH2 | ALDH1A1 | ALDH1A2 |
| 373 | 1.44 | 2.13 | >100 | 0.37 | 0.88 |
| 374 | 0.41 | 3.48 | >100 | 0.15 | 1.67 |
| 379 | 0.714 | 2.58 | | 0.736 | 2.58 |
| 380 | 0.023 | 8.7 | | 0.099 | >5 |
| 381 | 0.023 | 18.5 | | .059 | >5 |
| N104 | 0.141 | 6.5 | | | |

Methods

Cloning, Expression and Purification of Aldehyde Dehydrogenases (ALDHs)

ALDHs were cloned into bacterial expression vector for in vitro enzyme assays and into mammalian expression vectors for cell-based enzyme assays. Human ALDH1A1 cDNA and human ALDH2 cDNA were purchased from OriGene (SC321535) and Open Biosystems (MHS4771-99611182), respectively. and human ALDH1A2 cDNA was cloned from human testis RNA using RT-PCR (Population Division of the Department of Economic and Social Affairs of the United Nations Secretariat. World Population prospects: the 2008 revision. Available at http://www.un.org/esa/population/ (Retrieved Sep. 30, 2011)). For bacterial expression, an open reading frame of ALDH1A1 and ALDH2 were subcloned into the pETite vector (Lucigen) with a 5' histidine-tag and that of ALDH1A2 into a pET28 vector (Novagen) with a 3' histidine-tag. Correct frame and sequences were verified through DNA sequencing (UW DNA sequencing facility). ALDHs were induced with 1 mM IPTG and purified using His.Bind resin (Novagen, San Diego, Calif.) and stored in a buffer containing 20 mM Hepes (pH 8), 150 mM KCl and 1 mM EDTA as previously described (Fierce, Y., de Morais Vieira, M., Piantedosi, R., Wyss, A., Blaner, W. S., and Paik, J. (2008) In vitro and in vivo characterization of retinoid synthesis from beta-carotene. Archives of biochemistry and biophysics 472, 126-138).

Inhibitor Screening using Purified Enzymes

ALDH1A1 and ALDH1A2 activity was determined as previously reported (Beedle M T, Stevison F, Zhong G, Topping T, Hogarth C, Isoherranen N, Griswold M D. Sources of All-Trans Retinal Oxidation Independent of the Aldehyde Dehydrogenase 1A Isozymes Exist in the Postnatal Testis. Biol Reprod. 2018 Sep. 21. doi: 10.1093/biolre/ioy200). Briefly, purified enzymes were incubated in a buffer containing 10 mM HEPES buffer (pH 8.0), 150 mM potassium chloride and 2 mM EDTA with 2 mM NAD. Retinoic acid production was determined using HPLC as previously reported (Amory J K, Muller C H, Shimshoni A J, Isoherranen N, Paik J, Moreb J S, Amory D W, Evanoff R, Goldstein A S, Griswold M D. Suppression of spermatogenesis by bisdichloroacetyldiamines is mediated by inhibition of testicular retinoic acid biosynthesis. Journal of Andrology 2011; 32(1):111-119). Inhibitors were diluted in DMSO and added to the reactions. DMSO did not exceed 1% of total reaction volume. For initial screening of inhibitors for ALDH1A2, 1 µg ALDH1A2, 5 µM all-trans-retinal and 5 µM inhibitors were incubated for 15 min at 37° C. The compounds that resulted in >50% inhibition of ALDH1A2 activity were further analyzed by IC50 determination. For this purpose, 0.5 µg ALDH1A2 and 0.5 µg all-trans-retinal were incubated for 5 minutes at 37° C. with varying concentrations of inhibitors. To determine specificity toward ALDH1A2, the $IC_{50}$ for ALDH2 was determined for compounds that resulted in >50% inhibition of ALDH1A2. For this, 2 µg purified ALDH2, 20 µM propanal and varying concentrations of inhibitors were incubated at room temperature. Enzyme activity was determined by measuring fluorescence of NADH (Ex, 350 nm/Em, 460 nm) using a Victor3 plate reader (PerkinElmer), and initial velocity was calculated from two consecutive readings over 1 minute.

Generation of Stable Cell Lines Expressing ALDH1A1 or ALDH1A2

ALDH1A1 cDNA clone was purchased transfection-ready, and ALDH1A2 full-length cDNA was subcloned into pcDNA3, a mammalian expression vector. ALDH1A1 and ALDH1A2 were transfected into H1299 cells (CRL5803, ATCC) using Lipofectamine 3000 (Invitrogen) following the manufacturer's instructions. Stably transfected cells were selected with G418 (1.2 mg/ml) and referred to as ALDH1A1/H1299 and ALDH1A2/H1299. For the cell-based enzyme assays, H1299 cells were routinely grown in RPMI-1640 (ATCC) supplemented with 10% fetal bovine serum (Atlanta Biologicals) in a 37 C, 5% $CO_2$, moisture-saturated atmosphere. H1299, ALDH1A1/H1299 and ALDH1A2/H1299 cells were seeded into 12-well plates ($1 \times 10^5$ cells/well) and grown for 2 days to confluence. Confluent cells were treated for 20 hours in the above media excluding serum with 2 µM all-trans-retinal, and varying concentrations of inhibitors. Serum-free media was used for the treatment period to avoid retinoic acid in serum. Retinoic acid concentrations were determined from cells and media, and specificity of inhibitors was determined by comparing retinoic acid levels in the presence and absence of the inhibitors in ALDH1A1- vs. ALDH1A2-expressing cells.

ALDH1A2 High Through Put Assay

Enzyme soup (15 µl buffer (750 mM KCl, 50 mM HEPES pH 8, 10 mM EDTA), 15 µl 2 mM NAD (freshly prepared), 30 µl $H_2O$ and 0.4 µl ALDH1a2 enzyme (0.7 mg/ml) was added to black-walled, clear-bottom polystyrene 384-well plates (Matrix) using the Wellmate peristaltic microplate dispenser (Thermo Fisher Scientific, US). After enzyme addition, 50 nL of inhibitor diluted to 0.3 mM in 100% DMSO were added to the assay plates (final assay concentration 3 uM) via a slotted pin containing tool (VP Scientific, San Diego, Calif.) utilizing the CyBi Well Vario liquid handler (CyBio, US, Boston Mass.). Within 30 min of compound addition, background fluorescence within each well was determined using a Perkin Elmer EnVision Multilabel Platereader (10 flashes, top excitation filter—Umbelliferone 355 nm, emission filter-Umbelliferone 460 nm, measurement height at 4.7 mm, Excitation Light at 100%, Detector gain at 439) and the relative fluorescence signal captured digitally via computer. Plates were placed back onto the microplate dispenser and substrate (15 µL of 500 uM propanal (aq)) was added to each well. Following 30 min incubation at room temperature, relative fluorescence of each well was again determined as previously on the EnVision Plate reader. Each plate was tested in duplicate with vehicle (DMSO) controls and a positive control dose response utilizing WIN 18,499 ranging from 10 µM to 10 pM in half log units on each plate. Background fluorescence inherent to the compounds was subtracted from each corresponding well prior to determination of relative fluorescence intensity. Approximately 0.3% of the compounds within the library exhibited auto-fluorescence that interfered with the assay and were removed from further consideration. The following formula was used for calculation of percent activity of each sample:

$$\text{Percent activity} = \frac{\text{Unknown} - \text{Background}}{\text{Vehicle control} - \text{Background}} \times 100$$

Reliability of the assay was assessed by calculating the Z score:

$$Zscore = \frac{\text{Unknown} - \text{Mean}}{\text{Standard Deviation}}$$

Thus, a determination of the separation between the means and standard deviations of vehicle and negative controls on a plate by plate basis is assessed for each well. Furthermore, reliability of data from each plate was determined by the results of the WIN dose response curve. Inhibitors with activity at 3 uM or better compared to WIN 18,446 dose response were then assayed using the ALDH1A2 retinoic acid-HPLC assay and if potent inhibitors then using the ALDH2 assay.

The particulars shown herein are by way of example and for purposes of illustrative discussion of the preferred embodiments of the present invention only and are presented in the cause of providing what is believed to be the most useful and readily understood description of the principles and conceptual aspects of various embodiments of the invention. In this regard, no attempt is made to show structural details of the invention in more detail than is necessary for the fundamental understanding of the invention, the description taken with the drawings and/or examples making apparent to those skilled in the art how the several forms of the invention may be embodied in practice.

Definitions and explanations used in the present disclosure are meant and intended to be controlling in any future construction unless clearly and unambiguously modified in the following examples or when application of the meaning renders any construction meaningless or essentially meaningless. In cases where the construction of the term would render it meaningless or essentially meaningless, the definition should be taken from Webster's Dictionary, 3rd Edition or a dictionary known to those of ordinary skill in the art, such as the Oxford Dictionary of Biochemistry and Molecular Biology (Ed. Anthony Smith, Oxford University Press, Oxford, 2004).

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Unless the context clearly requires otherwise, throughout the description and the claims, the words 'comprise', 'comprising', and the like are to be construed in an inclusive sense as opposed to an exclusive or exhaustive sense; that is to say, in the sense of "including, but not limited to". Words using the singular or plural number also include the plural and singular number, respectively. Additionally, the words "herein," "above," and "below" and words of similar import, when used in this application, shall refer to this application as a whole and not to any particular portions of the application.

While illustrative embodiments have been illustrated and described, it will be appreciated that various changes can be made therein without departing from the spirit and scope of the invention.

The embodiments of the invention in which an exclusive property or privilege is claimed are defined as follows:

1. A compound having formula (I):

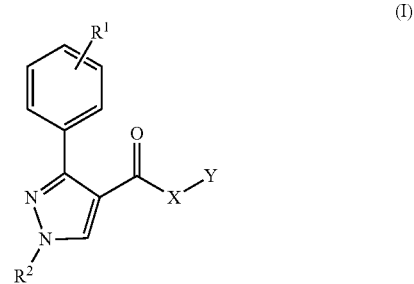

or a pharmaceutically acceptable salt thereof, wherein $R^1$ is selected from the group consisting of:
(a) $NO_2$,
(b) $SO_2R^a$, wherein $R^a$ is C1-C6 linear or branched alkyl or alkenyl,
(c) C(=O)$R^a$, wherein $R^a$ is hydrogen, C1-C6 linear or branched alkyl or alkenyl, optionally substituted with one or two halo groups, or $NR^cR^d$, wherein $R^c$ and $R^d$ are independently selected from hydrogen and C1-C3 linear or branched alkyl, and
(d) NH($R^e$) or N($R^a$)($R^e$), wherein $R^a$ is C1-C6 linear or branched alkyl, and wherein $R^e$ is selected from
(i) hydrogen,
(ii) C(=O)H,
(iii) C(=O)$R^f$, wherein $R^f$ is C1-C6 linear or branched alkyl or cyclo alkyl, optionally substituted with one or two halo groups,
(iv) C(=O)(CH$_2$)$_n$OH, wherein n is 1, 2, 3, or 4, or
(v) SO$_2R^g$, wherein $R^g$ is C1-C6 linear or branched alkyl;
$R^2$ is selected from the group consisting of:
(a) phenyl optionally substituted with
(i) C(=O)$R^a$, wherein $R^a$ is C1-C6 linear or branched alkyl, or $R^a$ is $NR^cR^d$, wherein $R^c$ and $R^d$ are independently selected from is hydrogen and C1-C3 linear or branched alkyl, or $R^c$ is hydrogen and $R^d$ is hydroxy,
(ii) CO$_2R^b$, wherein $R^b$ is hydrogen, or
(iii) cyano, (b) C1-C6 linear or branched alkyl, and
(c) C1-C6 linear or branched haloalkyl;
X is NH; and
Y is m-fluoro phenyl.

2. The compound of claim 1, or a pharmaceutically acceptable salt thereof, wherein $R^1$ is $C(=O)R^a$, wherein $R^a$ is C1-C6 linear or branched alkyl or alkenyl, optionally substituted with one or two halo groups, or $NH(C=O)R^f$, wherein $R^f$ is C1-C6 linear or branched alkyl, optionally substituted with one or two halo groups.

3. The compound of claim 1, or a pharmaceutically acceptable salt thereof, wherein $R^1$ is $C(=O)R^a$, wherein $R^a$ is C1-C6 linear or branched alkyl.

4. The compound of claim 1, or a pharmaceutically acceptable salt thereof, wherein $R^2$ is selected from phenyl optionally substituted with cyano or $CO_2R^a$, wherein $R^a$ is C1-C6 linear or branched alkyl.

5. A compound having formula (IV):

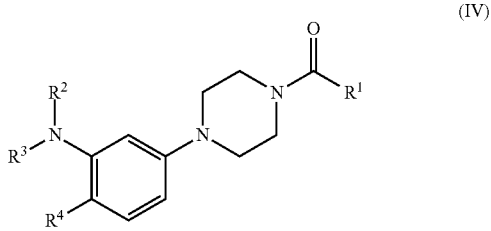

(IV)

or a pharmaceutically acceptable salt thereof, wherein
$R^1$ is N-methyl pyrrolyl;
$R^2$ and $R^3$ taken together with the nitrogen atom to which they are attached form a 4-, 5-, 6-, or 7-membered ring; and
$R^4$ is selected from the group consisting of:
(a) $NO_2$,
(b) $NH(R^e)$, wherein $R^e$ is
  $C(=O)R^f$, wherein $R^f$ is C1-C6 linear or branched alkyl, optionally substituted with one or two halo groups, and
(c) $N(R^g)C(=O)R^f$, wherein $R^g$ is C1-C6 linear or branched alkyl, and $R^f$ is C1-C6 linear or branched alkyl optionally substituted with one or two halo groups.

6. A compound of claim 1 selected from the group consisting of:
N-(3-fluorophenyl)-3-(4-nitrophenyl)-1-phenyl-1H-pyrazole-4-carboxamide;
3-(4-(methylsulfonyl)phenyl)-N-(3-fluorophenyl)-1-phenyl-1H-pyrazole-4-carboxamide;
3-(4-(ethylsulfonyl)phenyl)-N-(3-fluorophenyl)-1-phenyl-1H-pyrazole-4-carboxamide;
N-(4-cyanophenyl)-3-[4-(methylsulfonyl)phenyl]-1-(3-fluorophenyl)-1H-pyrazole-4-carboxamide;
1-(4-formylphenyl)-3-[4-(methylsulfonyl)phenyl]-N-(3-fluorophenyl)-1H-pyrazole-4-carboxamide;
3-{4-dichloroacetyl-N-methyl-aminophenyl}-N-(3-fluorophenyl)-1-phenyl-1H-pyrazole-4-carboxamide;
3-[4-(dichloroacetyl)phenyl]-N-(3-fluorophenyl)-1-phenyl-1H-pyrazole-4-carboxamide;
3-{[(dichloroacetyl)(ethyl)amino]methyl}-N-(3-fluorophenyl)-1-phenyl-1H-pyrazole-4-carboxamide; and
pharmaceutically acceptable salts thereof.

7. A pharmaceutical composition comprising a compound of claim 1, or a pharmaceutically acceptable salt thereof, and a pharmaceutically acceptable carrier.

8. An implantable device comprising a compound of claim 1, or a pharmaceutically acceptable salt thereof.

9. A method for inhibiting ALDH1A1 and ALDH1A2 in a subject, comprising administering a therapeutically effective amount of a compound of claim 1, or a pharmaceutically acceptable salt thereof, to subject in need thereof.

10. A method for preventing spermatogenesis in a subject, comprising administering a therapeutically effective amount of a compound of claim 1, or a pharmaceutically acceptable salt thereof, to subject in need thereof.

11. The method of claim 9, wherein the compound, or a pharmaceutically acceptable salt thereof, is administered systemically, intravenously, subcutaneously, intramuscularly, or topically.

12. The method of claim 9, wherein the compound, or a pharmaceutically acceptable salt thereof, is administered by release from an implantable device.

13. The method of claim 10, wherein the compound, or a pharmaceutically acceptable salt thereof, is administered systemically, intravenously, subcutaneously, intramuscularly, or topically.

14. The method of claim 10, wherein the compound, or a pharmaceutically acceptable salt thereof, is administered by release from an implantable device.

15. A compound of claim 5 selected from the group consisting of:
1-[4-(4-N-dichloroacetyl-3-(pyrrolidin-1-yl)phenyl]piperazin-1-yl](1-methyl-1H-pyrrol-2-yl)methanone;
1-[4-(4-N-chloroacetyl-3-(pyrrolidin-1-yl)phenyl]piperazin-1-yl](1-methyl-1H-pyrrol-2-yl)methanone;
1-[4-(4-nitrophenyl)-3-(azepan-1-yl)phenyl]piperazin-1-yl](1-methyl-1H-pyrrol-2-yl)methanone;
{4-[4-amino-3-(azepan-1-yl)phenyl]piperazin-1-yl}(1-methyl-1H-pyrrol-2-yl)methanone;
{4-[4-dichloroacetamido-3-(piperidin-1-yl)phenyl]piperazin-1-yl}(1-methyl-1H-pyrrol-2-yl)methanone;
{4-[4-dichloroacetamido-3-(azepan-1-yl)phenyl]piperazin-1-yl}(1-methyl-1H-pyrrol-2-yl)methanone;
1-[4-(4-nitrophenyl)-3-(azocan-1-yl)]piperazin-1-yl](1-methyl-1H-pyrrol-2-yl)methanone; and
pharmaceutically acceptable salts thereof.

16. A pharmaceutical composition comprising a compound of claim 5, or a pharmaceutically acceptable salt thereof, and a pharmaceutically acceptable carrier.

17. An implantable device comprising a compound of claim 5, or a pharmaceutically acceptable salt thereof.

18. A method for inhibiting ALDH1A1 and ALDH1A2 in a subject, comprising administering a therapeutically effective amount of a compound of claim 5, or a pharmaceutically acceptable salt thereof, to subject in need thereof.

19. A method for preventing spermatogenesis in a subject, comprising administering a therapeutically effective amount of a compound of claim 5, or a pharmaceutically acceptable salt thereof, to subject in need thereof.

20. The method of claim 18, wherein the compound, or a pharmaceutically acceptable salt thereof, is administered systemically, intravenously, subcutaneously, intramuscularly, or topically.

21. The method of claim 18, wherein the compound, or a pharmaceutically acceptable salt thereof, is administered by release from an implantable device.

22. The method of claim 19, wherein the compound, or a pharmaceutically acceptable salt thereof, is administered systemically, intravenously, subcutaneously, intramuscularly, or topically.

23. The method of claim 19, wherein the compound, or a pharmaceutically acceptable salt thereof, is administered by release from an implantable device.

\* \* \* \* \*

UNITED STATES PATENT AND TRADEMARK OFFICE
CERTIFICATE OF CORRECTION

PATENT NO. : 11,548,875 B2
APPLICATION NO. : 17/262877
DATED : January 10, 2023
INVENTOR(S) : A. Goldstein et al.

Page 1 of 1

It is certified that error appears in the above-identified patent and that said Letters Patent is hereby corrected as shown below:

In the Claims

| Column | Line | Claim | |
|--------|------|-------|---|
| 90 | 63 | 1 | change "from is hydrogen" to -- from hydrogen -- |

Signed and Sealed this
First Day of August, 2023

Katherine Kelly Vidal
*Director of the United States Patent and Trademark Office*